(12) United States Patent
Doudna et al.

(10) Patent No.: US 12,227,753 B2
(45) Date of Patent: *Feb. 18, 2025

(54) CASY COMPOSITIONS AND METHODS OF USE

(71) Applicant: The Regents of the University of California, Oakland, CA (US)

(72) Inventors: Jennifer A. Doudna, Berkeley, CA (US); David Burstein, Berkeley, CA (US); Janice S. Chen, Berkeley, CA (US); Lucas B. Harrington, Berkeley, CA (US); David Paez-Espino, Walnut Creek, CA (US); Jillian F. Banfield, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 432 days.

This patent is subject to a terminal disclaimer.

(21) Appl. No.: 16/755,534

(22) PCT Filed: Oct. 31, 2018

(86) PCT No.: PCT/US2018/058522
§ 371 (c)(1),
(2) Date: Apr. 10, 2020

(87) PCT Pub. No.: WO2019/089804
PCT Pub. Date: May 9, 2019

(65) Prior Publication Data
US 2020/0255858 A1  Aug. 13, 2020

Related U.S. Application Data

(60) Provisional application No. 62/580,393, filed on Nov. 1, 2017.

(51) Int. Cl.
| | | |
|---|---|---|
| C12N 15/82 | (2006.01) | |
| C12N 9/22 | (2006.01) | |
| C12N 15/113 | (2010.01) | |
| C12N 15/85 | (2006.01) | |

(52) U.S. Cl.
CPC .............. *C12N 15/85* (2013.01); *C12N 9/22* (2013.01); *C12N 15/113* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 6,773,885 B1 | 8/2004 | Walder et al. |
| 8,597,886 B2 | 12/2013 | Smith et al. |
| 8,815,782 B2 | 8/2014 | Zeiner et al. |
| 9,730,967 B2 | 6/2017 | Kovarik et al. |
| 9,790,490 B2 | 10/2017 | Zhang et al. |
| 10,253,365 B1 | 4/2019 | Doudna et al. |
| 10,266,886 B2 | 4/2019 | Abudayyeh et al. |
| 10,316,324 B2 * | 6/2019 | Begemann .......... C12N 15/825 |
| 10,337,051 B2 | 7/2019 | Doudna et al. |
| 10,494,664 B2 | 12/2019 | Doudna et al. |
| 10,570,415 B2 | 2/2020 | Doudna et al. |
| 11,180,743 B2 | 11/2021 | Doudna et al. |
| 11,371,031 B2 | 6/2022 | Doudna et al. |
| 11,441,137 B2 | 9/2022 | Doudna et al. |
| 11,453,866 B2 | 9/2022 | Doudna et al. |
| 11,459,599 B2 | 10/2022 | Doudna et al. |
| 11,459,600 B2 | 10/2022 | Doudna et al. |
| 11,739,335 B2 | 8/2023 | Chevessier-tünnesen et al. |
| 11,795,472 B2 | 10/2023 | Doudna et al. |
| 11,827,919 B2 | 11/2023 | Doudna et al. |
| 11,840,725 B2 | 12/2023 | Doudna et al. |
| 11,873,504 B2 | 1/2024 | Doudna et al. |
| 11,970,719 B2 | 4/2024 | Doudna et al. |
| 2013/0123129 A1 | 5/2013 | Zeiner et al. |

(Continued)

FOREIGN PATENT DOCUMENTS

| | | |
|---|---|---|
| CN | 1886512 A | 12/2006 |
| CN | 101283089 A | 10/2008 |

(Continued)

OTHER PUBLICATIONS

Burstein et al 2017 (Nature 542: p. p. 237-241) (Year: 2017).*
Genbank U2UMQ6, Jun. 2023.*
Koonin, et al.; "CRISPR-Cas: an adaptive immunity system in prokaryotes"; F1000 Biology Reports; vol. 1, No. 95, 6 pages (Dec. 9, 2009).
Abudayyeh, et al.; "C2c2 is a single-component programmable RNA-guided RNA-targeting CRISPR effector"; Science; vol. 353, No. 6299, 23 pages (Aug. 5, 2016).
Abudayyeh, et al.; "C2c2 is a single-component programmable RNA-guided RNA-targeting CRISPR effector; Supplementary Information"; Science; vol. 353, vol. 6299, 31 pages (Aug. 5, 2016).
Abudayyeh, et al.; "RNA targeting with CRISPR-Cas13"; Nature; vol. 550, 18 pages (Oct. 12, 2017).

(Continued)

*Primary Examiner* — Matthew R Keogh
(74) *Attorney, Agent, or Firm* — Bozicevic, Field & Francis LLP

(57) ABSTRACT

Provided are compositions and methods that include a CasY transactivating noncoding RNA (trancRNA) (referred to herein as a "CasY trancRNA"), nucleic acids encoding the CasY trancRNA, and/or a modified host cell comprising the CasY trancRNA (and/or a nucleic acid encoding the same). Subject compositions and methods can also include one or more of: (a) a "CasY" protein (also referred to as a CasY polypeptide, a Cas12d protein, and a Cas12d polypeptide), a nucleic acid encoding the CasY protein, and/or a modified host cell comprising the CasY protein (and/or a nucleic acid encoding the same); and (b) a CasY guide RNA (also referred to herein as a "Cas12d guide RNA") that binds to and provides sequence specificity to the CasY protein, a nucleic acid encoding the CasY guide RNA, and/or a modified host cell comprising the CasY guide RNA (and/or a nucleic acid encoding the same).

16 Claims, 35 Drawing Sheets

Specification includes a Sequence Listing.

(56) References Cited

U.S. PATENT DOCUMENTS

| | | | |
|---|---|---|---|
| 2013/0261196 A1 | 10/2013 | Diamond et al. | |
| 2014/0068797 A1 | 3/2014 | Doudna et al. | |
| 2014/0093883 A1 | 4/2014 | Maples et al. | |
| 2014/0273226 A1 | 9/2014 | Wu | |
| 2015/0020223 A1 | 1/2015 | Zhang et al. | |
| 2015/0211058 A1 | 7/2015 | Carstens | |
| 2016/0017366 A1 | 1/2016 | Chen et al. | |
| 2016/0138008 A1 | 5/2016 | Charpentier et al. | |
| 2016/0208243 A1 | 7/2016 | Zhang et al. | |
| 2016/0289659 A1 | 10/2016 | Doudna et al. | |
| 2017/0037432 A1 | 2/2017 | Donohoue et al. | |
| 2017/0051276 A1 | 2/2017 | May et al. | |
| 2017/0175104 A1 | 6/2017 | Doudna et al. | |
| 2017/0198277 A1* | 7/2017 | Kmiec | C12N 15/90 |
| 2017/0211142 A1 | 7/2017 | Smargon et al. | |
| 2017/0233756 A1 | 8/2017 | Begemann et al. | |
| 2017/0306335 A1 | 10/2017 | Zhang et al. | |
| 2017/0321198 A1 | 11/2017 | Severinov et al. | |
| 2017/0321214 A1 | 11/2017 | Zhang et al. | |
| 2017/0362644 A1 | 12/2017 | Doudna et al. | |
| 2017/0369870 A1 | 12/2017 | Gill et al. | |
| 2018/0208976 A1 | 7/2018 | Doudna et al. | |
| 2018/0208977 A1 | 7/2018 | Doudna et al. | |
| 2018/0320163 A1 | 11/2018 | Koonin et al. | |
| 2018/0340218 A1 | 11/2018 | Abudayyeh et al. | |
| 2018/0346927 A1 | 12/2018 | Doudna et al. | |
| 2019/0177775 A1 | 6/2019 | Doudna et al. | |
| 2019/0185933 A1 | 6/2019 | Zhang et al. | |
| 2019/0276842 A1 | 9/2019 | Doudna et al. | |
| 2019/0300908 A1 | 10/2019 | Doudna et al. | |
| 2020/0010878 A1 | 1/2020 | Doudna et al. | |
| 2020/0010879 A1 | 1/2020 | Doudna et al. | |
| 2020/0017879 A1 | 1/2020 | Doudna et al. | |
| 2020/0087640 A1 | 3/2020 | Doudna et al. | |
| 2020/0115688 A1 | 4/2020 | Doudna et al. | |
| 2020/0172886 A1 | 6/2020 | Doudna et al. | |
| 2020/0255858 A1 | 8/2020 | Doudna et al. | |
| 2020/0299660 A1 | 9/2020 | Doudna et al. | |
| 2020/0339967 A1 | 10/2020 | Doudna et al. | |
| 2020/0370028 A1 | 11/2020 | Doudna et al. | |
| 2021/0017508 A1 | 1/2021 | Doudna et al. | |
| 2021/0166783 A1 | 6/2021 | Shmakov et al. | |
| 2021/0209981 A1 | 7/2021 | Wang | |
| 2021/0214697 A1 | 7/2021 | Doudna et al. | |
| 2021/0284891 A1 | 9/2021 | Doudna et al. | |
| 2021/0309981 A1 | 10/2021 | Doudna et al. | |
| 2022/0396812 A1 | 12/2022 | Doudna et al. | |
| 2023/0332218 A1 | 10/2023 | Rauch et al. | |
| 2023/0348872 A1 | 11/2023 | Doudna et al. | |
| 2024/0167052 A1 | 5/2024 | Doudna et al. | |
| 2024/0182953 A1 | 6/2024 | Doudna et al. | |
| 2024/0301376 A1 | 9/2024 | Doudna et al. | |

FOREIGN PATENT DOCUMENTS

| | | |
|---|---|---|
| CN | 103088128 A | 5/2013 |
| CN | 104620107 A | 5/2015 |
| CN | 106701830 A | 5/2017 |
| CN | 110713940 A | 10/2019 |
| EP | 1580273 A1 | 9/2005 |
| EP | 3009511 A2 | 4/2016 |
| EP | 2825654 B1 | 4/2017 |
| EP | 3546573 A1 | 10/2019 |
| EP | 3283625 B1 | 12/2019 |
| EP | 3665279 A1 | 6/2020 |
| JP | 2004521606 A | 7/2004 |
| WO | WO 2014065596 A1 | 5/2014 |
| WO | WO 2015/071474 | 5/2015 |
| WO | WO 2015/139139 | 9/2015 |
| WO | WO 2015/191693 | 12/2015 |
| WO | WO 2016/094872 | 12/2015 |
| WO | WO 2016/106236 | 12/2015 |
| WO | WO 2016/028843 | 2/2016 |
| WO | WO 2016/094867 | 6/2016 |
| WO | WO 2016/205711 | 6/2016 |
| WO | WO 2016/123243 | 8/2016 |
| WO | WO 2016166340 A1 | 10/2016 |
| WO | WO 2016/205613 | 12/2016 |
| WO | WO 2016/205749 | 12/2016 |
| WO | WO 2016/205764 | 12/2016 |
| WO | WO 2017/070605 | 4/2017 |
| WO | WO 2017/205668 | 5/2017 |
| WO | WO 2017/120410 | 7/2017 |
| WO | WO 2017/147345 | 8/2017 |
| WO | WO 2017/176529 | 10/2017 |
| WO | WO 2017/218573 | 12/2017 |
| WO | WO 2017/219027 | 12/2017 |
| WO | WO 2017/223538 | 12/2017 |
| WO | WO 2017207589 A1 | 12/2017 |
| WO | WO 2018027078 A1 | 2/2018 |
| WO | WO 2018035250 A1 | 2/2018 |
| WO | WO 2018/064352 | 4/2018 |
| WO | WO 2018/064371 | 4/2018 |
| WO | WO 2018/107129 | 6/2018 |
| WO | WO 2018/172556 | 9/2018 |
| WO | WO 2018/195545 | 10/2018 |
| WO | WO 2018202800 A1 | 11/2018 |
| WO | WO 2019/030695 | 2/2019 |
| WO | WO 2019/089796 | 5/2019 |
| WO | WO 2019/089804 | 5/2019 |
| WO | WO 2019/089808 | 5/2019 |
| WO | WO 2019/089820 | 5/2019 |
| WO | WO 2019/126577 | 6/2019 |
| WO | WO 2019/022255 | 11/2019 |
| WO | WO 2020023529 A1 | 1/2020 |
| WO | WO 2020/098772 | 5/2020 |

OTHER PUBLICATIONS

Ambion; "RnaseAlert Lab Test Kit v2, User Guide"; 12 pages (Mar. 1, 2013).

Anantharaman, et al.; "Thousands of microbial genomes shed light on interconnected biogeochemical processes in an aquifer system"; Nature Communications; vol. 7, No. 13210, 11 pages (Oct. 24, 2016).

Applied Biosystems/Ambion; "RNaseAlert Lab Test Kit"; 12 pages (2008).

Armitage, et al.; "Hairpin-Forming Peptide Nucleic Acid Oligomers"; Biochemistry; vol. 37, No. 26, pp. 9417-9425 (1998).

Baker, et al.; "Enigmatic, ultrasmall, uncultivated Archaea"; PNAS; vol. 107, No. 19, pp. 8806-8811 (May 11, 2010).

Barrangou, et al.; "Expanding the CRISPR Toolbox: Targeting RNA with Cas13b"; Molecular Cell; vol. 65, No. 4, pp. 582-584 (Feb. 16, 2017).

Bautista, et al.; "Virus-Induced Dormancy in the Archaeon Sulfolobus islandicus"; mBio; vol. 6, No. 2, 8 pages (2015).

Burstein, et al.; "New CRISPR-Cas systems from uncultivated microbes"; Nature; vol. 542, No. 7640, pp. 237-241 (Feb. 9, 2017).

Choudhury, et al.; "CRISPR-dCas9 mediated TET1 targeting for selective DNA demethylation at BRCA1 promoter"; Oncotarget; vol. 7, No. 29, pp. 46545-46556 (2016).

Chylinski, et al.; "Classification and evolution of type II CRISPR-Cas systems"; Nucleic Acids Research; vol. 42, No. 10, pp. 6091-6105 (2014).

Cong, et al.; "Multiplex Genome Engineering Using CRISPR/Cas Systems"; Science; vol. 339, No. 6121, pp. 819-823 (Feb. 15, 2013).

Cox, et al.; "RNA editing with CRISPR-Cas13"; Science; vol. 358, No. 6366, 15 pages (Nov. 24, 2017).

CRZ3554.1 (hypothetical protein HHT344_2368 [Herbinix hemicellulosilytica], Gen Bank Accession sequence, priority to Jul. 24, 2015, 1 page) (Year: 2015).

Deltcheva, et al.; "CRISPR RNA maturation by trans-encoded small RNA and host factor RNase III"; Nature; vol. 471, pp. 1-19 (Mar. 31, 2011).

East-Seletsky, et al.; "RNA Targeting by Functionally Orthogonal Type VI-A CRISPR-Cas Enzymes"; Molecular Cell; vol. 66, pp. 373-383 (May 4, 2017).

East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).

(56) References Cited

OTHER PUBLICATIONS

Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
GenBank CRZ35554 1; "Hypothetical protein HHT355_2368 [Herbinix hemicellulosilytica]"; 1 page (Oct. 11, 2018).
GenBank OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).
Gootenberg, et al.; "Multiplexed and portable nucleic acid detection platform with Cas13, Cas12a, and Csm6"; Science; vol. 360, pp. 439-444 (2018).
Gootenberg, et al.; "Nucleic acid detection with CRISPR-Cas13a/C2c2"; Science; 9 pages (Apr. 13, 2017).
Hale, et al.; "RNA-Guided RNA Cleavage by a CRISPR RNA-Cas Protein Complex"; Cell; vol. 139, No. 5, pp. 945-956 (Nov. 25, 2009).
Hale, et al.; "Target RNA capture and cleavage by the Cmr type III-B CRISPR-Cas effector complex"; Genes & Development; vol. 28, No. 21, pp. 2432-2443 (Nov. 1, 2014).
Harrington, et al.; "Programmed DNA destruction by miniature CRISPR-Cas14 enzymes"; Science; vol. 362, pp. 839-842 (Nov. 16, 2018).
Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).
Karvelis, et al.; "PAM recognition by miniature CRISPR-Cas12f nucleases triggers programmable double-stranded DNA target cleavage"; Nucleic Acids Research; pp. 1-8 (2020).
Kelemen, et al.; "Hypersensitive substrate for ribonucleases"; Nucleic Acids Research; vol. 27, No. 18, pp. 3696-3701 (1999).
Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).
Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Koonin, et al.; "Diversity, classification and evolution of CRISPR-Cas systems"; Current Opinion in Microbiology; vol. 37, pp. 67-78 (2017).
Le Cong, et al.; "Multiplex Genome Engineering Using CRISPR/Cas Systems"; Science; vol. 339, pp. 819-823 (Feb. 15, 2013).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "CasX enzymes comprise a distinct family of RNA-guided genome editors"; Nature; vol. 566, pp. 23 pages (Feb. 14, 2019).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Makarova, et al.; "Evolutionary classification of CRISPR-Cas systems: a burst of class 2 and derived variants"; Nature Reviews Microbiology; vol. 18, pp. 67-83 (Feb. 2020).
Ngo, et al.; "Computational Complexity, Protein Structure Prediction, and the Levinthal Paradox"; The Protein Folding Problem and Tertiary Structure Prediction; pp. 433 and 492-495 (1994).
O'Connell; "Molecular Mechanisms of RNA Targeting by Cas13-containing Type VI CRISPR-Cas Systems"; J Mol Biol; vol. 431, pp. 66-87 (2019).
OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).
RNaseAlert Lab Test Kit (Applied Biosystems, Fluorometric RNase Detection Assay, 2008, 12 pages). (Year: 2008).
Sato, et al.; "Highly Sensitive Nuclease Assays Based on Chemically Modified DNA or RNA"; Sensors; vol. 14, No. 7, pp. 12437-12450 (2014).
Shmakov, et al.; "Discovery and functional characterization of diverse Class 2 CRISPR-Cas systems"; Mol. Cell.; vol. 60, No. 3, pp. 385-397 (Nov. 5, 2015).
Shmakov, et al.; "Diversity and evolution of class 2 CRISPR-Cas systems"; Nature Reviews Microbiology; vol. 15, pp. 169-182 (2017).
Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Strauß, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
Third Party Observations filed on Oct. 15, 2018 in UK patent application No. GB 1804822.3 (18 pages).
Yan, et al.; "Cas13d Is a Compact RNA-Targeting Type VI CRISPR Effector Positively Modulated by a WYL-Domain-Containing Accessory Protein"; Molecular Cell; vol. 70, pp. 327-339 (2018).
Yang, et al.; "New CRISPR-Cas systems discovered"; Cell Res.; vol. 27, pp. 313-314 (Feb. 21, 2017).
Yang, et al.; "Using Molecular Beacons for Sensitive Fluorescence Assays of the Enzymatic Cleavage of Nucleic Acids"; Methods in Molecular Biology, Fluorescent Energy Transfer Nucleic Acid Probes: Designs and Protocols; vol. 335, pp. 71-81 (2006).
Zhang, et al.; "Design of a Molecular Beacon DNA Probe with Two Fluorophores"; Angew. Chem.; vol. 113, No. 2, pp. 416-419 (2001).
GenBank CRL33181.1; Hypothetical protein T1815_05231 [[Eubacterium] rectale], priority to Apr. 6, 2016, 2 pages (Year: 2016).
NCBI Reference Sequence: WP_021746003.1 (Sep. 24, 2013).
NCBI Reference Sequence: WP_021746774.1 (Sep. 24, 2013).
NCBI Reference Sequence: WP_021747205.1 (Sep. 24, 2013).
Chen, et al.; "CRISPR-Cas12a target binding unleashes indiscriminate single-stranded DNase activity"; Science; vol. 360, pp. 436-439 (2018).
Liu, et al.; "Delivery strategies of the CRISPR-Cas9 gene-editing system for therapeutic applications"; Journal of Controlled Release; vol. 266, pp. 17-26 (2017).
Makarova, et al.; "An updated evolutionary classification of CRISPR-Cas systems"; Nat. Rev. Microbiol.; vol. 13, No. 11, pp. 722-736 (Nov. 2015).
Price, et al.; "Cas9-mediated targeting of viral RNA in eukaryotic cells"; PNAS; vol. 112, No. 19, pp. 6164-6169 (May 12, 2015).
Sampson, et al.; "A CRISPR/Cas system mediates bacterial innate immune evasion and virulence"; Nature; vol. 497, No. 7448; pp. 254-257 (May 9, 2013).
Wright, et al.; "Biology and Applications of CRISPR Systems: Harnessing Nature's Toolbox for Genome Engineering"; Cell; vol. 164, pp. 29-44 (2016).
Yamano, et al.; "Crystal Structure of Cpf1 in Complex with Guide RNA and Target DNA"; Cell; vol. 165, pp. 949-962 (2016).
Zetsche, et al.; "Cpf1 Is a Single RNA-Guided Endonuclease of a Class 2 CRISPR-Cas System"; Cell; vol. 163, pp. 759-771 (Oct. 22, 2015).
Clustl; "Omega Multiple Sequence Alignment. https://www.ebi.ac.uk/Tools/msa/clustalo/" [Retrieved from internet Feb. 2, 2022]. Alignment and Percent identity matrix. (Year: 2022).
NCBI Reference Sequence: WP_012985477.1 (May 18, 2013).
NCBI Reference Sequence: WP_015770004.1 (May 20, 2013).
NCBI Reference Sequence: WP_023911507.1 (Oct. 23, 2013).
NCBI Reference Sequence: WP_034560163.1 (Oct. 22, 2015).

(56) References Cited

OTHER PUBLICATIONS

Makarova, et al.; "SnapShot: Class 2 CRISPR-Cas Systems"; Cell; vol. 168, 2 pages (Jan. 12, 2017).
Mohanraju, et al.; "Diverse evolutionary roots and mechanistic variations of the CRISPR-Cas systems"; Science; vol. 353, No. 6299, 14 pages (Aug. 5, 2016).
Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).
Koonin, et al.; "Origins and evolution of CRISPR-Cas systems"; Phil. Trans. R. Soc. B.; vol. 374, No. 1772, 6 pages (Mar. 25, 2019).
Hyun, et al.; "Site-directed mutagenesis in *Arabidopsis thaliana* using dividing tissue-targeted RGEN of the CRISPR/Cas system to generate heritable null alleles"; Planta; vol. 241, pp. 271-284 (Jan. 2015).
NCBI Accession No. KZX85786; 2 pages (May 2, 2016).
Xie et al.; "RNA-Guided Genome Editing in Plants Using a CRISPR-Cas System." Molecular Plant, vol. 6, No. 6, pp. 1975-1983 (Nov. 2013).
Burstein, et al.; "New CRISPR-Cas systems from uncultivated microbes"; Nature; vol. 542, pp. 7640, pp. 237-241 (Feb. 9, 2017).
Shmakov, et al.; "Discovery and Functional Characterization of Diverse Class 2 CRISPR-Cas Systems"; Molecular Cell; vol. 60, pp. 385-397 (Nov. 5, 2015).
Burstein, et al.; "Major bacterial lineages are essentially devoid of CRISPR-Cas viral defence systems"; Nature Communications; vol. 7, No. 10613, 8 pages (Feb. 3, 2016).
GenBank KU516197.1; "Uncultured bacterium GWB1_scaffold_10668 CRISPR-Cas system-like gene, complete sequence"; 4 pages (2016).
Lander et al.; "Genome Editing by CRISPR/Cas9: a Game Change in the Genetic Manipulation of Protists"; J Eukaryot Microbial.; vol. 63, No. 5, pp. 679-690 (Sep. 2016).
Wright, et al.; "Rational design of a split-Cas9 enzyme complex"; PNAS; vol. 112, No. 10, pp. 2984-2989 (Mar. 10, 2015).
Sawamura, et al.; "Generation of biallelic F0 mutants in medaka using theCRISPR/Cas9 system"; Genes to Cells; No. 22, pp. 756-763 (2017).
Liu, et al.; "Synthetic chimeric nucleases funtion for efficient genome editing", Nature Communications; vol. 10, No. 5524, 11 pages (Dec. 2019).
Pausch, et al.; "CRISPR-Cas Phi from huge phages is a hypercompact genome editor", Science; vol. 369, No. 6501, pp. 333-337 (Jul. 17, 2020).
Thorne, et al., "Illuminating insights into firefly luciferase and other bioluminescent reporters used in chemical biology" Chem Biol., vol. 17, No. 6, pp. 646-657 (2010).
Extended European Search Report for EP Patent Application No. 17857442.2, mailed on Jan. 2, 2020, 8 pages.
"How to Choose the Right Cas Variant for Every CRISPR Experiment", Synthego, Chapter 5, Retrieved from the internet <https://www.synthego.com/guide/how-to-use-crispr/cas9-nuclease-variants> on Sep. 11, 2024, , 17 pages.
"Transposase", JGI Accession No. (Taxon ID:Gene ID) 3300013127.a:Ga0172365_100044211, Nov. 5, 2021, 2 pages.
"Transposase", JGI Accession No. (Taxon ID:Gene ID) 3300013123.a:Ga0172368_100090142, Nov. 5, 2021, 2 pages.
"Transposase", JGI Accession No. (Taxon ID:Gene ID) 3300025317.a:Ga0209541_ 1000016152, Nov. 5, 2021, 2 pages.
"Transposase", JGI Accession No. (Taxon ID:Gene ID) 3300025317.a:Ga0209541_1000046133, Nov. 5, 2021, 1 pages.
"Transposase", JGI Accession No. (Taxon ID:Gene ID) 3300013125.a:Ga0172369_100104642, Nov. 5, 2021, 2 pages.
"Transposase", JGI Accession No. (Taxon ID:Gene ID) 3300013130.a:Ga0172363_100165517, Nov. 5, 2021, 2 pages.
"Transposase", JGI Accession No. (Taxon ID:Gene ID) 3300025317.a:Ga0209541_100217848, Nov. 5, 2021, 2 pages.
"Transposase", JGI Accession No. (Taxon ID:Gene ID) 3300025323.a:Ga0209542_100271699, Nov. 5, 2021, 2 pages.
"Transposase", JGI Accession No. 3300025142.a:Ga0210019_10421012, Sep. 1, 2021, 2 pages.
"Transposase", JGI Accession No. 3300025308.a:Ga0209211_100536734, Nov. 9, 2021, 2 pages.
"Transposase", JGI Accession No. 3300025317.a:Ga0209541_100096836, Nov. 9, 2021, 2 pages.
"Transposase", JGI Accession No. 3300025323.a:Ga0209542_1000010711, Nov. 9, 2021, 2 pages.
"Transposase", JGI Accession No. 3300025323.a:Ga0209542_10000107204, Nov. 9, 2021, 2 pages.
"Transposase and inactivated derivatives", JGI Accession No. (Taxon ID: Gene ID) 3300000353.a:ElkS_mat_MD6ADRAFT_10068983, Nov. 5, 2021, 2 pages.
"Transposase and inactivated derivatives", JGI Accession No. 3300002105.a:C687J26635_100228363, Nov. 9, 2021, 2 pages.
"Transposase and inactivated derivatives", JGI Accession No. (Taxon ID:Gene ID) 3300002966.a:JGI24721J44947_100297402, Nov. 5, 2021, 2 pages.
"Transposase and inactivated derivatives", JGI Accession No. (Taxon ID:Gene ID) 3300002502.a:C687J35174_100502431, Nov. 5, 2021, 2 pages.
"Transposase and inactivated derivatives", JGI Accession No. (Taxon ID:Gene ID) 3300001245.a:JGI12048J13642_102012859, Nov. 5, 2021, 2 pages.
"Transposase and inactivated derivatives", JGI Accession No. (Taxon ID:Gene ID) 3300001245.a:JGI12048J13642_102012865, Nov. 5, 2021, 2 pages.
"Transposase and inactivated derivatives", JGI Accession No. (Taxon ID:Gene ID) 3300001256.a:JGI12210J13797_103875826, Nov. 5, 2021, 2 pages.
"Transposase and inactivated derivatives", JGI Accession No. (Taxon ID:Gene ID) 3300001256.a:JGI12210J13797_103875833, Nov. 5, 2021, 2 pages.
"Transposase and inactivated derivatives", JGI Accession No. (Taxon ID:Gene ID) 3300005573.a:Ga0078972_100101520, Nov. 5, 2021, 1 page.
"Transposase and inactivated derivatives", JGI Accession No. 3300002502.a:C687J35174_100538264, Sep. 1, 2021, 2 pages.
Bhattacharya et al., "Impact of genetic variation on three dimensional structure and function of proteins", PLoS One, Mar. 15, 2017, 12(3):e0171355:1-22.
Bork et al., "Go hunting in sequence databases but watch out for the traps", Trends in Genetics, Oct. 1996, 12(10):425-427.
Bork, P., "Powers and pitfalls in sequence analysis: the 70% hurdle", Genome Research, Apr. 2000, 10(4):398-400.
Brenner et al., "Errors in genome annotation", Outlook, Apr. 1, 1999, 15(4):132-133.
Doerks et al., "Protein annotation: detective work for function prediction", Trends in Genetics, Jan. 2000, 14(6):248-50.
Fenton et al., "Rheostat positions: A new classification of protein positions relevant to pharmacogenomics", Med Chem Res., Jul. 2020, 9(7):1133-1146.
GenBank, "Type VI-a CRISPR-Associated RNA-Guided Ribonuclease Cas13a [Leptotrichia Buccalis]", GenBank: WP_015770004, Retrieved from: https://www.ncbi.nlm.nih.gov/protein/WP_015770004.1, Sep. 28, 2020, 2 pages.
Pausch, et al., "DNA Interference States of the Hypercompact CRISPR-CasΦ Effector", Nat Struct Mol Biol., Aug. 2021, 28(8):652-661.
Skolnick et al., "From genes to protein structure and function: novel applications of computational approaches in the genomic era", Trends in Biotechnology, Jan. 1, 2000, 18(1):34-39.
Smith et al., "The challenges of genome sequence annotation or "the devil is in the details"", Nature Biotechnology, Nov. 1, 1997, 15(12):1222-1223.
Tokuriki et al., "Stability effects of mutations and protein evolvability", Current Opinion in Structural Biology, Oct. 2009, 19(5):596-604.
Xie et al., "sgRNAcas9: A Software Package for Designing CRISPR sgRNA and Evaluating Potential Off-Target Cleavage Sites", PLoS One, Jun. 23, 2014, 9(6):e100448, 9 pages.

(56) References Cited

OTHER PUBLICATIONS

Harrington, et al.; "A scoutRNA Is Required for Some Type V CRISPR-Cas Systems"; Molecular Cell; vol. 79, pp. 416-424 (Aug. 6, 2020).

* cited by examiner

FIG. 1

>CasY1
MRKKLFKGYILHNKRLVYTGKAAIRSIKYPLVAPNKTALNNLSEKIIYDYEHLFGPLNVA
SYARNSNRYSLVDFWIDSLRAGVIWQSKSTSLIDLISKLEGSKSPSEKIFEQIDFELKNK
LDKEQFKDIILLNTGIRSSSNVRSLRGRFLKCFKEEFRDTEEVIACVDKWSKDLIVEGKS
ILVSKQFLYWEEEFGIKIFPHFKDNHDLPKLTFFVEPSLEFSPHLPLANCLERLKKFDIS
RESLLGLDNNFSAFSNYFNELFNLLSRGEIKKIVTAVLAVSKSWENEPELEKRLHFLSEK
AKLLGYPKLTSSWADYRMIIGGKIKSWHSNYTEQLIKVREDLKKHQIALDKLQEDLKKVV
DSSLREQIEAQREALLPLLDTMLKEKDFSDDLELYRFILSDFKSLLNGSYQRYIQTEEER
KEDRDVTKKYKDLYSNLRNIPRFFGESKKEQFNKFINKSLPTIDVGLKILEDIRNALETV
SVRKPPSITEEYVTKQLEKLSRKYKINAFNSNRFKQITEQVLRKYNNGELPKISEVFYRY
PRESHVAIRILPVKISNPRKDISYLLDKYQISPDWKNSNPGEVVDLIEIYKLTLGWLLSC
NKDFSMDFSSYDLKLFPEAASLIKNFGSCLSGYYLSKMIFNCITSEIKGMITLYTRDKFV
VRYVTQMIGSNQKFPLLCLVGEKQTKNFSRNWGVLIEEKGDLGEEKNQEKCLIFKDKTDF
AKAKEVEIFKNNIWRIRTSKYQIQFLNRLFKKTKEWDLMNLVLSEPSLVLEEEWGVSWDK
DKLLPLLKKEKSCEERLYYSLPLNLVPATDYKEQSAEIEQRNTYLGLDVGEFGVAYAVVR
IVRDRIELLSWGFLKDPALRKIRERVQDMKKKQVMAVFSSSSTAVARVREMAIHSLRNQI
HSIALAYKAKIIYEISISNFETGGNRMAKIYRSIKVSDVYRESGADTLVSEMIWGKKNKQ
MGNHISSYATSYTCCNCARTPFELVIDNDKEYEKGGDEFIFNVGDEKKVRGFLQKSLLGK
TIKGKEVLKSIKEYARPPIREVLLEGEDVEQLLKRRGNSYIYRCPFCGYKTDADIQAALN
IACRGYISDNAKDAVKEGERKLDYILEVRKLWEKNGAVLRSAKFL (SEQ ID NO: 1)

>CasY2
MQKVRKTLSEVHKNPYGTKVRNAKTGYSLQIERLSYTGKEGMRSFKIPLENKNKEVFDEF
VKKIRNDYISQVGLLNLSDWYEHYQEKQEHYSLADFWLDSLRAGVIFAHKETEIKNLISK
IRGDKSIVDKFNASIKKKHADLYALVDIKALYDFLTSDARRGLKTEEEFFNSKRNTLFPK
FRKKDNKAVDLWVKKFIGLDNKDKLNFTKKFIGFDPNPQIKYDHTFFFHQDINFDLERIT
TPKELISTYKKFLGKNKDLYGSDETTEDQLKMVLGFHNNHGAFSKYFNASLEAFRGRDNS
LVEQIINNSPYWNSHRKELEKRIIFLQVQSKKIKETELGKPHEYLASFGGKFESWVSNYL
RQEEEVKRQLFGYEENKKGQKKFIVGNKQELDKIIRGTDEYEIKAISKETIGLTQKCLKL
LEQLKDSVDDYTLSLYRQLIVELRIRLNVEFQETYPELIGKSEKDKEKDAKNKRADKRYP
QIFKDIKLIPNFLGETKQMVYKKFIRSADILYEGINFIDQIDKQITQNLLPCFKNDKERI
EFTEKQFETLRRKYYLMNSSRFHHVIEGIINNRKLIEMKKRENSELKTFSDSKFVLSKLF
LKKGKKYENEVYYTFYINPKARDQRRIKIVLDINGNNSVGILQDLVQKLKPKWDDIIKKN
DMGELIDAIEIEKVRLGILIALYCEHKFKIKKELLSLDLFASAYQYLELEDDPEELSGTN
LGRFLQSLVCSEIKGAINKISRTEYIERYTVQPMNTEKNYPLLINKEGKATWHIAAKDDL
SKKKGGGTVAMNQKIGKNFFGKQDYKTVFMLQDKRFDLLTSKYHLQFLSKTLDTGGGSWW
KNKNIDLNLSSYSFIFEQKVKVEWDLTNLDHPIKIKPSENSDDRRLFVSIPFVIKPKQTK
RKDLQTRVNYMGIDIGEYGLAWTIINIDLKNKKINKISKQGFIYEPLTHKVRDYVATIKD
NQVRGTFGMPDTKLARLRENAITSLRNQVHDIAMRYDAKPVYEFEISNFETGSNKVKVIY
DSVKRADIGRGQNNTEADNTEVNLVWGKTSKQFGSQIGAYATSYICSFCGYSPYYEFENS
KSGDEEGARDNLYQMKKLSRPSLEDFLQGNPVYKTFRDFDKYKNDQRLQKTGDKDGEWKT
HRGNTAIYACQKCRHISDADIQASYWIALKQVVRDFYKDKEMDGDLIQGDNKDKRKVNEL
NRLIGVHKDVPIINKNLITSLDINLL (SEQ ID NO: 2)

FIG. 1 (Cont.)

```
>CasY3
MKAKKSFYNQKRKFGKRGYRLHDERIAYSGGIGSMRSIKYELKDSYGIAGLRNR
IADATISDNKWLYGNINLNDYLEWRSSKTDKQIEDGDRESSLLGFWLEALRLGFVFSKQS
HAPNDFNETALQDLFETLDDDLKHVLDRKKWCDFIKIGTPKTNDQGRLKKQIKNLLKGNK
REEIEKTLNESDDELKEKINRIADVFAKNKSDKYTIFKLDKPNTEKYPRINDVQVAFFCH
PDFEEITERDRTKTLDLIINRFNKRYEITENKKDDKTSNRMALYSLNQGYIPRVLNDLFL
FVKDNEDDFSQFLSDLENFFSFSNEQIKIIKERLKKLKKYAEPIPGKPQLADKWDDYASD
FGGKLESWYSNRIEKLKKIPESVSDLRNNLEKIRNVLKKQNNASKILELSQKIIEYIRDY
GVSFEKPEIIKFSWINKTKDGQKKVFYVAKMADREFIEKLDLWMADLRSQLNEYNQDNKV
SFKKKGKKIEELGVLDFALNKAKKNKSTKNENGWQQKLSESIQSAPLFFGEGNRVRNEEV
YNLKDLLFSEIKNVENILMSSEAEDLKNIKIEYKEDGAKKGNYVLNVLARFYARFNEDGY
GGWNKVKTVLENIAREAGTDFSKYGNNNNRNAGRFYLNGRERQVFTLIKFEKSITVEKIL
ELVKLPSLLDEAYRDLVNENKNHKLRDVIQLSKTIMALVLSHSDKEKQIGGNYIHSKLSG
YNALISKRDFISRYSVQTTNGTQCKLAIGKGKSKKGNEIDRYFYAFQFFKNDDSKINLKV
IKNNSHKNIDFNDNENKINALQVYSSNYQIQFLDWFFEKHQGKKTSLEVGGSFTIAEKSL
TIDWSGSNPRVGFKRSDTEEKRVFVSQPFTLIPDDEDKERRKERMIKTKNRFIGIDIGEY
GLAWSLIEVDNGDKNNRGIRQLESGFITDNQQQVLKKNVKSWRQNQIRQTFTSPDTKIAR
LRESLIGSYKNQLESLMVAKKANLSFEYEVSGFEVGGKRVAKIYDSIKRGSVRKKDNNSQ
NDQSWGKKGINEWSFETTAAGTSQFCTHCKRWSSLAIVDIEEYELKDYNDNLFKVKINDG
EVRLLGKKGWRSGEKIKGKELFGPVKDAMRPNVDGLGMKIVKRKYLKLDLRDWVSRYGNM
AIFICPYVDCHHISHADKQAAFNIAV    (SEQ ID NO: 3)

>CasY4
MSKRHPRISGVKGYRLHAQRLEYTGKSGAMRTIKYPLYSSPSGGRTVPREIVSAINDDYV
GLYGLSNFDDLYNAEKRNEEKVYSVLDFWYDCVQYGAVFSYTAPGLLKNVAEVRGGSYEL
TKTLKGSHLYDELQIDKVIKFLNKKEISRANGSLDKLKKDIIDCFKAEYRERHKDQCNKL
ADDIKNAKKDAGASLGERQKKLFRDFFGISEQSENDKPSFTNPLNLTCCLLPFDTVNNNR
NRGEVLFNKLKEYAQKLDKNEGSLEMWEYIGIGNSGTAFSNFLGEGFLGRLRENKITELK
KAMMDITDAWRGQEQEEELEKRLRILAALTIKLREPKFDNHWGGYRSDINGKLSSWLQNY
INQTVKIKEDLKGHKKDLKKAKEMINRFGESDTKEEAVVSSLLESIEKIVPDDSADDEKP
DIPAIAIYRRFLSDGRLTLNRFVQREDVQEALIKERLEAEKKKKPKKRKKKSDAEDEKET
IDFKELFPHLAKPLKLVPNFYGDSKRELYKKYKNAAIYTDALWKAVEKIYKSAFSSSLKN
SFFDTDFDKDFFIKRLQKIFSVYRRFNTDKWKPIVKNSFAPYCDIVSLAENEVLYKPKQS
RSRKSAAIDKNRVRLPSTENIAKAGIALARELSVAGFDWKDLLKKEEHEEYIDLIELHKT
ALALLLAVTETQLDISALDFVENGTVKDFMKTRDGNLVLEGRFLEMFSQSIVFSELRGLA
GLMSRKEFITRSAIQTMNGKQAELLYIPHEFQSAKITTPKEMSRAFLDLAPAEFATSLEP
ESLSEKSLLKLKQMRYYPHYFGYELTRTGQGIDGGVAENALRLEKSPVKKREIKCKQYKT
LGRGQNKIVLYVRSSYYQTQFLEWFLHRPKNVQTDVAVSGSFLIDEKKVKTRWNYDALTV
ALEPVSGSERVFVSQPFTIFPEKSAEEEGQRYLGIDIGEYGIAYTALEITGDSAKILDQN
FISDPQLKTLREEVKGLKLDQRRGTFAMPSTKIARIRESLVHSLRNRIHHLALKHKAKIV
YELEVSRFEEGKQKIKKVYATLKKADVYSEIDADKNLQTTVWGKLAVASEISASYTSQFC
GACKKLWRAEMQVDETITTQELIGTVRVIKGGTLIDAIKDFMRPPIFDENDTPFPKYRDF
CDKHHISKKMRGNSCLFICPFCRANADADIQASQTIALLRYVKEEKKVEDYFERFRKLKN
IKVLGQMKKI    (SEQ ID NO: 4)
```

FIG. 1 (Cont.)

```
>CasY5
MAESKQMQCRKCGASMKYEVIGLGKKSCRYMCPDCGNHTSARKIQNKKKRD
KKYGSASKAQSQRIAVAGALYPDKKVQTIKTYKYPADLNGEVHDSGVAEKIAQAIQEDEI
GLLGPSSEYACWIASQKQSEPYSVVDFWFDAVCAGGVFAYSGARLLSTVLQLSGEESVLR
AALASSPFVDDINLAQAEKFLAVSRRTGQDKLGKRIGECFAEGRLEALGIKDRMREFVQA
IDVAQTAGQRFAAKLKIFGISQMPEAKQWNNDSGLTVCILPDYYVPEENRADQLVVLLRR
LREIAYCMGIEDEAGFEHLGIDPGALSNFSNGNPKRGFLGRLLNNDIIALANNMSAMTPY
WEGRKGELIERLAWLKHRAEGLYLKEPHFGNSWADHRSRIFSRIAGWLSGCAGKLKIAKD
QISGVRTDLFLLKRLLDAVPQSAPSPDFIASISALDRFLEAAESSQDPAEQVRALYAFHL
NAPAVRSIANKAVQRSDSQEWLIKELDAVDHLEFNKAFPFFSDTGKKKKKGANSNGAPSE
EEYTETESIQQPEDAEQEVNGQEGNGASKNQKKFQRIPRFFGEGSRSEYRILTEAPQYFD
MFCNNMRAIFMQLESQPRKAPRDFKCFLQNRLQKLYKQTFLNARSNKCRALLESVLISWG
EFYTYGANEKKFRLRHEASERSSDPDYVVQQALEIARRLFLFGFEWRDCSAGERVDLVEI
HKKAISFLLAITQAEVSVGSYNWLGNSTVSRYLSVAGTDTLYGTQLEEFLNATVLSQMRG
LAIRLSSQELKDGFDVQLESSCQDNLQHLLVYRASRDLAACKRATCPAELDPKILVLPVG
AFIASVMKMIERGDEPLAGAYLRHRPHSFGWQIRVRGVAEVGMDQGTALAFQKPTESEPF
KIKPFSAQYGPVLWLNSSSYSQSQYLDGFLSQPKNWSMRVLPQAGSVRVEQRVALIWNLQ
AGKMRLERSGARAFFMPVPFSFRPSGSGDEAVLAPNRYLGLFPHSGGIEYAVVDVLDSAG
FKILERGTIAVNGFSQKRGERQEEAHREKQRRGISDIGRKKPVQAEVDAANELHRKYTDV
ATRLGCRIVVQWAPQPKPGTAPTAQTVYARAVRTEAPRSGNQEDHARMKSSWGYTWGTYW
EKRKPEDILGISTQVYWTGGIGESCPAVAVALLGHIRATSTQTEWEKEEVVFGRLKKFFP
S      (SEQ ID NO: 6)

>CasY6
MAESKQMQCRKCGASMKYEVIGLGKKSCRYMCPDCGNHTSARKIQNKKKRD
KKYGSASKAQSQRIAVAGALYPDKKVQTIKTYKYPADLNGEVHDRGVAEKIEQAIQEDEI
GLLGPSSEYACWIASQKQSEPYSVVDFWFDAVCAGGVFAYSGARLLSTVLQLSGEESVLR
AALASSPFVDDINLAQAEKFLAVSRRTGQDKLGKRIGECFAEGRLEALGIKDRMREFVQA
IDVAQTAGQRFAAKLKIFGISQMPEAKQWNNDSGLTVCILPDYYVPEENRADQLVVLLRR
LREIAYCMGIEDEAGFEHLGIDPGALSNFSNGNPKRGFLGRLLNNDIIALANNMSAMTPY
WEGRKGELIERLAWLKHRAEGLYLKEPHFGNSWADHRSRIFSRIAGWLSGCAGKLKIAKD
QISGVRTDLFLLKRLLDAVPQSAPSPDFIASISALDRFLEAAESSQDPAEQVRALYAFHL
NAPAVRSIANKAVQRSDSQEWLIKELDAVDHLEFNKAFPFFSDTGKKKKKGANSNGAPSE
EEYTETESIQQPEDAEQEVNGQEGNGASKNQKKFQRIPRFFGEGSRSEYRILTEAPQYFD
MFCNNMRAIFMQLESQPRKAPRDFKCFLQNRLQKLYKQTFLNARSNKCRALLESVLISWG
EFYTYGANEKKFRLRHEASERSSDPDYVVQQALEIARRLFLFGFEWRDCSAGERVDLVEI
HKKAISFLLAITQAEVSVGSYNWLGNSTVSRYLSVAGTDTLYGTQLEEFLNATVLSQMRG
LAIRLSSQELKDGFDVQLESSCQDNLQHLLVYRASRDLAACKRATCPAELDPKILVLPAG
AFIASVMKMIERGDEPLAGAYLRHRPHSFGWQIRVRGVAEVGMDQGTALAFQKPTESEPF
KIKPFSAQYGPVLWLNSSSYSQSQYLDGFLSQPKNWSMRVLPQAGSVRVEQRVALIWNLQ
AGKMRLERSGARAFFMPVPFSFRPSGSGDEAVLAPNRYLGLFPHSGGIEYAVVDVLDSAG
FKILERGTIAVNGFSQKRGERQEEAHREKQRRGISDIGRKKPVQAEVDAANELHRKYTDV
ATRLGCRIVVQWAPQPKPGTAPTAQTVYARAVRTEAPRSGNQEDHARMKSSWGYTWSTYW
EKRKPEDILGISTQVYWTGGIGESCPAVAVALLGHIRATSTQTEWEKEEVVFGRLKKFFP
S      (SEQ ID NO: 7)
```

FIG. 1 (Cont.)

```
>CasY7
MKRILNSLKVAALRLLFRGKGSELVKTVKYPLVSPVQGAVEELAEAIRHDNLHLFGQKEI
VDLMEKDEGTQVYSVVDFWLDTLRLGMFFSPSANALKITLGKFNSDQVSPFRKVLEQSPF
FLAGRLKVEPAERILSVEIRKIGKRENRVENYAADVETCFIGQLSSDEKQSIQKLANDIW
DSKDHEEQRMLKADFFAIPLIKDPKAVTEEDPENETAGKQKPLELCVCLVPELYTRGFGS
IADFLVQRLTLLRDKMSTDTAEDCLEYVGIEEEKGNGMNSLLGTFLKNLQGDGFEQIFQF
MLGSYVGWQGKEDVLRERLDLLAEKVKRLPKPKFAGEWSGHRMFLHGQLKSWSSNFFRLF
NETRELLESIKSDIQHATMLISYVEEKGGYHPQLLSQYRKLMEQLPALRTKVLDPEIEMT
HMSEAVRSYIMIHKSVAGFLPDLLESLDRDKDREFLLSIFPRIPKIDKKTKEIVAWELPG
EPEEGYLFTANNLFRNFLENPKHVPRFMAERIPEDWTRLRSAPVWFDGMVKQWQKVVNQL
VESPGALYQFNESFLRQRLQAMLTVYKRDLQTEKFLKLLADVCRPLVDFFGLGGNDIIFK
SCQDPRKQWQTVIPLSVPADVYTACEGLAIRLRETLGFEWKNLKGHEREDFLRLHQLLGN
LLFWIRDAKLVVKLEDWMNNPCVQEYVEARKAIDLPLEIFGFEVPIFLNGYLFSELRQLE
LLLRRKSVMTSYSVKTTGSPNRLFQLVYLPLNPSDPEKKNSNNFQERLDTPTGLSRRFLD
LTLDAFAGKLLTDPVTQELKTMAGFYDHLFGFKLPCKLAAMSNHPGSSSKMVVLAKPKKG
VASNIGFEPIPDPAHPVFRVRSSWPELKYLEGLLYLPEDTPLTIELAETSVSCQSVSSVA
FDLKNLTTILGRVGEFRVTADQPFKLTPIIPEKEESFIGKTYLGLDAGERSGVGFAIVTV
DGDGYEVQRLGVHEDTQLMALQQVASKSLKEPVFQPLRKGTFRQQERIRKSLRGCYWNFY
HALMIKYRAKVVHEESVGSSGLVGQWLRAFQKDLKKADVLPKKGGKNGVDKKKRESSAQD
TLWGGAFSKKEEQQIAFEVQAAGSSQFCLKCGWWFQLGMREVNRVQESGVVLDWNRSIVT
FLIESSGEKVYGFSPQQLEKGFRPDIETFKKMVRDFMRPPMFDRKGRPAAAYERFVLGRR
HRRYRFDKVFEERFGRSALFICPRVGCGNFDHSSEQSAVVLALIGYIADKEGMSGKKLVY
VRLAELMAEWKLKKLERSRVEEQSSAQ    (SEQ ID NO: 5)

>CasY18
MKRIAKFRHDKPVKREAWSKGYRVHKNRIINKVTRSIKYPLVVKDEWKKRLIDDAAHDYRWLVG
PINYSDWCRDPNQYSILEFWIDFLCVGGVFQSSHSNICRLAIQLSGGSVFEQEWKDLSPFVRAN
LIQGIKPAEFIGFLTAEFRSSSNPKNFISKFFEGSNEDLESLTNEFASIVDFIKAKDISLLRKS
LPSCKKIAPNLWEKAVGSHSTNELLKLLTKYTRVMLVAEPSHSDRVFSQTVLQSNDQDDPELTG
PLPSHKVGKASYLFIPEFIREVNLDKISKLDLSAKSKLAVEQVKKLSELTSDFKQIENQSEAYF
GLSTSFNELSNFLGILIRTLRNAPEAILKDQIALCAPLDKDILKITLDWLCDRAQALPENPRFE
TNWAEYRSYLGGKIKSWFSNYENFFEIPQAASSQQNNNREKKLGNRSAIRALNLKKEAFEKARE
TFKGDKGTLEKIDLAYRLLGSISPEVLQCDEGLKLYQQFNDELLVLNETINQKFQDAKRDIKAK
KEKESFEKLQRNLSSPLPRIPEFFGERAKKGYQKARVSPKLARHLLECLNDWLARFAKVEESAF
SEKEFQRILDWLRTSDFLPVFIRKSKDPPSWLRYIARVATGKYYFWVSEYSRKRVQIIDKPIAQ
NPLKELISWFLLNKDAFSRDNELFKGLSSKMVTLARIMAGILRDRGEGLKELQAMTSKLDNIGL
LHPSFSVPVTDSLKDAAFYRAFFSELEGLLNIGRSRLIIERITLQSQQSKNKKTRRPLMPEPFI
NEDKEVFLAFPKFETKNKVKGTRVVYNSPDEVNWLLSPIRSSKGQLSFMFRCLSEDAKIMTTSG
GCSYIVEFKKLLEAQEEVLSIHDCDIIPRAFVSIPFTLERESEETKPDWKPNRFMGVDIGEYAV
AYCVIEKGTDSIEILDCGIVRNGAHRVLKEKVDRLKRRQRSMTFGAMDTSIAAARESLVGNYRN
RLHAIALKHGAKLVYEYEVSAFESGGNRIKKVYETLKKSDCTGETEADKNARKHIWGETNAVGD
QIGAGWTSQTCAKCGRSFGADLKAGNFGVAVPVPEKVEDSKGHYAYHEFPFEDGLKVRGFLKPN
KIISDQKELAKAVHAYMRPPLVALGKRKLPKNARYRRGNSSLFRCPFSDCGFTADADIQAAYNI
AVKQLYKPKKGYPKERKWQDFVILKPKEPSKLFDKQFYRPN    (SEQ ID NO: 8)
```

FIG. 1 (Cont.)

>CasY9
mdkkitgyrlhfkrilfsggeivrtikfplsstslssgkndlinnfegqlinddlkirgd
vnlndyliyefsgkpiytlfnfwidslksgiiwadkpaslidfinefyjlikspydlvwer
ateefkkyfdkksfkeilisgpirktknpskkesfkkkdnklpdeyvikegnslsvespe
vlkfinkivssffdedgnlilegkkqdnfwlnefgidksiiqktkpegelkditfviipe
livdsfnkeyevdsliekrrvwlkkrfnkekeieknlqlilglsnnfngfsnflgkglra
fqggkilmifeamskinpsiknqenkekvlealnflsdkskffplrpslnivkswadyrt
ffggklqswysngirrknelkvqvkeiyefltkaqdylaakisfndenkryarkelesin
lkinrlkqfienenfdissedrylifdtllsslrtqlnlyyqkylsseednirenkdlkg
iyqkiykpiaffgkatkrknkkvieetvpiiesginnlfslmkklektflpkntfskvkn
knedeetnlrnlvdyyqnkvshkmlnsltfvnkleevmksvieendwdklhsnkyvfyks
eyqkgalelipIkkgswidifekiilemtsylltfdltdllkdkkilldwieiakntlak
likfntcdvftldelnldlrnfpkamdyikifkitkvdknelnfivqsfilselkgaatl
fskekylakynvqvinadkkfklfykpndgfierevdrknllkphqyfvaldkiedkkik
ekanfllitkedikpvfikeenfsklykisssfyqiqfldkfiympeefkdlgirlsewn
fvlereykidwdlctkrpkmtfiensktknklylsipfnvfykskkkdvslskvisnrlsy
pilgidvgeyglayllaefsdkkikilkkgfiedrnianikdkfaeiqlkartgifneed
ttiarvrenaignlrnkvhyiltsdrgasiiyersisnfetgsgrtttkiydsvkradtef
eteadkfihnhvwgkntkyvgrslsayqssyicskchrsiyqfkkedlreikllmregni
ltfltpigkvwgyskdekfkkdyqfkptekdfkefikilkdfarppvgknktevlekffl
kdndkkakidefrkkrgasaificpfcgfiadadiqaafvmavrgyirfkesqikeenks
lilektinylkevqfkpediflpf (SEQ ID NO: 51)

>CasY10
mkdskinapininannvsknktpkkkprrksgkrgyrlhderiaysggtgscrsikyell
npdatrknllrgsglqheiisavrqdnlllygplnfndyifdkdapnllhfwtlalslgf
vfsnqnsierefkdylgvsteeavlfgklnetlkavfdeakfisgflyrnfrglasktre
qriklltdtlrepldgvngdsvseiikpyaekwaeydgecdqfvfkcelfsikstdkpre
ntrlsfaidpafevmklddktvffddlithykencsdeaqakrflgigdngnyfngifgg
lfelltdgdekicettdhlariygfdetkkteinkrlvrlaeyarqinrrpclvkrwsey
rsdfngtieswysnrqskqndtlkqldeklklleemrasfptdsdlcgiksIsetiefir
slkgeriarkvtdelesylavlgselnqytqqnkdhalplgwqkklskhiqssplffgen
kialweklinlkeliktevkelevvlaedfddyeitdkqvdnlaalagrfsespdgsghp
lvterlakiestlgvdfthknnrakfylsgfergkfgkldvpnkikvshlfeladlsily
navanspedgyilrdtaqlskiilsaklrdadrekqrktvlahstlqgysaliskrefvs
ryplqavngsqnlmaydanrkyyyaynsekfagtkeltvalrgnnfgpeafggkfkkvpa
lrvqsskyqiqfldwffekqkkrktelgaggsftiaeisckvnwddktpvifekpdprlf
vsqpftinppensakkdyaryigidigeyglawhlvevfedanediggagknavriksve
kgfftdpqqislkedvkklrenqvratftspdtkiarvresligsyrnlledlavrkdar
lcfeyevsgfesggariskvydsikrssvakkenkaenkqswgklfgpefsfkaieitaa
gtsqyctkckrwaslaikdnnnyqllewdngetgdkrgsdgllavtldgegketnrtvrl
fpkdgkkagdtikgkdlksaiyramrpnmrpsedgsislgagmeavrrdlmpeqwekltl
efgqgkprgnmaiyvcpycghisdadmqaafniavrgylanrdekkvklgkeyltdeqs
kltfdpvgilehtt (SEQ ID NO: 52)

FIG. 1 (Cont.)

>CasY11
mfnqkkgyrlhleriiysggeitrsikyllashsdsqknkellnnfsqdlynddlkirgclnln
dlvnnnqiynladfwidslragviwqssasslidfikrlnhqetigekifnnanerikrffnse
kfikeiilsepkrisskkqafynslfdilkdefkkqeknekiiidnkaeqlikeivdafysndg
vflmegeekqnnfwqekfnidknmikkekedilkdvgditafihppliilkgdvsqliderkky
fsekdleeilglsdnfnafshyfnkfflllyqdkqekifecyqkifsfsqedrkrikdaldfll
ekskllglpkivnswsdyrsvfggkikswfsnylnredkakkqekkikeglekvnkflldfiqk
nqvdsdlqqeikfyydklnqfinsyqnqeffhqqelfllfsdllaeyreklnrfyqkylsdkek
eekkvdefplfkdlfekyegpisfygktklednkkiidltfktikvglnlirrllidlynssdf
knsdnnnqerdlrrifefllnkipatktfrekylsilkdnfdqqtykemtlkpsrytfveniys
renrklielpsknfeellskiikdltdfslsfknddlfvdiyllsdlvelaktlislvinysnk
sqfdsykneliddtyqkakkyletfkisffnskkeanyfyqtrvlselkgavalfskkyyqaky
niqilksneifplfvkfsdllkkeeindinklklifkkpyrylialkkikfkkkqqqssvihld
kknkdlvlispqdedflfkltssfyqlqfldrfvypvkkwlnvditlsewsfilekkykinwdf
nngkpefseidsrlylnipfkikainqqkilkpkelflgidvgeygvgyalvnfkdeeikiiks
gfirskniasirdkyrllqdrskkgvyfsstnvvqevrenaigeirnqihdiliknnadliyey
nisnfetgsgritkiydsikksdvyaeneadksviqhvwgikksiashlsaygssytcsncgrs
ifsfsendifsskvikrdgniitiqtpkgevfayskdkkfnigysfsqeknkeemknlfmkivk
ayarppllksevlltqkkldreflekfkkergnsaifvcpfvdcqsladsdiqaafimalrgyl
kkkkgkdinyleeslnylqnfkginfsnllh (SEQ ID NO: 53)

>CasY12
mnkkssnstgyrlhkdrilfsggeimrtikyplvveknnlnseeivekirqaiinddrvirsdi
nlndyieytkkgnrlytlidfwqdclragviwqpstsfllylinklyskpkaielienakpdis
rffdvdkfskcfilpgeiregkilktfkrelieaIkgefkkgkkekikdeddylekfvekdark
lireiadcffsndilvthdlkegkkeyqdrlweekfgikkgkllenfklpdhlrnfknisffii
pelsdksknfdelielrrkwllerkicvredgdylenekkldeelrnlvglsdncnplsnflgt
vfcellvpnnlnednalekfydvftivepkiaelnikdqimgsleflrlrakqlgspnlvnfsk
sqnlkanesikldgwslyrqnfgskmqswftsyiernklledslknfkekikkaqnfiknlkni
seepqqeeeaqqekeeivelfekifsslekvnrenfevfdsllsslrkrlnffyqqylyneake
gddvkkhkilgpifkniekpiafygetqrkknekfvedtipileegtvflttlisnlldsfspk
qvfpdvrkkdeteeiiyrkelqffwnklkdlavnskefekeyqdiiesavdeselsklkelfvn
kkkngskynkytfykskytkgsieeiklkgskeeyllrfekliksltnfltqfnrnkllqdkdl
lldwvelaknivsvlirfstntefslneikaqsqfkkaknylelfklkkakkkefgfiiqsfil
seikgaatlyskrkyiasysvqivgsnnkfklfyqpldssinisggpkdfvtkkhkylivfqdl
knvknkdatenrinllrlnkerkiplvaykddlvsksllIssspyqlqfldkylyrprgwenid
iklnewsfvveeaydiewdlnsktpklipspksnrnklylaipftlkgnvkeppldkivlkset
kkdhsrdknrlnypilgvdvgeygvawcltkfdynqdfslrdidiqgkgfiedrnigkikdyfa
eiqqksrkgaydeddttiakvrenaigklrnaihsiltgslegaspvyedaisnfetgsgktik
iynsvkradtefkseadkaehslvwgkkdrnqetkyigrnvsayassytcvnclhtlfkvkked
lsnikilekdgrivtmsspygpdkkvrgylsekekyeigyqfkeseedlkafrkivrdfarppv
nknsevlekyakeilagnkieefrkkrgnsaifvcpfcqfkadadiqaafmmamrgylrfsgiv
pskensknnpqesedkslknskkqsetgdtfltktaeylqqlrfeikekikeavkvdf
(SEQ ID NO: 54)

FIG. 1 (Cont.)

>CasY13
mtkrksrlagyrlhkerilfaggqiirtikypltpsypteemtqflkdfeeaviaddlkirgdl
nindyltytakgkplytlfdfwvdslrngviwmskgtmlidflatqyninspfdnvwkkaspri
tsffkkdefkeiilcdpvrsssstknsfhkritgylkdhlkvkngdsytivsndaqkvvefivhs
ffnnegklilegeeqfkfwkkeynldkaiiesakpkgkyaditfviipelisnlnpkqsledli
nkrdvwlqgrrfdkedklllsilglsdnfngfsnflgvvlrdlqkengnkevlydaqktvfpll
gnskdevlealdflsqkakllgvtslplvngwheyrsifggklkswftnsqnrkeeldgqisrf
keslfkarnylqtenfgeeankekedilsflsllenfftdekrsikveenyqlfepllalvkrr
lnffyqryiqkegdetkvnelghfkglyekiykpvafygyaakkvnkkfvnqtfpiledgieni
eklisylqnsfsvqetfeevkqgkeeiddpyrkllqffwnkyledsinshlfaekykdilkgni
ednewekvidktkkgkyvfykspyakgsleeipigtsnyleqlqisilelskfilsykkdills
dvglllldwvelsknvisillrfntkktyriddlrldnfsqakryqelfkhgdypknefsfiiqs
lvlseirgaatlyskreyiasysvqvvgsdskyriyyipkekisitpdvvksrpesserkqlmg
phyyavalgkvlekkkseifnsialfkknikaiflpesslrgvfrlssspyqlqfldkfiyrpf
gwenidvslsewsfivekrytinwdlrskkpkllpvtdteriknknkvyiaipfnlipskevrqa
aplktiakgketrekdlsrlnfpimgvdvgeyglayclvkiifdkntykilaielvsdkkeafg
fiedrnignikdkfaeiqhrarqgsfdeedtvitrvrenavghlrnrlhvivtlqrssssvyeds
isnfetgsgrttkiynsvkradtesdtnadkmthnhvwgektkwvgrnvsayassytcvsclks
lyqvrkedlskmritqrggrivtisgphgdikgyvskeekynlgyhfretddelknfrkivqdf
arppvgdhsevlkkyakqilekgkieewrkrrgnssificpfcqyitdadvqaafmmairgylr
fsgivpsrgnkkdqdqeqedektagesfleqtqrqlgdvnlskileafslki
    (SEQ ID NO: 55)

>CasY14
mvfpamlfytrpeyafltililislessvlflpkkiivmtaktqknknskktkhfgqtgyalhksr
lvytgkeairsikfplkstsqvklddfankvisdysliqgatnineylteyqnaqhsyslidfw
vdslragvvfaktpaaltdflhvvyqrtspsrlafdqmykslrskldyelflqkiilstgirks
agkhgilscfkkewqsdpsvlkevdyifsnlikngatlsqeeqrnfwksaynlqlpakqkganl
tfyvlpelkfdsnmnistcfsdrfsffkkqndskldaifgfdnnfsafsnyfgeilqlfkeqkt
qkiadylinffdiwrgmedelnrrlvflsnqaklvqaniatnyadfrmsfggklqswfsgyqn
qnqkiieqlndhgedlkkindavtkqnvkpedeerktdlltdladlqkyqselaggkelefakl
dlyrdllaffrsdfnwffqnylleekekkadkdisvnkkykklfknlrlvpeffglarkkayqk
yidstipiiktgwqvvtdalpilrenmsyefllnpkkkdyfianlekfnrklktktwnrpkfsq
lsekivrhynnnqvptsnqvfyknrfsnsrqeiilidglnqekelkwlvnscleclakpvlsad
aglmidqleltkmvlgwlingnndsiinfdkydlanfikaskfievfktnqfagrqlsrflmsy
ifgelrgavglfsrqsfvnryvvspmaslsnyplvndgakwylalgksskkpkegmkefteyad
kesdkaksahffpddllyvsssiyqmqflhalkrqkegkkwhkwqqinlklsdhafivedeyqv
kwdlitgkpnlkrvaenrrvfvsvpfilnplseqktqsenianryrylgidvgeyglayavldf
snkkraeiidqgfiydgslrkirdhfdlikdtqtkgtfsvpstalsrvrenaitalrnkihdlv
lrfnakpvyefsisnfetgsgkvtkiynsvkkadiypeidtdkavqkhiwgknpkligqevsay
atsytcskchqsiydqgldkeskikanqiinasptglikiklvskveawgfvkgsrkleitene
rtvslfkgqkigdevaqrlvknfarppineaseaiklamsqkklnsnminfeklaedrgnmamf
vcpfclhvddadiqaaqnialrgflknefekdnngkkesfnyiqavknffqsggmadyne
    (SEQ ID NO: 56)

FIG. 1 (Cont.)

>CasY15
mnekktatqrmarrrrgerartksqelrgyrlhdariefsgglgsmrtvkvellnpdssredp
qrgqglqgkvakavfddyralygpmniedylsdpdcpsflglwvkavclgvimsrktatdfgel
rggsksgqafdsipehlrrqliklkwldwydkgirksssskasrlksltdvfanpkqpdqgvmaa
weqgeklaessrdiaalgrrefkdklfaippptssvvldddvkatkvsrdwqwavdpqfklpst
dlditraleevdrqwferlgnnrgmvqqffaigdngnhlnnglfghffasirsanladivaemg
tafgfsaeerdivrqrletlheyaqglpekpvlasrwaeyrtdmtaklgswysnrtskgaasit
qvwgtintetgevkddglvrtleniqsdlpdscsikegilqetldfigdrrsstdraftdelel
ylatlrsdlntwcqeqsalweekqrqvatpasdekskkadnpwagkgsktdkwlgalhtriqss
plfwgvdklelwktlanlkqairdeidklneqvevfgrsaydepvgkdadsgegdrrvdqlsyl
sarlgdqaheevrqrldaialalgvkfserddlhrffvssrarrraallampntitvgklrela
dltplwerikkkpeeprlladtvalskvvnsacasranpsdqielttihsrldgysknightef
isratvqstngaqntvaldslvsprlfyynfpnivesaephvshlevatrgnlgsfeefaakeh
rtfdrenpqkdsrnridsvnplavassryqiqfftwwaglhrsketalevggsftiaerqvrld
wsqekpqavvseelrvfvsqpftivpddkkrpatsgtryigvdigeyglawscwefapgywngs
vvnpskvtcldygflaepgqrrivervkklresqatktftspdtyiarlrenvvatyqaqleal
mmaynaqlvfeseisafetggnrvkkiydaikrssvfgrsdaeatdnnqhwgkngnrssvkdpd
klrlneagqvaarvpwaepvsawmtsqtcsacgrvyvrayrgknsnepdsgatgevryfdnkqq
kiltktigadtvwvtdqerkefergvynamrpnafmpdgrwtaageileaalksrgtldggrgf
aglhltskaqvheyiegtgkshrdahgnsaificpytdcghiadadlqasynialrgfayaivr
kkhpelfagsgsstdgdegggkkpqqkqafideivraagras (SEQ ID NO: 57)

>CasY16 (truncated)
Manrqispvdstnnfiftlyvsfdtvlyarilaflltlscllvgfleyiyplgviylimptnqqy
dgltgyqlhterlrhtgksgirtfklplktndqelfgnffenikhdhegqigatnittwteeqk
ssrqiyslldfwldsvragvvfassssaelnellsvcgdedavdeqvktamrainptffkhlkfn
dfkeeialkegmrssstknsvtrrlykcldcteedapeeiqqavadliktffttdgkiisrndq
ddywqvhfgldkslykldsdikltfsflpdipftpeadahmcldkyrcwidenaekfqlesked
ktnflqihwgiegnynafsnyfnqiidllreeegrqklldallntsdlwegaetelqkrfdflv
dkakqlpkakcvdswsdyrttfggrlsswlsntlnqeefikdtvsdqkeelkqiiknseknlyk
kafsaaddnravelsheaviaqktleklqksssfepqllgvyrdnlgrlrsllnkahqllpdei
enksahevysalherirlmpkfiggakaarfekyvkslqilkqgasflenfeekvkeamkssvs
veveeisegyflrqlntlkrfydnandsrfkgklsslfdkdlgvnieavsnretfyispyskhd
nravisvevanyqqllkswvnelkpywgniiatenwgeiidamqleririgwiyklypkltfai
sddldelfakaatyrdlhgh (SEQ ID NO: 58)

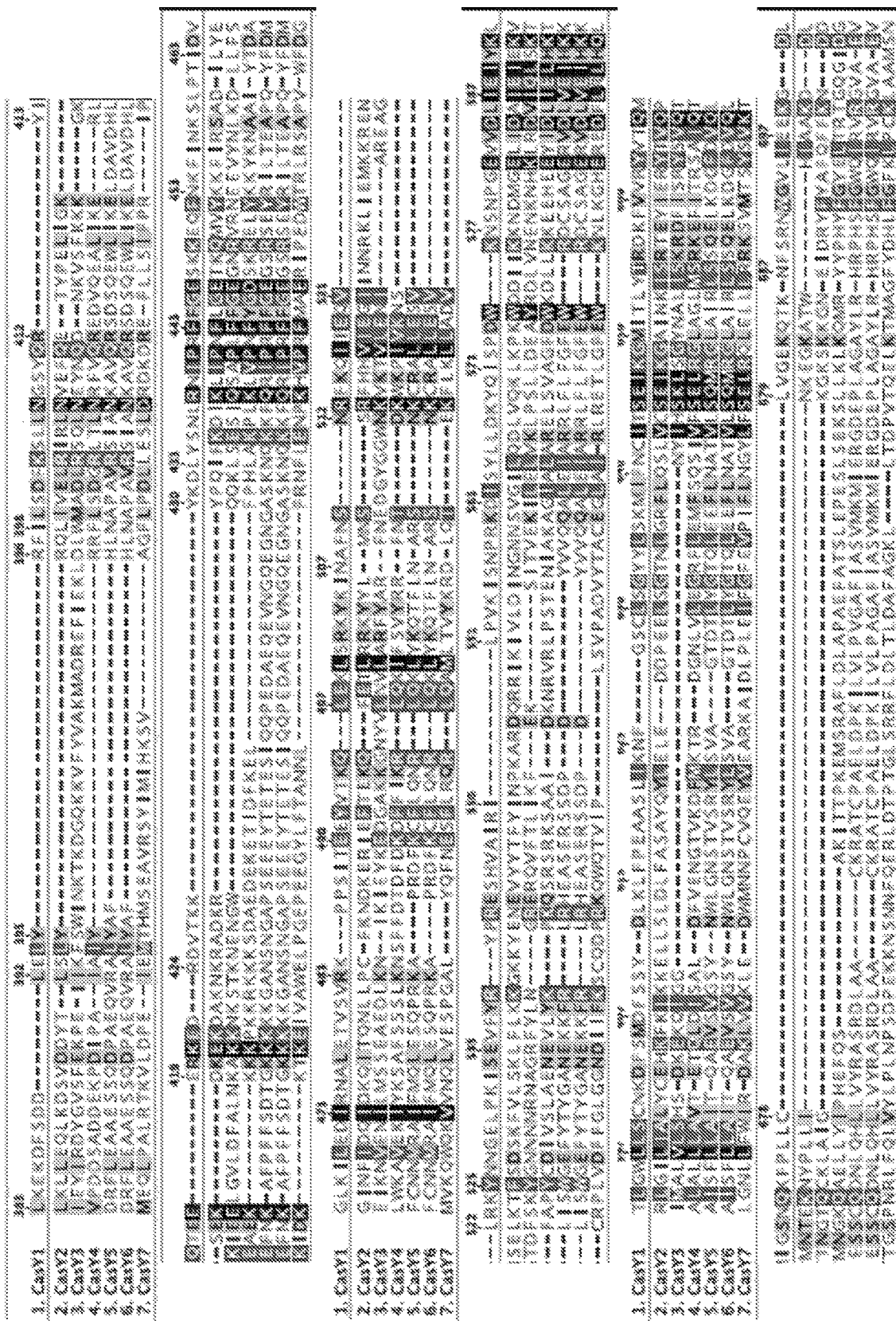
Figure 2 (Cont. 1)

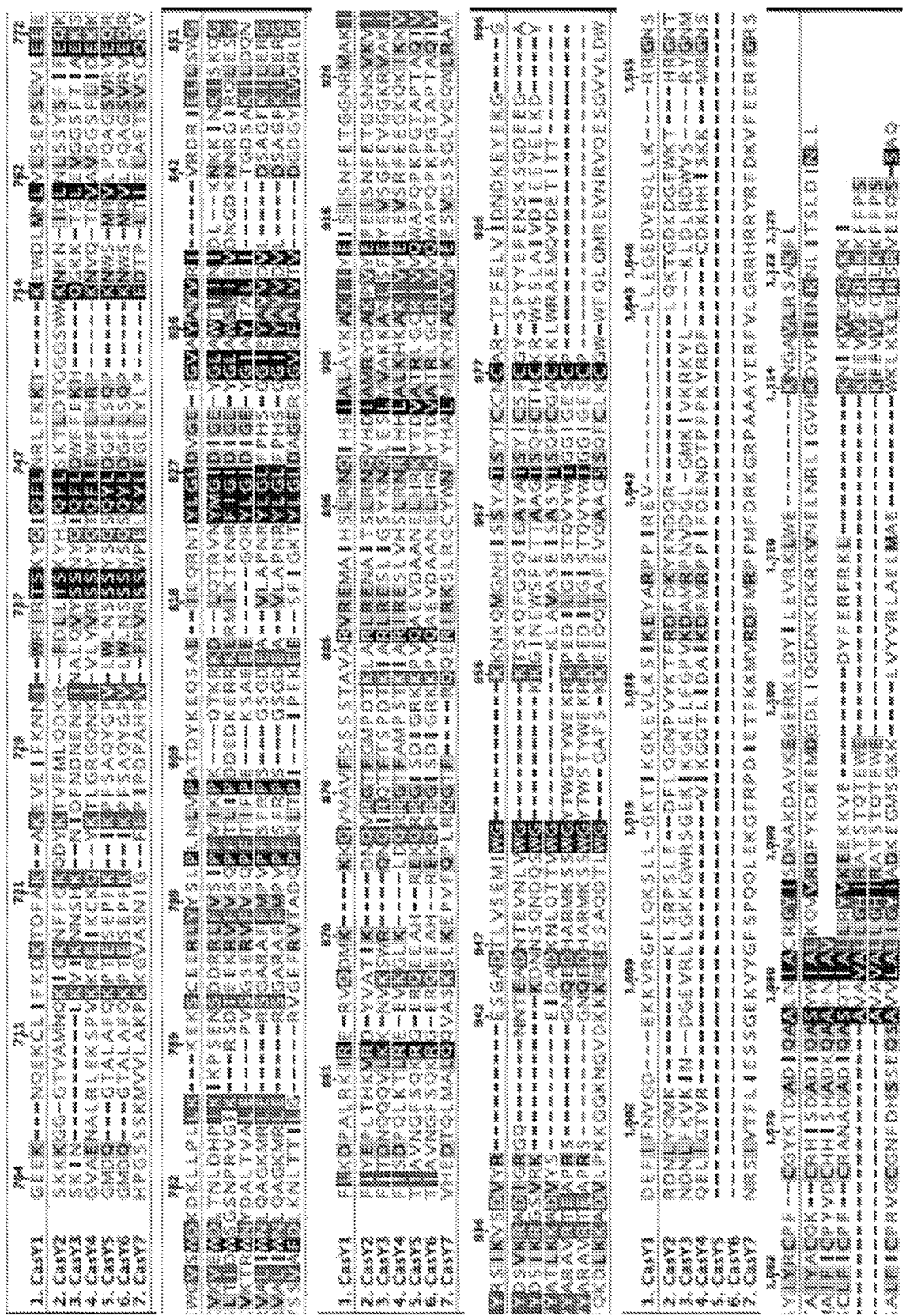
Figure 2 (Cont. 2)

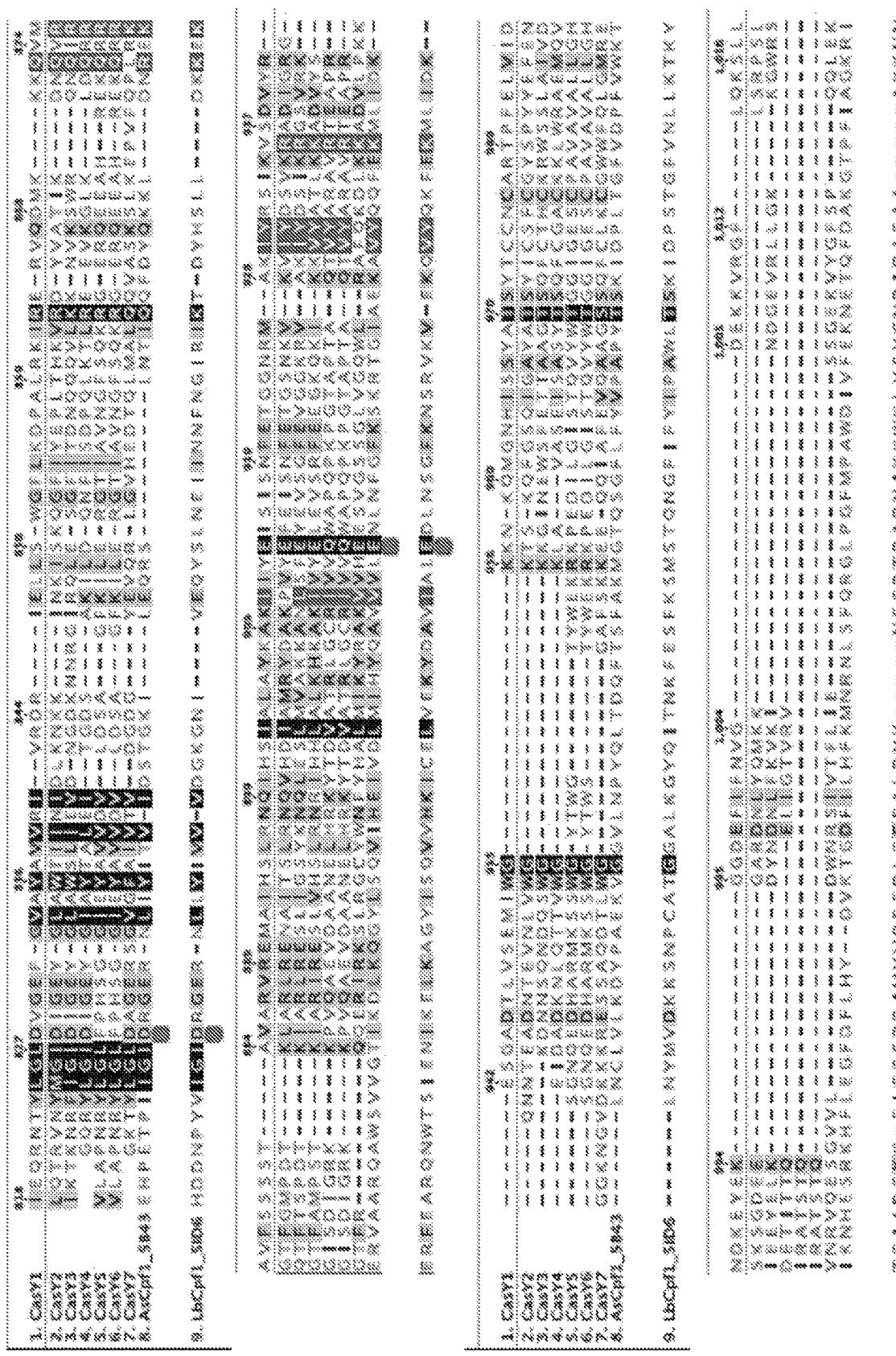
Figure 2 (Cont. 3)

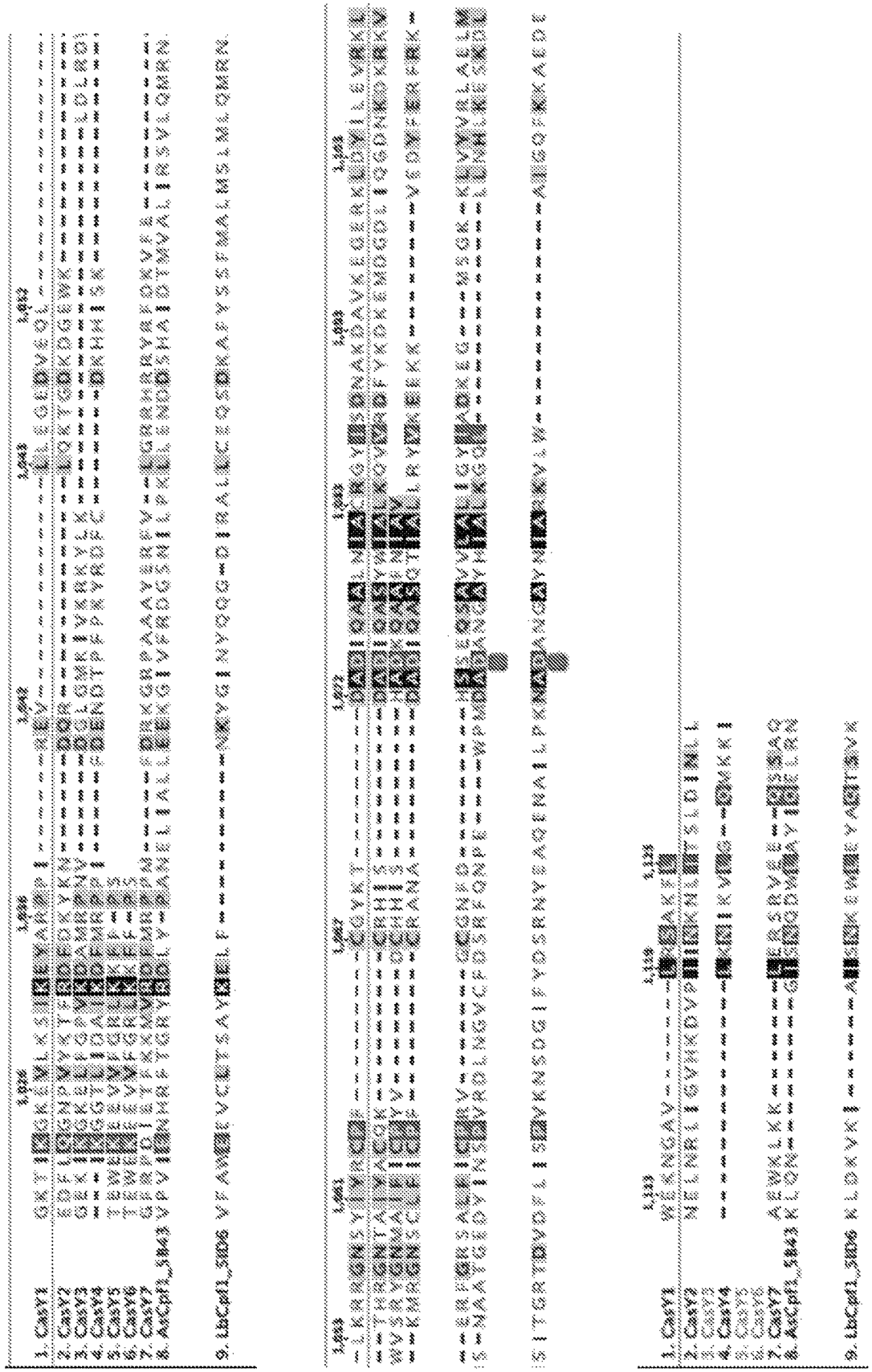
Figure 2 (Cont. 4)

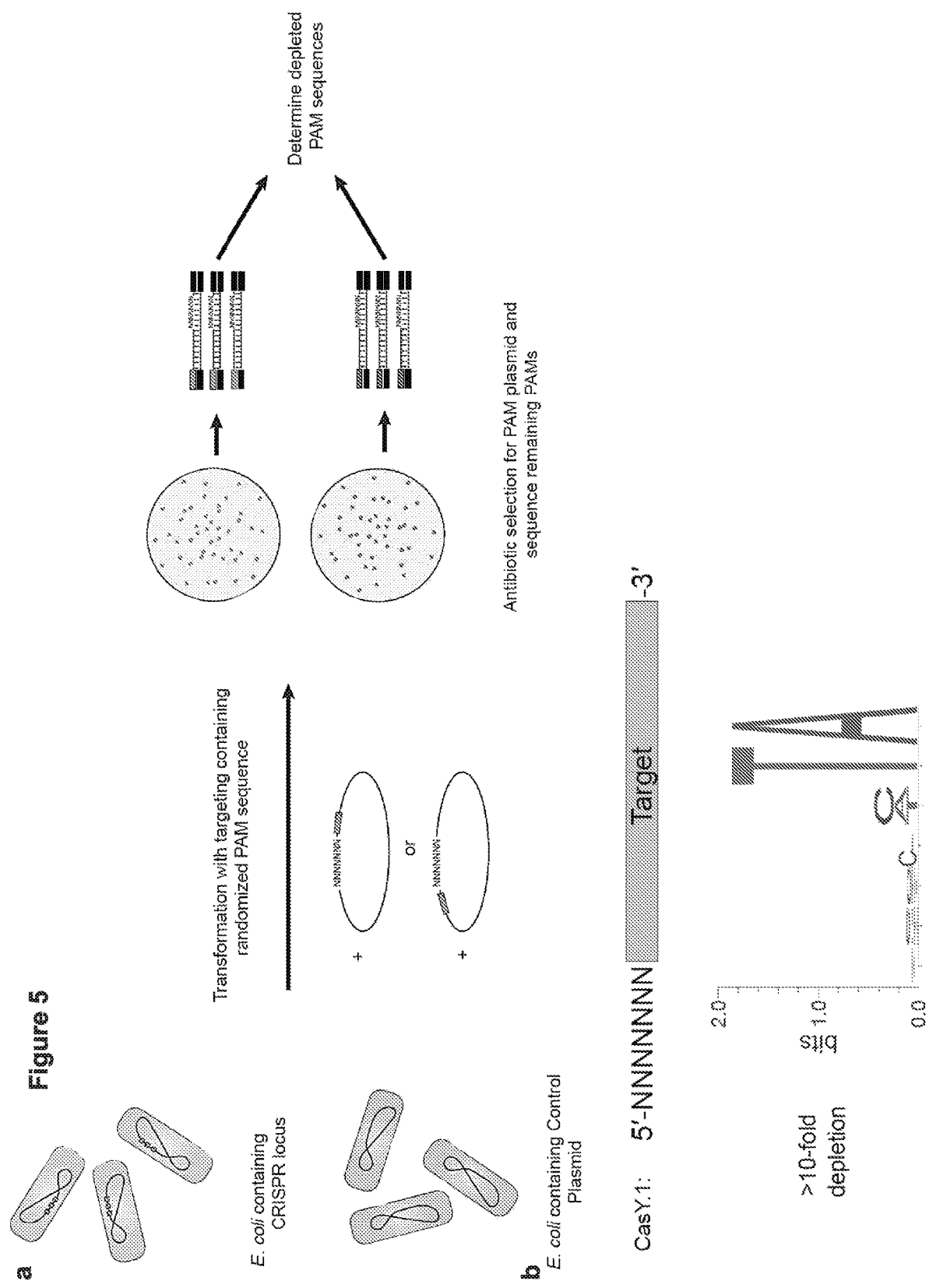

Figure 5
c
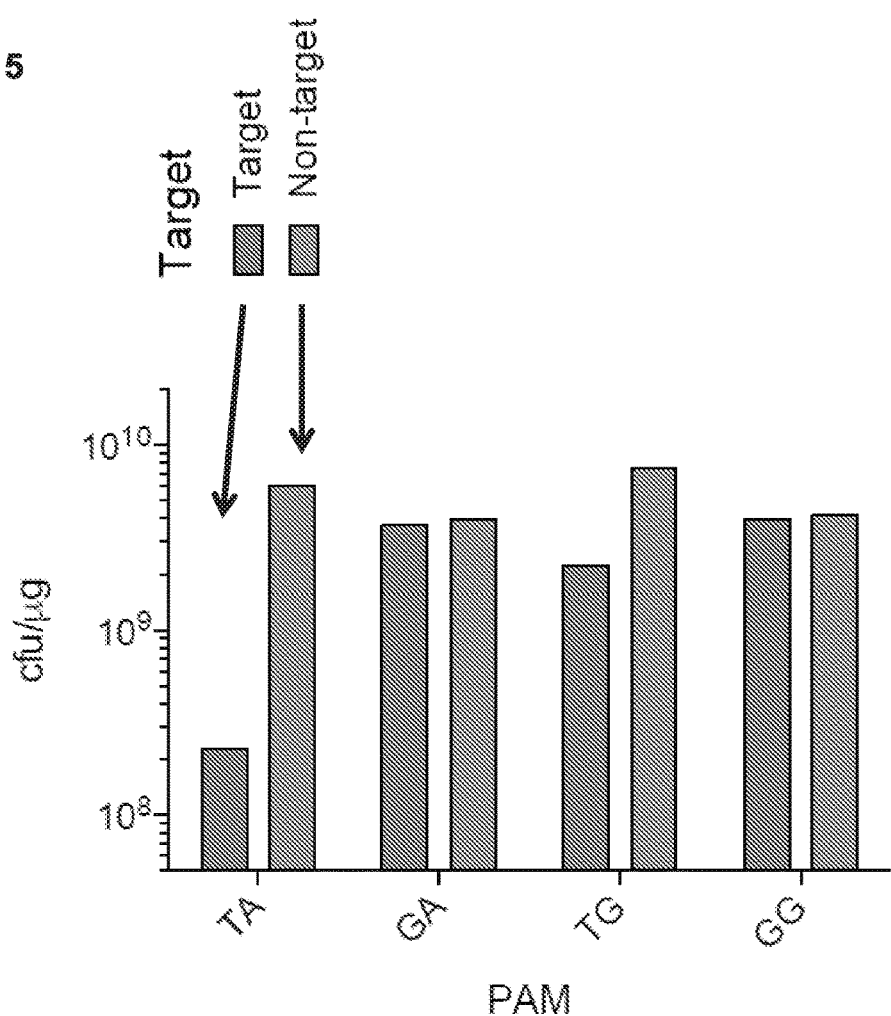
d
Lower threshold
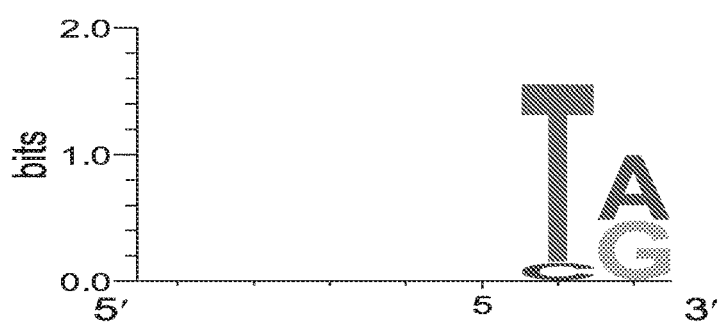
Higher threshold
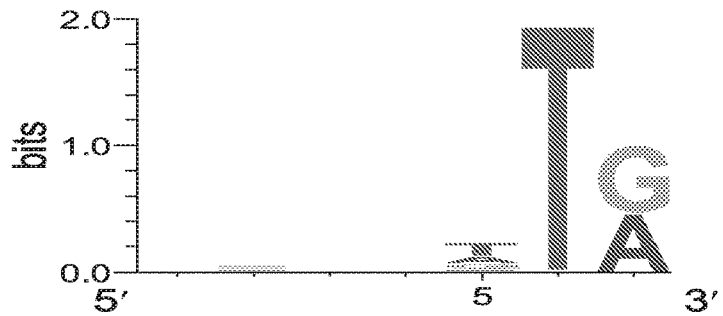

Repeat

CasY1 CTCCGAAAGTATCGGGGATAAAGGC (SEQ ID NO:31)
CasY2 CACCGAAATTTGGAGAGGATAAGGC (SEQ ID NO:32)
CasY3 CTCCGAATTATCGGGAGGATAAGGC (SEQ ID NO:33)
CasY4 CCCCGAATATAGGGGACAAAAGGC (SEQ ID NO:34)

CasY5 GTCTAGACATACAGGTGGAAGGTGAGAGTAAAGAC
(and Y6) (SEQ ID NO:35)

B

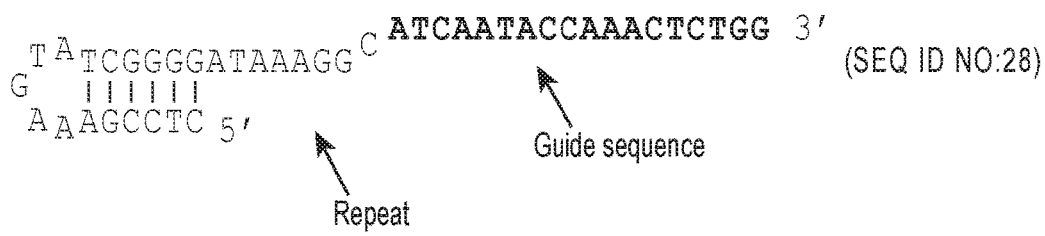

```
                    PAM
5' GACATGATCGCTAATCAATACCAAACTCTGGACCGAATTC (SEQ ID NO:9)
   ||||||||||||||||||||||||||||||||||||||||
3' CTGTACTAGCGATTAGTTATGGTTTGAGACCTGGCTTAAG (SEQ ID NO:10)
                       C ATCAATACCAAACTCTGG 3'
  T A TCGGGGATAAAGG                                    (SEQ ID NO:28)
 G      ||||||                   ↑
  A AGCCTC  5'              Guide sequence
  A       ↑
        Repeat
```

C trancRNAs

CasY1 (76 nt)
   CUCCGAAAGUAUCAAAAUAAAAAGGGUUUCCAGUUUUUAACUAAA
   CUUUAGCCUUCCACCCUUUCCUGAUUUUGUU (SEQ ID NO: 41)

CasY2 (79 nt)
   ACCUGCCAAAAUUUCGUUCAACGAAACUUAAGCAGGCAAGAAAAU
   UUAAAAUUAAAUCCGCUGGUGGGCGGAUAAAGUC
                                   (SEQ ID NO: 42)

CasY4 (51 nt)
   GGUAUUUCCGGACAGCGGCUUGACCGCAUCGUCCUCGCCUUUU
   CCUAAAAU (SEQ ID NO: 43)

Figure 7
a
CasY.1, 2 (Katanobacteria, Parcubacteria)
CasY.3 (Parcubacteria)
CasY.4 (Parcubacteria)
CasY.5/6 (Novel phyla)
CasY.7 (Kerfeldbacteria)
b
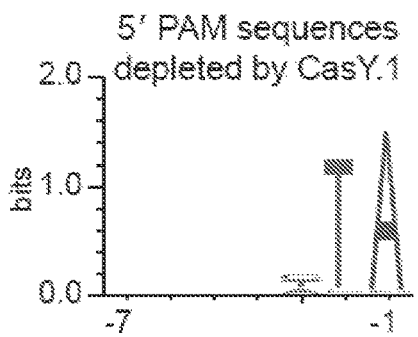
c
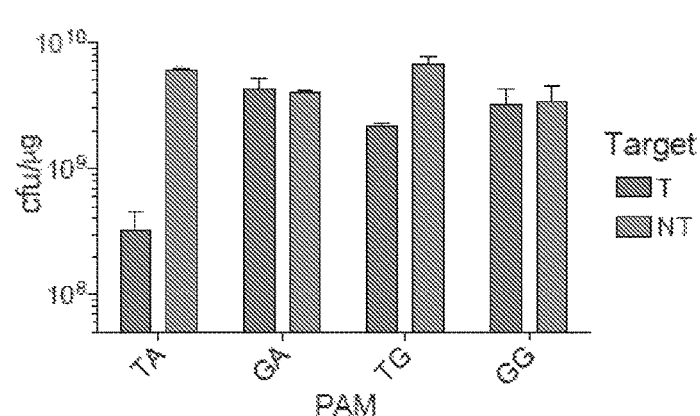

Figure 14
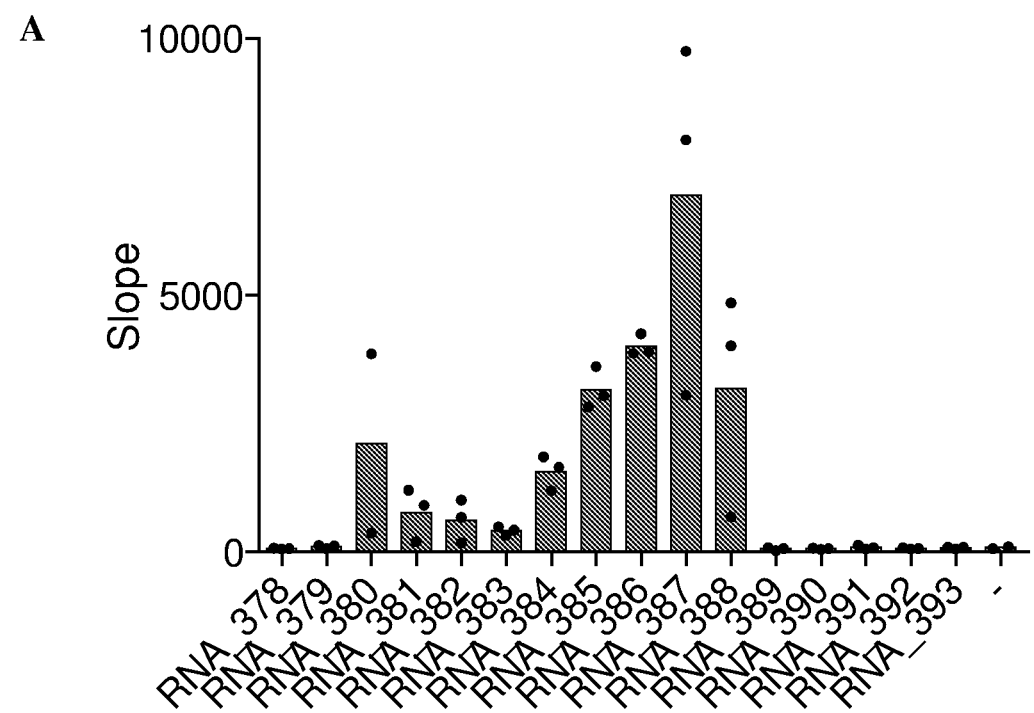
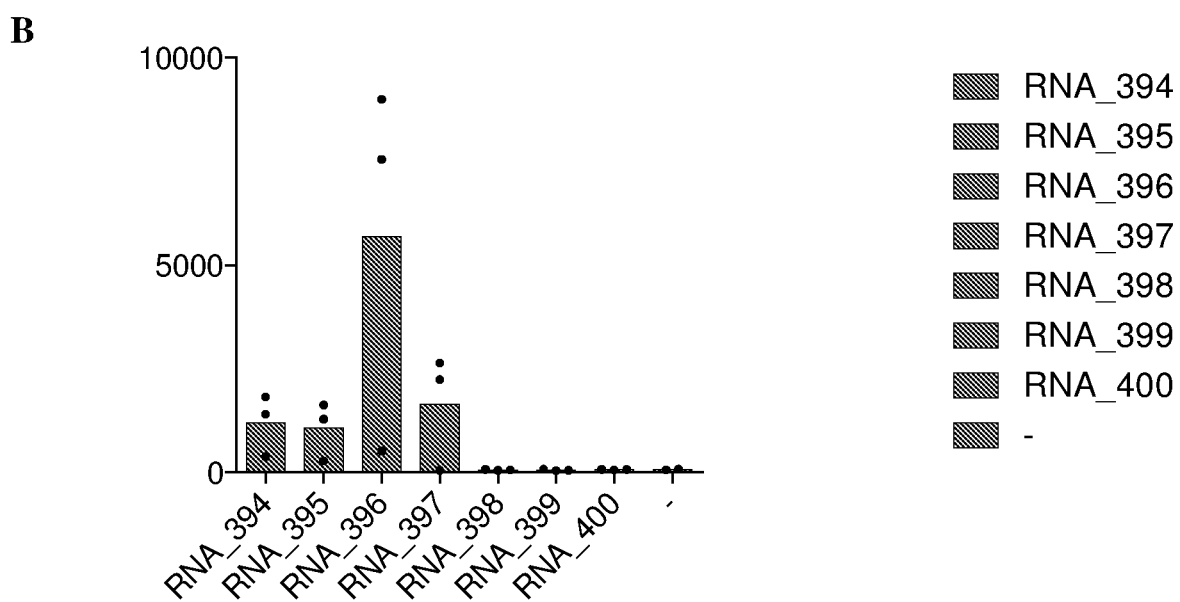

FIG. 15

Table 2

| RNA | RNA SEQUENCE | SEQ ID NO: |
|---|---|---|
| RNA_378 | atcaataccaaactctgg | 135 |
| RNA_379 | AAGGCatcaataccaaactctgg | 136 |
| RNA_380 | GCGATGAAGGCatcaataccaaactctgg | 137 |
| RNA_381 | CAGAGCGATGAAGGCatcaataccaaactctgg | 138 |
| RNA_382 | ACCCGTAAAGCAGAGCGATGAAGGCatcaataccaaactctgg | 139 |
| RNA_383 | GCGATGAAGGCatcaataccaaactctggCGG | 140 |
| RNA_384 | GCGATGAAGGCatcaataccaaactctggCG | 141 |
| RNA_385 | GCGATGAAGGCatcaataccaaactctggC | 142 |
| RNA_386 | GCGATGAAGGCatcaataccaaactctgg | 143 |
| RNA_387 | GCGATGAAGGCatcaataccaaactctg | 144 |
| RNA_388 | GCGATGAAGGCatcaataccaaactct | 145 |
| RNA_389 | atcaataccaaactctggACCCGTAAAGCAGAGCGATGAAGGC | 146 |
| RNA_390 | ACCCGTAAAGCAGAGCGATGGGCGTatcaataccaaactctgg | 147 |
| RNA_391 | GCGATGGGCGTatcaataccaaactctgg | 148 |
| RNA_392 | ACCCGTAAAGCAGAGCGATGAAGGCatcaataccaaactctggACCCGTAAAGCAGAGCGATGAAGGC | 149 |
| RNA_393 | GCCTTCATCGCTCTGCTTTACGGGTccagagtttggtatgatGCCTTCATCGCTCTGCTTTACGGGT | 150 |
| RNA_394 | CTTAGTTAAGGATGTTCCAGGTTCTTTCGGGAGCCTTGGCCTTCTCCCTT | 151 |
| RNA_395 | CCGACTTCGCTGATAAAATCTTAGTTAAGGATGTTCCAGGTTCTTTCGGGAGCCTTGGCCTTCTCCCTT | 152 |
| RNA_396 | CTTAGTTAAGGATGTTCCAGGTTCTTTCGGGAGCCTTGGCCTTCTCCCTTAACCTATGCCACTAATGATT | 153 |
| RNA_397 | CTTAGTTAAGGATGTTCCAGGTTCTTTCGGGAGCCTTGGCCTTCTCCCTTAACCTATGCCACTAATGATTAGGAACACGATGAATGAAAGAAGACGGCGA | 154 |
| RNA_398 | CTTAGTTAAGGATGTTCCAGGTTCTTTCGGGAACGCCGGCCTTCTCCCTT | 155 |

FIG. 15 (Cont.)

| RNA | RNA SEQUENCE | SEQ ID NO: |
|---|---|---|
| RNA_399 | CTTAGTTAAGGATGTTCCAGGTTCTTTCGGGAGCCTTGACGCCCTCCCTT | 156 |
| RNA_400 | CTTAGTTAAGGATGTTCCAGGTTCTTTCGGGAACGCCGACGCCCTCCCTT | 157 |
| RNA_401 | GGAGAGCAACTACCCGTAAAGCAGAGCGATGAAGGCatcaataccaaactctggACCCGTAAAGCAGAGCGATGAAGGCttgtcgtgtgagcagcttACCCGTAAAGCAGAGCGATGAAGGCACATTGGCCGACTTCGCTGATAAAAATCTTAGTTAAGGATGTTCCAGGTTCTTTCGGGAGCCTTGGCCTTCTCCCTTAACCT | 158 |
| RNA_402 | CTTAGTTAAGGATGTTCCAGGTTCTTTCGGGAGCCTTGGCCTTCTCCCTTAACCTATGCCACTAATGATTgaaaGCGATGAAGGCatcaataccaaactctgg | 159 |
| RNA_403 | CTTAGTTAAGGATGTTCCAGGTTCTTTCGGGAGCCTTGGCCTTCTCCCTTAACCTATGCCACTAATGATTgaaaaaaaaaaaGCGATGAAGGCatcaataccaaactctgg | 160 |
| RNA_404 | GGAGAGCAACTACCCGTAAAGCAGAGCGATGAAGGCatcaataccaaactctggACCCGTAAAGCAGAGCGATGAAGGCttgtcgtgtgagcagcttACCCGTAAAGCAGAGCGATGAAGGCA | 161 |

FIG. 16

Table 3

| DNA substrates | DNA Sequence | SEQ ID NO: |
|---|---|---|
| LβH_4421_CasY target 1 | GCCTGCCCGcagactaATCAATACCAAACTCTGGCGGCGTAAACTTTCCAGTC | 162 |
| LβH_4422_CasY Target 2 | GCCTGCCCGcagactaTACTGTTATTGTTGTACTCGGCGTAAACTTTCCAGTC | 163 |
| LβH_4423_CasY target 1 PAM TG | GCCTGCCCGcagactgATCAATACCAAACTCTGGCGGCGTAAACTTTCCAGTC | 164 |
| LβH_4424_CasY target 1 PAM TC | GCCTGCCCGcagactcATCAATACCAAACTCTGGCGGCGTAAACTTTCCAGTC | 165 |
| LβH_4425_CasY target 1 PAM TT | GCCTGCCCGcagacttATCAATACCAAACTCTGGCGGCGTAAACTTTCCAGTC | 166 |
| LβH_4426_CasY target 1 PAM AA | GCCTGCCCGcagacaaATCAATACCAAACTCTGGCGGCGTAAACTTTCCAGTC | 167 |
| LβH_4427_CasY target 1 PAM GA | GCCTGCCCGcagacGAATCAATACCAAACTCTGGCGGCGTAAACTTTCCAGTC | 168 |
| LβH_4428_CasY target 1 PAM CA | GCCTGCCCGcagaccaATCAATACCAAACTCTGGCGGCGTAAACTTTCCAGTC | 169 |
| LβH_4429_CasY target 1 PAM CC | GCCTGCCCGcagacccATCAATACCAAACTCTGGCGGCGTAAACTTTCCAGTC | 170 |
| LβH_4430_CasY target 1 PAM TTa | GCCTGCCCGcagattgATCAATACCAAACTCTGGCGGCGTAAACTTTCCAGTC | 171 |
| LβH_4431_CasY target 1 PAM gTa | GCCTGCCCGcagagtaATCAATACCAAACTCTGGCGGCGTAAACTTTCCAGTC | 172 |
| LβH_4432_CasY target 1 PAM aTa | GCCTGCCCGcagaataATCAATACCAAACTCTGGCGGCGTAAACTTTCCAGTC | 173 |
| LβH_4433_CasY target 1 MM 1-2 | GCCTGCCCGcagactaGCCAATACCAAACTCTGGCGGCGTAAACTTTCCAGTC | 174 |
| LβH_4434_CasY target 1 MM 3-4 | GCCTGCCCGcagactaATTGATACCAAACTCTGGCGGCGTAAACTTTCCAGTC | 175 |
| LβH_4435_CasY target 1 MM 5-6 | GCCTGCCCGcagactaATCAGCACCAAACTCTGGCGGCGTAAACTTTCCAGTC | 176 |

FIG. 16 (Cont.)

| DNA substrates | DNA Sequence | SEQ ID NO: |
|---|---|---|
| LβH_4436_CasY target 1 MM 7-8 | GCCTGCCCGcagactaATCAATGTCAAACTCTGGCGGCGTAAACTTTCCAGTC | 177 |
| LβH_4437_CasY target 1 MM 9-10 | GCCTGCCCGcagactaATCAATACTGAACTCTGGCGGCGTAAACTTTCCAGTC | 178 |
| LβH_4438_CasY target 1 MM 11-12 | GCCTGCCCGcagactaATCAATACCAGGCTCTGGCGGCGTAAACTTTCCAGTC | 179 |
| LβH_4439_CasY target 1 MM 13-14 | GCCTGCCCGcagactaATCAATACCAAATCCTGGCGGCGTAAACTTTCCAGTC | 180 |
| LβH_4440_CasY target 1 MM 15-16 | GCCTGCCCGcagactaATCAATACCAAACTTCGGCGGCGTAAACTTTCCAGTC | 181 |
| LβH_4441_CasY target 1 MM 17-18 | GCCTGCCCGcagactaATCAATACCAAACTCTAACGGCGTAAACTTTCCAGTC | 182 |
| LβH_4442_CasY target 1 MM 19-20 | GCCTGCCCGcagactaATCAATACCAAACTCTGGTAGCGTAAACTTTCCAGTC | 183 |
| LβH_4443_CasY target 1 | GACTGGAAAGTTTACGCCGCCAGAGTTTGGTATTGATtagtctgCGGGCAGGC | 184 |
| LβH_4444_CasY Target 2 | GACTGGAAAGTTTACGCCGAGTACAACAATAACAGTAtagtctgCGGGCAGGC | 185 |
| LβH_4445_CasY target 1 PAM TG | GACTGGAAAGTTTACGCCGCCAGAGTTTGGTATTGATcagtctgCGGGCAGGC | 186 |
| LβH_4446_CasY target 1 PAM TC | GACTGGAAAGTTTACGCCGCCAGAGTTTGGTATTGATgagtctgCGGGCAGGC | 187 |
| LβH_4447_CasY target 1 PAM TT | GACTGGAAAGTTTACGCCGCCAGAGTTTGGTATTGATaagtctgCGGGCAGGC | 188 |
| LβH_4448_CasY target 1 PAM AA | GACTGGAAAGTTTACGCCGCCAGAGTTTGGTATTGATttgtctgCGGGCAGGC | 189 |
| LβH_4449_CasY target 1 PAM GA | GACTGGAAAGTTTACGCCGCCAGAGTTTGGTATTGATTCgtctgCGGGCAGGC | 190 |
| LβH_4450_CasY target 1 PAM CA | GACTGGAAAGTTTACGCCGCCAGAGTTTGGTATTGATtggtctgCGGGCAGGC | 191 |

FIG. 16 (Cont.)

| DNA substrates | DNA Sequence | SEQ ID NO: |
|---|---|---|
| LβH_4451_CasY target 1 PAM CC | GACTGGAAAGTTTACGCCGCCAGAGTTTGGTATTGATgggtctgCGGGCAGGC | 192 |
| LβH_4452_CasY target 1 PAM TTa | GACTGGAAAGTTTACGCCGCCAGAGTTTGGTATTGATcaatctgCGGGCAGGC | 193 |
| LβH_4453_CasY target 1 PAM gTa | GACTGGAAAGTTTACGCCGCCAGAGTTTGGTATTGATtactctgCGGGCAGGC | 194 |
| LβH_4454_CasY target 1 PAM aTa | GACTGGAAAGTTTACGCCGCCAGAGTTTGGTATTGATtattctgCGGGCAGGC | 195 |
| LβH_4455_CasY target 1 MM 1-2 | GACTGGAAAGTTTACGCCGCCAGAGTTTGGTATTGGCtagtctgCGGGCAGGC | 196 |
| LβH_4456_CasY target 1 MM 3-4 | GACTGGAAAGTTTACGCCGCCAGAGTTTGGTATCAATtagtctgCGGGCAGGC | 197 |
| LβH_4457_CasY target 1 MM 5-6 | GACTGGAAAGTTTACGCCGCCAGAGTTTGGTGCTGATtagtctgCGGGCAGGC | 198 |
| LβH_4458_CasY target 1 MM 7-8 | GACTGGAAAGTTTACGCCGCCAGAGTTTGACATTGATtagtctgCGGGCAGGC | 199 |
| LβH_4459_CasY target 1 MM 9-10 | GACTGGAAAGTTTACGCCGCCAGAGTTCAGTATTGATtagtctgCGGGCAGGC | 200 |
| LβH_4460_CasY target 1 MM 11-12 | GACTGGAAAGTTTACGCCGCCAGAGCCTGGTATTGATtagtctgCGGGCAGGC | 201 |
| LβH_4461_CasY target 1 MM 13-14 | GACTGGAAAGTTTACGCCGCCAGGATTTGGTATTGATtagtctgCGGGCAGGC | 202 |
| LβH_4462_CasY target 1 MM 15-16 | GACTGGAAAGTTTACGCCGCCGAAGTTTGGTATTGATtagtctgCGGGCAGGC | 203 |
| LβH_4463_CasY target 1 MM 17-18 | GACTGGAAAGTTTACGCCGTTAGAGTTTGGTATTGATtagtctgCGGGCAGGC | 204 |
| LβH_4464_CasY target 1 MM 19-20 | GACTGGAAAGTTTACGCTACCAGAGTTTGGTATTGATtagtctgCGGGCAGGC | 205 |

Figure 18

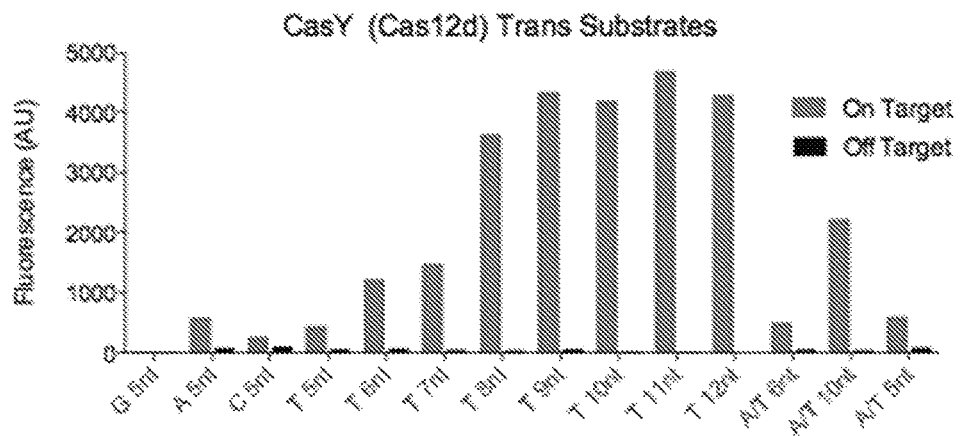

| Probe Name | Sequence | SEQ ID NO: |
|---|---|---|
| F-Q 5nt | /56-FAM/TTTTT/3IABkFQ/ | 206 |
| F-Q 6nt | /56-FAM/TTTTTT/3IABkFQ/ | 207 |
| F-Q 7nt | /56-FAM/TTTTTTT/3IABkFQ/ | 208 |
| F-Q 8nt | /56-FAM/TTTTTTTT/3IABkFQ/ | 209 |
| F-Q 9nt | /56-FAM/TTTTTTTTT/3IABkFQ/ | 210 |
| F-Q 10nt | /56-FAM/TTTTTTTTTT/3IABkFQ/ | 211 |
| F-Q 11nt | /56-FAM/TTTTTTTTTTT/3IABkFQ/ | 212 |
| F-Q 12nt | /56-FAM/TTTTTTTTTTTT/3IABkFQ/ | 213 |
| F-Q 10nt A/T | /56-FAM/TATATATATA/3IABkFQ/ | 214 |
| F-Q 6nt A/T | /56-FAM/TATATA/3IABkFQ/ | 215 |
| F-Q 5nt A/T | /56-FAM/TATAT/3IABkFQ/ | 216 |

SEQUENCE LISTING

```
<160> NUMBER OF SEQ ID NOS: 216

<210> SEQ ID NO 1
<211> LENGTH: 1125
<212> TYPE: PRT
<213> ORGANISM: Unknown
<220> FEATURE:
<223> OTHER INFORMATION: Synthetic sequence

<400> SEQUENCE: 1

Met Arg Lys Lys Leu Phe Lys Gly Tyr Ile Leu His Asn Lys Arg Leu
1               5                   10                  15

Val Tyr Thr Gly Lys Ala Ala Ile Arg Ser Ile Lys Tyr Pro Leu Val
            20                  25                  30
```

```
Ala Pro Asn Lys Thr Ala Leu Asn Asn Leu Ser Glu Lys Ile Ile Tyr
             35                  40                  45
Asp Tyr Glu His Leu Phe Gly Pro Leu Asn Val Ala Ser Tyr Ala Arg
 50                  55                  60
Asn Ser Asn Arg Tyr Ser Leu Val Asp Phe Trp Ile Asp Ser Leu Arg
 65                  70                  75                  80
Ala Gly Val Ile Trp Gln Ser Lys Ser Thr Ser Leu Ile Asp Leu Ile
                 85                  90                  95
Ser Lys Leu Glu Gly Ser Lys Ser Pro Ser Lys Ile Phe Glu Gln
                100                 105                 110
Ile Asp Phe Glu Leu Lys Asn Lys Leu Asp Lys Glu Gln Phe Lys Asp
                115                 120                 125
Ile Ile Leu Leu Asn Thr Gly Ile Arg Ser Ser Ser Asn Val Arg Ser
                130                 135                 140
Leu Arg Gly Arg Phe Leu Lys Cys Phe Lys Glu Glu Phe Arg Asp Thr
145                 150                 155                 160
Glu Glu Val Ile Ala Cys Val Asp Lys Trp Ser Lys Asp Leu Ile Val
                165                 170                 175
Glu Gly Lys Ser Ile Leu Val Ser Lys Gln Phe Leu Tyr Trp Glu Glu
                180                 185                 190
Glu Phe Gly Ile Lys Ile Phe Pro His Phe Lys Asp Asn His Asp Leu
                195                 200                 205
Pro Lys Leu Thr Phe Phe Val Glu Pro Ser Leu Glu Phe Ser Pro His
                210                 215                 220
Leu Pro Leu Ala Asn Cys Leu Glu Arg Leu Lys Lys Phe Asp Ile Ser
225                 230                 235                 240
Arg Glu Ser Leu Leu Gly Leu Asp Asn Asn Phe Ser Ala Phe Ser Asn
                245                 250                 255
Tyr Phe Asn Glu Leu Phe Asn Leu Leu Ser Arg Gly Glu Ile Lys Lys
                260                 265                 270
Ile Val Thr Ala Val Leu Ala Val Ser Lys Ser Trp Glu Asn Glu Pro
                275                 280                 285
Glu Leu Glu Lys Arg Leu His Phe Leu Ser Glu Lys Ala Lys Leu Leu
                290                 295                 300
Gly Tyr Pro Lys Leu Thr Ser Ser Trp Ala Asp Tyr Arg Met Ile Ile
305                 310                 315                 320
Gly Gly Lys Ile Lys Ser Trp His Ser Asn Tyr Thr Glu Gln Leu Ile
                325                 330                 335
Lys Val Arg Glu Asp Leu Lys Lys His Gln Ile Ala Leu Asp Lys Leu
                340                 345                 350
Gln Glu Asp Leu Lys Lys Val Val Asp Ser Ser Leu Arg Glu Gln Ile
                355                 360                 365
Glu Ala Gln Arg Glu Ala Leu Leu Pro Leu Leu Asp Thr Met Leu Lys
                370                 375                 380
Glu Lys Asp Phe Ser Asp Asp Leu Glu Leu Tyr Arg Phe Ile Leu Ser
385                 390                 395                 400
Asp Phe Lys Ser Leu Leu Asn Gly Ser Tyr Gln Arg Tyr Ile Gln Thr
                405                 410                 415
Glu Glu Glu Arg Lys Glu Asp Arg Asp Val Thr Lys Lys Tyr Lys Asp
                420                 425                 430
Leu Tyr Ser Asn Leu Arg Asn Ile Pro Arg Phe Phe Gly Glu Ser Lys
                435                 440                 445
Lys Glu Gln Phe Asn Lys Phe Ile Asn Lys Ser Leu Pro Thr Ile Asp
```

-continued

```
            450             455             460
Val Gly Leu Lys Ile Leu Glu Asp Ile Arg Asn Ala Leu Glu Thr Val
465                     470                     475                 480

Ser Val Arg Lys Pro Pro Ser Ile Thr Glu Glu Tyr Val Thr Lys Gln
                    485                     490                 495

Leu Glu Lys Leu Ser Arg Lys Tyr Lys Ile Asn Ala Phe Asn Ser Asn
                500                     505                 510

Arg Phe Lys Gln Ile Thr Glu Gln Val Leu Arg Lys Tyr Asn Asn Gly
            515                     520                 525

Glu Leu Pro Lys Ile Ser Glu Val Phe Tyr Arg Tyr Pro Arg Glu Ser
            530                     535                 540

His Val Ala Ile Arg Ile Leu Pro Val Lys Ile Ser Asn Pro Arg Lys
545                     550                     555                 560

Asp Ile Ser Tyr Leu Leu Asp Lys Tyr Gln Ile Ser Pro Asp Trp Lys
                    565                     570                 575

Asn Ser Asn Pro Gly Glu Val Val Asp Leu Ile Glu Ile Tyr Lys Leu
                580                     585                 590

Thr Leu Gly Trp Leu Leu Ser Cys Asn Lys Asp Phe Ser Met Asp Phe
            595                     600                 605

Ser Ser Tyr Asp Leu Lys Leu Phe Pro Glu Ala Ala Ser Leu Ile Lys
            610                     615                 620

Asn Phe Gly Ser Cys Leu Ser Gly Tyr Tyr Leu Ser Lys Met Ile Phe
625                     630                     635                 640

Asn Cys Ile Thr Ser Glu Ile Lys Gly Met Ile Thr Leu Tyr Thr Arg
                    645                     650                 655

Asp Lys Phe Val Val Arg Tyr Val Thr Gln Met Ile Gly Ser Asn Gln
                660                     665                 670

Lys Phe Pro Leu Leu Cys Leu Val Gly Glu Lys Gln Thr Lys Asn Phe
            675                     680                 685

Ser Arg Asn Trp Gly Val Leu Ile Glu Glu Lys Gly Asp Leu Gly Glu
            690                     695                 700

Glu Lys Asn Gln Glu Lys Cys Leu Ile Phe Lys Asp Lys Thr Asp Phe
705                     710                     715                 720

Ala Lys Ala Lys Glu Val Glu Ile Phe Lys Asn Asn Ile Trp Arg Ile
                    725                     730                 735

Arg Thr Ser Lys Tyr Gln Ile Gln Phe Leu Asn Arg Leu Phe Lys Lys
                740                     745                 750

Thr Lys Glu Trp Asp Leu Met Asn Leu Val Leu Ser Glu Pro Ser Leu
            755                     760                 765

Val Leu Glu Glu Glu Trp Gly Val Ser Trp Asp Lys Asp Lys Leu Leu
            770                     775                 780

Pro Leu Leu Lys Lys Glu Lys Ser Cys Glu Glu Arg Leu Tyr Tyr Ser
785                     790                     795                 800

Leu Pro Leu Asn Leu Val Pro Ala Thr Asp Tyr Lys Glu Gln Ser Ala
                    805                     810                 815

Glu Ile Glu Gln Arg Asn Thr Tyr Leu Gly Leu Asp Val Gly Glu Phe
                820                     825                 830

Gly Val Ala Tyr Ala Val Val Arg Ile Val Arg Asp Arg Ile Glu Leu
            835                     840                 845

Leu Ser Trp Gly Phe Leu Lys Asp Pro Ala Leu Arg Lys Ile Arg Glu
            850                     855                 860

Arg Val Gln Asp Met Lys Lys Lys Gln Val Met Ala Val Phe Ser Ser
865                     870                     875                 880
```

```
Ser Ser Thr Ala Val Ala Arg Val Arg Glu Met Ala Ile His Ser Leu
            885                 890                 895

Arg Asn Gln Ile His Ser Ile Ala Leu Ala Tyr Lys Ala Lys Ile Ile
        900                 905                 910

Tyr Glu Ile Ser Ile Ser Asn Phe Glu Thr Gly Gly Asn Arg Met Ala
        915                 920                 925

Lys Ile Tyr Arg Ser Ile Lys Val Ser Asp Val Tyr Arg Glu Ser Gly
    930                 935                 940

Ala Asp Thr Leu Val Ser Glu Met Ile Trp Gly Lys Asn Lys Gln
945                 950                 955                 960

Met Gly Asn His Ile Ser Ser Tyr Ala Thr Ser Tyr Thr Cys Cys Asn
                965                 970                 975

Cys Ala Arg Thr Pro Phe Glu Leu Val Ile Asp Asn Asp Lys Glu Tyr
            980                 985                 990

Glu Lys Gly Gly Asp Glu Phe Ile Phe Asn Val Gly Asp Glu Lys Lys
        995                 1000                1005

Val Arg Gly Phe Leu Gln Lys Ser Leu Leu Gly Lys Thr Ile Lys
    1010                1015                1020

Gly Lys Glu Val Leu Lys Ser Ile Lys Glu Tyr Ala Arg Pro Pro
    1025                1030                1035

Ile Arg Glu Val Leu Leu Glu Gly Glu Asp Val Glu Gln Leu Leu
    1040                1045                1050

Lys Arg Arg Gly Asn Ser Tyr Ile Tyr Arg Cys Pro Phe Cys Gly
    1055                1060                1065

Tyr Lys Thr Asp Ala Asp Ile Gln Ala Ala Leu Asn Ile Ala Cys
    1070                1075                1080

Arg Gly Tyr Ile Ser Asp Asn Ala Lys Asp Ala Val Lys Glu Gly
    1085                1090                1095

Glu Arg Lys Leu Asp Tyr Ile Leu Glu Val Arg Lys Leu Trp Glu
    1100                1105                1110

Lys Asn Gly Ala Val Leu Arg Ser Ala Lys Phe Leu
    1115                1120                1125

<210> SEQ ID NO 2
<211> LENGTH: 1226
<212> TYPE: PRT
<213> ORGANISM: Unknown
<220> FEATURE:
<223> OTHER INFORMATION: Synthetic sequence

<400> SEQUENCE: 2

Met Gln Lys Val Arg Lys Thr Leu Ser Glu Val His Lys Asn Pro Tyr
1               5                   10                  15

Gly Thr Lys Val Arg Asn Ala Lys Thr Gly Tyr Ser Leu Gln Ile Glu
                20                  25                  30

Arg Leu Ser Tyr Thr Gly Lys Glu Gly Met Arg Ser Phe Lys Ile Pro
            35                  40                  45

Leu Glu Asn Lys Asn Lys Glu Val Phe Asp Glu Phe Val Lys Lys Ile
        50                  55                  60

Arg Asn Asp Tyr Ile Ser Gln Val Gly Leu Leu Asn Leu Ser Asp Trp
65                  70                  75                  80

Tyr Glu His Tyr Gln Glu Lys Gln Glu His Tyr Ser Leu Ala Asp Phe
                85                  90                  95

Trp Leu Asp Ser Leu Arg Ala Gly Val Ile Phe Ala His Lys Glu Thr
            100                 105                 110
```

Glu Ile Lys Asn Leu Ile Ser Lys Ile Arg Gly Asp Lys Ser Ile Val
            115                 120                 125

Asp Lys Phe Asn Ala Ser Ile Lys Lys His Ala Asp Leu Tyr Ala
    130                 135                 140

Leu Val Asp Ile Lys Ala Leu Tyr Asp Phe Leu Thr Ser Asp Ala Arg
145                 150                 155                 160

Arg Gly Leu Lys Thr Glu Glu Phe Phe Asn Ser Lys Arg Asn Thr
                165                 170                 175

Leu Phe Pro Lys Phe Arg Lys Lys Asp Asn Lys Ala Val Asp Leu Trp
            180                 185                 190

Val Lys Lys Phe Ile Gly Leu Asp Asn Lys Asp Lys Leu Asn Phe Thr
        195                 200                 205

Lys Lys Phe Ile Gly Phe Asp Pro Asn Pro Gln Ile Lys Tyr Asp His
        210                 215                 220

Thr Phe Phe Phe His Gln Asp Ile Asn Phe Asp Leu Glu Arg Ile Thr
225                 230                 235                 240

Thr Pro Lys Glu Leu Ile Ser Thr Tyr Lys Lys Phe Leu Gly Lys Asn
                245                 250                 255

Lys Asp Leu Tyr Gly Ser Asp Glu Thr Thr Glu Asp Gln Leu Lys Met
            260                 265                 270

Val Leu Gly Phe His Asn Asn His Gly Ala Phe Ser Lys Tyr Phe Asn
        275                 280                 285

Ala Ser Leu Glu Ala Phe Arg Gly Arg Asp Asn Ser Leu Val Glu Gln
        290                 295                 300

Ile Ile Asn Asn Ser Pro Tyr Trp Asn Ser His Arg Lys Glu Leu Glu
305                 310                 315                 320

Lys Arg Ile Ile Phe Leu Gln Val Gln Ser Lys Lys Ile Lys Glu Thr
                325                 330                 335

Glu Leu Gly Lys Pro His Glu Tyr Leu Ala Ser Phe Gly Gly Lys Phe
            340                 345                 350

Glu Ser Trp Val Ser Asn Tyr Leu Arg Gln Glu Gly Glu Val Lys Arg
        355                 360                 365

Gln Leu Phe Gly Tyr Glu Glu Asn Lys Lys Gly Gln Lys Phe Ile
        370                 375                 380

Val Gly Asn Lys Gln Glu Leu Asp Lys Ile Ile Arg Gly Thr Asp Glu
385                 390                 395                 400

Tyr Glu Ile Lys Ala Ile Ser Lys Glu Thr Ile Gly Leu Thr Gln Lys
                405                 410                 415

Cys Leu Lys Leu Leu Glu Gln Leu Lys Asp Ser Val Asp Asp Tyr Thr
            420                 425                 430

Leu Ser Leu Tyr Arg Gln Leu Ile Val Glu Leu Arg Ile Arg Leu Asn
        435                 440                 445

Val Glu Phe Gln Glu Thr Tyr Pro Glu Leu Ile Gly Lys Ser Glu Lys
450                 455                 460

Asp Lys Glu Lys Asp Ala Lys Asn Lys Arg Ala Asp Lys Arg Tyr Pro
465                 470                 475                 480

Gln Ile Phe Lys Asp Ile Lys Leu Ile Pro Asn Phe Leu Gly Glu Thr
                485                 490                 495

Lys Gln Met Val Tyr Lys Lys Phe Ile Arg Ser Ala Asp Ile Leu Tyr
            500                 505                 510

Glu Gly Ile Asn Phe Ile Asp Gln Ile Asp Lys Gln Ile Thr Gln Asn
        515                 520                 525

-continued

```
Leu Leu Pro Cys Phe Lys Asn Asp Lys Glu Arg Ile Glu Phe Thr Glu
530                 535                 540
Lys Gln Phe Glu Thr Leu Arg Arg Lys Tyr Tyr Leu Met Asn Ser Ser
545                 550                 555                 560
Arg Phe His His Val Ile Glu Gly Ile Ile Asn Asn Arg Lys Leu Ile
                565                 570                 575
Glu Met Lys Lys Arg Glu Asn Ser Glu Leu Lys Thr Phe Ser Asp Ser
            580                 585                 590
Lys Phe Val Leu Ser Lys Leu Phe Leu Lys Gly Lys Lys Tyr Glu
        595                 600                 605
Asn Glu Val Tyr Tyr Thr Phe Tyr Ile Asn Pro Lys Ala Arg Asp Gln
610                 615                 620
Arg Arg Ile Lys Ile Val Leu Asp Ile Asn Gly Asn Asn Ser Val Gly
625                 630                 635                 640
Ile Leu Gln Asp Leu Val Gln Lys Leu Lys Pro Lys Trp Asp Asp Ile
                645                 650                 655
Ile Lys Lys Asn Asp Met Gly Glu Leu Ile Asp Ala Ile Glu Ile Glu
            660                 665                 670
Lys Val Arg Leu Gly Ile Leu Ile Ala Leu Tyr Cys Glu His Lys Phe
        675                 680                 685
Lys Ile Lys Lys Glu Leu Leu Ser Leu Asp Leu Phe Ala Ser Ala Tyr
690                 695                 700
Gln Tyr Leu Glu Leu Glu Asp Asp Pro Glu Glu Leu Ser Gly Thr Asn
705                 710                 715                 720
Leu Gly Arg Phe Leu Gln Ser Leu Val Cys Ser Glu Ile Lys Gly Ala
                725                 730                 735
Ile Asn Lys Ile Ser Arg Thr Glu Tyr Ile Glu Arg Tyr Thr Val Gln
            740                 745                 750
Pro Met Asn Thr Glu Lys Asn Tyr Pro Leu Leu Ile Asn Lys Glu Gly
        755                 760                 765
Lys Ala Thr Trp His Ile Ala Ala Lys Asp Asp Leu Ser Lys Lys Lys
770                 775                 780
Gly Gly Gly Thr Val Ala Met Asn Gln Lys Ile Gly Lys Asn Phe Phe
785                 790                 795                 800
Gly Lys Gln Asp Tyr Lys Thr Val Phe Met Leu Gln Asp Lys Arg Phe
                805                 810                 815
Asp Leu Leu Thr Ser Lys Tyr His Leu Gln Phe Leu Ser Lys Thr Leu
            820                 825                 830
Asp Thr Gly Gly Gly Ser Trp Trp Lys Asn Lys Asn Ile Asp Leu Asn
        835                 840                 845
Leu Ser Ser Tyr Ser Phe Ile Phe Glu Gln Lys Val Lys Val Glu Trp
850                 855                 860
Asp Leu Thr Asn Leu Asp His Pro Ile Lys Ile Lys Pro Ser Glu Asn
865                 870                 875                 880
Ser Asp Asp Arg Arg Leu Phe Val Ser Ile Pro Phe Val Ile Lys Pro
                885                 890                 895
Lys Gln Thr Lys Arg Lys Asp Leu Gln Thr Arg Val Asn Tyr Met Gly
            900                 905                 910
Ile Asp Ile Gly Glu Tyr Gly Leu Ala Trp Thr Ile Asn Ile Asp
        915                 920                 925
Leu Lys Asn Lys Lys Ile Asn Lys Ile Ser Lys Gln Gly Phe Ile Tyr
930                 935                 940
Glu Pro Leu Thr His Lys Val Arg Asp Tyr Val Ala Thr Ile Lys Asp
```

```
                   945                 950                 955                 960
Asn Gln Val Arg Gly Thr Phe Gly Met Pro Asp Thr Lys Leu Ala Arg
                    965                 970                 975

Leu Arg Glu Asn Ala Ile Thr Ser Leu Arg Asn Gln Val His Asp Ile
            980                 985                 990

Ala Met Arg Tyr Asp Ala Lys Pro Val Tyr Glu Phe Glu Ile Ser Asn
                995                 1000                1005

Phe Glu Thr Gly Ser Asn Lys Val Lys Val Ile Tyr Asp Ser Val
        1010                1015                1020

Lys Arg Ala Asp Ile Gly Arg Gly Gln Asn Asn Thr Glu Ala Asp
        1025                1030                1035

Asn Thr Glu Val Asn Leu Val Trp Gly Lys Thr Ser Lys Gln Phe
        1040                1045                1050

Gly Ser Gln Ile Gly Ala Tyr Ala Thr Ser Tyr Ile Cys Ser Phe
        1055                1060                1065

Cys Gly Tyr Ser Pro Tyr Tyr Glu Phe Glu Asn Ser Lys Ser Gly
        1070                1075                1080

Asp Glu Glu Gly Ala Arg Asp Asn Leu Tyr Gln Met Lys Lys Leu
        1085                1090                1095

Ser Arg Pro Ser Leu Glu Asp Phe Leu Gln Gly Asn Pro Val Tyr
        1100                1105                1110

Lys Thr Phe Arg Asp Phe Asp Lys Tyr Lys Asn Asp Gln Arg Leu
        1115                1120                1125

Gln Lys Thr Gly Asp Lys Asp Gly Glu Trp Lys Thr His Arg Gly
        1130                1135                1140

Asn Thr Ala Ile Tyr Ala Cys Gln Lys Cys Arg His Ile Ser Asp
        1145                1150                1155

Ala Asp Ile Gln Ala Ser Tyr Trp Ile Ala Leu Lys Gln Val Val
        1160                1165                1170

Arg Asp Phe Tyr Lys Asp Lys Glu Met Asp Gly Asp Leu Ile Gln
        1175                1180                1185

Gly Asp Asn Lys Asp Lys Arg Lys Val Asn Glu Leu Asn Arg Leu
        1190                1195                1200

Ile Gly Val His Lys Asp Val Pro Ile Asn Lys Asn Leu Ile
        1205                1210                1215

Thr Ser Leu Asp Ile Asn Leu Leu
        1220                1225

<210> SEQ ID NO 3
<211> LENGTH: 1160
<212> TYPE: PRT
<213> ORGANISM: Unknown
<220> FEATURE:
<223> OTHER INFORMATION: Synthetic sequence

<400> SEQUENCE: 3

Met Lys Ala Lys Lys Ser Phe Tyr Asn Gln Lys Arg Lys Phe Gly Lys
1               5                   10                  15

Arg Gly Tyr Arg Leu His Asp Glu Arg Ile Ala Tyr Ser Gly Gly Ile
            20                  25                  30

Gly Ser Met Arg Ser Ile Lys Tyr Glu Leu Lys Asp Ser Tyr Gly Ile
        35                  40                  45

Ala Gly Leu Arg Asn Arg Ile Ala Asp Ala Thr Ile Ser Asp Asn Lys
    50                  55                  60

Trp Leu Tyr Gly Asn Ile Asn Leu Asn Asp Tyr Leu Glu Trp Arg Ser
```

```
                65                  70                  75                  80
        Ser Lys Thr Asp Lys Gln Ile Glu Asp Gly Asp Arg Glu Ser Ser Leu
                         85                  90                  95
        Leu Gly Phe Trp Leu Glu Ala Leu Arg Leu Gly Phe Val Phe Ser Lys
                        100                 105                 110
        Gln Ser His Ala Pro Asn Asp Phe Asn Glu Thr Ala Leu Gln Asp Leu
                        115                 120                 125
        Phe Glu Thr Leu Asp Asp Leu Lys His Val Leu Asp Arg Lys Lys
                130                 135                 140
        Trp Cys Asp Phe Ile Lys Ile Gly Thr Pro Lys Thr Asn Asp Gln Gly
        145                 150                 155                 160
        Arg Leu Lys Lys Gln Ile Lys Asn Leu Leu Lys Gly Asn Lys Arg Glu
                        165                 170                 175
        Glu Ile Glu Lys Thr Leu Asn Glu Ser Asp Asp Glu Leu Lys Glu Lys
                        180                 185                 190
        Ile Asn Arg Ile Ala Asp Val Phe Ala Lys Asn Lys Ser Asp Lys Tyr
                        195                 200                 205
        Thr Ile Phe Lys Leu Asp Lys Pro Asn Thr Glu Lys Tyr Pro Arg Ile
                        210                 215                 220
        Asn Asp Val Gln Val Ala Phe Phe Cys His Pro Asp Phe Glu Glu Ile
        225                 230                 235                 240
        Thr Glu Arg Asp Arg Thr Lys Thr Leu Asp Leu Ile Ile Asn Arg Phe
                        245                 250                 255
        Asn Lys Arg Tyr Glu Ile Thr Glu Asn Lys Lys Asp Asp Lys Thr Ser
                        260                 265                 270
        Asn Arg Met Ala Leu Tyr Ser Leu Asn Gln Gly Tyr Ile Pro Arg Val
                        275                 280                 285
        Leu Asn Asp Leu Phe Leu Phe Val Lys Asp Asn Glu Asp Asp Phe Ser
                        290                 295                 300
        Gln Phe Leu Ser Asp Leu Glu Asn Phe Phe Ser Phe Ser Asn Glu Gln
        305                 310                 315                 320
        Ile Lys Ile Ile Lys Glu Arg Leu Lys Lys Leu Lys Lys Tyr Ala Glu
                        325                 330                 335
        Pro Ile Pro Gly Lys Pro Gln Leu Ala Asp Lys Trp Asp Asp Tyr Ala
                        340                 345                 350
        Ser Asp Phe Gly Gly Lys Leu Glu Ser Trp Tyr Ser Asn Arg Ile Glu
                        355                 360                 365
        Lys Leu Lys Lys Ile Pro Glu Ser Val Ser Asp Leu Arg Asn Asn Leu
        370                 375                 380
        Glu Lys Ile Arg Asn Val Leu Lys Lys Gln Asn Asn Ala Ser Lys Ile
        385                 390                 395                 400
        Leu Glu Leu Ser Gln Lys Ile Ile Glu Tyr Ile Arg Asp Tyr Gly Val
                        405                 410                 415
        Ser Phe Glu Lys Pro Glu Ile Ile Lys Phe Ser Trp Ile Asn Lys Thr
                        420                 425                 430
        Lys Asp Gly Gln Lys Lys Val Phe Tyr Val Ala Lys Met Ala Asp Arg
                        435                 440                 445
        Glu Phe Ile Glu Lys Leu Asp Leu Trp Met Ala Asp Leu Arg Ser Gln
                        450                 455                 460
        Leu Asn Glu Tyr Asn Gln Asp Asn Lys Val Ser Phe Lys Lys Gly
        465                 470                 475                 480
        Lys Lys Ile Glu Glu Leu Gly Val Leu Asp Phe Ala Leu Asn Lys Ala
                        485                 490                 495
```

```
Lys Lys Asn Lys Ser Thr Lys Asn Glu Asn Gly Trp Gln Gln Lys Leu
            500                 505                 510

Ser Glu Ser Ile Gln Ser Ala Pro Leu Phe Phe Gly Glu Gly Asn Arg
            515                 520                 525

Val Arg Asn Glu Glu Val Tyr Asn Leu Lys Asp Leu Leu Phe Ser Glu
            530                 535                 540

Ile Lys Asn Val Glu Asn Ile Leu Met Ser Ser Glu Ala Glu Asp Leu
545                 550                 555                 560

Lys Asn Ile Lys Ile Glu Tyr Lys Glu Asp Gly Ala Lys Lys Gly Asn
                565                 570                 575

Tyr Val Leu Asn Val Leu Ala Arg Phe Tyr Ala Arg Phe Asn Glu Asp
            580                 585                 590

Gly Tyr Gly Gly Trp Asn Lys Val Lys Thr Val Leu Glu Asn Ile Ala
            595                 600                 605

Arg Glu Ala Gly Thr Asp Phe Ser Lys Tyr Gly Asn Asn Asn Asn Arg
            610                 615                 620

Asn Ala Gly Arg Phe Tyr Leu Asn Gly Arg Glu Arg Gln Val Phe Thr
625                 630                 635                 640

Leu Ile Lys Phe Glu Lys Ser Ile Thr Val Glu Lys Ile Leu Glu Leu
                645                 650                 655

Val Lys Leu Pro Ser Leu Leu Asp Glu Ala Tyr Arg Asp Leu Val Asn
            660                 665                 670

Glu Asn Lys Asn His Lys Leu Arg Asp Val Ile Gln Leu Ser Lys Thr
            675                 680                 685

Ile Met Ala Leu Val Leu Ser His Ser Asp Lys Glu Lys Gln Ile Gly
            690                 695                 700

Gly Asn Tyr Ile His Ser Lys Leu Ser Gly Tyr Asn Ala Leu Ile Ser
705                 710                 715                 720

Lys Arg Asp Phe Ile Ser Arg Tyr Ser Val Gln Thr Thr Asn Gly Thr
                725                 730                 735

Gln Cys Lys Leu Ala Ile Gly Lys Gly Lys Ser Lys Lys Gly Asn Glu
            740                 745                 750

Ile Asp Arg Tyr Phe Tyr Ala Phe Gln Phe Phe Lys Asn Asp Asp Ser
            755                 760                 765

Lys Ile Asn Leu Lys Val Ile Lys Asn Ser His Lys Asn Ile Asp
            770                 775                 780

Phe Asn Asp Asn Glu Asn Lys Ile Asn Ala Leu Gln Val Tyr Ser Ser
785                 790                 795                 800

Asn Tyr Gln Ile Gln Phe Leu Asp Trp Phe Phe Glu Lys His Gln Gly
                805                 810                 815

Lys Lys Thr Ser Leu Glu Val Gly Gly Ser Phe Thr Ile Ala Glu Lys
            820                 825                 830

Ser Leu Thr Ile Asp Trp Ser Gly Ser Asn Pro Arg Val Gly Phe Lys
            835                 840                 845

Arg Ser Asp Thr Glu Glu Lys Arg Val Phe Val Ser Gln Pro Phe Thr
            850                 855                 860

Leu Ile Pro Asp Asp Glu Asp Lys Glu Arg Arg Lys Glu Arg Met Ile
865                 870                 875                 880

Lys Thr Lys Asn Arg Phe Ile Gly Ile Asp Ile Gly Glu Tyr Gly Leu
                885                 890                 895

Ala Trp Ser Leu Ile Glu Val Asp Asn Gly Asp Lys Asn Asn Arg Gly
            900                 905                 910
```

-continued

Ile Arg Gln Leu Glu Ser Gly Phe Ile Thr Asp Asn Gln Gln Val
            915                 920                 925

Leu Lys Lys Asn Val Lys Ser Trp Arg Gln Asn Gln Ile Arg Gln Thr
930                 935                 940

Phe Thr Ser Pro Asp Thr Lys Ile Ala Arg Leu Arg Glu Ser Leu Ile
945                 950                 955                 960

Gly Ser Tyr Lys Asn Gln Leu Glu Ser Leu Met Val Ala Lys Lys Ala
                965                 970                 975

Asn Leu Ser Phe Glu Tyr Glu Val Ser Gly Phe Glu Val Gly Gly Lys
            980                 985                 990

Arg Val Ala Lys Ile Tyr Asp Ser Ile Lys Arg Gly Ser Val Arg Lys
            995                 1000                1005

Lys Asp Asn Asn Ser Gln Asn Asp Gln Ser Trp Gly Lys Lys Gly
    1010                1015                1020

Ile Asn Glu Trp Ser Phe Glu Thr Thr Ala Ala Gly Thr Ser Gln
    1025                1030                1035

Phe Cys Thr His Cys Lys Arg Trp Ser Ser Leu Ala Ile Val Asp
    1040                1045                1050

Ile Glu Glu Tyr Glu Leu Lys Asp Tyr Asn Asp Asn Leu Phe Lys
    1055                1060                1065

Val Lys Ile Asn Asp Gly Glu Val Arg Leu Leu Gly Lys Lys Gly
    1070                1075                1080

Trp Arg Ser Gly Glu Lys Ile Lys Gly Lys Glu Leu Phe Gly Pro
    1085                1090                1095

Val Lys Asp Ala Met Arg Pro Asn Val Asp Gly Leu Gly Met Lys
    1100                1105                1110

Ile Val Lys Arg Lys Tyr Leu Lys Leu Asp Leu Arg Asp Trp Val
    1115                1120                1125

Ser Arg Tyr Gly Asn Met Ala Ile Phe Ile Cys Pro Tyr Val Asp
    1130                1135                1140

Cys His His Ile Ser His Ala Asp Lys Gln Ala Ala Phe Asn Ile
    1145                1150                1155

Ala Val
    1160

<210> SEQ ID NO 4
<211> LENGTH: 1210
<212> TYPE: PRT
<213> ORGANISM: Unknown
<220> FEATURE:
<223> OTHER INFORMATION: Synthetic sequence

<400> SEQUENCE: 4

Met Ser Lys Arg His Pro Arg Ile Ser Gly Val Lys Gly Tyr Arg Leu
1               5                   10                  15

His Ala Gln Arg Leu Glu Tyr Thr Gly Lys Ser Gly Ala Met Arg Thr
            20                  25                  30

Ile Lys Tyr Pro Leu Tyr Ser Ser Pro Ser Gly Gly Arg Thr Val Pro
        35                  40                  45

Arg Glu Ile Val Ser Ala Ile Asn Asp Asp Tyr Val Gly Leu Tyr Gly
    50                  55                  60

Leu Ser Asn Phe Asp Asp Leu Tyr Asn Ala Glu Lys Arg Asn Glu Glu
65                  70                  75                  80

Lys Val Tyr Ser Val Leu Asp Phe Trp Tyr Asp Cys Val Gln Tyr Gly
                85                  90                  95

```
Ala Val Phe Ser Tyr Thr Ala Pro Gly Leu Leu Lys Asn Val Ala Glu
            100                 105                 110

Val Arg Gly Gly Ser Tyr Glu Leu Thr Lys Thr Leu Lys Gly Ser His
            115                 120                 125

Leu Tyr Asp Glu Leu Gln Ile Asp Lys Val Ile Lys Phe Leu Asn Lys
        130                 135                 140

Lys Glu Ile Ser Arg Ala Asn Gly Ser Leu Asp Lys Leu Lys Lys Asp
145                 150                 155                 160

Ile Ile Asp Cys Phe Lys Ala Glu Tyr Arg Glu Arg His Lys Asp Gln
                165                 170                 175

Cys Asn Lys Leu Ala Asp Asp Ile Lys Asn Ala Lys Lys Asp Ala Gly
            180                 185                 190

Ala Ser Leu Gly Glu Arg Gln Lys Lys Leu Phe Arg Asp Phe Phe Gly
            195                 200                 205

Ile Ser Glu Gln Ser Glu Asn Asp Lys Pro Ser Phe Thr Asn Pro Leu
        210                 215                 220

Asn Leu Thr Cys Cys Leu Leu Pro Phe Asp Thr Val Asn Asn Asn Arg
225                 230                 235                 240

Asn Arg Gly Glu Val Leu Phe Asn Lys Leu Lys Glu Tyr Ala Gln Lys
                245                 250                 255

Leu Asp Lys Asn Glu Gly Ser Leu Glu Met Trp Glu Tyr Ile Gly Ile
            260                 265                 270

Gly Asn Ser Gly Thr Ala Phe Ser Asn Phe Leu Gly Glu Gly Phe Leu
            275                 280                 285

Gly Arg Leu Arg Glu Asn Lys Ile Thr Glu Leu Lys Lys Ala Met Met
            290                 295                 300

Asp Ile Thr Asp Ala Trp Arg Gly Gln Glu Gln Glu Glu Leu Glu
305                 310                 315                 320

Lys Arg Leu Arg Ile Leu Ala Ala Leu Thr Ile Lys Leu Arg Glu Pro
                325                 330                 335

Lys Phe Asp Asn His Trp Gly Gly Tyr Arg Ser Asp Ile Asn Gly Lys
            340                 345                 350

Leu Ser Ser Trp Leu Gln Asn Tyr Ile Asn Gln Thr Val Lys Ile Lys
            355                 360                 365

Glu Asp Leu Lys Gly His Lys Lys Asp Leu Lys Lys Ala Lys Glu Met
        370                 375                 380

Ile Asn Arg Phe Gly Glu Ser Asp Thr Lys Glu Glu Ala Val Val Ser
385                 390                 395                 400

Ser Leu Leu Glu Ser Ile Glu Lys Ile Val Pro Asp Asp Ser Ala Asp
                405                 410                 415

Asp Glu Lys Pro Asp Ile Pro Ala Ile Ala Ile Tyr Arg Arg Phe Leu
            420                 425                 430

Ser Asp Gly Arg Leu Thr Leu Asn Arg Phe Val Gln Arg Glu Asp Val
            435                 440                 445

Gln Glu Ala Leu Ile Lys Glu Arg Leu Glu Ala Glu Lys Lys Lys Lys
        450                 455                 460

Pro Lys Lys Arg Lys Lys Ser Asp Ala Glu Asp Glu Lys Glu Thr
465                 470                 475                 480

Ile Asp Phe Lys Glu Leu Phe Pro His Leu Ala Lys Pro Leu Lys Leu
                485                 490                 495

Val Pro Asn Phe Tyr Gly Asp Ser Lys Arg Glu Leu Tyr Lys Lys Tyr
            500                 505                 510

Lys Asn Ala Ala Ile Tyr Thr Asp Ala Leu Trp Lys Ala Val Glu Lys
```

```
                515                 520                 525
Ile Tyr Lys Ser Ala Phe Ser Ser Leu Lys Asn Ser Phe Phe Asp
    530                 535                 540

Thr Asp Phe Asp Lys Asp Phe Phe Ile Lys Arg Leu Gln Lys Ile Phe
545                 550                 555                 560

Ser Val Tyr Arg Arg Phe Asn Thr Asp Lys Trp Lys Pro Ile Val Lys
                565                 570                 575

Asn Ser Phe Ala Pro Tyr Cys Asp Ile Val Ser Leu Ala Glu Asn Glu
                580                 585                 590

Val Leu Tyr Lys Pro Lys Gln Ser Arg Ser Lys Ser Ala Ala Ile
                595                 600                 605

Asp Lys Asn Arg Val Arg Leu Pro Ser Thr Glu Asn Ile Ala Lys Ala
            610                 615                 620

Gly Ile Ala Leu Ala Arg Glu Leu Ser Val Ala Gly Phe Asp Trp Lys
625                 630                 635                 640

Asp Leu Leu Lys Glu Glu His Glu Glu Tyr Ile Asp Leu Ile Glu
                645                 650                 655

Leu His Lys Thr Ala Leu Ala Leu Leu Leu Ala Val Thr Glu Thr Gln
                660                 665                 670

Leu Asp Ile Ser Ala Leu Asp Phe Val Glu Asn Gly Thr Val Lys Asp
            675                 680                 685

Phe Met Lys Thr Arg Asp Gly Asn Leu Val Leu Glu Gly Arg Phe Leu
690                 695                 700

Glu Met Phe Ser Gln Ser Ile Val Phe Ser Glu Leu Arg Gly Leu Ala
705                 710                 715                 720

Gly Leu Met Ser Arg Lys Glu Phe Ile Thr Arg Ser Ala Ile Gln Thr
                725                 730                 735

Met Asn Gly Lys Gln Ala Glu Leu Leu Tyr Ile Pro His Glu Phe Gln
            740                 745                 750

Ser Ala Lys Ile Thr Thr Pro Lys Glu Met Ser Arg Ala Phe Leu Asp
            755                 760                 765

Leu Ala Pro Ala Glu Phe Ala Thr Ser Leu Glu Pro Glu Ser Leu Ser
        770                 775                 780

Glu Lys Ser Leu Leu Lys Leu Lys Gln Met Arg Tyr Tyr Pro His Tyr
785                 790                 795                 800

Phe Gly Tyr Glu Leu Thr Arg Thr Gly Gln Gly Ile Asp Gly Gly Val
                805                 810                 815

Ala Glu Asn Ala Leu Arg Leu Glu Lys Ser Pro Val Lys Lys Arg Glu
            820                 825                 830

Ile Lys Cys Lys Gln Tyr Lys Thr Leu Gly Arg Gly Gln Asn Lys Ile
        835                 840                 845

Val Leu Tyr Val Arg Ser Ser Tyr Tyr Gln Thr Gln Phe Leu Glu Trp
    850                 855                 860

Phe Leu His Arg Pro Lys Asn Val Gln Thr Asp Val Ala Val Ser Gly
865                 870                 875                 880

Ser Phe Leu Ile Asp Glu Lys Lys Val Lys Thr Arg Trp Asn Tyr Asp
                885                 890                 895

Ala Leu Thr Val Ala Leu Glu Pro Val Ser Gly Ser Glu Arg Val Phe
                900                 905                 910

Val Ser Gln Pro Phe Thr Ile Phe Pro Glu Lys Ser Ala Glu Glu Glu
            915                 920                 925

Gly Gln Arg Tyr Leu Gly Ile Asp Ile Gly Glu Tyr Gly Ile Ala Tyr
        930                 935                 940
```

Thr Ala Leu Glu Ile Thr Gly Asp Ser Ala Lys Ile Leu Asp Gln Asn
945                 950                 955                 960

Phe Ile Ser Asp Pro Gln Leu Lys Thr Leu Arg Glu Glu Val Lys Gly
            965                 970                 975

Leu Lys Leu Asp Gln Arg Arg Gly Thr Phe Ala Met Pro Ser Thr Lys
        980                 985                 990

Ile Ala Arg Ile Arg Glu Ser Leu Val His Ser Leu Arg Asn Arg Ile
    995                 1000                1005

His His Leu Ala Leu Lys His Lys Ala Lys Ile Val Tyr Glu Leu
    1010                1015                1020

Glu Val Ser Arg Phe Glu Glu Gly Lys Gln Lys Ile Lys Lys Val
    1025                1030                1035

Tyr Ala Thr Leu Lys Lys Ala Asp Val Tyr Ser Glu Ile Asp Ala
    1040                1045                1050

Asp Lys Asn Leu Gln Thr Thr Val Trp Gly Lys Leu Ala Val Ala
    1055                1060                1065

Ser Glu Ile Ser Ala Ser Tyr Thr Ser Gln Phe Cys Gly Ala Cys
    1070                1075                1080

Lys Lys Leu Trp Arg Ala Glu Met Gln Val Asp Glu Thr Ile Thr
    1085                1090                1095

Thr Gln Glu Leu Ile Gly Thr Val Arg Val Ile Lys Gly Gly Thr
    1100                1105                1110

Leu Ile Asp Ala Ile Lys Asp Phe Met Arg Pro Pro Ile Phe Asp
    1115                1120                1125

Glu Asn Asp Thr Pro Phe Pro Lys Tyr Arg Asp Phe Cys Asp Lys
    1130                1135                1140

His His Ile Ser Lys Lys Met Arg Gly Asn Ser Cys Leu Phe Ile
    1145                1150                1155

Cys Pro Phe Cys Arg Ala Asn Ala Asp Ala Asp Ile Gln Ala Ser
    1160                1165                1170

Gln Thr Ile Ala Leu Leu Arg Tyr Val Lys Glu Glu Lys Lys Val
    1175                1180                1185

Glu Asp Tyr Phe Glu Arg Phe Arg Lys Leu Lys Asn Ile Lys Val
    1190                1195                1200

Leu Gly Gln Met Lys Lys Ile
    1205                1210

<210> SEQ ID NO 5
<211> LENGTH: 1287
<212> TYPE: PRT
<213> ORGANISM: Unknown
<220> FEATURE:
<223> OTHER INFORMATION: Synthetic sequence

<400> SEQUENCE: 5

Met Lys Arg Ile Leu Asn Ser Leu Lys Val Ala Ala Leu Arg Leu Leu
1               5                   10                  15

Phe Arg Gly Lys Gly Ser Glu Leu Val Lys Thr Val Lys Tyr Pro Leu
            20                  25                  30

Val Ser Pro Val Gln Gly Ala Val Glu Glu Leu Ala Glu Ala Ile Arg
        35                  40                  45

His Asp Asn Leu His Leu Phe Gly Gln Lys Glu Ile Val Asp Leu Met
    50                  55                  60

Glu Lys Asp Glu Gly Thr Gln Val Tyr Ser Val Val Asp Phe Trp Leu
65                  70                  75                  80

-continued

```
Asp Thr Leu Arg Leu Gly Met Phe Phe Ser Pro Ser Ala Asn Ala Leu
                85                  90                  95
Lys Ile Thr Leu Gly Lys Phe Asn Ser Asp Gln Val Ser Pro Phe Arg
            100                 105                 110
Lys Val Leu Glu Gln Ser Pro Phe Phe Leu Ala Gly Arg Leu Lys Val
        115                 120                 125
Glu Pro Ala Glu Arg Ile Leu Ser Val Glu Ile Arg Lys Ile Gly Lys
    130                 135                 140
Arg Glu Asn Arg Val Glu Asn Tyr Ala Ala Asp Val Glu Thr Cys Phe
145                 150                 155                 160
Ile Gly Gln Leu Ser Ser Asp Glu Lys Gln Ser Ile Gln Lys Leu Ala
                165                 170                 175
Asn Asp Ile Trp Asp Ser Lys Asp His Glu Glu Gln Arg Met Leu Lys
            180                 185                 190
Ala Asp Phe Phe Ala Ile Pro Leu Ile Lys Asp Pro Lys Ala Val Thr
        195                 200                 205
Glu Glu Asp Pro Glu Asn Glu Thr Ala Gly Lys Gln Lys Pro Leu Glu
    210                 215                 220
Leu Cys Val Cys Leu Val Pro Glu Leu Tyr Thr Arg Gly Phe Gly Ser
225                 230                 235                 240
Ile Ala Asp Phe Leu Val Gln Arg Leu Thr Leu Leu Arg Asp Lys Met
                245                 250                 255
Ser Thr Asp Thr Ala Glu Asp Cys Leu Glu Tyr Val Gly Ile Glu Glu
            260                 265                 270
Glu Lys Gly Asn Gly Met Asn Ser Leu Leu Gly Thr Phe Leu Lys Asn
        275                 280                 285
Leu Gln Gly Asp Gly Phe Glu Gln Ile Phe Gln Phe Met Leu Gly Ser
    290                 295                 300
Tyr Val Gly Trp Gln Gly Lys Glu Asp Val Leu Arg Glu Arg Leu Asp
305                 310                 315                 320
Leu Leu Ala Glu Lys Val Lys Arg Leu Pro Lys Pro Lys Phe Ala Gly
                325                 330                 335
Glu Trp Ser Gly His Arg Met Phe Leu His Gly Gln Leu Lys Ser Trp
            340                 345                 350
Ser Ser Asn Phe Phe Arg Leu Phe Asn Glu Thr Arg Glu Leu Leu Glu
        355                 360                 365
Ser Ile Lys Ser Asp Ile Gln His Ala Thr Met Leu Ile Ser Tyr Val
    370                 375                 380
Glu Glu Lys Gly Gly Tyr His Pro Gln Leu Leu Ser Gln Tyr Arg Lys
385                 390                 395                 400
Leu Met Glu Gln Leu Pro Ala Leu Arg Thr Lys Val Leu Asp Pro Glu
                405                 410                 415
Ile Glu Met Thr His Met Ser Glu Ala Val Arg Ser Tyr Ile Met Ile
            420                 425                 430
His Lys Ser Val Ala Gly Phe Leu Pro Asp Leu Leu Glu Ser Leu Asp
        435                 440                 445
Arg Asp Lys Asp Arg Glu Phe Leu Leu Ser Ile Phe Pro Arg Ile Pro
    450                 455                 460
Lys Ile Asp Lys Lys Thr Lys Glu Ile Val Ala Trp Glu Leu Pro Gly
465                 470                 475                 480
Glu Pro Glu Glu Gly Tyr Leu Phe Thr Ala Asn Asn Leu Phe Arg Asn
                485                 490                 495
```

```
Phe Leu Glu Asn Pro Lys His Val Pro Arg Phe Met Ala Glu Arg Ile
            500                 505                 510

Pro Glu Asp Trp Thr Arg Leu Arg Ser Ala Pro Val Trp Phe Asp Gly
        515                 520                 525

Met Val Lys Gln Trp Gln Lys Val Val Asn Gln Leu Val Glu Ser Pro
        530                 535                 540

Gly Ala Leu Tyr Gln Phe Asn Glu Ser Phe Leu Arg Gln Arg Leu Gln
545                 550                 555                 560

Ala Met Leu Thr Val Tyr Lys Arg Asp Leu Gln Thr Glu Lys Phe Leu
                565                 570                 575

Lys Leu Leu Ala Asp Val Cys Arg Pro Leu Val Asp Phe Phe Gly Leu
            580                 585                 590

Gly Gly Asn Asp Ile Ile Phe Lys Ser Cys Gln Asp Pro Arg Lys Gln
            595                 600                 605

Trp Gln Thr Val Ile Pro Leu Ser Val Pro Ala Asp Val Tyr Thr Ala
            610                 615                 620

Cys Glu Gly Leu Ala Ile Arg Leu Arg Glu Thr Leu Gly Phe Glu Trp
625                 630                 635                 640

Lys Asn Leu Lys Gly His Glu Arg Glu Asp Phe Leu Arg Leu His Gln
                645                 650                 655

Leu Leu Gly Asn Leu Leu Phe Trp Ile Arg Asp Ala Lys Leu Val Val
            660                 665                 670

Lys Leu Glu Asp Trp Met Asn Pro Cys Val Gln Glu Tyr Val Glu
            675                 680                 685

Ala Arg Lys Ala Ile Asp Leu Pro Leu Glu Ile Phe Gly Phe Glu Val
            690                 695                 700

Pro Ile Phe Leu Asn Gly Tyr Leu Phe Ser Glu Leu Arg Gln Leu Glu
705                 710                 715                 720

Leu Leu Leu Arg Arg Lys Ser Val Met Thr Ser Tyr Ser Val Lys Thr
                725                 730                 735

Thr Gly Ser Pro Asn Arg Leu Phe Gln Leu Val Tyr Leu Pro Leu Asn
            740                 745                 750

Pro Ser Asp Pro Glu Lys Lys Asn Ser Asn Asn Phe Gln Glu Arg Leu
            755                 760                 765

Asp Thr Pro Thr Gly Leu Ser Arg Arg Phe Leu Asp Leu Thr Leu Asp
            770                 775                 780

Ala Phe Ala Gly Lys Leu Leu Thr Asp Pro Val Thr Gln Glu Leu Lys
785                 790                 795                 800

Thr Met Ala Gly Phe Tyr Asp His Leu Phe Gly Phe Lys Leu Pro Cys
                805                 810                 815

Lys Leu Ala Ala Met Ser Asn His Pro Gly Ser Ser Ser Lys Met Val
            820                 825                 830

Val Leu Ala Lys Pro Lys Gly Val Ala Ser Asn Ile Gly Phe Glu
            835                 840                 845

Pro Ile Pro Asp Pro Ala His Pro Val Phe Arg Val Arg Ser Ser Trp
            850                 855                 860

Pro Glu Leu Lys Tyr Leu Glu Gly Leu Leu Tyr Leu Pro Glu Asp Thr
865                 870                 875                 880

Pro Leu Thr Ile Glu Leu Ala Glu Thr Ser Val Ser Cys Gln Ser Val
            885                 890                 895

Ser Ser Val Ala Phe Asp Leu Lys Asn Leu Thr Thr Ile Leu Gly Arg
            900                 905                 910

Val Gly Glu Phe Arg Val Thr Ala Asp Gln Pro Phe Lys Leu Thr Pro
```

```
             915                 920                 925
Ile Ile Pro Glu Lys Glu Ser Phe Ile Gly Lys Thr Tyr Leu Gly
    930                 935                 940
Leu Asp Ala Gly Glu Arg Ser Gly Val Gly Phe Ala Ile Val Thr Val
945                 950                 955                 960
Asp Gly Asp Gly Tyr Glu Val Gln Arg Leu Gly Val His Glu Asp Thr
                965                 970                 975
Gln Leu Met Ala Leu Gln Gln Val Ala Ser Lys Ser Leu Lys Glu Pro
            980                 985                 990
Val Phe Gln Pro Leu Arg Lys Gly Thr Phe Arg Gln Gln Glu Arg Ile
        995                1000                1005
Arg Lys Ser Leu Arg Gly Cys Tyr Trp Asn Phe Tyr His Ala Leu
    1010                1015                1020
Met Ile Lys Tyr Arg Ala Lys Val Val His Glu Glu Ser Val Gly
    1025                1030                1035
Ser Ser Gly Leu Val Gly Gln Trp Leu Arg Ala Phe Gln Lys Asp
    1040                1045                1050
Leu Lys Lys Ala Asp Val Leu Pro Lys Lys Gly Gly Lys Asn Gly
    1055                1060                1065
Val Asp Lys Lys Lys Arg Glu Ser Ser Ala Gln Asp Thr Leu Trp
    1070                1075                1080
Gly Gly Ala Phe Ser Lys Lys Glu Glu Gln Gln Ile Ala Phe Glu
    1085                1090                1095
Val Gln Ala Ala Gly Ser Ser Gln Phe Cys Leu Lys Cys Gly Trp
    1100                1105                1110
Trp Phe Gln Leu Gly Met Arg Glu Val Asn Arg Val Gln Glu Ser
    1115                1120                1125
Gly Val Val Leu Asp Trp Asn Arg Ser Ile Val Thr Phe Leu Ile
    1130                1135                1140
Glu Ser Ser Gly Glu Lys Val Tyr Gly Phe Ser Pro Gln Gln Leu
    1145                1150                1155
Glu Lys Gly Phe Arg Pro Asp Ile Glu Thr Phe Lys Lys Met Val
    1160                1165                1170
Arg Asp Phe Met Arg Pro Pro Met Phe Asp Arg Lys Gly Arg Pro
    1175                1180                1185
Ala Ala Ala Tyr Glu Arg Phe Val Leu Gly Arg Arg His Arg Arg
    1190                1195                1200
Tyr Arg Phe Asp Lys Val Phe Glu Glu Arg Phe Gly Arg Ser Ala
    1205                1210                1215
Leu Phe Ile Cys Pro Arg Val Gly Cys Gly Asn Phe Asp His Ser
    1220                1225                1230
Ser Glu Gln Ser Ala Val Val Leu Ala Leu Ile Gly Tyr Ile Ala
    1235                1240                1245
Asp Lys Glu Gly Met Ser Gly Lys Lys Leu Val Tyr Val Arg Leu
    1250                1255                1260
Ala Glu Leu Met Ala Glu Trp Lys Leu Lys Lys Leu Glu Arg Ser
    1265                1270                1275
Arg Val Glu Glu Gln Ser Ser Ala Gln
    1280                1285

<210> SEQ ID NO 6
<211> LENGTH: 1192
<212> TYPE: PRT
<213> ORGANISM: Unknown
```

```
<220> FEATURE:
<223> OTHER INFORMATION: Synthetic sequence

<400> SEQUENCE: 6

Met Ala Glu Ser Lys Gln Met Gln Cys Arg Lys Cys Gly Ala Ser Met
1               5                   10                  15

Lys Tyr Glu Val Ile Gly Leu Gly Lys Ser Cys Arg Tyr Met Cys
            20                  25                  30

Pro Asp Cys Gly Asn His Thr Ser Ala Arg Lys Ile Gln Asn Lys Lys
            35                  40                  45

Lys Arg Asp Lys Lys Tyr Gly Ser Ala Ser Lys Ala Gln Ser Gln Arg
        50                  55                  60

Ile Ala Val Ala Gly Ala Leu Tyr Pro Asp Lys Lys Val Gln Thr Ile
65                  70                  75                  80

Lys Thr Tyr Lys Tyr Pro Ala Asp Leu Asn Gly Glu Val His Asp Ser
                85                  90                  95

Gly Val Ala Glu Lys Ile Ala Gln Ala Ile Gln Glu Asp Glu Ile Gly
                100                 105                 110

Leu Leu Gly Pro Ser Ser Glu Tyr Ala Cys Trp Ile Ala Ser Gln Lys
            115                 120                 125

Gln Ser Glu Pro Tyr Ser Val Val Asp Phe Trp Phe Asp Ala Val Cys
        130                 135                 140

Ala Gly Gly Val Phe Ala Tyr Ser Gly Ala Arg Leu Leu Ser Thr Val
145                 150                 155                 160

Leu Gln Leu Ser Gly Glu Glu Ser Val Leu Arg Ala Ala Leu Ala Ser
                165                 170                 175

Ser Pro Phe Val Asp Asp Ile Asn Leu Ala Gln Ala Glu Lys Phe Leu
                180                 185                 190

Ala Val Ser Arg Arg Thr Gly Gln Asp Lys Leu Gly Lys Arg Ile Gly
                195                 200                 205

Glu Cys Phe Ala Glu Gly Arg Leu Glu Ala Leu Gly Ile Lys Asp Arg
            210                 215                 220

Met Arg Glu Phe Val Gln Ala Ile Asp Val Ala Gln Thr Ala Gly Gln
225                 230                 235                 240

Arg Phe Ala Ala Lys Leu Lys Ile Phe Gly Ile Ser Gln Met Pro Glu
                245                 250                 255

Ala Lys Gln Trp Asn Asn Asp Ser Gly Leu Thr Val Cys Ile Leu Pro
            260                 265                 270

Asp Tyr Tyr Val Pro Glu Glu Asn Arg Ala Asp Gln Leu Val Val Leu
        275                 280                 285

Leu Arg Arg Leu Arg Glu Ile Ala Tyr Cys Met Gly Ile Glu Asp Glu
290                 295                 300

Ala Gly Phe Glu His Leu Gly Ile Asp Pro Gly Ala Leu Ser Asn Phe
305                 310                 315                 320

Ser Asn Gly Asn Pro Lys Arg Gly Phe Leu Gly Arg Leu Leu Asn Asn
                325                 330                 335

Asp Ile Ile Ala Leu Ala Asn Asn Met Ser Ala Met Thr Pro Tyr Trp
                340                 345                 350

Glu Gly Arg Lys Gly Glu Leu Ile Glu Arg Leu Ala Trp Leu Lys His
            355                 360                 365

Arg Ala Glu Gly Leu Tyr Leu Lys Glu Pro His Phe Gly Asn Ser Trp
        370                 375                 380

Ala Asp His Arg Ser Arg Ile Phe Ser Arg Ile Ala Gly Trp Leu Ser
385                 390                 395                 400
```

-continued

```
Gly Cys Ala Gly Lys Leu Lys Ile Ala Lys Asp Gln Ile Ser Gly Val
                405                 410                 415
Arg Thr Asp Leu Phe Leu Leu Lys Arg Leu Leu Asp Ala Val Pro Gln
            420                 425                 430
Ser Ala Pro Ser Pro Asp Phe Ile Ala Ser Ile Ser Ala Leu Asp Arg
        435                 440                 445
Phe Leu Glu Ala Ala Glu Ser Ser Gln Asp Pro Ala Glu Gln Val Arg
    450                 455                 460
Ala Leu Tyr Ala Phe His Leu Asn Ala Pro Ala Val Arg Ser Ile Ala
465                 470                 475                 480
Asn Lys Ala Val Gln Arg Ser Asp Ser Gln Glu Trp Leu Ile Lys Glu
                485                 490                 495
Leu Asp Ala Val Asp His Leu Glu Phe Asn Lys Ala Phe Pro Phe Phe
            500                 505                 510
Ser Asp Thr Gly Lys Lys Lys Lys Gly Ala Asn Ser Asn Gly Ala
        515                 520                 525
Pro Ser Glu Glu Glu Tyr Thr Glu Thr Glu Ser Ile Gln Gln Pro Glu
    530                 535                 540
Asp Ala Glu Gln Glu Val Asn Gly Gln Glu Gly Asn Gly Ala Ser Lys
545                 550                 555                 560
Asn Gln Lys Lys Phe Gln Arg Ile Pro Arg Phe Phe Gly Glu Gly Ser
                565                 570                 575
Arg Ser Glu Tyr Arg Ile Leu Thr Glu Ala Pro Gln Tyr Phe Asp Met
            580                 585                 590
Phe Cys Asn Asn Met Arg Ala Ile Phe Met Gln Leu Glu Ser Gln Pro
        595                 600                 605
Arg Lys Ala Pro Arg Asp Phe Lys Cys Phe Leu Gln Asn Arg Leu Gln
    610                 615                 620
Lys Leu Tyr Lys Gln Thr Phe Leu Asn Ala Arg Ser Asn Lys Cys Arg
625                 630                 635                 640
Ala Leu Leu Glu Ser Val Leu Ile Ser Trp Gly Glu Phe Tyr Thr Tyr
                645                 650                 655
Gly Ala Asn Glu Lys Lys Phe Arg Leu Arg His Glu Ala Ser Glu Arg
            660                 665                 670
Ser Ser Asp Pro Asp Tyr Val Val Gln Gln Ala Leu Glu Ile Ala Arg
        675                 680                 685
Arg Leu Phe Leu Phe Gly Phe Glu Trp Arg Asp Cys Ser Ala Gly Glu
    690                 695                 700
Arg Val Asp Leu Val Glu Ile His Lys Lys Ala Ile Ser Phe Leu Leu
705                 710                 715                 720
Ala Ile Thr Gln Ala Glu Val Ser Val Gly Ser Tyr Asn Trp Leu Gly
                725                 730                 735
Asn Ser Thr Val Ser Arg Tyr Leu Ser Val Ala Gly Thr Asp Thr Leu
            740                 745                 750
Tyr Gly Thr Gln Leu Glu Glu Phe Leu Asn Ala Thr Val Leu Ser Gln
        755                 760                 765
Met Arg Gly Leu Ala Ile Arg Leu Ser Ser Gln Glu Leu Lys Asp Gly
    770                 775                 780
Phe Asp Val Gln Leu Glu Ser Ser Cys Gln Asp Asn Leu Gln His Leu
785                 790                 795                 800
Leu Val Tyr Arg Ala Ser Arg Asp Leu Ala Ala Cys Lys Arg Ala Thr
                805                 810                 815
```

Cys Pro Ala Glu Leu Asp Pro Lys Ile Leu Val Leu Pro Val Gly Ala
            820                 825                 830

Phe Ile Ala Ser Val Met Lys Met Ile Glu Arg Gly Asp Glu Pro Leu
            835                 840                 845

Ala Gly Ala Tyr Leu Arg His Arg Pro His Ser Phe Gly Trp Gln Ile
            850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
            885                 890                 895

Ser Ala Gln Tyr Gly Pro Val Leu Trp Leu Asn Ser Ser Tyr Ser
            900                 905                 910

Gln Ser Gln Tyr Leu Asp Gly Phe Leu Ser Gln Pro Lys Asn Trp Ser
            915                 920                 925

Met Arg Val Leu Pro Gln Ala Gly Ser Val Arg Val Glu Gln Arg Val
            930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
            965                 970                 975

Gly Ser Gly Asp Glu Ala Val Leu Ala Pro Asn Arg Tyr Leu Gly Leu
            980                 985                 990

Phe Pro His Ser Gly Gly Ile Glu Tyr Ala Val Val Asp Val Leu Asp
            995                 1000                1005

Ser Ala Gly Phe Lys Ile Leu Glu Arg Gly Thr Ile Ala Val Asn
            1010                1015                1020

Gly Phe Ser Gln Lys Arg Gly Glu Arg Gln Glu Glu Ala His Arg
            1025                1030                1035

Glu Lys Gln Arg Arg Gly Ile Ser Asp Ile Gly Arg Lys Lys Pro
            1040                1045                1050

Val Gln Ala Glu Val Asp Ala Ala Asn Glu Leu His Arg Lys Tyr
            1055                1060                1065

Thr Asp Val Ala Thr Arg Leu Gly Cys Arg Ile Val Gln Trp
            1070                1075                1080

Ala Pro Gln Pro Lys Pro Gly Thr Ala Pro Thr Ala Gln Thr Val
            1085                1090                1095

Tyr Ala Arg Ala Val Arg Thr Glu Ala Pro Arg Ser Gly Asn Gln
            1100                1105                1110

Glu Asp His Ala Arg Met Lys Ser Ser Trp Gly Tyr Thr Trp Gly
            1115                1120                1125

Thr Tyr Trp Glu Lys Arg Lys Pro Glu Asp Ile Leu Gly Ile Ser
            1130                1135                1140

Thr Gln Val Tyr Trp Thr Gly Gly Ile Gly Glu Ser Cys Pro Ala
            1145                1150                1155

Val Ala Val Ala Leu Leu Gly His Ile Arg Ala Thr Ser Thr Gln
            1160                1165                1170

Thr Glu Trp Glu Lys Glu Glu Val Val Phe Gly Arg Leu Lys Lys
            1175                1180                1185

Phe Phe Pro Ser
        1190

<210> SEQ ID NO 7
<211> LENGTH: 1192
<212> TYPE: PRT

<213> ORGANISM: Artificial Sequence
<220> FEATURE:
<223> OTHER INFORMATION: Synthetic sequence

<400> SEQUENCE: 7

```
Met Ala Glu Ser Lys Gln Met Gln Cys Arg Lys Cys Gly Ala Ser Met
1               5                   10                  15

Lys Tyr Glu Val Ile Gly Leu Gly Lys Lys Ser Cys Arg Tyr Met Cys
            20                  25                  30

Pro Asp Cys Gly Asn His Thr Ser Ala Arg Lys Ile Gln Asn Lys Lys
        35                  40                  45

Lys Arg Asp Lys Lys Tyr Gly Ser Ala Ser Lys Ala Gln Ser Gln Arg
    50                  55                  60

Ile Ala Val Ala Gly Ala Leu Tyr Pro Asp Lys Lys Val Gln Thr Ile
65                  70                  75                  80

Lys Thr Tyr Lys Tyr Pro Ala Asp Leu Asn Gly Glu Val His Asp Arg
                85                  90                  95

Gly Val Ala Glu Lys Ile Glu Gln Ala Ile Gln Glu Asp Glu Ile Gly
            100                 105                 110

Leu Leu Gly Pro Ser Ser Glu Tyr Ala Cys Trp Ile Ala Ser Gln Lys
        115                 120                 125

Gln Ser Glu Pro Tyr Ser Val Val Asp Phe Trp Phe Asp Ala Val Cys
    130                 135                 140

Ala Gly Gly Val Phe Ala Tyr Ser Gly Ala Arg Leu Leu Ser Thr Val
145                 150                 155                 160

Leu Gln Leu Ser Gly Glu Glu Ser Val Leu Arg Ala Ala Leu Ala Ser
                165                 170                 175

Ser Pro Phe Val Asp Asp Ile Asn Leu Ala Gln Ala Glu Lys Phe Leu
            180                 185                 190

Ala Val Ser Arg Arg Thr Gly Gln Asp Lys Leu Gly Lys Arg Ile Gly
        195                 200                 205

Glu Cys Phe Ala Glu Gly Arg Leu Glu Ala Leu Gly Ile Lys Asp Arg
    210                 215                 220

Met Arg Glu Phe Val Gln Ala Ile Asp Val Ala Gln Thr Ala Gly Gln
225                 230                 235                 240

Arg Phe Ala Ala Lys Leu Lys Ile Phe Gly Ile Ser Gln Met Pro Glu
                245                 250                 255

Ala Lys Gln Trp Asn Asn Asp Ser Gly Leu Thr Val Cys Ile Leu Pro
            260                 265                 270

Asp Tyr Tyr Val Pro Glu Glu Asn Arg Ala Asp Gln Leu Val Val Leu
        275                 280                 285

Leu Arg Arg Leu Arg Glu Ile Ala Tyr Cys Met Gly Ile Glu Asp Glu
    290                 295                 300

Ala Gly Phe Glu His Leu Gly Ile Asp Pro Gly Ala Leu Ser Asn Phe
305                 310                 315                 320

Ser Asn Gly Asn Pro Lys Arg Gly Phe Leu Gly Arg Leu Leu Asn Asn
                325                 330                 335

Asp Ile Ile Ala Leu Ala Asn Asn Met Ser Ala Met Thr Pro Tyr Trp
            340                 345                 350

Glu Gly Arg Lys Gly Glu Leu Ile Glu Arg Leu Ala Trp Leu Lys His
        355                 360                 365

Arg Ala Glu Gly Leu Tyr Leu Lys Glu Pro His Phe Gly Asn Ser Trp
    370                 375                 380

Ala Asp His Arg Ser Arg Ile Phe Ser Arg Ile Ala Gly Trp Leu Ser
```

-continued

```
         385                 390                 395                 400
Gly Cys Ala Gly Lys Leu Lys Ile Ala Lys Asp Gln Ile Ser Gly Val
                 405                 410                 415

Arg Thr Asp Leu Phe Leu Leu Lys Arg Leu Leu Asp Ala Val Pro Gln
                 420                 425                 430

Ser Ala Pro Ser Pro Asp Phe Ile Ala Ser Ile Ser Ala Leu Asp Arg
                 435                 440                 445

Phe Leu Glu Ala Ala Glu Ser Ser Gln Asp Pro Ala Glu Gln Val Arg
                 450                 455                 460

Ala Leu Tyr Ala Phe His Leu Asn Ala Pro Ala Val Arg Ser Ile Ala
465                 470                 475                 480

Asn Lys Ala Val Gln Arg Ser Asp Ser Gln Glu Trp Leu Ile Lys Glu
                 485                 490                 495

Leu Asp Ala Val Asp His Leu Glu Phe Asn Lys Ala Phe Pro Phe Phe
                 500                 505                 510

Ser Asp Thr Gly Lys Lys Lys Lys Gly Ala Asn Ser Asn Gly Ala
                 515                 520                 525

Pro Ser Glu Glu Glu Tyr Thr Glu Thr Glu Ser Ile Gln Gln Pro Glu
                 530                 535                 540

Asp Ala Glu Gln Glu Val Asn Gly Gln Glu Asn Gly Ala Ser Lys
545                 550                 555                 560

Asn Gln Lys Lys Phe Gln Arg Ile Pro Arg Phe Phe Gly Glu Gly Ser
                 565                 570                 575

Arg Ser Glu Tyr Arg Ile Leu Thr Glu Ala Pro Gln Tyr Phe Asp Met
                 580                 585                 590

Phe Cys Asn Asn Met Arg Ala Ile Phe Met Gln Leu Glu Ser Gln Pro
                 595                 600                 605

Arg Lys Ala Pro Arg Asp Phe Lys Cys Phe Leu Gln Asn Arg Leu Gln
                 610                 615                 620

Lys Leu Tyr Lys Gln Thr Phe Leu Asn Ala Arg Ser Asn Lys Cys Arg
625                 630                 635                 640

Ala Leu Leu Glu Ser Val Leu Ile Ser Trp Gly Glu Phe Tyr Thr Tyr
                 645                 650                 655

Gly Ala Asn Glu Lys Lys Phe Arg Leu Arg His Glu Ala Ser Glu Arg
                 660                 665                 670

Ser Ser Asp Pro Asp Tyr Val Val Gln Gln Ala Leu Glu Ile Ala Arg
                 675                 680                 685

Arg Leu Phe Leu Phe Gly Phe Glu Trp Arg Asp Cys Ser Ala Gly Glu
                 690                 695                 700

Arg Val Asp Leu Val Glu Ile His Lys Lys Ala Ile Ser Phe Leu Leu
705                 710                 715                 720

Ala Ile Thr Gln Ala Glu Val Ser Val Gly Ser Tyr Asn Trp Leu Gly
                 725                 730                 735

Asn Ser Thr Val Ser Arg Tyr Leu Ser Val Ala Gly Thr Asp Thr Leu
                 740                 745                 750

Tyr Gly Thr Gln Leu Glu Glu Phe Leu Asn Ala Thr Val Leu Ser Gln
                 755                 760                 765

Met Arg Gly Leu Ala Ile Arg Leu Ser Ser Glu Leu Lys Asp Gly
                 770                 775                 780

Phe Asp Val Gln Leu Glu Ser Ser Cys Gln Asp Asn Leu Gln His Leu
785                 790                 795                 800

Leu Val Tyr Arg Ala Ser Arg Asp Leu Ala Ala Cys Lys Arg Ala Thr
                 805                 810                 815
```

Cys Pro Ala Glu Leu Asp Pro Lys Ile Leu Val Leu Pro Ala Gly Ala
            820                 825                 830

Phe Ile Ala Ser Val Met Lys Met Ile Glu Arg Gly Asp Glu Pro Leu
            835                 840                 845

Ala Gly Ala Tyr Leu Arg His Arg Pro His Ser Phe Gly Trp Gln Ile
            850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
            885                 890                 895

Ser Ala Gln Tyr Gly Pro Val Leu Trp Leu Asn Ser Ser Tyr Ser
            900                 905                 910

Gln Ser Gln Tyr Leu Asp Gly Phe Leu Ser Gln Pro Lys Asn Trp Ser
            915                 920                 925

Met Arg Val Leu Pro Gln Ala Gly Ser Val Arg Val Glu Gln Arg Val
            930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
            965                 970                 975

Gly Ser Gly Asp Glu Ala Val Leu Ala Pro Asn Arg Tyr Leu Gly Leu
            980                 985                 990

Phe Pro His Ser Gly Gly Ile Glu Tyr Ala Val Val Asp Val Leu Asp
            995                 1000                1005

Ser Ala Gly Phe Lys Ile Leu Glu Arg Gly Thr Ile Ala Val Asn
            1010                1015                1020

Gly Phe Ser Gln Lys Arg Gly Glu Arg Gln Glu Glu Ala His Arg
            1025                1030                1035

Glu Lys Gln Arg Arg Gly Ile Ser Asp Ile Gly Arg Lys Lys Pro
            1040                1045                1050

Val Gln Ala Glu Val Asp Ala Ala Asn Glu Leu His Arg Lys Tyr
            1055                1060                1065

Thr Asp Val Ala Thr Arg Leu Gly Cys Arg Ile Val Val Gln Trp
            1070                1075                1080

Ala Pro Gln Pro Lys Pro Gly Thr Ala Pro Thr Ala Gln Thr Val
            1085                1090                1095

Tyr Ala Arg Ala Val Arg Thr Glu Ala Pro Arg Ser Gly Asn Gln
            1100                1105                1110

Glu Asp His Ala Arg Met Lys Ser Ser Trp Gly Tyr Thr Trp Ser
            1115                1120                1125

Thr Tyr Trp Glu Lys Arg Lys Pro Glu Asp Ile Leu Gly Ile Ser
            1130                1135                1140

Thr Gln Val Tyr Trp Thr Gly Gly Ile Gly Glu Ser Cys Pro Ala
            1145                1150                1155

Val Ala Val Ala Leu Leu Gly His Ile Arg Ala Thr Ser Thr Gln
            1160                1165                1170

Thr Glu Trp Glu Lys Glu Val Val Phe Gly Arg Leu Lys Lys
            1175                1180                1185

Phe Phe Pro Ser
            1190

<210> SEQ ID NO 8
<211> LENGTH: 1193

```
<212> TYPE: PRT
<213> ORGANISM: Artificial Sequence
<220> FEATURE:
<223> OTHER INFORMATION: Synthetic sequence

<400> SEQUENCE: 8

Met Lys Arg Ile Ala Lys Phe Arg His Asp Lys Pro Val Lys Arg Glu
1               5                   10                  15

Ala Trp Ser Lys Gly Tyr Arg Val His Lys Asn Arg Ile Ile Asn Lys
            20                  25                  30

Val Thr Arg Ser Ile Lys Tyr Pro Leu Val Val Lys Asp Glu Trp Lys
                35                  40                  45

Lys Arg Leu Ile Asp Asp Ala Ala His Asp Tyr Arg Trp Leu Val Gly
    50                  55                  60

Pro Ile Asn Tyr Ser Asp Trp Cys Arg Asp Pro Asn Gln Tyr Ser Ile
65                  70                  75                  80

Leu Glu Phe Trp Ile Asp Phe Leu Cys Val Gly Val Phe Gln Ser
                85                  90                  95

Ser His Ser Asn Ile Cys Arg Leu Ala Ile Gln Leu Ser Gly Gly Ser
                100                 105                 110

Val Phe Glu Gln Glu Trp Lys Asp Leu Ser Pro Phe Val Arg Ala Asn
            115                 120                 125

Leu Ile Gln Gly Ile Lys Pro Ala Glu Phe Ile Gly Phe Leu Thr Ala
    130                 135                 140

Glu Phe Arg Ser Ser Ser Asn Pro Lys Asn Phe Ile Ser Lys Phe Phe
145                 150                 155                 160

Glu Gly Ser Asn Glu Asp Leu Glu Ser Leu Thr Asn Glu Phe Ala Ser
                165                 170                 175

Ile Val Asp Phe Ile Lys Ala Lys Asp Ile Ser Leu Leu Arg Lys Ser
                180                 185                 190

Leu Pro Ser Cys Lys Lys Ile Ala Pro Asn Leu Trp Glu Lys Ala Val
            195                 200                 205

Gly Ser His Ser Thr Asn Glu Leu Leu Lys Leu Leu Thr Lys Tyr Thr
            210                 215                 220

Arg Val Met Leu Val Ala Glu Pro Ser His Ser Asp Arg Val Phe Ser
225                 230                 235                 240

Gln Thr Val Leu Gln Ser Asn Asp Gln Asp Asp Pro Glu Leu Thr Gly
                245                 250                 255

Pro Leu Pro Ser His Lys Val Gly Lys Ala Ser Tyr Leu Phe Ile Pro
            260                 265                 270

Glu Phe Ile Arg Glu Val Asn Leu Asp Lys Ile Ser Lys Leu Asp Leu
            275                 280                 285

Ser Ala Lys Ser Lys Leu Ala Val Glu Gln Val Lys Lys Leu Ser Glu
    290                 295                 300

Leu Thr Ser Asp Phe Lys Gln Ile Glu Asn Gln Ser Glu Ala Tyr Phe
305                 310                 315                 320

Gly Leu Ser Thr Ser Phe Asn Glu Leu Ser Asn Phe Leu Gly Ile Leu
                325                 330                 335

Ile Arg Thr Leu Arg Asn Ala Pro Glu Ala Ile Leu Lys Asp Gln Ile
                340                 345                 350

Ala Leu Cys Ala Pro Leu Asp Lys Asp Ile Leu Lys Ile Thr Leu Asp
            355                 360                 365

Trp Leu Cys Asp Arg Ala Gln Ala Leu Pro Glu Asn Pro Arg Phe Glu
    370                 375                 380
```

```
Thr Asn Trp Ala Glu Tyr Arg Ser Tyr Leu Gly Gly Lys Ile Lys Ser
385                 390                 395                 400

Trp Phe Ser Asn Tyr Glu Asn Phe Phe Glu Ile Pro Gln Ala Ala Ser
            405                 410                 415

Ser Gln Gln Asn Asn Asn Arg Glu Lys Lys Leu Gly Asn Arg Ser Ala
        420                 425                 430

Ile Arg Ala Leu Asn Leu Lys Lys Glu Ala Phe Glu Lys Ala Arg Glu
        435                 440                 445

Thr Phe Lys Gly Asp Lys Gly Thr Leu Glu Lys Ile Asp Leu Ala Tyr
    450                 455                 460

Arg Leu Leu Gly Ser Ile Ser Pro Glu Val Leu Gln Cys Asp Glu Gly
465                 470                 475                 480

Leu Lys Leu Tyr Gln Gln Phe Asn Asp Glu Leu Leu Val Leu Asn Glu
            485                 490                 495

Thr Ile Asn Gln Lys Phe Gln Asp Ala Lys Arg Asp Ile Lys Ala Lys
        500                 505                 510

Lys Glu Lys Glu Ser Phe Glu Lys Leu Gln Arg Asn Leu Ser Ser Pro
    515                 520                 525

Leu Pro Arg Ile Pro Glu Phe Phe Gly Glu Arg Ala Lys Lys Gly Tyr
530                 535                 540

Gln Lys Ala Arg Val Ser Pro Lys Leu Ala Arg His Leu Leu Glu Cys
545                 550                 555                 560

Leu Asn Asp Trp Leu Ala Arg Phe Ala Lys Val Glu Glu Ser Ala Phe
            565                 570                 575

Ser Glu Lys Glu Phe Gln Arg Ile Leu Asp Trp Leu Arg Thr Ser Asp
        580                 585                 590

Phe Leu Pro Val Phe Ile Arg Lys Ser Lys Asp Pro Pro Ser Trp Leu
    595                 600                 605

Arg Tyr Ile Ala Arg Val Ala Thr Gly Lys Tyr Tyr Phe Trp Val Ser
610                 615                 620

Glu Tyr Ser Arg Lys Arg Val Gln Ile Ile Asp Lys Pro Ile Ala Gln
625                 630                 635                 640

Asn Pro Leu Lys Glu Leu Ile Ser Trp Phe Leu Leu Asn Lys Asp Ala
            645                 650                 655

Phe Ser Arg Asp Asn Glu Leu Phe Lys Gly Leu Ser Ser Lys Met Val
        660                 665                 670

Thr Leu Ala Arg Ile Met Ala Gly Ile Leu Arg Asp Arg Gly Glu Gly
    675                 680                 685

Leu Lys Glu Leu Gln Ala Met Thr Ser Lys Leu Asp Asn Ile Gly Leu
690                 695                 700

Leu His Pro Ser Phe Ser Val Pro Val Thr Asp Ser Leu Lys Asp Ala
705                 710                 715                 720

Ala Phe Tyr Arg Ala Phe Phe Ser Glu Leu Glu Gly Leu Leu Asn Ile
            725                 730                 735

Gly Arg Ser Arg Leu Ile Ile Glu Arg Ile Thr Leu Gln Ser Gln Gln
        740                 745                 750

Ser Lys Asn Lys Lys Thr Arg Arg Pro Leu Met Pro Glu Pro Phe Ile
    755                 760                 765

Asn Glu Asp Lys Glu Val Phe Leu Ala Phe Pro Lys Phe Glu Thr Lys
    770                 775                 780

Asn Lys Val Lys Gly Thr Arg Val Val Tyr Asn Ser Pro Asp Glu Val
785                 790                 795                 800

Asn Trp Leu Leu Ser Pro Ile Arg Ser Ser Lys Gly Gln Leu Ser Phe
```

```
                    805                 810                 815
Met Phe Arg Cys Leu Ser Glu Asp Ala Lys Ile Met Thr Thr Ser Gly
                820                 825                 830

Gly Cys Ser Tyr Ile Val Glu Phe Lys Lys Leu Leu Glu Ala Gln Glu
            835                 840                 845

Glu Val Leu Ser Ile His Asp Cys Asp Ile Ile Pro Arg Ala Phe Val
        850                 855                 860

Ser Ile Pro Phe Thr Leu Glu Arg Glu Ser Glu Thr Lys Pro Asp
865                 870                 875                 880

Trp Lys Pro Asn Arg Phe Met Gly Val Asp Ile Gly Glu Tyr Ala Val
                885                 890                 895

Ala Tyr Cys Val Ile Glu Lys Gly Thr Asp Ser Ile Glu Ile Leu Asp
            900                 905                 910

Cys Gly Ile Val Arg Asn Gly Ala His Arg Val Leu Lys Glu Lys Val
        915                 920                 925

Asp Arg Leu Lys Arg Arg Gln Arg Ser Met Thr Phe Gly Ala Met Asp
930                 935                 940

Thr Ser Ile Ala Ala Ala Arg Glu Ser Leu Val Gly Asn Tyr Arg Asn
945                 950                 955                 960

Arg Leu His Ala Ile Ala Leu Lys His Gly Ala Lys Leu Val Tyr Glu
                965                 970                 975

Tyr Glu Val Ser Ala Phe Glu Ser Gly Gly Asn Arg Ile Lys Lys Val
            980                 985                 990

Tyr Glu Thr Leu Lys Lys Ser Asp Cys Thr Gly Glu Thr Glu Ala Asp
            995                 1000                1005

Lys Asn Ala Arg Lys His Ile Trp Gly Glu Thr Asn Ala Val Gly
    1010                1015                1020

Asp Gln Ile Gly Ala Gly Trp Thr Ser Gln Thr Cys Ala Lys Cys
    1025                1030                1035

Gly Arg Ser Phe Gly Ala Asp Leu Lys Ala Gly Asn Phe Gly Val
    1040                1045                1050

Ala Val Pro Val Pro Glu Lys Val Glu Asp Ser Lys Gly His Tyr
    1055                1060                1065

Ala Tyr His Glu Phe Pro Phe Glu Asp Gly Leu Lys Val Arg Gly
    1070                1075                1080

Phe Leu Lys Pro Asn Lys Ile Ile Ser Asp Gln Lys Glu Leu Ala
    1085                1090                1095

Lys Ala Val His Ala Tyr Met Arg Pro Pro Leu Val Ala Leu Gly
    1100                1105                1110

Lys Arg Lys Leu Pro Lys Asn Ala Arg Tyr Arg Arg Gly Asn Ser
    1115                1120                1125

Ser Leu Phe Arg Cys Pro Phe Ser Asp Cys Gly Phe Thr Ala Asp
    1130                1135                1140

Ala Asp Ile Gln Ala Ala Tyr Asn Ile Ala Val Lys Gln Leu Tyr
    1145                1150                1155

Lys Pro Lys Lys Gly Tyr Pro Lys Glu Arg Lys Trp Gln Asp Phe
    1160                1165                1170

Val Ile Leu Lys Pro Lys Glu Pro Ser Lys Leu Phe Asp Lys Gln
    1175                1180                1185

Phe Tyr Arg Pro Asn
    1190

<210> SEQ ID NO 9
```

```
<211> LENGTH: 40
<212> TYPE: DNA
<213> ORGANISM: Artificial Sequence
<220> FEATURE:
<223> OTHER INFORMATION: Synthetic sequence

<400> SEQUENCE: 9
gacatgatcg ctaatcaata ccaaactctg gaccgaattc                            40

<210> SEQ ID NO 10
<211> LENGTH: 40
<212> TYPE: DNA
<213> ORGANISM: Artificial Sequence
<220> FEATURE:
<223> OTHER INFORMATION: Synthetic sequence

<400> SEQUENCE: 10
ctgtactagc gattagttat ggtttgagac ctggcttaag                            40

<210> SEQ ID NO 11
<211> LENGTH: 25
<212> TYPE: RNA
<213> ORGANISM: Artificial sequence
<220> FEATURE:
<223> OTHER INFORMATION: Synthetic sequence

<400> SEQUENCE: 11
cuccgaaagu aucggggaua aaggc                                            25

<210> SEQ ID NO 12
<211> LENGTH: 25
<212> TYPE: RNA
<213> ORGANISM: Artificial sequence
<220> FEATURE:
<223> OTHER INFORMATION: Synthetic sequence

<400> SEQUENCE: 12
caccgaaauu uggagaggau aaggc                                            25

<210> SEQ ID NO 13
<211> LENGTH: 25
<212> TYPE: RNA
<213> ORGANISM: Artificial sequence
<220> FEATURE:
<223> OTHER INFORMATION: Synthetic sequence

<400> SEQUENCE: 13
cuccgaauua ucgggaggau aaggc                                            25

<210> SEQ ID NO 14
<211> LENGTH: 25
<212> TYPE: RNA
<213> ORGANISM: Artificial sequence
<220> FEATURE:
<223> OTHER INFORMATION: Synthetic sequence

<400> SEQUENCE: 14
ccccgaauau aggggacaaa aaggc                                            25

<210> SEQ ID NO 15
<211> LENGTH: 36
<212> TYPE: RNA
<213> ORGANISM: Artificial sequence
<220> FEATURE:
<223> OTHER INFORMATION: Synthetic sequence

<400> SEQUENCE: 15
```
gucuagacau acaggnggaa aggugagagu aaagac                                    36

<210> SEQ ID NO 16
<211> LENGTH: 25
<212> TYPE: RNA
<213> ORGANISM: Artificial sequence
<220> FEATURE:
<223> OTHER INFORMATION: Synthetic sequence

<400> SEQUENCE: 16
cuccgugaau acgugggguagua aaggc                                            25

<210> SEQ ID NO 17
<211> LENGTH: 76
<212> TYPE: RNA
<213> ORGANISM: Artificial sequence
<220> FEATURE:
<223> OTHER INFORMATION: Synthetic sequence

<400> SEQUENCE: 17
cuccgaaagu aucaaaauaa aaaggguuuc caguuuuuaa cuaaacuuua gccuuccacc         60
cuuuccugau uuuguu                                                        76

<210> SEQ ID NO 18
<211> LENGTH: 79
<212> TYPE: RNA
<213> ORGANISM: Artificial sequence
<220> FEATURE:
<223> OTHER INFORMATION: Synthetic sequence

<400> SEQUENCE: 18
accugccaaa auuucguuca acgaaacuua agcaggcaag aaaauuuaaa auuaaauccg         60
cuggugggcg gauaaaguc                                                     79

<210> SEQ ID NO 19
<211> LENGTH: 51
<212> TYPE: RNA
<213> ORGANISM: Artificial sequence
<220> FEATURE:
<223> OTHER INFORMATION: Synthetic sequence

<400> SEQUENCE: 19
gguauuuccg gacagcggcu ugaccgcauc guccucgccu uuuccuaaaa u                  51

<210> SEQ ID NO 20
<211> LENGTH: 43
<212> TYPE: RNA
<213> ORGANISM: Artificial sequence
<220> FEATURE:
<223> OTHER INFORMATION: Synthetic sequence

<400> SEQUENCE: 20
cuccgaaagu aucggggaua aaggcaucaa uaccaaacuc ugg                           43

<210> SEQ ID NO 21
<211> LENGTH: 6430
<212> TYPE: DNA
<213> ORGANISM: Artificial sequence
<220> FEATURE:
<223> OTHER INFORMATION: Synthetic sequence

<400> SEQUENCE: 21
ttaaaaggac agtttctaat agcatataat cattatagca ttcatacgg aaaactactt         60

```
caaatttgcg gcagatcgga ttttgctggc ccagagatat attttccttc tttgttaaaa      120
gcggatttat ggcaagggca gagccagttt ttatttttat cttcccattc aacgatgcat      180
ccaagatgtg ggcaaattgg agagagtttt aaaatttctc cttttttcatt tttgtatacg     240 gcaactttct ttccttctat ctcaacaatt tttcctgtgt tgttttttaa attgtctaaa      300
gtacccgaag ttttcataaa gcgccccttc ataaaagat aaggaaaaag aaatatttgt       360
tttaataatg ttaacatata gcttgttgaa ttataacatt tatccgagag gtggtctaac      420
ttatgcaact tattgattct tactttagga gaatagttct actctaggcg tatagagaac      480
ttttgttgaa aggttttgc aatatctcta ctttctggcc aaaaatcggt ttttcccgcg       540
aatctgccgt atagtttgta tcctgcttta acaggtctgc ctccgctagg ttttcccggg      600
aaaggtacta taaatctctt atttcctaag agataagagc gcaaaccgag aattaagcca      660
tgatagagtt cctgaaaagt agcagtttgg cgagttgctg caacataaat ttctgtatcc      720
atgaaatcct ttaggttttc cattgtatag ggaagtgttt tactttcatc cccaccgttt      780
tcttgtatct ctttattgt attaaaggcg actccgtcga taaaacctct atatggttcc       840
atcaaatcgt agattagaga ggggtaatct gaaggtgtgt gggtgtatcc gtgaaaagga     900
ctaaaatgat ggtaaaccac ccaacgcaag ataataccgc taacaaattt tgaagaagca     960
tctaaaacat tacagataaa attacctttt gatcgtcgcc tatctttagg atatcccaaa    1020
gacttgtaga aatgttccca atatctttg gcatgccacg attccactcc aactatagac      1080
tccacggacg ataagccctg cagttcctgc gttgggctg ggattaacca ttccatggat      1140
ttgaatttag cgtaaatcaa tcttttcgtt atatatgcgc gtttcttttc attttgtctg     1200
aatagaatct gttttgttag taaatcttct ctattagatg ttgtagaagg aacgatccaa     1260
acaccgcggg gcatatttcg tcgatgtatt gttaaaggaa tgccccaagc actgcatttt     1320
tctagaaatt cttgttctag cggacaaacg ctaccataaa acatgataga gtgaatctct     1380
ggaaaggaca aatccagctc accacctttg taagagaatt taacactctt tcccgataag    1440
tctatggatt ttacataggg taaccagata aattgtttac gcttggcgaa atatctcctc    1500
atttcgtatt ggatatatgt ctcaaattat gctatattta aggtacattt tcaagcggtt    1560
tttagctcgt ttacatttta atatcaacaa atcggggag aagtctccga agtatcggg      1620 gataaaggca tcaataccaa actctggctc cgaaagtatc ggggataaag gcattcccaa    1680
tatctcatta ctccgaaagt atcggggata aaggctcctc ccgtatctgt caactccgaa    1740
agtatcgggg ataaaggctt aaaaaggaat accccactcc gaaagtatcg gggataaagg    1800
cttgtactcc acatccgcta ctccgaaagt atcggggata aaggcactga aacttgaatt    1860
gtactccgaa agtatcgggg ataaaggcat cttgcgactt tctcttctcc gaaagtatcg    1920
gggataaagg ctcttcggtt ggtacgggtt ctccgaaagt atcggggata aaggcttatg    1980
gcagtatcgc atactccgaa agtatcgggg ataaaggctt cataagtacg cctaaactcc    2040
gaaagtatcg gggataaagg cagatgaggc tatacttaac tccgaaagta tcgggggataa   2100 aggcacaaac ataaagggaa aactccgaaa gtatcgggga taaaggcata atctggtga    2160 acttactccg aaagtatcgg ggataaaggc tactgttatt gttgtacact ccgaaagtat    2220
cggggataaa ggcataacta gcgttcccat tctccgaaag tatcaaaata aaagggttt     2280 ccagttttta actaaacttt agccttccac cctttcctga ttttgttgat aattaataat    2340
gcgcaaaaaa ttgtttaagg gttacatttt acataataag aggcttgtat atacaggtaa    2400
agctgcaata cgttctatta aatatccatt agtcgctcca aataaaacag ccttaaacaa    2460
```

```
tttatcagaa aagataattt atgattatga gcatttattc ggacctttaa atgtggctag    2520
ctatgcaaga aattcaaaca ggtacagcct tgtggatttt tggatagata gcttgcgagc    2580
aggtgtaatt tggcaaagca aaagtacttc gctaattgat ttgataagta agctagaagg    2640
atctaaatcc ccatcagaaa agatatttga acaaatagat tttgagctaa aaataagtt     2700 ggataaagag caattcaaag atattattct tcttaataca ggaattcgtt ctagcagtaa    2760
tgttcgcagt ttgaggggc gctttctaaa gtgttttaaa gaggaattta gagataccga    2820
agaggttatc gcctgtgtag ataaatggag caaggacctt atcgtagagg gtaaaagtat    2880
actagtgagt aaacagtttc tttattggga agaagagttt ggtattaaaa ttttcctca    2940 ttttaaagat aatcacgatt taccaaaact aactttttt gtggagcctt ccttggaatt    3000
tagtccgcac ctcccttag ccaactgtct tgagcgtttg aaaaaattcg atatttcgcg    3060
tgaaagtttg ctcgggttag acaataattt ttcggccttt tctaattatt tcaatgagct    3120
ttttaactta ttgtccaggg gggagattaa aaagattgta acagctgtcc ttgctgtttc    3180
taaatcgtgg gagaatgagc cagaattgga aaagcgctta catttttga gtgagaaggc    3240 aaagttatta gggtacccta agcttacttc ttcgtgggcg gattatagaa tgattattgg    3300
cggaaaaatt aaatcttggc attctaacta taccgaacaa ttaataaaag ttagagagga    3360
cttaaagaaa catcaaatcg cccttgataa attacaggaa gatttaaaaa agtagtaga    3420 tagctctta agagaacaaa tagaagctca acgagaagct ttgcttcctt tgcttgatac    3480
catgttaaaa gaaaaagatt tttccgatga tttagagctt tacagattta tcttgtcaga    3540
ttttaagagt ttgttaaatg ggtcttatca aagatatatt caaacagaag aggagagaaa    3600
ggaggacaga gatgttacca aaaaatataa agatttatat agtaatttgc gcaacatacc    3660
tagatttttt ggggaaagta aaaaggaaca attcaataaa tttataaata aatctctccc    3720
gaccatagat gttggtttaa aaatacttga ggatattcgt aatgctctag aaactgtaag    3780
tgttcgcaaa cccccttcaa taacagaaga gtatgtaaca aagcaacttg agaagttaag    3840
tagaaagtac aaaattaacg cctttaattc aaacagattt aaacaaataa ctgaacaggt    3900
gctcagaaaa tataataacg gagaactacc aaagatctcg gaggttttt atagataccc    3960 gagagaatct catgtggcta taagaatatt acctgttaaa ataagcaatc caagaaagga    4020
tatatcttat cttctcgaca aatatcaaat tagccccgac tggaaaaaca gtaacccagg    4080
agaagttgta gatttgatag agatatataa attgacattg ggttggctct tgagttgtaa    4140
caaggatttt tcgatggatt tttcatcgta tgacttgaaa ctcttcccag aagccgcttc    4200
cctcataaaa aattttggct cttgcttgag tggttactat ttaagcaaaa tgatatttaa    4260
ttgcataacc agtgaaataa aggggatgat tactttatat actagagaca gtttgttgt    4320 tagatatgtt acacaaatga taggtagcaa tcagaaattt cctttgttat gtttggtggg    4380
agagaaacag actaaaaact tttctcgcaa ctggggtgta ttgatagaag agaagggaga    4440 tttggggag gaaaaaaacc aggaaaaatg tttgatattt aaggataaaa cagattttgc    4500
taaagctaaa gaagtagaaa ttttaaaaa taatatttgg cgtatcagaa cctctaagta    4560
ccaaatccaa ttttgaata ggcttttaa gaaaaccaaa gaatgggatt taatgaatct    4620
tgtattgagc gagcctagct tagtattgga ggaggaatgg ggtgtttcgt gggataaaga    4680 taaacttta cctttactga agaaagaaaa atcttgcgaa gaaagattat attactcact    4740
tccccttaac ttggtgcctg ccacagatta taaggagcaa tctgcagaaa tagagcaaag    4800
```

```
gaatacatat ttgggtttgg atgttggaga atttggtgtt gcctatgcag tggtaagaat    4860
agtaagggac agaatagagc ttctgtcctg gggattcctt aaggacccag ctcttcgaaa    4920
aataagagag cgtgtacagg atatgaagaa aaagcaggta atggcagtat tttctagctc    4980
ttccacagct gtcgcgcgag tacgagaaat ggctatacac tctttaagaa atcaaattca    5040
tagcattgct ttggcgtata aagcaaagat aatttatgag atatctataa gcaattttga    5100
gacaggtggt aatagaatgg ctaaaatata ccgatctata aaggtttcag atgtttatag    5160
ggagagtggt gcggataccc tagtttcaga gatgatctgg ggcaaaaaga ataagcaaat    5220
gggaaaccat atatcttcct atgcgacaag ttacacttgt tgcaattgtg caagaacccc    5280
ttttgaactt gttatagata atgacaagga atatgaaaag ggaggcgacg aatttatttt    5340
taatgttggc gatgaaaaga aggtaagggg gttttttacaa aagagtctgt taggaaaaac    5400
aattaaaggg aaggaagtgt tgaagtctat aaaagagtac gcaaggccgc ctataaggga    5460
agtcttgctt gaaggagaag atgtagagca gttgttgaag aggagaggaa atagctatat    5520
ttatagatgc ccttttttgtg gatataaaac tgatgcggat attcaagcgg cgttgaatat    5580
agcttgtagg ggatatattt cggataacgc aaaggatgct gtgaaggaag gagaaagaaa    5640
attagattac atttttggaag ttagaaaatt gtgggagaag aatggagctg ttttgagaag    5700
cgccaaattt ttatagttat attggatata tcttttcaaa aaatctgaat tggtctagga    5760
ccgcggaatc ctatggtaat ttctacgtcc agaatgtagc gccatgccat tagaccagtc    5820
cccgaattaa acatcgccga acttcttggt gatgttatgg caaagagaat gcgacagcgc    5880
ctattcattg agcaagatat ggaaagtatt cctccagggc aaacaatggt tttgaatatg    5940
ggggagcctg ttgtgggaac ggaatttaca catcggcgga atattaatgg gaaagagtgc    6000 gtttatttt ttgcagttga acttttttaaa gacgacagcg cgtagtcagt acatcttcgg    6060
cccatcttaa tcttccattg gggttattaa gactgcccac tttagcagca agatttttaa    6120
ggtgactcct taattctttc tcgtgcggag ttagatctat ttttccaaaa tctttatccg    6180
catggtttag gaatatttgt atagagtcta ggggaatttc cttaccgatg tcccccgctg    6240
cggtaacaac tctgtaaaga tccatcttta ttgaatttaa tataaactgt ctgtcttttt    6300
tcatatttct aaatgctttt ttgttaattc aaataaccta ccccctcacat tcttatcgta    6360 tatctcatat gtatacttac ctagtgcagg tttgtaattt ctcatagcca tatattcaac    6420
ttcttttgaa                                                           6430

<210> SEQ ID NO 22
<211> LENGTH: 13819
<212> TYPE: DNA
<213> ORGANISM: Artificial sequence
<220> FEATURE:
<223> OTHER INFORMATION: Synthetic sequence

<400> SEQUENCE: 22 ctcttttct tgactatggt catcgcttag cttggcgggg acgtttgatc tttgcttcta      60
gtttaatcct ttttctgtcc ttgttgtttt taatgaatta ccctctaatt tggggtttat    120 tagcttgag tttattggct ttagtgattc taacttggtg gaaaaaggct tggactaaat     180
ggttgttagt cccactgata atttttctgc tggctggcac tctagcgatt tttgcttcaa    240
aacctatttt agctaaacca attttttgatc taaatcaaag tttgaaaatt aatagttttg    300
attcgcgacc taatttagat agcactgctc aagtgactaa agccagtttg aaagctcatc    360 ccttttttagg ttttggtcca aatcgttttt ggcgagcttg gactctttat aagccaaaat    420
```

```
tatttaatca atcagtaatc tggtcagttg attatcgtct ggcttatggt tttattccaa    480
caatgttagt aactcaaggt ggcctcggtt ttctggcttg gttaattctg ataatttcta    540
gttttattta tctttatcat ttattcaaac aaagttcagt agaagatttt tccacgataa    600
ttttattgag tctaagtttt atttatctct ggttaaattt actcattctt aatcctaatt    660
ttgttatcct ctctctggct tttgggtgct tggggtggtt gttagttttt aatcataaaa    720
tttctaatca gctttcttgg cacattaaat tagatacgtt tctaaaaagt ttagtggcaa    780
aactaggtct tagtattatt ttgggttttt tattttttaat cattatttg tcactgctta    840 attatagttc tttgatctta tttcatcggg gtctttcatc tttggatcgg ggggattttt    900
ccgccaccga aaaaaattgg cgtttagcta gtcgtttgag tcctcagaca gtttataatc    960
gttctttggc tgatcttaaa ctgcgtcaga ttaatcaact tctgacgact cctaattctg   1020
attctcaaaa aactttagcc gagttttccc gttttatgg tgagtcaatt ggatttggct   1080
tgactgctcg tgaccaagat ccttttgatt atttaaattg gttaatttta ggtcaagttt   1140
atgaagctgg gattccgctt aaaattaaag gggccgatat tcaagctcgg aaaatttatc   1200
aagaagtgct tagattaaac ccggtttggc cagtcatttg gctaaatttg gctcgagtgg   1260
aattaggctc tgatcaccct gatttagcgc gagaagattt acttaaagct ttggaattaa   1320
aagccgatta ttccgatgct ctgttagctt tagccgaatt agattatagt caaggtcgat   1380
tatcaaaagc tttagcggga gctaaggtgg cagttctgaa agaaccaaat aatttgggag   1440
cttggttttc ccttggtttt ttccagtatc aaattggaca ttatgatgaa gctgtcattt   1500
ctttagaaaa agtcttaacc tttaatcaaa attcagctga tactaaatat tttcttggtt   1560
taagtttagc tgaacttgat cgaacgactg aggcgattga cctatttcaa tctttagttc   1620
gggctaatcc cgacaatcaa gagcttaaaa atattttaac taatctcaaa gctggtcgaa   1680
cagctttagc gccaccagag accaaaacca aacaaaaata taattcatg gtgtctaaaa   1740 ttactcgctt acttcaaaaa gaatttacca atcttcacca agcagctttt ttgttggcta   1800
cttcggcctt gctgtctcaa tttttgggtt tgtggcggga tcgtttatta gcctctggtt   1860
ttggagctag tcatcaatta gatatttatt atacggcttt tcgcttaccg gatttaattt   1920
acgtttcggt ggcttcttttt gtttcgatca cggtccatat tcctttgatt attaataaga   1980
tggaaactgg tggtaaaccg gcggtggaaa aatttctcaa ttcagtgctg acagtttttt   2040
taattgggat ggtttcagtt tccgcgttat tatttatttt tatgccctgg ttatcgaaaa   2100
ttaccgctcc cgggttttct tcagttgatc aacaaacctt agtcaccta tctcgaattt   2160 tattgttgtc tcccttattg ttgggttttgt ctaatctctt gggaggagcc actcaagctt   2220
ttcgtaaatt tgccgcctat gcctttagtc ctatttttta taatttggga attattttg    2280 ggattttctt tttctatcct ttgcttggtt tgccgggctt agtctgggga gtaattctcg   2340
gtgcagtctt acatttatca attcaattgc cagttttaag tcaattaggt ttacgtcttc   2400
gtttatcgag attaattaat tggccggaaa tgagaaaagt gatgctcata tccctaccgc   2460
gaactattac cttatcggct aatcaactat ctttattagt tttagtggct ttagcttcgt   2520
ttttgcccaa agggtcaatt tcggtttta attttcgct caatcttcaa tcagtccccc    2580
tgtcgattat cggagtttct tattcggtgg cggcttttcc cgtcttggcc aaatttttg    2640 tcgctggtca acacaaagaa tttgctggtg aaattatcgc cgccattcga catattattt    2700
tttggtctgc tccagtggtc gttttgttta ttgttttacg agctcaaatc gtccgggtga   2760
```

```
ttttaggttc aggacgtttt gattggtcgg ccactcgatt gacggcagct tgtttggcga    2820
tttttttctgt gtcagtgatt gctcaaagtt tgattttagt tttagtccga gcttactatg   2880
ccgctgggga aaccaaaact cccttgatca ttaattcctt atcatctttg ggaacaatta    2940
ttttggcttt aattttatgg caactgttca aagtttggcc ggcctttcat ctgattttgg    3000
aacaaattct aagattgaaa gatttaccag ggacaattat tttagtctta cctctcgctt    3060
tttcgattgg agcgattatc aatgttttg ttttatggtg ggcttgcgaa cgacgctttg     3120
ctatcggaat ttggcgcaat ttagaggtag ttagtcttca gtctttagtc gcttctttat    3180
ttggtggctt tgtggcctat aacttactaa atgtctttag tctgtattat aaattagata    3240
ctttttggtc aatctttgag cagggatttt tagccggtat tttgggctta attgcctgga    3300
tttcggtctt aattcttttg aaaagtgaag aattggctga attgggacgt tctctgtcag    3360
cccgagtctg gaaagttgtc cctattgtcc cagaacgaga agaactgtag gatgggaaag    3420
tctttatatg gatttaaaac actatcgtaa ttttttctatt attgctcacc ccagtagaac   3480
agccaagctg tctacggggc aagtattgat cataaattag tcttatggat ttaaaacact    3540
atcgtaatt ttctattatt gcccatatag atcatgggaa gagtactttg tctgatcggc     3600
ttttagattt gacagggaca attgaaaagc gaaaatgcg agaacaagtc cttgattcga     3660
tggagttaga acgtgaacga ggaataacca tcaaaatgca accagtccga atgaattata    3720
aattggctgg tgaagattat attctgaatc taattgatac tccgggtcat attgattttt    3780
cttatgaagt gtctcgttcg cttcaagcag tggaaggggt cttgcttttg gttgacgcca   3840
ctcaaggggt ccaagctcaa acttttactg ttttagcgat ggctcaagaa ttgggtttaa   3900
cgattattcc cgttttaaac aaaattgatt taccaattgc tcgaacagct gaagtcaaac   3960
aagagattgt taatctatta aaatgtcagc ccgaagatat tatggcggtt tctggcaaaa   4020
ccggtgaagg agtagataaa ttattaattg agattattaa aaaaattcct agtccaattt   4080
cagaaataaa agttgttaaa ccttgccgag cgctggtatt tgattttgaa tattctattc   4140
ataaaggagt ggtggtctat gttcgagttt tagatggcga aattactccc gctgatcaac   4200
taaactttgt cgcttctggt gaaaaatttt cggttttaga attaggttat tttcgacctc   4260
aagctgaacc acaaaaaaaa ttacaggcgg gtgacattgg ttatttagtc actggaatta   4320
aaaaaccagg caatgctaaa gtgggggata cgattaccac tttagtgagt cctcttccag   4380
ctgtaccggg ctatatgact cctcgaccgg tggtctgggc ttctctttat ccagctagcc   4440
aagatgattt tgctctactc aagcaatccc tcgaacgatt aaatcttcaa gatgccgctc   4500
tgtctttttga agaggaaagc tcgggtgctt tgggacgagg ttttagagct ggttttctgg   4560
gaatgcttca tttggaaatc attagcgaac gattgaagcg agaattttct ttaaatttaa   4620
ttgtgacgac accgagtatt agttatcgtc taattaatac tcggaccaaa gaagaagtca   4680
ggattttctc tcctcacctt tttccacttg aaatcaagga ttatgaaatt tacgaatctt   4740
gggtagcggt tagaattatt agtcccgccg attatcttag tccgattatt caattacttc   4800
atgaacacga agcggaagta atgactatgg aaactttttag ttctagtcgc accgctttgt   4860
ctatcctcat gcctttacga gaattgatgc gtaatttttt tgatagtttta aaagtgtct   4920
cttctggctt tgcttctttt tcttatgaat tagccgaaga acgtctcgct gatgtctctc   4980
gcttggatat tttaattaat ggtgaaataa ttccggcttt ttcgcgaatt gtttcgcgtc    5040
gacgaatcga aaaggatgct tcggaaatgg ctgaacgttt agagggttg attcccaaac     5100
aattgattac gattaaaatc caagttcaag gtttagggcg aattttggcg gcgcgttcaa    5160
```

```
tttccgctct acgaaaagat gtcactgact atctctatgg cggcgatatt actcgaaaaa    5220
tgaaattacg agaaaagcag aaaaaaggca agaaaaaaat gcaacagctg ggtaaggtaa    5280
atatccccca agaagttttt ctaaagatga tgcgaaatgc ggactagcgc ggactggacg    5340
cagactaatg cgaatttacc ctatggagta gcttgctata ctccataggg taaacgcaga    5400
tagtcacaaa caagacactg atcagatcag cgttttttta gcattgatcg gcgttttatc    5460
taaacaagaa ggggagagag taaagggcga ccatacttaa aataacaaga ataccaactg    5520
tcgctgagat gatttgaaag attttttttgt gtttgctctg aaataacatt agttgtagta    5580
taaggctgtg accagatttt atcaagtcga aaaacatttt aagtggctaa atgttctctt    5640
tcttattgtc actttaatct tggtgatttt tttggctcga ggggtttggc gagtttataa    5700
tcagagtcgt tttgctaatt ctaattatct tttgactaaa gatcgtctta ctaaattaga    5760
agacagacaa aaacaaatta ctgatcgtct agaaaaatta tcaaccgatc gtggtttaga    5820
agaagaattt agaaataatt tttcagtcgt gcgaccaggg gaaaaaatga ttttaattgt    5880
cgatagtatt gaaacagcta ctgatacagc cactactagt gaggctagtc tttggggac    5940 tttaaaagcc ttattattaa gtcgttaatt aaaaaagcga gattggttca gcttgccctc    6000
ttaaatttct tgtgcaaata tgcgggtatg gtttagtttg cccttttaaaa ttttttgtcc    6060 gaacatgcga gtatggttta gtggtagaat gcgaccttcc caaggttgag acgcgagttc    6120
gattctcgct actcgcacaa aaaactttt agggtgaata aatgcgacc cccgaagaac    6180 agcaaagctg tctacggggc aggcttccca agcataagac gctggttcga ttcccgcatt    6240
tcgcacaatt ggccgattaa aatagtattt tattttttta tgtcctccac ctttaaacga    6300
actatcgaaa attttacttg tgctcattgt ggagcggagg tgattggtaa tggttatact    6360
gatcactgtc ctaaatgcct ctggggcctc catgtagatg atttcccggg agatcgagct    6420
aatccttgtt tgggcttaat gaagccgatt ggagtggatt tagcgaaggg agattatact    6480
ttaagctatc aatgtgaaaa atgtcacatc attaaaacta ataaaactgc tccggacgat    6540
gaacttaaca agtacttgac cggtatgtta taattgttaa ataagttaaa tttaaaatat    6600
aaaatgaaga aagttaccat ttattccact cccacttgtg gttattgtaa aattgctaaa    6660 caattctttta aagataaggg aattgatttt acagagattg atgtcactac tgatttagct    6720
gggcgacagg ccttagaaca aaaaattggc cgaattacgg gtgtgccagt aattacgatt    6780
gacgaagaag ccgtcgtggg ttttgatcaa gctcatattg cgaagatgtt agggatttaa    6840
actagtgaca atttaccccg ccttctgcca gccggtagag gatgggtttt tttggtaatt    6900
tgctaacaac aaacaaggag tctattatga agattaagtt tttgcctctg tagttcccgc    6960
cataatcctt aaataaattt aggattatgg cgggcgggaa acaagccggt taacgctctc    7020
atagttcaaa ggatagaact gtctcgtcct aagagaccaa tctccgttcg agtcggagtg    7080
agagcacaga ttaaaaaaca ttgactagag tcctacttgc cagcctaaga tttgctttag    7140
taaagttttg gcgggaggga aagatgtagg ttcgattcct accagaggca caattcgtaa    7200
cttggtcaaa tcattttcaa aacaaatgat accacacaca gaggagagga tatggggcac    7260
agccttcgtc agtttgataa ctcaaggaaa caaatctaaa aataaaactt caccgatgtt    7320
atcatttgga agccatctgc ttttcgtgcg tatttgaaac attttttggca acactccaga    7380 aatcggtagg gccggccgtc cttccatata gtttgtaacc aacttttact ggtcggccac    7440
cgtttggttt tcctggaatt ggtacgatga attgtcgcga tattccctgt aagtatgatc    7500
```

```
gtaacgataa tacagacccg tgtaataatt cttgaaaagt tactatctga cgagtagtgt    7560
tggtataaag atttgagtcg agataatctt caacggcgat tatacacctt gccagaaaat    7620
ccttttcttc aaccttttcc gatttagctt gctgtattgt attgaataca attttttcaa    7680
tatttcctct ataaggttcc attagatcgt aaactaaaga aggataatct gtcggaatgt    7740
ggagaaatcc atgataggg ctcattcggt ggtaaattat ataacgcagt gtaataccgc    7800
ttattaattt tgaaaccgcg tccaaaatag atttttatcgt atttgcccct cctctgcgtg    7860
aatatccact gtatccgagt atttttataat attttttcca ataccctttt gcatgctgtg    7920
cctcaatgtt taccatttgt ttaatagaat atcttttacc gtcaaataac attggatatg    7980
aaaccagcca actcatactt tgaatttgg cttgtaaaat cttcttggca atgtggacac    8040
gtttcttctc attatttcta aatgagattt gcttacttaa gatatcatct ttggccgagg    8100
tttttacgct tggagtaatc catacggcat tactcattgt tcttcggtgt agacatatag    8160
gaacgccata ttttgcgcaa agttgtaaaa aatttttcact taaatcacaa gttccaccat    8220
aaagcataat cgaaagaatg ttttttaatgt ttgcggtata tttgccacct ttatattgaa    8280
aagttacaat attttttcttt acttctattt ggaaggtgta gggtagccat aagggtatct    8340
ttttattctt gctaatagac atgtttttg atattattac cctagaaaga gttaggtttt    8400
gaatacaaaa tctaacttat attttgtatt ttgtcaagta aaataaagag aaaagagaga    8460
acctcaccga aatttggaga ggataaggca agacaacaca catcttgcac cgaaatttgg    8520
agaggataag gcataccgct ctggctttga acaccgaaat ttggagagga taaggcaata    8580
ttcaaaatat ctagcaccga aatttggaga ggataaggct caatcttttt atagcctaca    8640
ccgaaatttg gagaggataa ggcaactcaa cataaagggt gcaccgaaat ttggagagga    8700
taaggcggat cgagataagt cgaacaccga aatttggaga ggataaggcg ctaacaaaat    8760
taccacccac cgaaatttgg agaggataag gcaaccagc agggacttca caccgaaatt    8820
tggagaggat aaggcacaat tgtcatgttt attcaccgaa atttggagag gataaggctc    8880
gtttatgtta gcgaccacac cgaaatttgg agaggataag gcaagaaaca ataaccgcag    8940
aacaccgaaa tttggagagg ataaggccaa ttataatata gcctgcaccg aaatttggag    9000
aggataaggc aagatactgt tccaataaca ccgaaatttg gagaggataa ggcaaattat    9060
cataatccat tcaccgaaat ttggagagga taaggcatgg cttgtttttg taatcaccga    9120
aatttggaga ggataaggca cagggagaaa ttgcgaacac cgaaatttgg agaggataag    9180
gcgtttggca ataagtctcg caccgaaatt tggagaggat aaggcatggg tcaatccaac    9240
ccgtcaccga aatttggaga ggatgatggg tttggttcaa aaattctaag aatctgcttt    9300
attttcttca cttcacctac acggtctttc gtctcgttcc ttctagtaac acgagacctc    9360
gcctttccga ccgttctctt tgtctcttta ttttatctga cagaatatgc aaaaagtaag    9420
aaaaacttta tcagaggtac ataaaaatcc ttatggtaca aaagtccgta atgcaaagac    9480
tggctactca ctacagatag agaggctttc gtatactgga aaagagggga tgagaagttt    9540
taagattcca ctcgaaaata aaaataaaga agttttgat gaattcgtaa aaagatcag    9600 gaatgattat atcagtcagg ttgggttgct caatcttct gattggtatg aacattatca    9660
ggagaaacaa gaacattatt ctttggcgga ttttggtta gatagtttga gggccggagt    9720
gatttttgcg cacaaagaaa ctgagataaa gaatcttatc tctaagatac gtggtgataa    9780
atcgattgtt gataaattta atgcaagtat aaagaaaaaa cacgccgatc tttatgccct    9840
tgtcgatata aaagctctct acgatttct tacctccgac gcaagaaggg gattaaagac    9900
```

```
cgaagaagaa tttttaact caaaaaggaa taccttgttt ccgaaattta gaaaaaaga    9960
taacaaagcc gtcgaccttt gggtcaaaaa atttattggg ctggataata aagacaaatt  10020
aaattttacc aaaaagttta tcggtttcga tccaaatcct cagattaaat atgaccatac  10080
tttcttcttt catcaagaca ttaattttga tctagagaga atcacgactc cgaaggaact  10140
tatttcgact tataagaaat tcttaggaaa aaataaggat ctatacggtt ctgatgaaac  10200
aacgaaagat caacttaaaa tggtattagg ttttcataat aatcacggcg ctttttctaa  10260
gtatttcaac gcgagcttgg aagcttttag ggggagagac aactccttgg ttgaacaaat  10320
aattaataat tctccttact ggaatagcca tcggaaagaa ttggaaaaga gaatcattt   10380
tttgcaagtt cagtctaaaa aaataaaaga gaccgaactg ggaaagcctc acgagtatct  10440
tgcgagtttt ggcgggaagt ttgaatcttg ggtttcaaac tatttacgtc aggaagaaga  10500
ggtcaaacgt caacttttg gttatgagga gaataaaaaa ggccagaaaa aatttatcgt   10560
gggcaacaaa caagagctag ataaaatcat cagagggaca gatgagtatg agattaaagc  10620
gatttctaag gaaaccattg gacttactca gaaatgttta aaattacttg aacaactaaa  10680
agatagtgtc gatgattata cacttagcct atatcggcaa ctcatagtcg aattgagaat  10740
cagactgaat gttgaattcc aagaaactta tccggaatta atcggtaaga gtgagaaaga  10800
taaagaaaaa gatgcgaaaa ataaacgggc agacaagcgt tacccgcaaa ttttaagga   10860
tataaaatta atccccaatt ttctcggtga aacgaaacaa atggtatata agaaatttat  10920
tcgttccgct gacatccttt atgaaggaat aaattttatc gaccagatcg ataaacagat  10980
tactcaaaat ttgttgcctt gttttaagaa cgacaaggaa cggattgaat ttaccgaaaa  11040
acaatttgaa actttacggc gaaaatacta tctgatgaat agttcccgtt ttcaccatgt  11100
tattgaagga ataatcaata ataggaaact tattgaaatg aaaaagagag aaaatagcga  11160
gttgaaaact ttctccgata gtaagtttgt tttatctaag cttttttctta aaaaaggcaa  11220
aaaatatgaa aatgaggtct attatacttt ttatataaat ccgaaagctc gtgaccagcg  11280
acggataaaa attgttcttg atataaatgg gaacaattca gtcggaattt tacaagatct  11340
tgtccaaaag ttgaaaccaa aatgggacga catcataaag aaaaatgata tgggagaatt  11400
aatcgatgca atcgagattg agaaagtccg gctcggcatc ttgatagcgt tatactgtga  11460
gcataaattc aaaattaaaa aagaactctt gtcattagat ttgtttgcca gtgcctatca  11520
atatctagaa ttggaagatg accctgaaga actttctggg acaaacctag gtcggttttt  11580
acaatccttg gtctgctccg aaattaaagg tgcgattaat aaaataagca ggacagaata  11640
tatagagcgg tatactgtcc agccgatgaa tacggagaaa aactatcctt tactcatcaa  11700
taaggaggga aaagccactt ggcatattgc tgctaaggat gacttgtcca agaagaaggg  11760
tggggcact gtcgctatga atcaaaaaat cggcaagaat ttttttggga aacaagatta   11820
taaaactgtg tttatgcttc aggataagcg gtttgatcta ctaacctcaa agtatcactt  11880
gcagttttta tctaaaactc ttgatactgg tggagggtct tggtggaaaa acaaaaatat  11940
tgatttaaat ttaagctctt attctttcat tttcgaacaa aaagtaaaag tcgaatggga  12000
tttaaccaat cttgaccatc ctataaagat taagcctagc gagaacagtg atgatagaag  12060
gcttttcgta tccattcctt ttgttattaa accgaaacag acaaaaagaa aggatttgca  12120
aactcgagtc aattatatgg ggattgatat cggagaatat ggtttggctt ggacaattat  12180
taatattgat ttaaagaata aaaaaataaa taagatttca aaacaaggtt tcatctatga  12240
```

```
gccgttgaca cataaagtgc gcgattatgt tgctaccatt aaagataatc aggttagagg    12300 aactttggc atgcctgata cgaaactagc cagattgcga gaaaatgcca ttaccagctt     12360
gcgcaatcaa gtgcatgata ttgctatgcg ctatgacgcc aaaccggtat atgaatttga    12420
aatttccaat tttgaaacgg ggtctaataa agtgaaagta atttatgatt cggttaagcg    12480
agctgatatc ggccgaggcc agaataatac cgaagcagac aatactgagg ttaatcttgt    12540 ctggggaag acaagcaaac aatttggcag tcaaatcggc gcttatgcga caagttacat     12600
ctgttcattt tgtggttatt ctccatatta tgaatttgaa aattctaagt cgggagatga    12660 agaagggggct agatataatc tatatcagat gaagaaattg agtcgcccct ctcttgaaga   12720
tttcctccaa ggaaatccgg tttataagac atttagggat tttgataagt ataaaaacga   12780
tcaacggttg caaagacgg gtgataaaga tggtgaatgg aaaacacaca gagggaatac     12840
tgcaatatac gcctgtcaaa agtgtagaca tatctctgat gcggatatcc aagcatcata    12900
ttggattgct ttgaagcaag ttgtaagaga ttttttataaa gacaaagaga tggatggtga   12960
tttgattcaa ggagataata aagacaagag aaaagtaaac gagcttaata gacttattgg    13020
agtacataaa gatgtgccta taataaataa aaatttaata acatcactcg acataaaactt   13080 actatagagt tctcttcatt ggattgaaaa tagatccgat tcctaccaga gacaccaaat    13140
aaatttaaaa ttaaaaatta cctgccaaaa tttcgttcaa cgaaacttaa gcaggcaaga    13200
aaatttaaaa ttaaatccgc tggtgggcgg ataaagtcaa aaattgaaaa tatattaaat    13260
tgacaatatg ttctttatta gagtgcgatg tttgaatacc tcggggcttc gaatcagtag    13320
attcgtggct tggccataaa tccacaggta ttcaaacacg cgatgtgttt tgtatggccg    13380
ggtgggccat acctattcta acaaaacaac catggtgttt ggcgtgccta atacctcatc    13440
ggctctgccg tgaggatagg acacgcaact tgttttatta tgatataatg aaaggtagaa    13500
attgtcattt tgtaatggaa cagtaaaaaa gaggtgccgg tgatgaacaa agagtgact     13560 aaaggagaca tcaggattta cctgatgatg tggaagggtg ctattatgac cgtcgtgtc    13620 gcgagtctgg ttggcatcat ccttggtcca gtctatcttt tgatcatttt tccgttgaag    13680
aaaatgatca gaaggtattc gatcgatttt tcggattgc tcaaaggtct ttgatgactt    13740
ttaggcaaga agattgtttg ttagctctct accgcaagga ggagggcttt ttcttttttt    13800
taaattaatt tacctttca                                                 13819
```

<210> SEQ ID NO 23
<211> LENGTH: 34045
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (29562)..(29573)
<223> OTHER INFORMATION: n is a, c, g, or t

<400> SEQUENCE: 23

```
atgttccctc ttcttttcgt tgcctctgaa taagatttgc ttactcaaga tatcttcctt      60
agaagacgtc tttatgcttg gggtaatcca gatcgcggta ctcatcgttc tgcgatggat     120
gcaaacagga acactatatt tagtgcatag ttgcaagaaa tcctccttta aatcacaggt     180
gccgccataa agcattatcg ataagatgtt tttgacgtca gcagaataga cacctccttt     240 gtaatgaaa gttatcttat cttttttcac ctctattgcg gaagtataag ggaaccatag      300
ggggattctt ctgttgttat ttttcatgtt ttgatatata attcacactag atatgggcac    360
```

```
atttcaggag taaaatctaa cccattttt gtattttgtc aaataaaata aaggtaaagg      420
agagaacctc tccgaattat cgggaggata aggcagcgtc tgataattct tcctccgaat      480
tatcgggagg ataaggcaag actggtaaac tctagctccg aattatcggg aggataaggc      540
acagtaacaa catacgggct ccgaattatc gggaggataa ggcaaactaa ccgttgctct      600
actccgaatt atcgggagga taaggcaaag cgtttaaagc cgacactccg aattatcggg      660
aggataaggc aaacgcccta taacgcaatc tccgaattat cggaggata aggcgtagtt       720
agtggataat ttactccgaa ttatcgggag gataaggcga cgctgacgat aaactgctcc      780
gaattatcgg gaggataagg cacaaacatt tcctcgacat ctccgaatta tcggaggat       840
aaggcataat tactcgctcg acactccgaa ttatcgggag gataaggcaa aatcatatcg      900
ttcttgctcc gaattatcgg gaggataagg caccccgaca aaattaagcc tccgaattat      960
cgggaggata agtatggata tttccacaat cttgaaagaa agatttgtta gcctttaatc     1020
cattctcctt tccctttatt ttatctgaca acatatgaaa gctaaaaaaa gtttttataa     1080
tcaaaagcgg aagttcggta aagaggtta tcgtcttcac gatgaacgta tcgcgtattc      1140
aggagggatt ggatcgatgc gatctattaa atatgaattg aaggattcgt atggaattgc     1200
tgggcttcgt aatcgaatcg ctgacgcaac tatttctgat aataagtggc tgtacgggaa     1260
tataaatcta aatgattatt tagagtggcg atcttcaaag actgacaaac agattgaaga     1320
cggagaccga gaatcatcac tcctgggttt ttggctggaa gcgttacgac tgggattcgt     1380
gttttcaaaa caatctcatg ctccgaatga ttttaacgag accgctctac aagatttgtt     1440
tgaaactctt gatgatgatt tgaaacatgt tcttgatagg aaaaaatggt gtgactttat     1500
caagatagga acacctaaga caaatgacca aggtcgttta aaaaaacaaa tcaagaattt     1560
gttaaaagga acaagagag aggaaattga aaaaactctc aatgaatcag acgatgaatt      1620
gaaagagaaa ataaacagaa ttgccgatgt ttttgcaaaa aataagtctg ataaatacac     1680
aattttcaaa ttagataaac ccaatacgga aaaatacccc agaatcaacg atgttcaggt     1740
ggcgtttttt tgtcatcccg attttgagga aattacagaa cgagatagaa caaagactct     1800
agatctgatc attaatcggt ttaataagag atatgaaatt accgaaaata aaaaagatga     1860
caaaacttca aacaggatgg ccttgtattc cttgaaccag ggctatattc ctcgcgtcct     1920
gaatgattta ttcttgtttg tcaaagacaa tgaggatgat tttagtcagt ttttatctga     1980
tttggagaat ttcttctctt tttccaacga acaaattaaa ataataaagg aaaggttaaa     2040
aaaacttaaa aaatatgctg aaccaattcc cggaaagccg caacttgctg ataaatggga     2100
cgattatgct tctgatttg gcggtaaatt ggaaagctgg tactccaatc gaatagagaa       2160
attaaagaag attccggaaa gcgtttccga tctgcggaat aatttggaaa agatacgcaa     2220
tgttttaaaa aaacaaaata tgcatctaa atcctggag ttatctcaaa agatcattga       2280
atacatcaga gattatggag tttcttttga aaagccggag ataattaagt tcagctggat     2340
aaataagacg aaggatggtc agaaaaaagt tttctatgtt gcgaaaatgg cggatagaga     2400
attcatagaa aagcttgatt tatggatggc tgatttacgc agtcaattaa atgaatacaa     2460
tcaagataat aaagtttctt tcaaaaagaa aggtaaaaaa atagaagagc tcggtgtctt     2520
ggattttgct cttaataaag cgaaaaaaaa taaagtaca aaaaatgaaa atggctggca      2580
acaaaaattg tcagaatcta ttcaatctgc ccgttatttt tttggcgaag ggaatcgtgt     2640
acgaaatgaa gaagtttata atttgaagga ccttctgttt tcagaaatca agaatgttga     2700
```

```
aaatatttta atgagctcgg aagcggaaga cttaaaaaat ataaaaattg aatataaaga    2760
agatggcgcg aaaaaaggga actatgtctt gaatgtcttg gctagatttt acgcgagatt    2820
caatgaggat ggctatggtg gttggaacaa agtaaaaacc gttttggaaa atattgcccg    2880
agaggcgggt actgattttt caaaatatgg aaataataac aatagaaatg ccggcagatt    2940
ttatctaaac ggccgcgaac gacaagtttt tactctaatc aagtttgaaa aaagtatcac    3000
ggtggaaaaa atacttgaat tggtaaaatt acctagccta cttgatgaag cgtatagaga    3060
tttagtcaac gaaaataaaa atcataaatt acgcgacgta attcaattga gcaagacaat    3120
tatggctctg gttttatctc attctgataa agaaaaacaa attggaggaa attatatcca    3180
tagtaaattg agcggataca atgcgcttat ttcaaagcga gattttatct cgcggtatag    3240
cgtgcaaacg accaacggaa ctcaatgtaa attagccata ggaaaaggca aaagcaaaaa    3300
aggtaatgaa attgacaggt atttctacgc ttttcaattt tttaagaatg acgacagcaa    3360
aattaattta aaggtaatca aaaataattc gcataaaaac atcgatttca acgcaatga    3420 aaataaaatt aacgcattgc aagtgtattc atcaaactat cagattcaat tcttagactg    3480
gttttttgaa aaacatcaag ggaagaaaac atcgctcgag gtcggcggat cttttaccat    3540
cgccgaaaag agtttgacaa tagactggtc ggggagtaat ccgagagtcg gttttaaaag    3600
aagcgacacg gaagaaaaga gggttttttgt ctcgcaacca tttacattaa taccagacga    3660
tgaagacaaa gagcgtcgta aagaaagaat gataaagacg aaaaaccgtt ttatcggtat    3720
cgatatcggt gaatatggtc tggcttggag tctaatcgaa gtggacaatg gagataaaaa    3780
taatagagga attagacaac ttgagagcgg ttttattaca gacaatcagc agcaagtctt    3840
aaagaaaaac gtaaaatcct ggaggcaaaa ccaaattcgt caaacgttta cttcaccaga    3900
cacaaaaatt gctcgtcttc gtgaaagttt gatcggaagt tacaaaaatc aactggaaag    3960
tctgatggtt gctaaaaaag caaatcttag ttttgaatac gaagtttccg ggtttgaagt    4020
tgggggaaag agggttgcaa aaatatacga tagtataaag cgtgggtcgg tgcgtaaaaa    4080
ggataataac tcacaaaatg atcaaagttg gggtaaaaag ggaattaatg agtggtcatt    4140
cgagacgacg gctgccggaa catcgcaatt ttgtactcat tgcaagcggt ggagcagttt    4200
agcgatagta gatattgaag aatatgaatt aaaagattac aacgataatt tatttaaggt    4260
aaaaattaat gatggtgaag ttcgtctcct tggtaagaaa ggttggagat ccggcgaaaa    4320
gatcaagggg aaagaattat ttggtcccgt caaagacgca atgcgcccaa atgttgacgg    4380
actagggatg aaaattgtaa aaagaaaata tctaaaactt gatctccgcg attgggtttc    4440
aagatatggg aatatggcta ttttcatctg tccttatgtc gattgccacc atatctctca    4500
tgcggataaa caagctgctt ttaatattgc cgtgcgaggg tatttgaaaa gcgttaatcc    4560
tgacagagca ataaaacacg gagataaagg tttgtctagg acttttttgt gccaagaaga    4620
gggtaagctt aattttgaac aaataggggtt attatgaatc taaaaatagt cgtgatcaac    4680
aaactcaatc atttgaaaaa ttttttatcgt cgccatccaa agaaaatcct ttggttgggg    4740
gtgccattgc tattgcttat cgggttgggg gcttgggctt atactcggag gactcaaccc    4800
gagttcgaaa cagaggtggt gaagttggc gaggtggccg atgtggtgag cgatactggt    4860
ttggtgacgg ccgagaatga tctcactctc tcgttcgaga cgggcggggt cgttcgcacg    4920
gttaaggtta ccgaaggtga cgcggtttat cgaggacaga cgttagtctc gctggatgcc    4980
agtttgaagg cggcggaagt ggcgagcgcg cgcgccacgt tggccgctca agaagccaaa    5040
ttggctgaac tggtggcggg cccgaccaag ctagatttag cttcggccaa gacgaaactc    5100
```

```
gagaacgccc gcaagacctt gctgaccgcc gacctgcaag cgtacttcgc cggtccttca   5160
gccgattatg cggcttcttc attcacttat acggcgccga cggttttggg gacttacaat   5220
tccgatcaag agggcgaata cgtgcttgag ttatatcaat caggcgcgcc gtcgggctac   5280
tcggtggagt actccggttt ggagacgggg attatggagg cgccgaagg acgagccgag    5340
cccttgggcc ggcgcggtct ctatctccaa ttcccggaga acttcattcg ggcgccagag   5400
gtaatttggc gcgtgcctat ccccaacacc aagtccgctt cttatgctac taaccggcgc   5460
gcctacgaac aggctcaagc cgattacgac ctgaaagtgg ctggcactcg cgccgaacaa   5520
attgtcgccg ccgaagccca agcgcgccaa gcccgcgcca ccctccaatc ggcgcaggcc   5580
tcgctgtcca agctctccct tacggcgccg gtggccggtt tggtgaagtc cgttccggtt   5640
accgtagggg agacggttac cgttggttca ccagctgtgg cgttggtctc ggatcataat   5700
tattacgtga ccctctatgt gccggaggct gagatggcca acttgacggt cggcgacttg   5760
gccgagatcc ggctcaaggc cttccccgat cgcgtcttcc gcgccaccgt ggggagtgtg   5820
gccccggcgg ccgaagatcg tgatggcgtg gcttcgttta agttaaaatt atatttccaa   5880
gaatccgatc cccaaattag agtggggatg tcggctgacg tcgaccttga ggcgcttaag   5940
aagaccgacg tcatggtggt gcccgggcgg gcggtggtgc gctctaatgg gcgaatcttt   6000
gtccgggttt ggagcaataa gaccgtcgag gaacgctcgg tggagattgg tctgcgtggc   6060
tctgatggct cggtggagat tgtctcggga ctctcggtgg gcgaagaggt gattactttt   6120
atccgtgacg aggagttgga tcgcttggcg gactaattcc ctttcggcgt ttatggcttt   6180
acttgaactc gaccaagtta ctaaatctta ttatagcgac gatctcacca ctcagatctt   6240
gcgcgggatt tcgtttacca ttaatgaagg cgaattcgtc tcgattatgg gcccgtccgg   6300
ttcgggcaaa tcaaccctct tgcacgttct cggattcttg gctgatcgca ccgccggtac   6360
ttaccgcttc aacggcaagc aatttgccga acataccgat gaggagatcg cgcgggtacg   6420
caatgaagaa atggggttcg tcttccagac ttttcaactta cttggtcgta ataccgtctt   6480
cgaaaatgtg cgcttgccgc tcatctactc gcgcgtgccc gaaggagagt ggccggcctt   6540
ggttgatcag gctatcgccc aagttaagct tgatcatcgg cgcgactatg cctgctccaa   6600
gctctccggc ggcgagcaac aacgcgtcgc catcgctcgc gccttggtca accgacccaa   6660
cgtcctcttc gccgacgaac cgaccggcaa cttagactcc gcttcggggg gagcggtgat   6720
ggatacttta caacacttgc atgaagattc tggtcagacg gtgatcttaa tcactcacga   6780
gacctatacc gccgagcatg ctcagcggat catcaagatt ttggatggcc gggtcgaagc   6840
cgatttcaga cttgagacca gacgacgcgc cagcgagggt tatcataagt agttcgattt   6900
aatttatcct gagggtaatc gaaggactca ccacaagtaa aatgcaacgt acaaatttta   6960
gcttcctttc ggccttggag gcgatcaaaa ccaatcgtac gcgctctatc ctcaccactt   7020
tggggatcgt tattgggggtg gcggcgatca ttgtgattat gtcgttgggc gccggcgccc   7080
agagtttaat tttaaatgag atcaatcaga tgggggccga cggtcatc gtgttgccgg     7140
gtgagatcac tgatgccgcg gcggttttct cggactcact gacgcaacgt gacctggccg   7200
cggtgaaggt taagtccaat gtgcccaatt ggcgcgcgc cgcgccggcg gtcatcgtcc    7260
caggcaagac cacttataga ggtacgactt ataccccgc catgattatc ggcactgaag    7320
cggaattctt cggtgaggtt tttaatattt accctaaggt gggcacaatc tatgatcaag   7380
atgatatcga gacagcggcg cgggtggcga ttattggcga caaggttaag accgagcttt   7440
```

```
ttggcgcttc tgacgcggtg ggcgagcgga tcgatatcaa gggcaagcaa ttccgcgtgg   7500 tggggggtgta tccaacgacg gggcaaaaag gacctttcga tatcgacggc ttggtgatga   7560
ttccgcacac caccgcccag acttatctct taggcactaa ctattatcat cgccttatga   7620
ctcaagccga cagttcggac aatgtcgaga aattggcaca cgacatcacc gcgaccctgc   7680
gggagactca tggtctttat cctggtgatg acgacgactt ctcggtggta actcaacaag   7740
cgctggtgga tcaaatttcg atcattatca acattctcac ggccttcttg gcggccgtgg   7800
tggcgatctc cttggtggtg ggcggtatcg gcgtgatgaa tattatgctc gtgtcggtga   7860
ccgaacgcac taaagagatt ggtttgcgca aggcgctcgg ggcgaccgcc tcggccatta   7920
tgacgcaatt tctctttgag gcgattgcgc tgaccttgtt tggggcgtg ctggggatca   7980 tgatcggcgc ctcgctctcg ctcgtgctct cggggattct cacttacgcc gtggggctca   8040
attggtcctt ccacttcccc attagcgccg cgatgctcgg ggtcacggtc tcggcggcgg   8100
tcggactggt gtttggcctc tatccggcgc gtcgcgccgc cgccaaagac ccaatcgaag   8160
cgttgcggta tgaatagaac cggggaggtt tgacgtgact attgattagt gttagactat   8220
tgaaggaagt taatttgatt ttttgttcga aacaaagaaa aaagaagga ggttaccatg   8280 tcggataaaa tcgtgagatt gcctcacctt aaagtttggc aacgagatcg gtgttggtgg   8340
ggacaattac tcttcactga tcgctcgatg agcgaagagt tcaacggcaa gttcttggcc   8400
ttggtcgctc tgcttgaagc ccaagagcga aaaagtgttg ttaatgaaga catcctcgat   8460
ctacttgatc agattgggaa atccccattg tcggagacag attgtcttcg gctacgacgt   8520
gacggtcatg ataaggtaga tgtggttctg gttaaaatta tgagaaattg ggtccgcgac   8580
tcggctcaaa atgagcgacg tgaatttgag ctcgtaagtt ttaaaaccac cattatgtcc   8640
aaacaggcgg cgaaagccac cttcaactga aatttttctc gcctgcgaat ctccaagcag   8700
accggtccga gcacgtgttg ctcgggccct ttatttttaa taaatatttg cccgaggatt   8760
gttttctcaa attctctttt ttctttaagt cggggttttt ggactgaaac ggaagagttg   8820
taatctagaa actcactttt tttggatggt ttttcaacaa atagctgtta caatagaaga   8880
gtggaaaaat aaaatgagtt gttttaaacc aggtacgggt aatcgaaagc tcagcacaat   8940
tccgggtttt accttgattg aaatcttggt ggtggttgcc attatcggta ttttgtcggg   9000
aataatttcg aataatttaa ggggtgctaa aattaaagcc cgagaagcct cggcccttca   9060
aaatgcgcgg caattagatt tggcggtatc gcttttttgaa atagataaag gttattatcc   9120
gggaaccctg ggggttgaga caaatcaaga tgaccaaacg actggttgga agaaggacc   9180 aggaaccctg cacgacgatc tggttcccaa atatatttct aaattaccca cgagtgatga   9240
gataaagttt atttatcttg ccgatgaacc atgtcccaac gaccagacga aaccttgtcg   9300
agctaagata gttatcgata ctgaccaaat tgtcgatggt gacggaggga caccccccacc   9360 accccaccaa ccccccaccac cagctaaggt gattgttccg gacttggtta ataaaaccga   9420
agccgaagcc ctcggggcca tctcggcggc taatttagca gtaggcttca atgatgatgg   9480
gtgtagtgat atggtttctt ctggttatgt ttttctcaa tcgttgacgg ccggtgctag   9540
tgttgatgaa ggtacggcga ttaatattgt tgtttctgcc ggagggtgta tttctccgcc   9600
accggtcggg tcgatccta tctcaagttg tggcacaata ataactcaac ctggagatta   9660
ccatctggcc ctggtggagg agaccgagtt gaatcaaact aattccggga tctgtattta   9720
tgttaacaat gttgataatg ttaatttaga ctgtcagaat ataagataa agggtaccga   9780 taccacagag tcatcgaaac aatatggcgt aattgtcggt aattcgtctg ggtggccgt   9840
```

```
taaaaattgt ctgattgaaa acgtcggcac cggaattagg gtatattcgt ctgataacat    9900
ctcgattgaa aacaatcgac tgtcaaactt aggcagggaa gggatgtatc ttaaagataa    9960
ttcagatgtg attattcgaa ataatcagct gaccaacgcc ggtgcaagag cgattgctat   10020
ttatcgagaa tgggcgagtc ttatttccgg ttacgctgtt gataataaca ccatcaaggg   10080
ggggtcctat ggtattacgt tcgggcatct gtttaccgac agtcgtcctc ccggtgagat   10140
taaagagatc gttataaacg gcaataattt atatgatatt gtcactacgg ctctatcctt   10200
aaatttagtc gagaacctct caatcattaa taattacatt tatgacccga aaatattcct   10260
ccaaatagac gattctaaaa atttactcat agacaacaac ttcggccaaa atatcacctg   10320
ggacatgttt atcggctatt cagataatgt aaccttttct aacaataagc ttaagagcgc   10380
ttcggcgact aaatcggtgg ttttagtttg gatgttaagg gttaataact tagatttctc   10440
tcgcaacgaa attgaaggct acaatcgtaa tttgttaaaa cttgacgata gttatgattt   10500
ctcgatcaaa aataatattt tcaatagccg ggttggtgtt tatgaagggg tgattttggg   10560
taaaggtttt ctcggtgtat ctggtgaagt ttctgaaaat gattttacg gcggtggcga   10620
gggcgtctct ttagctttag atatttatca taattcggcc aaccgtctgg cgatcttta   10680
taataatttt attgattatt tggggcgtc gttaagatat gattctagtt ttttggattt   10740
aggagctaat tattatggta caaccgactg tgccttattg cgggcgacaa cttgccccga   10800
ctgggtgata ataccacctt cttctggttt acccagtcct ttgctttact tggattcgtt   10860
ttggcctaaa gggaacgttc aaacttgcaa ttaatttagg ctaaactgcg agtgaggtgt   10920
ttttcttgat atttagatta aaaagtgata taagtataaa agagaaagga ggttctgatg   10980
tctcaaatgg gtattgccca cgcgctcttt tacaagcgag gggattgtct ccaagctcgg   11040
atcgttttcg gcgacggtcg cttgagcgaa gagttcagct cccgtctcga agggatggag   11100
attctgacaa aatctcgtca ggataagctc atttctcatc aagagatgac ctctctggcg   11160
ttggaatttg cggaatcgac tttgccggcg agaactccgt cggcggaaat tgttgacggc   11220
cttctgatgg cgatgaagct tgacctttga aagctttatc aaaaccgctc tccggctgat   11280
ctcggggcgg ttttttttgtt taaatttaaa gggatggagt tatttcgagc gggggatgcg   11340
atgcttctga tgagtgaagt tggcgttgaa gtttgacttg aagttttgat tgttcggccc   11400
gcccgatttc tgaaacttga agactgacgg ggtgcgaaaa ccggcgttgc ccggttgttg   11460
ctgtttgttt tgtttgctcc gattggtgtt tttcatatcc tttaattata aatcgaagtt   11520
ggattatggc aagcagtaag ataaacgtcc taattgtgac gtgattgaca gaaaagataa   11580
aacaatgtag gatagatttc ggatcctgaa ccttcaactc tcctcaacag aatcaacaga   11640
aaggaagaca gaatgaagaa gatgcttgtc ttgttgtccg cgtttgtctt gaccatcgcc   11700
gagctggctt cggccggatc gttctctgac ccgttcgatg cccttgattc ggcttgggtg   11760
accgatcggt tcgagccggc cggattctcc agcgtcgtct tcgacggcga caatcggttg   11820
gagattgcga ttagcgcgac cgactcggag gctaatcgtc cggccgggtt cactagtggg   11880
ttttataaca cgcaaggccg tcaacgagat gccttgatgg cggaaccttg ggtcatctcc   11940
ggcgatcttt acttgtcgct ggatatgctc ttgggcgaca atttgcgccg gactgatctc   12000
tgggcgcgaa cttcggacgg tccggaggct aatgcgcaat acccgattat cgggatgcgt   12060
cggtttgacc cgcttgatcc cttcaacccg ctggcgggtg atattgcctc aacttggcga   12120
gtctgggatt cggacacggt cgacggttgg gtcaatttgg ccacgccgat ggtggctggt   12180
```

```
tggaacacgc tttcgattga gagtgacggt ctatcatatc tctatcggat caacggggtt  12240
gaggtctatg aggacctcac catcagcgct ttcgcgaccg atctgaccac ggtctttctc  12300
caaggttata acttcggcgg tgactacgaa gtctattggg acaatgtctc tgccgccacc  12360
ttggctccgg tgcccgagcc ggccacgatc ttgcttttaa tgctggggc cggcgtggtg   12420 gcgattcgtc gtcatttcgc gaaacaacaa taactaactt gagaggttag ggtccgccaa  12480
cccgttcgct gtcgcgagcg ggttttttta ttggcgagaa gttaagggg gatgtttagt   12540 tgaccaaggt aatagcgaag ggtgtagagc caatcctcgt cttcttcgcc ggcttccagt  12600
ttttgtttca gaagccattc gagataaccg cgatcggtct tggccacttc ggcgagcgtt  12660
cggtctttat gcttgccaaa accgaatttt ttgaagagtg acggacgaga cgagatctca  12720
atcattttgg cgagcgtttc ttcgtcggag agttcgcgcg aacccaagag cgagccgtcg  12780
ccggctttca atttttgcca taaccgatta aacagcgctt cggtcaccaa aacatcgccc  12840
acggcgtcat gagcggtgcc atcaagatcc aagtcgagat aataacgcaa gaattgcaga  12900
ttgtattccg gaatcacccc ttcggtatcc agttcgcgag ccaagcgcag ggtgcagata  12960
tattgcggca ctttgactcc ttcggcggcc aagatagcga tgtcgaattt ggcattgtgc  13020
gccaccaaca cgtgatcagc gagaagggtt tccagctcgc gacggaaggc gctctcggcg  13080
aagggttctt tgtcggccac cagcttattg gtgatgtgag tgatactcat cgacttaacc  13140
gagatgggga ctggcggctt gaagtaggcg gtgcgagtgg tggttttggt tttgtagcag  13200
acctgacaaa ggcgatcttt ggtcacgtcg ttgccggtgg tttcggtatc taagaataag  13260
atttccatgg tcggttaagc ggccggttgg tcggtcgaat caaccttaac gttttggata  13320
attacgggcg tgacggggcg atcgttttgg tcagtggcga cttggccgat ctggtttaca  13380
atttcttgtc caacagttac ccgaccgaag atggtgtagt tattgggtag cggataatct  13440
tcgagcatga taaagaattg actgccgttg gtattgggac cggcgttggc catcgccaac  13500
acgccttgcc ggtagccggc ctggtatgac ggagtggccg gatcgagctc gtcggcgaat  13560
tggtaaccgg ggccgccggt accgcagggg ccggtggcgg ggactttggc ggattcaggt  13620
gaacagttcg ggtcgccgcc ttggatcata aaccccttga tcactcgatg gaaggtgaga  13680
ccgttgtaat aaccggctcg ggccagcttg ataaagttgg caaccgtgtt ggggggcgtct  13740 ttttcgtaga gaacgagggt aatctcgcca agattggttt gcaaggtgat ttggttaggc  13800
atagttgagg tggtcagtcc cgagcttgct cgcggtgagt tcgtcgaatc cgtcgaggtg  13860
gcttgagatt gataaatgtt acttgttaaa tcggcaggat tgggcgctct ctgatttaac  13920
ttttgccaac caaaaagtcc agccaggccg agtaaaataa taagaactaa aatcacctgt  13980
ttgttcatgg gaattgagaa acgggttaaa gatgggctga taattgtgaa ttataacaat  14040
aaccgttaga gtaaggcaat gaagagtgaa gaaccggaag attatcggct aggttggcgg  14100
cccttcttgg gttgccaagt ggatctctct cagcgaccgt tgattccgcg cgaggagacg  14160
gaattctggg ttgatcaagc aatcaaggaa cttaaaccag aatcaaccgc cggcaaacaa  14220
gtcttggact tgtttgccgg ttccggttgc atcggcttgg cggtgcttga gcactgtccg  14280
ggcgtggcgg tgactttcgg cgaaagggag gaaaaatttt gtgggcagat tcggaagaac  14340
ctcaagttaa acccgccagc cagatttgat ttcccgccag accttcgggc ggcctctcaa  14400
ggtctggcgg gtgaaggac catggcctct caaggtctgg cgggtgaaag gaccatggcc   14460
tctcaaggtc tggcggggcg aattagagtc gagtcgtcgg gaaaggttgt ccaaaccgac  14520
attttttcca aaatcaaagg gcagtttgat tttattttcg ccaacccgcc ttatgtcgcg  14580
```

```
accagaagaa gtcgggttca agcctcggtg cgcgactggg agccggccgg agcgctcttt   14640
gccggccccg acggtttggc ggtgattcga ccgttttttgg ttgaagcgaa aaaacgtttg   14700
cacccgggtg gccggattta tttggaattc ggttacggcc aaaaaggcgc tctggaagag   14760
ttattgcggc aaaacggata taaaggttgg tcgtttcggc gcgaccagtt tggccgctgg   14820
cgttgggtcg tgatacaata gcggtatcaa aagttaattt tttaattcta aaattttatg   14880
acagacaaaa acaaagcttt cattctctgg ttcaatgatt tgacaattgg cgacgtcggt   14940
ttggttggcg gcaagaacgc cgctttgggc gaaatggtca acaacctggt tccgcttgga   15000
gttaatgtgc cgaatggttt cgcgattacg gcgcacgctt acgcctactt cttagacaag   15060
acaggcttaa acagaggat taaggaaatt ttgaccgatc tcaatactca caatatcaac   15120
gatttgcaaa aacgcggcgc ccaagtccgc gccgcgatta ttaaagaaga attgccggaa   15180
gaactgcaag tggagattat caacgcttat cgcaagctta gcgccaacta tcacagccag   15240
gccgtggatg tggcggtgcg gtcttccgcc acggccgagg atttgcccgg ggcctcgttt   15300
gccggtcaac aagaaactta tcttaatgtc gccagcgaaa aggagttgat gttgtcggtg   15360
cgcaagtgct tcgcctcgct ctttaccaat cgcgccatct cttatcgggt tgataagggt   15420
ttctcaatgt ttgatgtttt gctttcggtc ggggtacaga agatggtgcg cagcgatttg   15480
gccgcggccg gcgtgatgtt ttcggtcgac accgaaaccg gtttcgataa ggtggtggtg   15540
atcaacggtg cctacggttt gggcgagatg gtggtcttgg gcaaagtcac tcccgatgaa   15600
ttcgtggtct tcaagccgtc gctggagcgc ggttatcagg cgattctctc caagacgctt   15660
ggtcgcaagg acgtgaagtt ggtttacggc gccaagggca ccaaacaggt gtcggtgccg   15720
gccaaagagg tgaaccgttt ttgtctcaaa gacgaggagg tttccaaact ggccgcttgg   15780
ggcctgacca ttgagaaata ttttttccggc aaacacaatc gctatcaacc gatggatatg   15840
gagtgggcca aggacggcaa gaccggcgaa ctctttattg ttcaagctcg ccccgagacg   15900
gtccacgccg aagccgacaa gaatgtttac gaagagcata ttttgaaaga gaaaggcaag   15960
gagttggttc gtggcaacgc catcggcgcc aagatcactg ccggcaaagt gcgcctgatc   16020
aagagcgcca accagatgaa caccttcaag ccgggcgaga tcttggttac cgagatcacc   16080
gatccggatt gggaaccgat tatgaagatc gcggcggcga ttatcaccga aagggcggg   16140 cggaccagtc atgcggccat tgtctcgcgt gagcttggag tgccctccat cgtgggcacg   16200
ggcaacgcca ccaaggtgct aaaaaacggc cagctggtga ccgtggattg ttcctccggc   16260
aaagaaggag tggtttacga aggcaagctt gcctttgaga aaaagaaca tcgtctaacc   16320 gctaccgcca agacgcgcac caaggtaatg gtcaatatcg gttcacccga cgatgccttc   16380
cgcaatttct atttgcccgt ttccggggtc ggtttaggtc ggttggaatt tatcattaat   16440
tcttacatca aggttcaccc caacgcgctc ttggattaca aagagcttaa ggccagtcgc   16500
gatccgcgcg ccaagaaggc ggttaaggcg attgatgagt tgacggttga atacaaaaac   16560
aagaccgatt attacgtcgg cgaattggcc gaagggttg ccaaaatcgc ggccaccttc   16620
tacccgcacg acgtgattat ccgtttctcc gatttcaaga ccaacgagta ccgcactctg   16680
atcggcggcg atctctacga gccggaagag gagaacccga tgatcggttg gcgcggcgct   16740
tcgcgttatt atgatcccaa tttccgtcgc gctttcgcct tggaatgtcg cgctctctac   16800
caagtgcgta gcgagatggg cctttccaac gtgatcccga tgattcccctt ctgtcgcacg   16860 gcggaagaag gccggcaagt ggtggagatt atgaccgaag ccggtctgga ccgtcaggct   16920
```

```
gacccttcgc tcaagattta tgtgatgtgc gagattcctt ccaacgtggt ggaggccgat   16980
gccttttttgg aagtcttcga cgggatgtcg atcggttcca acgacctgac ccagctgatg   17040
cttggtttgg atcgcgattc caacttgatc agccatatcg ccaacgagaa tcatccggcc   17100
gtcaagaaga tgattgaggt ggcgattaaa gcttgtcggg ccaagggcaa gtatatcggc   17160
atttgcggtc aggcgccgtc cgattatccg gagtttgccg atttttttggt gcagaacggg   17220
atcgggagca tctcgctcaa tcccgattcg gtgattaaga ccttacccgt gattgaggcg   17280
gccgaagaga agtatcccca aagataataa aaatatgaaa atcgcttttt ttgaattgga   17340
gacttgggaa aaaaaatact tgcaagagcg aactctgccc ggcgaggtcg tttttatcga   17400
cggaccgttg gatgagacca agttgccgga gcaaaacgat ttcgacgcca tttcggtttt   17460
tgttaattcc attgtcggcg acaaagtgtt gggacatttt cccaatctcc agttgattgc   17520
cacccgctcg accggttatg atcattttga cctgccaact tgcgccgctc gggggggtcaa   17580
ggtggccaac gtgccgagtt acggcgaaga taccgtggcc gagtacgcct tcgccttaat   17640
gctcactctc tcgcgcaaga tttgcgagag ttatgagcgt attcgcgaga ccggcagttt   17700
cgatctcacc ggcctgcgcg gctttgatct gaagggcaag accttggggg tgatcggcac   17760
tggtcggatc ggcaaaaacg cgatcgagat cgcgcggggc ttcaatatga atatcgtcgc   17820
ttacgacaaa tttcccgacc cggtttatgc cgaaaagatg ggctatcgtt atctgtctct   17880
ggacgaggtg ctggccacgg ccgatatctt gaccttgcac gtgccctacc tgccggagaa   17940
tcatcatttg atcaatgccg aaacgctggc caaaatgaag tcggggggctt acctgatcaa   18000
caccgctcgc ggtggcttga ttgacaccgc ggctctgctc gtggcgctta agtcggggca   18060
aattgccgga gccggtttgg acgtgctcga agaggagggc gtaatcaaag atgaggtcaa   18120
tttcttaacc aacggtcgct tggatcaagg cgatctgaag acggtgctcg gcaatcatat   18180
tttgattgat ttgcccaacg tgatcattac tccgcataat gccttcaaca cttgggaggc   18240
gctgaagcgc attttagaca ccaccgtggc gaatctggtg gcttttgaag ctggaatgcc   18300
gcaaaatttg atcagtggcg attaaggcgg tttattgacg ttttaccttg ataacggtac   18360
aataaggtca gattccgttc ggggtgagtg gaaaaacgtc ggttctagac aacgaaagga   18420
gattttatgg cccagaagtc tgccactgaa attgtttgag ctcgtctgtc tgcgtgaccg   18480
acgagcttgt gttttgttta aataaaaaga tggctgaatt caatttcaaa atcgaaaaga   18540
aaattgccgg ccgtctcggc cgagcgggaa caataatgac gcctcacgga gacatctcca   18600
ctccggcgtt tatcaccgtg gggaccaagg ccaccgtcaa ggcgctctcg ccggagcaag   18660
taatggcctc cggttcaccg gcggcgttgg ccaatactta ccacctcctc ttggagccgg   18720
gcgcggaagc ggtggcgcgg gctggcggtt tgcatcgcta tatgaattgg ccggggccgc   18780
tgattaccga ttcgggcggc ttccaggtct tctcgctcgg cgcggcttat gacgagggcg   18840
ggatcaataa attcctcaag ccgggcctac cctcgcggac cgcaccgaag cgaccttcgg   18900
aagaaggtcc gcgggagccg aagccggcca agattgacga gacggagtg acgtttcgtt   18960
cgcctttgga tggcgccgaa caccgcctga cgccggagag ctcgattcaa attcaacatc   19020
aacttggcgc cgatattatt tttgctttcg acgaatgcac ggcgcccacg gccgattacg   19080
tttatcagaa ggaagccatg aatcgcactc accgctgggc cgagcggagt ttggctgaac   19140
acgagcggct aacccaggct aagactcggg aaaatgcttc taaaaaagtc ctcggtcctc   19200
ttcaggcttc gcttgaggcc agactttttg ataagcattt tcccgagtct tattcggcct   19260
tgttcggcat cgtccaaggc ggccgcttcc aagacttgag ggaggcgagc gccaaattta   19320
```

```
ttgccagctt gcctttcgcc ggttttggga ttggcggttc cttcgataag accgatatgg   19380
gcacggcggt cgggtgggtc aatgcgatct tgccgaccga caaaccgcgc cacctgctgg   19440
ggattggcga accggaggat atgtttgagg cggtggcgca aggggccgac actttcgatt   19500
gtgtcactcc aacgcgcttg gcgcgccatg ccactttatt gacggcgacc ggccggctca   19560
atattttgaa tgccgctcac cgtgacgatc cgacatcgat cgaagccgat tgtgactgtt   19620
acgcctgcca aaattattcg cgcgcttact ggctcacct tttccgcgcc ggtgagattt   19680
ttggcgccac tttggccacg attcacaatt tgcgctttat gaatcgtctg tcggagcaaa   19740
tgcgcgccgc gattttggcc gagcgatttt tggagttcaa ggccgagtgg ctagccaaat   19800
atcaaagatg aagaaacccc cctcaacccc aaaactttt cgtttggaaa gcgccttcgc   19860
gccgccggc gatcaaccgg cagcgattaa ggcgctgacc gaaggtctgg cacgcaatct   19920
tcgtcatcaa accttgttgg gggtgaccgg ttcgggcaaa acttttacca tggcgggagt   19980
gattgccgct tacaacaagc cgaccttggt gattgcccat aataaaactt tggcggccca   20040
attggcgcag gagtatcgaa gttttttccc cgaccacgcg gtgcattact ttgtttctta   20100
ttacgattat tatcaaccgg aggcttacgt ggcggccagc gacacttata tcgagaaaga   20160
cgccagcatc aacgaagaga tcgaacggct tcgtcacgcc tctaccgaag cgcttctgac   20220
gcggcgcgac gtgatcattg tcgcttcggt gtcgtgcatc tacggtttgg gcagtccgga   20280
ggaatacgcc aaaagttta tcaattttaa tcttggcggg aaaattgaac gccaagcctt   20340
gattgagaaa ctggtcagtc tttattatga gcgaatcaac gccgatctct cgcccggcac   20400
ctttcgcgcc atcggcaatt ctgtggagat tatgccgccc ggtcaacgag agatcatcaa   20460
tctcaagttg accggggacc accttgccga aattttgatc gttgacgctg tttcgcgccg   20520
agtggtgaac cagccgggcg agatttcaat ttatccggct aagcacttta tcaccagcgc   20580
cgacgaacgc cagcgcgcca tcgctttgat taagaccgag ttggctgaga ggttgaaaga   20640
gttggttgcc gccggcaaga atctggaggc cgaacgcctg aagcgccgca ccaattacga   20700
tttggcgatg atcaaagaaa tcggctactg caatggcatt gagaattatt cacgccacct   20760
ctcggggcgg gcggcgggcg aggcgccggc caccttgctt gattattttc ctaagacttc   20820
tttcggtcgg cccgattttt tgaccatcat tgatgagtct cacgtaacgg tgccgcagct   20880
tggcgggatg tttgccggcg acgagaaccg gaagaaaaat ttggtggcct atggttttcg   20940
tctgcccagc gctctggaca atcgcccgct caagtttccc gagtttgaag cccgaattgg   21000
tcccactatc tataccagcg ccaccccggg caaatacgag cttgaagcca gtaatcccca   21060
aaaaggcggg cagatcatcg aacagattat ccggcccacc ggcctggtgg atccggcaat   21120
tgaaattaaa ccgatcgttt cgaccgcgcg ctatctcggg caaatccagg attttatcgc   21180
cgaggtgaaa aagaaattg ctcaaggtcg gcgggctatc gccacgacct taaccaaacg   21240
gatggccgaa gatttgagcg agtatttgaa aggtgagggg attaaggccg aatatttgca   21300
cagcgagatc aaaacgttgg agcggatcaa aatcctcacc gacttccgcc gcggcgagtt   21360
cgactgcttg gtcggcgtta atctcttgcg cgaaggtttg gatctgcccg aagtgtcgct   21420
gatcggcatt ttggatgctg ataaggaggg cttcttgcgg tcggaagtgg cgttgatcca   21480
gaccattggc cggcggcgc gcaatttggc cggccgggtg attctctacg cggagacgat   21540
aaccgactcg atgaagcggg cgatggatga cggcgcgc cggcggacca acaactggc   21600
ttacaatcag caacatggca ttcgccggt ttcaatcgtg aagaagatta aagacatcac   21660
```

```
cgacagtttg gctaaagatc ggcaacaatc ggttaccgct ctcttggcaa tagatgaaga    21720
gctttatggt aaaaacaaga aaaaattaat cagggagaag gtcaagcaaa tgagcgaagc    21780
ggtcaagaac ctcgatttcg aaaccgccgc tctcctccgc gacgaaatca agatcttgga    21840
aaacgtcaag actaaggcca aatgatatcg gaggatgatg ttggcgtgac atcccgccga    21900 caattttat cccaattcat acacgaccgt gcacggatag ggatgattag gaagtctgag    21960
gcaggttgaa aaattttctc aaccaacgat cattttcgat ttgggtgact tccagatata    22020
aaatttcatt tccgattcgg taattggctt taatcatcgc gacaatttcg cggcaatcat    22080
aaggcgaaac ccagacgctg ttttgcaatc tgactaagcc aaggtggtgt aaccaacgac    22140
gaagtttgtc tcgggtgctt cgcttccatt ccttaatatc aaagatgatg attcgatatt    22200
tgcggtccca tttggacggt ttttttatgg tcaacttctt taactggtat tctcttaatc    22260
tcgcttgacc ttttttagtt aaacgaacaa ttttttgatt ttgatgattg gtttgaatct    22320
caagcaaccc ttggttcttc attttctcta ttaccgtatt ggtgtaatat ttttctttg    22380 attgttgtcc gggcaaatat tttagcagtt gaacgcagtt gggggccaac aaggtaaaag    22440
caatcacccc ggtgataccg atgatactta aaataagctc ttgataatcc gctttgtcta    22500
ttcgtgacat ataccttatt ataaacggtc gtataagata agggaagata gaaaagatag    22560
gaaaagaggg aatccctcaa agcttttttg tttgggtcgg atgtgttata atcgctaggt    22620
tccctatggg ccggcccacg gggggtttcg gcgtcatccg gaataagatt aagaaatttt    22680
tatggatcag aaacatcagg ataaaatcaa aatcaaaggg gcgcggacgc acaacctgaa    22740
gaatatcagt ttggagattc cgcgcgatca actcacggtg attaccggtt tatcgggctc    22800
gggcaagtct agcttggctt tcgacactat ttttgccgaa ggccagcgac gctatattga    22860
gtcactttca gcttacgcgc gccaattttt gaaacaatta cccaaaccgg aggtggacga    22920
gatctctggt ctctcgccgg cgattgccat tgaccagaaa tcgcgttcgc acaatccgcg    22980
ctcaaccgtg gcgaccgtga ccgagatcta cgattatctg cgcgtgctct acgcgcggat    23040
cggccggccg cactgtccgg tgtgtggagt ggcgattgag aaactctcgc tggaggaaat    23100
cgtgaatttc gccaaagaga aaattgccgt cagtcatcgg ggtaaaaaaa atctcaagat    23160
ttcaattacc gcgcccttgg tgcgcggacg gaaagggggag tattatcagc tcctctacga    23220
tttactggac aagggttacc tcgaagtgtt ggtggacggt caaacttatc aactgcgcga    23280
acgcatcgta atgaccaaga ccaagaagca tgatattgac gccgtggtcg acatgattga    23340
ttggagcgat cagggcgagg ttgtcgcggc cggccagcgt ttggccgagg cggtggaacg    23400
ggcgctcaaa gagtcggacg gtctagtgaa gattgtgatt gataacgaga acttcctgct    23460
ttcctccaaa ttttcttgcc ccaacgatgg ctttctcttt cccgagattg aaccgcgact    23520
cttctccttc aattcgcctt acggcgcttg tcccacttgt cacggtattg gcaccaagca    23580
cctcttcggt ggcgaacctt gcgatacttg ccaaggggct cgcctgcgtc gggaggcctt    23640
ggaggtgaga attggcggca aaacattat ggaagcggtg tcgctctcaa ttgccgacgc    23700
ggccagcttt ttcgacaagc tgaagttgac cccgaaagag aaaacaattt ccgaggtgct    23760
gtggcgcgag atcaaggcgc gattgaagtt tttgctcgat gtgggtttgg attacgtgga    23820
gttgaatcgc cgcgccgaca cgctctcggg cggtgaggcc caacgcatcc gcctggcttc    23880
gcagttgggg tcgcgtttgg tcggcacgct ctacgtgctt gatgaaccca cgattggttt    23940
gcatgctcgc gataacgcca aactgattaa gactttgctt gagttgcgcg atttgggcaa    24000
caccattgtg gtggtggagc acgacgaaga cacaattttt gcctctgatt atttggtgga    24060
```

```
tatcggccct ggggccgggg tgcacggggg caaggtggtg gccgccggtc caaccgagaa    24120 attttttaacc agcaagaaga acgattataa ttctttgacg attgattacc ttcggggcga    24180
caagactatc gctttgccgg aaaaacggcg aggaaaccag aagggcgcgc tgaaaattcg    24240 cggggggcaaa attttttaaca tcaagaatct caatgtggac ctgccgctct cgcgcttggt    24300
ggcgattacc ggcgtgtcgg gttcgggcaa atcctctttc gtctacgaaa ttctttataa    24360
aaatttgcag gccaaactgg agcgtcgtta tcgcaccaac accttgttta attgtcggga    24420
atttggcgga acggaatact tgagccgagt ggtcttagtg gatcagtcac cgatcggtcg    24480
gaccccgcgc tccaatccgg ccacttatac cggcgccttc accttcatcc gggaactttt    24540
tgcggcttcg gctctggccc gggcgcgcgg ctggaagccg tctcgcttct ccttcaacgt    24600
ggctggcggc cggtgcgagg cctgccaagg taacggcgaa gtggcggtgg agatgcattt    24660
cttacctacc atctttgttc cttgcgatgt ttgcggcggc aaacgctacg agaaggaaac    24720
tctggaagcg ctctataaag gaaaaaatat ttacgaagtg ttgcagatga cggtggaaga    24780
agcctttagt tttttcgaag atattccggc catcttcgac cggctcaaaa cgttgaacga    24840
agtcggtttg ggttatttgg aattgggtca atcggccacc accctctcgg gaggcgaggc    24900
ccaacgggtc aaaatctcca ctgaacttta tcggccgttt accgaacgca cgatttatat    24960 cttgacgaa ccaacggtcg gattgcatta cgaagatgtt aaaaacctaa acgaaatttt    25020
gcaaaaattg gtgaccaaag gcaataccgt ggtggtgatt gagcataatt tggaagtggt    25080
caagagcgcc gattacgtga ttgatctcgg gcccgccggc ggcaaagacg gcggcgagtt    25140
ggtggcggtc ggaacgccgg aagaattggc ctacgctcct ggctcccata ccgggaaata    25200
tctcaagcgt ctgttgaaac aacaataatt aaagttgaaa gatggaaagc cgggagctta    25260
aaaaatatca attgcccgat gggcccgggg tctacttctt caagcagggc cggcgaatcc    25320
tttatgtggg caaagccacg tcgctcaagg atcgggtgcg cagttatttt gccggtgatt    25380
tgggcgaaac gcgcggacca aaaattgagc ggatgcttga gttggccaac cgcgtggact    25440
ggcaaaccac ggactcggtg ttggaagcgc tcttgctgga gtcggccttg atcaagaaac    25500
atcaaccgcc ctataacacc agagaaaaag atgacaagag ctactggttc gtggtgatta    25560
ctcacgaacc ttttcccga gtattgttgt gtcggggccg gcaattgtcg aacggttcat    25620
tctctcttgc gcttaaaatc aaaaaaatttt tcggccctttt tccccgttca agcgaaatca    25680
aggccgcctt gctcgtgatc cgaaaaattt ttccttatcg cgaccgttgt caactggcgg    25740
tggccggccg accctgtttt aatcgtcagc tcggactctg ccccggggtg tgcaccggcg    25800
aaattaacca aaccgattat cggcggctga ttgccaacat tgaacgcttg tttgccgggc    25860
gtaaaaggga attgctcgtt cgtctggaac gcgccatgaa acgagcggcc agaactcaac    25920
gtttcgaagc ggcgggtcaa attgcaatc aaattttcgc cctcaaacat attcaagatt    25980
tggcgttgtt gaaatcaagc cccaaccgcc tcaagggaaa atccgttcgg atcgaggctt    26040
acgatgtggc tcattggcaa ggcgaggccg cggtgggagc catggcggtt tggcaagacg    26100
gagagttgga tcgaagtcag ttccgccaat tcaaacttcg ggcgacaacg ccggggggacg    26160 atttggccgg gttgcgcgaa atcttgactc gacgtctggg tcatcgggag tggcccgagc    26220
cctctctggt ggtggtggat ggagaccagc gacaggtcgc cacggcccaa gtcgcattgg    26280
ctcgtcaagg tcttgactgg ccggtagtcg gagtgaccaa agaccgtcat caccgcgccg    26340
tcgctttggc gggcaatctt gaggcagaga gttttgaccg tcaagccgtg attgaagtca    26400
```

```
acgacgcggc tcatcgcgtg gccattgctc atcatcgccg acgtttgcgt ttgggtcggt    26460
aaggtcaggg cttatcccct ggagcgctct tccgaaatat ggtaaaataa aggtcggata    26520
atcaacttta tgttttggtc tgacttagtc gcaaagttgc ccaccgagcc ctcggtttgg    26580
attgccgcgt tgggtttgtt tggggtcgcc ttttccttg gttatttttg gcaggatcaa     26640
tcgaccagga cgagatggca ggtcaagcag gagatgttga agaaccagca gattattgaa    26700
ctggaaaaag tcaaccagaa cttggcggcc aaaaatcgtg aactctatgc caaagaattg    26760
gagctgacca tcgccaacaa acatctccaa gcgctggaag cagccaaatc caaatttatc    26820
gccgtgacca ctcaccaatt gcgcacgccg ctctcggctg tgaagtggac gctggatttg    26880
gcggccaaag gtcaattggg caaggtcgac gaagagcaaa aaagtttctt aaacaaaggc    26940
ttgattagtg tcaaccgggt tattgccatc gtgaacgaac tcttgcgcgt ggactcggtg    27000
gagaccgatc aagtcgtcta ttgtttccaa cccgtcaatt ttatcaagct gttcgacgaa    27060
gtgttgtttg aattcgaagt gcaggccaag agcaaagggg tgaaactctc ggtgcgtcgg    27120
ccggagactg acctgcctcc aattgatttg gatgaaacca agattaaaat ggtgatggaa    27180
aatcttttcg acaacgccat taaatacacg ccggtggggcg gtctggtgga agtggttgtc    27240
tccgacaagc gtctcaaccg cgccgaaggg gcgattgagg tgacggtgcg cgattccggc    27300
atcggcatcc cgagcgagga aaagaacaac atttttccaaa aatttttccg cgcgaccaac    27360
gcgatcaagg ccgagcccga cggttccggt ctcggtctct ttatcgctca cgatattgtg    27420
actcggcata atggctcaat gtggtttgag ccggccgcgg gcggaggcac gattttttacc    27480 ttcactttac cgattcatca gaagacgcta aatttttaaa gactcttatc aatttaatct    27540
taaaagacaa tggacaagaa aaaaatccta atcgtggagg acgacgagtt cctccgttcc    27600
ctcaacgcca agaagctgga gagcgagggt tatgccgtta gtgtgtcgcc cgacgggacc    27660
agcgcgatcg aattgattcc tgaagaattg cccgacttgg tgtttctgga tcttctgttg    27720
ccgggcggca aagacggttt cgatgtttta acggcgatca aggccgacga aaaaaccaag    27780
aatattccgg tcgtggtttt ctccaatctc ggccaagccg aggatatcaa gaaggctaag    27840
gacttgggcg cgattgactt tttgatcaaa gccaacttta cccttgacga cgtggtgacg    27900
aaaattaaag aaattttgaa ataaaacaaa tcaatggcgc ccattcgagt cggtatcttg    27960
cgcggtggca tcggatccga gtatgaagtt tcgcttcgaa ccggcgccgg tgttttgcgc    28020
cacttgccgg gcgacaagta tcagccggtg gatattttgc tgtctcgaga cggggcgtgg    28080
tatgccggcg gtttgcgcgc caccccgag cgggcggtac ggggagtcga tgtgatcttc    28140
aacgccttgc acggcgagtt cggcgaagac ggtcaagcgc aacaactgct tgattatctg    28200
ttcaagccct atactggttc cggcgcggtc gccagcgctc tggggatgga taagcctcga    28260
gccaaagagc tcttccggca ggctggtctg cgggtgccca acgcgcggt gcttcggcga    28320 gcggatcgtc ccgaggaaac cgatgccgag cggtggcctt acgatgtctt caaaaaaatt    28380
ccgccgcctt ggatcgtgaa gccggccagc ggtggctcct cggtggatct ccggctggcg    28440
cgccattacc ccgagttagt ggcggcggtg gccgccggcc ttaagcagaa cgatcgaatc    28500
ttggttgagg aatacgtgcg cggtcaagaa gccacggtgg gggtcgtcga tcgtctgcgc    28560
ggccgcgatc attatccgtt gttgccggtt gagattgtca cgctgccaga caaggtcttg    28620
tttgattacg aagcgaagta cggcggccaa accaaagaaa tttgcccgg ccgctttcgg    28680 ccggaagaca agcttgagtt ggaacgtcaa gccgttttga ttcatcaaca attaggcctg    28740
cgtcactatt ctcgttccga ttttatcatc tcgcctcgcg gtatctacgt gctggaagtc    28800
```

```
aacactttgc ccggcctgac cgaagagtct ctggtgccca aggcgctggc cgctgccggc   28860
atcgcttacc cgcagttttt ggatcacttg gtgaccttgg cgttagaacg acgctgaatt   28920
tgaaggacaa aaaagccccg cgagagaaga tgcagtgatc tcaaggpggc aagaggaggg   28980 gatgaaaggt atgaaggaac taccaatgaa ggggatggaa ctgggacaaa agaacaaatt   29040
aggtggcaga gccttcagtg ccactcgaaa gctctgccgg ttagggtgta aaggtcgagc   29100
gagcgaccta tcttcaggtt atcataaggt gtgatttttt gcaagggcgg agggattatc   29160
ttggtggtgt tattataata gcatttgctc gaacttattt tcaagacaaa atgaaggact   29220
gaacgccccg ccacccgcct cgcggacttg gcggacacca gaaacaaaaa attttcttaa   29280
cattttccga tttggcgcga ggaagaattt ctcttaaatg gaaagaaaaa ttttgtttct   29340
ggtgttctgt cctcaaggtc tcgggcagtt ggcggggctt cagaaattcg gacagaaaat   29400
taaaaagtgt catcccccce aaaccccaac cactttttaa ttttctgatt cctacaatgt   29460
ttcgtttggt ggtgttatt t tagcatttgc tcgaacttat ttccaagaaa aaatgaaaga   29520
ctagcgttcc ccgcgcgctg aagcgcctct gtgcaaagca cnnnnnnnnn nnnggggatt   29580
ttgaattttg tccgcgcgga ggcagggtct gggagggaat ccgcgcgggc tttatttttt   29640 tgaattt ttt tggcgtagag cttgtataaa atacaattat atggtataaa aatagtaaga   29700
gaaagtcatc gtggctttct caaaaccgct cattgacaac taaaaaagga ggatccaatg   29760
attatttcat tcagtgggcc ctccggtatc ggtaagggct tcatcaaaga acgactatta   29820
cagctttatc cagacatcca agaattggtg tggtatacaa ctcgcacctt gcgaccaaac   29880
gaacaagggt caaacagaat tcaagtttca ctttccgagt ttaaccagtc ggttgaactt   29940
ggcaagctta ctttagtgca agatcttttt ggtcatcgtt atggtctaaa aaagagaagat  30000 ctcgtaacga gttcgggtat caagttgact gagttgcatc cagcaaatct agtggaagca   30060
ctcaaaatca acccgaagat ttttgcaatt ggtcttgtaa cttctgattt atcactactt   30120
cgtaaaagac ttactgttgt gagaaagacg gaaagcgaag cagagataga gaaaagagtt   30180
acgaaagcta aaagcgagat cgagataatt ctacaacaca ggtcttttta tgcttccgtg   30240
attgaaatta cagaagctga agaagatcaa gtgttcaaca aggttcatgc aatattgcaa   30300
tcacaaatca aaccgaaagg aggaaaaaat gaaactagaa acacaagttg gtagtctgaa   30360
gttgcacaca ccgttgttgc tggcttcagg ttacattacc gaaacaccag agttctttct   30420
gagagctcaa ccctacggct gttcgggtat cgttacccga tcacttaaac aaaatgttcc   30480
agcggaacga tcacggatta catctccacg ctatgcagtc tttggtaatg acagcatgct   30540
taactgcgag tggggaaatg aaagaccgtg gacggattgg cgagatcatg gagtgcaaca   30600
ggtcaaagca attggttgtc taatcatcat ttcgctttcg gggcgagatt tggatagctg   30660
ttgtaatttg attcgtgcat tcgataagat cggtgttgat gcctacgaaa tcaacatctc   30720
atgttcgcat tctggagcac tgcatgggaa tctgaatgtt gatgtgcttc acctagaaca   30780
actgatgaaa agagtgcgta acattacgac gactccaatc tggatcaagt tgtcgtattc   30840
aaacctgctg ttctcaatgg caaaacaagc cgaagagttt agagcagatg cgatagtgtg   30900
cacaaatagc atcggtccag gaatgttgat cgacaccaaa accgctaaac cgaaactcgg   30960
aatcaagggc ggaggcggtg gaatgacggg aaaagcaatt ttcccgatcg ctctatggtg   31020
tgtgcatcag ctttcaaaaa ccgtgagtat ccctgttgtc ggttgtggtg gaattttcac   31080
cgcagacgat gtaattcaaa tgctcatggc aggtgctagt gcagttcaac tctacacagc   31140
```

```
tcctgcgctg aaaggtccta cggtctttag acgagtaaag gctggactac aaaggtttct  31200
cgatgagaat ccgaagtatg cttcagtcaa agacctcgtt ggacttacgc tcgacaaaac  31260
aggtgagcat aagttttctt cacctcgtcc agtcgtgatt gaagaaaagt gcacaggatg  31320
tggaatctgt attcaatcct gtgcatttga cgccctgtca atggttcgta gtgctgatag  31380
caaagcactg gcggtcattg ccgataactg catctcatgc aacgcttgcg ttggagtatg  31440
tcctccgaaa ttcgacgcta tcaaagcatc attctaggag gtaatacaga atgaaaaaa   31500
aacacataca tcatcgcggt tcactgcaat gcgtgtcgaa ccctactgta tcgttacaaa  31560
aaagaaggtg gtggacatct cctcaagtgt tatgccgaca tgataatgtc ggattacact  31620
aaaggcgatc taaggtgtcc ttcttgcggt caagagtttg ctcgacatgc aatcatccac  31680
aatcgctcag cacataagat aatccgaggg agagtctttg tgaagggtca tcatggataa  31740
catcatcaca acgggtggtt tgattcaatc agaccacccg ttattttttt attttagttc  31800
aaatctgttt ttgaaataat tagatgtata gttttatata tcaaaaatct cattagattc  31860
tttatttagt ttttctacat attcaaaaaa ttgttttta tcaaaaatat caagactaag   31920
ttctttacaa acatttgcaa ttcctttaac caattcatcg ccatttcat taccagaggc    31980
cattttttct gcttcgtaat aataactatg tcccggtact tctaccaatg caaattcaat  32040
atccttatat tcatatactt tactttttct aacacaaagc atacctttac caaatccaag  32100
ttcgccgaaa atttcaacca acgtgtcaaa atcgccttgt ttagtgaaaa ccgagagctc  32160
tttacgttgc tcatttcctc cccattcgcc aattttaaga ataatttcag gaattccatt  32220
ggtcactcgc aatcgtatat ctttttttct atgttctacc cctccctcta aaaagttga   32280
ataatcaatc aatactctat tttttctctga tttcttttt ccactactgt caaaaattt    32340
taccagattc tcaaattctc cttttgataa aggtcctcgt atttcaattt ctatattttc  32400
atccatattt attgatttt taggtttata aatagttgct ttattatcat ggtcgcataa   32460
ctaccagtag gtaagtaaaa ggaaagtgta attttcattt tattttatg aagatcgtca    32520
gactctaaat catgagcata catattagtg gcgaccaaga gatttctctt gttcagtttt   32580
ggttttgcta aaaaatttc tggaattagt tcaaaccctc cagcttcaca aatatgtgga   32640
cattgaaata cagcatttgt tggcaaatat aatttgccaa cattttgaa tataaatttt     32700
ttacttttag tattttctc tatcaacaaa gatgcctgtg tattccacag aaaactatta    32760
tatgcggaca caaaaaaga actttttttt ggattcatga catcaaaaac cttttgtag    32820
tctgagatat cttttgcttt tagttcagct ccttgcgtaa tattatttgt aatttttagt  32880
tgttcataag cctgtttcca attatcttct actattgcct taccaatcag atgagtatta  32940
tagggccac caggcattcc aaatctttga ttgtcatagt aatttataaa ataaagttgt    33000
ttgtgattgt ggacataatt tgaaagatta tctgcaatcg tagaatttaa atttcttacc   33060
actattttaa aagcatttcc gtgtaaagcc ctttctttta ttggttttc cccatgaccc    33120
attacaaact taatttttga aaattgattt ttaaatttgt gtttcttgtt aaatactatg  33180
atatcttttt ctttcaagat tttttgatg gaaataagtt gttcggtaat agcatcctca    33240
tcttttaatc cttggctaca tacatcctca aatgaaagtt taaaaaatag ctttatttgt  33300
tctaaggctt caaatgttgt aaatccagat ttttgtagcc aaatataagt aaacttacgt  33360
ttacctttg atataaatga tggcataaga gagacctccg tcatctgaaa gtcttcgttt    33420
atgtgtttta ttttataatc ctcatatttta tccataatat aaataattta acataaataa  33480
ccttatttgt aaataattcg ccaaaaaatc ccaaaaaaca aaagcccgcg cggattccct  33540
```

```
cccagaccct gcctccgcgc ggacaaaatt caaaatcccc gccgaatttc aaaaacatta    33600
gtctcggttt tgcgaaccct tctcccagaa aatagttttt gcaaaaccga gtccatattt    33660
gcatttctgc acctcgcctc attctcccag attattagtg gcgaggggca gggcgtttcc    33720
ccgcacttct gcttcagcag aagctctgtg ctttgcacag aggcgcttca gcgcgcgggg    33780
aacgctagtc tttcattttt tcttggaaat aagttcgagc aaatgctaaa ataacaccac    33840
caaacgaaac ttgttcggaa ttaagaaagc ggagcgattt tgcgggagcc aaaatcgcgc    33900
tatcattttt ttcaaaaccc tttccgccta cggcggaagc ggtgaattcc caaagttccc    33960
cccaattgaa atcatgaaag acctcaaacc aaaatatttt ctctacgcga ggaaatcaac    34020
agaggatgat gaccaccaaa taatg                                          34045

<210> SEQ ID NO 24
<211> LENGTH: 11142
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (6655)..(6659)
<223> OTHER INFORMATION: n is a, c, g, or t

<400> SEQUENCE: 24
catcttcatt tgtatgcgta tcagagagat caaaaactat gttatcaatg atggcgcggt      60
atggttcaat gagatcgaag gcgagagcgg ggtaatcagt cgtctcgtgc aggaacccat     120
ggaagggaga gaggtgatgg tagtgaatcc atcggagaaa aattcctatt aaaaattttg     180
acatcgcatt cagcgcgttg ctggccgggt ttttaccgcg cctcatgaag gctgaatgtc     240
cgagcttctt gaaatatgcg ctccaatagc gctggctgtg gagcgcttcg tgattgcgca     300
gttcctgaat ggtcatggtg cgggagagtt ttttgcagg aggaacgata agccacgcca     360
tgctgttgaa ttttgcgttt agaatttgcc gcgcgatata cttttttgatg cgcaaatcag     420 agcgctttac aagttgttga gaaagcaggt catttccatc tgcacggtta ctggcggtaa     480
tccagactgt attggttaaa tttctcctat gaataatgat aggaattta tgacgcgctg     540 tgaattcaag tgtgctcggg gctaaggag ggctatctcc gtaaatcatg atggagagga     600
gcttggcagg attgcaggtt acttcgcctc ctttatactt aatgtgaata ttttccctt     660 tgacttcaaa tgtttcaaca taaggcgccc aaagaggtat ttttgcgag tatgttttca     720 tgttatagaa taaagtgagt attgaaatat aaaactttat atggtaatgt aagacacata     780
attttgcaag atgtgttgca aaaagcgat tttttgaggg gtcgccccga atataggga     840 caaaaggct agcatacttt tttggaaccc cgaatatagg ggacaaaaag gcttatgagc     900
tgaaaaagat ccccgaatat aggggacaaa aaggcacgcc gctttcgcgt tcaaccccga     960 atataggga caaaaaggca attaccgcat aaatcatccc cgaatatagg ggacaaaaag    1020
gcaacatgac ccaccctcct ccccgaatat aggggacaaa aaggctatga gacttctgaa    1080 atcccccga atataggga caaaaaggct aagccccat gctttctccc cgaatatagg    1140
ggacaaaaag gctgaagtac gcaatctgca accccgaata taggggacaa aaaggcatgc    1200
tgtttgtatc ttcaccccga atataggga caaaaaggca aggatattca agcgcacccc    1260
ccgaatatag gggacaaaaa ggcttaccac acaacttatt gaccccgaat ataggggaca    1320 aaaggctgt gagcgatgta aaccacccg aatataggag acaaaaaggc gcgtggtcaa    1380
```

```
tgctcgtgcc ccgaatatag gggacaaaaa ggcctttagc ttcatttaag attttaggta    1440
tttccggaca gcggcttgac cgcatcgtcc tcgccttttc ctaaaatcgc ccctcttaaa    1500
tcgcttgcct tacagacgca tgtataaaga tattttgaag attaagttat cgcatacttt    1560
atgagtaagc gacatcctag aattagcggc gtaaagggt accgtttgca tgcgcaacgg    1620
ctggaatata ccggcaaaag tggggcaatg cgaacgatta aatatcctct ttattcatct    1680
ccgagcggtg gaagaacggt tccgcgcgag atagtttcag caatcaatga tgattatgta    1740
gggctgtacg gtttgagtaa ttttgacgat ctgtataatg cggaaaagcg caacgaagaa    1800
aaggtctact cggttttaga tttttggtac gactgcgtcc aatacggcgc ggttttttcg    1860
tatacagcgc cgggtctttt gaaaaatgtt gccgaagttc gcggggaag ctacgaactt     1920 acaaaaacgc ttaagggag ccatttatat gatgaattgc aaattgataa agtaattaaa     1980 ttttgaata aaaagaaat ttcgcgagca acggatcgc ttgataaact gaagaaagac       2040
atcattgatt gcttcaaagc agaatatcgg gaacgacata agatcaatg caataaactg     2100 gctgatgata ttaaaaatgc aaaaaaagac gcgggagctt ctttagggga gcgtcaaaaa    2160
aaattatttc gcgattttt tggaatttca gagcagtctg aaaatgataa accgtctttt      2220
actaatccgc taaacttaac ctgctgttta ttgccttttg acacagtgaa taacaacaga    2280
aaccgcggcg aagttttgtt taacaagctc aaggaatatg ctcaaaaatt ggataaaaac     2340
gaagggtcgc ttgaaatgtg ggaatatatt ggcatcggga acagcggcac tgccttttct    2400 aatttttag gagaagggtt tttgggcaga ttgcgcgaga ataaaattac agagctgaaa     2460
aaagccatga tggatattac agatgcatgg cgtgggcagg aacaggaaga agagttagaa    2520
aaacgtctgc ggatacttgc cgcgcttacc ataaaattgc gcgagccgaa atttgacaac    2580
cactggggag ggtatcgcag tgatataaac ggcaaattat ctagctggct tcagaattac    2640
ataaatcaaa cagtcaaaat caaagaggac ttaaagggac acaaaaagga cctgaaaaaa    2700
gcgaaagaga tgataaatag gtttggggaa agcgacacaa aggaagaggc ggttgtttca    2760
tctttgcttg aaagcattga aaaaattgtt cctgatgata gcgctgatga cgagaaaccc    2820
gatattccag ctattgctat ctatcgccgc tttctttcgg atggacgatt aacattgaat    2880 cgcttttgtcc aaagagaaga tgtgcaagag gcgctgataa agaaagatt ggaagcggag    2940 aaaaagaaaa aaccgaaaaa gcgaaaaaag aaagtgacg ctgaagatga aaagaaaca     3000 attgacttca aggagttatt tcctcatctt gccaaaccat taaaattggt gccaaacttt    3060
tacggcgaca gtaagcgtga gctgtacaag aaatataaga acgccgctat ttatacagat    3120
gctctgtgga aagcagtgga aaaatatac aaaagcgcgt tctcgtcgtc tctaaaaaat     3180
tcattttttg atacagattt tgataaagat ttttttatta gcggcttca gaaaattttt    3240 tcggtttatc gtcggtttaa tacagacaaa tggaaaccga ttgtgaaaaa ctctttcgcg    3300
ccctattgcg acatcgtctc acttgcggag aatgaagttt tgtataaacc gaaacagtcg    3360
cgcagtagaa aatctgccgc gattgataaa acagagtgc gtctcccttc cactgaaaat     3420
atcgcaaaag ctggcattgc cctcgcgcgg gagctttcag tcgcaggatt tgactggaaa    3480
gatttgttaa aaaagagga gcatgaagaa tacattgatc tcatagaatt gcacaaaacc    3540 gcgcttcgc ttcttcttgc cgtaacagaa acacagcttg acataagcgc gttggatttt     3600
gtagaaaatg ggacggtcaa ggattttatg aaaacgcggg acggcaatct ggttttggaa    3660
gggcgttttc ttgaaatgtt ctcgcagtca attgtgtttt cagaattgcg cgggcttgcg    3720
ggtttaatga gccgcaagga atttatcact cgctccgcga ttcaaactat gaacggcaaa    3780
```

```
caggcggagc ttctctacat tccgcatgaa ttccaatcgg caaaaattac aacgccaaag   3840
gaaatgagca gggcgtttct tgaccttgcg cccgcggaat ttgctacatc gcttgagcca   3900
gaatcgcttt cggagaagtc attattgaaa ttgaagcaga tgcggtacta tccgcattat   3960
tttggatatg agcttacgcg aacaggacag gggattgatg gtggagtcgc ggaaaatgcg   4020
ttacgacttg agaagtcgcc agtaaaaaaa cgagagataa aatgcaaaca gtataaaact   4080 tgggacgcg gacaaaataa aatagtgtta tatgtccgca gttcttatta tcagacgcaa   4140
tttttggaat ggttttgca tcggccgaaa aacgttcaaa ccgatgttgc ggttagcggt   4200
tcgtttctta tcgacgaaaa gaaagtaaaa actcgctgga attatgacgc gcttacagtc   4260
gcgcttgaac cagtttccgg aagcgagcgg gtctttgtct cacagccgtt tactattttt   4320
ccggaaaaaa gcgcagagga agaaggacag aggtatcttg gcatagacat cggcgaatac   4380
ggcattgcgt atactgcgct tgagataact ggcgacagtg caaagattct tgatcaaaat   4440
tttatttcag accccccagct taaaactctg cgcgaggagg tcaaaggatt aaaacttgac   4500
caaaggcgcg ggacatttgc catgccaagc acgaaaatcg cccgcatccg cgaaagcctt   4560
gtgcatagtt tgcggaaccg catacatcat cttgcgttaa agcacaaagc aaagattgtg   4620
tatgaattgg aagtgtcgcg ttttgaagag ggaaagcaaa aaattaagaa agtctacgct   4680
acgttaaaaa aagcggatgt gtattcagaa attgacgcgg ataaaaattt acaaacgaca   4740
gtatggggaa aattggccgt tgcaagcgaa atcagcgcaa gctatacaag ccagttttgt   4800
ggtgcgtgta aaaaattgtg gcgggcggaa atgcaggttg acgaaacaat tacaacccaa   4860
gaactaatcg gcacagttag agtcataaaa gggggcactc ttattgacgc gataaaggat   4920
tttatgcgcc cgccgatttt tgacgaaaat gacactccat ttccaaaata tagagacttt   4980
tgcgacaagc atcacatttc caaaaaaatg cgtggaaaca gctgtttgtt catttgtcca   5040
ttctgccgcg caaacgcgga tgctgatatt caagcaagcc aaacaattgc gcttttaagg   5100
tatgttaagg aagagaaaaa ggtagaggac tactttgaac gatttagaaa gctaaaaaac   5160
attaaagtgc tcggacagat gaagaaaata tgatagacgt tgtttttaca ccatcgctat   5220
tgactaggtg atctttacgt cagaacccca tcagaaattc cttaaactcc tcaaacttgt   5280
ttgaaagcgg gagaacctgt ttttgtttgt gtagaagctt tttgagatca gcggggagag   5340 gtatttttt gccgatgagt ggttccacta ttgcgttgaa tttcactgga tgcgcggtct   5400
caagaaaaat gccgagagta ttttctttt tattttgagc acaatatttt ttgaggccta   5460
aataggcaac cgcgccgtgc ggatctgcac tatagccaca gcggttatac agttcagaaa   5520
ttgccccgcg cgtttcagcg tcagtaaacg atgcgccgaa aatatctttt tgcatttcag   5580
cgcgttcatc atgatacaga gtgcgcatac gcgcgaagtt actcggattt ccgatatcca   5640
tggcatttga aattgttcgt attgacggtt ttggaatgaa cggctcaccg cataaatatc   5700
gcgggacgac atcattgctg tttgtggcgg cgatgaattg tctcacagga agccccattt   5760
tttttgcaat gagccctgcg gtgaggttgc caaaatttcc gcacggcact gaaaatacaa   5820
gcggcgggca tacagcgaac gagcgagctt gcgcttgggc atacgcgtaa aaataataga   5880
atgtctgcga aataagccgc gcgatattga ttgaatttgc agaggcaagg cgcaatgttc   5940
gggcaagctc ccgatcggca aatgcttgtt ttacgagggt ttggcagtcg tcaaacgtgc   6000
cgtttatctc aagcgccgtg atgttttgc ctaagccagt aatctgtttt tcctgaatag   6060
cacttactcc gtcttttggg tatagaatta taatgtgcac gcgctcactt tgaaaaagc   6120
```

```
tgtgcgccac tgccgcgccg gtgtctccgc ttgttgcggc aagaatggtt aaacatctgt    6180
cgtcattttc caaaaaataa cacatcaatt ccgccatgaa tcgcgcgcca aaatctttaa    6240
acgagagtgt ttggccgtga aaaagttcaa gtacagcgag cgtttcattt aaaaacacaa    6300
gaggcgcgtc aaatgtgaga gattttcaa taatgcggtt gatgtcttgt tttggaattt     6360
tagggaacca caactcgctt gtttcccgcg caatatcttt gagggatttt ttggcaatgc    6420
ttttgaaaaa tgatgaagag agccggggaa tttcaagcgg catgaacagg ccgccatccg    6480
gcgcgagcgg ggaaaagaga ccatgtttaa aggaaaaaat tttattgttt ctatttgtgc    6540
ttttaagctt catggcaggt ttgtataaaa ttctctgctg aaaattcggg cgaccgtagt    6600
ctgtgatagg ggatggttgc gtgcgcgtat tgtttatagc gattggtgcg atagnnnnnc    6660
agttttgggt aacatcgcgc gagcgcagag cgattgtttt cgttattccg cttttcaaac    6720
atattccccc acagcacggg ctttggatcg cgaaggtact gttcaaacat ttctttgcgt    6780
acttttgccg gcgtgtataa atataccaca cgcgtatatt ttttgagcag attgcataat    6840
gcggggtcaa cataaataac actccctgtc gtgtcaataa ctgtgcgaca atcaagtttt    6900
cttttttgta ttaaaccgat aattttcgt ataacgctac gctcgcaacg caaataatgg     6960
ctttgattcg cgttgtattg ggactcgtat ggctggccaa gccatcgcga tacatcttga    7020
atgcccttat agccgtgctt tttaagcaag gaagcaagct ttttttcaat taaatcgtca    7080
cagcagatat gcgcgtaccc aaagcgcgca agctgttgcg cccagtatga ttttcccgcg    7140
cctgacatgc cgataagcgc gattggtttt tcttgcacac tatatatgtt cataaacgca    7200
ctgccttaaa aatatctgaa aaaactcctg cggatgtcac ctctgcgcct gctcctttgc    7260
ctcgtacgat aagcggtgtt tcatggtaat gatcggtggt aaatgaaaat atattgtcgc    7320
tcccgcggag cccggcaaac ggatgattag aggcaacttc tttaagaaac atttttgcct    7380
tgccattttc tatttcagca acaaagcgaa gcactgcgcc gcgtgcgatc gcgcgttgtt    7440
tttttgcttc aaattgggcg tcgtaccgtt caagtgtttt taaaaattct ttaacggttt    7500
ccttttttct gccttgcgga atgagctgtt ctatttcaac atccgcgcat tccatgggga    7560
gagcgcactc tcttgcaaca atcaccaatt tcgcgccgc gtccatgccg tttaagtcgt     7620
ttcgcggatc tggttccgtg taaccgagct tctgcgcctc gcgcaccgct ttgctcaatg    7680
ttgtatttcc ctcaaatgag ttaaagatat agcttagcgt tccagaaacg attgctgaaa    7740 tttttttctac gcggtcgccg cagagcatga aatctcgtat ggtggaaagc acaggaagcc    7800
ctgccccgac ggttgtttca tataaaaacc gcgtatggtt ttgagaggcg agtagtttta    7860 aattttata gaatttaaaa ttggatgaaa ggcctttttt attcggcgtt acaatggcaa      7920
tgcgctctgc aagtatggtg ttatagaggg cgggaatttc ttcgctcgcg gtgcagtcca    7980
caaacacggc gtttggaagg cgcattgcct tcatgccggc gacaaattga gcaagatcag    8040 cttttttgtcc gcgcgtgtta agctcttctt tccagccaga aagcgtgccg aggtgttccc    8100
caagaaccat tttcttggtg ttgacgatgc ctgcaacttt gagcgcaata ccctcctctg    8160
ccaaaagccg ctctctttga gcattgattt tcgtaagaag cgcagatccg ataagcccgc    8220
ttcccgcgag aaaacacgtga atgttttgtg gtgccatagg tataaaaaaa ccgctccaga    8280
catgtgggta atgtccggag cggaagaagt tataatgcgc cttgttttta tttttaactc    8340
ttcacaacca aacatcaccc gccttttgcg gtaatagtgg tgatgatggt agtgatgcta    8400
ttttgacgca taagaatttt tttgactctc atagtatagc acaagtaaaa tttttgcgc     8460 aaggttttgg tgagttgata gagttttgag gttgatatct aattgtcaag aaacggggat    8520
```

```
aatgtgcaca cattatcaca acagattgaa tatatgcggg ttttgtgaaa taatggcatt    8580
atatatcttg atgaacctca ccaaactcgc caattttttc tttgaacttg gcatgatgaa    8640
acgggaaaag catcagggtt ttgctattgc gggcgtgcat cacgacatgg ggtctttagc    8700
ggatcatacg tgtcgcgcgg ctttaattgg cgcaatttta gcggaaatgg aaggcgcgga    8760
cgtgaataaa gttgccatga tggtgctttt gcacgatata ccggaaacgc gcattgggga    8820
tcatcataaa gttgcggcgc ggtatttgga tacgaaaaaa gtggaacgcg ctattttttt    8880
agaacaaatt cagtttctgc ctgatccttt gcaaaaaaaa tggctcgcgc tctacgacga    8940
aaaagcaaag agaagcacta aagagggtat tgtcgcaaaa gacgcggact ggcttgaact    9000
ggcgatttcc gcgcgtgaat acatacacat cggctataaa gatttgcagt tgtgggttga    9060
taatgttcgg agcgcgcttg aaactgaatc cgccaaaaaa cttcttgcag aaatagaaaa    9120
acaaggcacc tacgactggg cccgcggttt agaaaagatg acatatcaga aattatcgtg    9180
atctgcaatt ttttgctata attataaaaa agtttcattc caacatctaa cgcaacattg    9240
aggaaaaact tcaatgcaat gatgagtatt gtgaaaaagt tgggaccagc tctctttccc    9300
atttgcagg atatgcgtct ctcgtatcag gtgcatggaa aggagtaaaa aaatacacgc    9360
cgcttgcaaa tttagaagac gtacggaata gagccgttgc gattagaaaa gaagcagaca    9420
aagaaaagcc agatagttta gagattgatc gtattttaac ggattttatg aatgcggagc    9480
taaaggaatt atggaatacc atagataaac gtattgttga tgcggcgaaa aagtttatac    9540
aaaacttcaa agatcatccc gaagacgcga ggagagcgaa ggtggagagt tggggactag    9600
aagaatggaa aagagattta gaacggatag tcaaaacccc aattaatcaa atgatggggg    9660
acgcatcatt tgtgattaac agaggagtgg atcagtatcg tgcgcgcgat atggcgaaaa    9720
ttatgggtaa gataagtgtt ttttatcaac cccttgtgtg ggagaaggcg tcataaccca    9780
tgagaattat cacaaaattc tctgcttcat atacaccatc gctccgtaaa gccccgagga    9840
atcgcagagc tttgattttt gaatcggcgg aaaggacggg aacaggggtt gatttgattt    9900
cttgacacgc tgtgagttgg gcagtagagt agtaagaaag taatatttt ttatattcat    9960
gaacactaag ataatacaaa aagctacatc tcggggaaa attacgcttc caggacagtg    10020
gcgtaaaaag tttcctacga accaatatct tgttgaagtg gaagaagatt tgcttaagat    10080
taagcctttt gaagtggaca cggcggggca attagaagaa caagtaaaag tgttgaattg    10140
tgtcaataga tttgagggac ttgcgataaa aggaagaaaa tttgctaaaa agagaggaat    10200
taaaatggac gatgttttaa aagatgatta aagcagtact tgatacgaat attttaattt    10260
ccgcactttt ttggaaaggc accccatata ttattgtgca ggatggatta gagggtgtgt    10320
ttgaaatggt tacttcaaaa gcaataatga gtgaaacgaa agagaagttg attcaaaaat    10380
ttgaattttc tgttgaagat actctaagat acttggaact cttggtttgt aagtcgttcg    10440
ttgtatcacc gatggtacag cataatgtgg tgaaaatga tagtactgat aataaaattc    10500
ttgagtgtgc ggtaagcgcc aacgcagatt atattgtgac aggagataaa catctactaa    10560
atatcaagca ttatcaaggg atcactattc tcactgcacg cagatttgat gagatacttg    10620
aaaatgaacg gagtagaatg agaagaaata agcgataggc acagaataac ttggatccaa    10680
ccttctaacg caacagcgtt aagaatgaat taattgattg aaaacctcgt atggtgtttg    10740
aaagtcgagt gttttttctcg gtcggccatt caggagatgt tgcgctcgtt tcacttcgta    10800
ccgcgatacc ttggtaaagt tggttccttt cggaaaaaat tgtctgatga gtccattggt    10860
```

| | |
|---|---:|
| gttttcgttc gtgcctcgtt cccatggact ccggggatgg gcgaagtaga ctttgactcc | 10920 |
| ggtcagattc gtgaataatt tgtggctggc catttcccgc ccttggtcgt atgtcatcgt | 10980 |
| cagtctcatt tgtttcggca attttttcac ttccttggca aacgctttgg ccacatcttc | 11040 |
| ggcagatttg cttttcacgg ggataaggat agtcgtgcgg gtcgtgcgct caaccagagt | 11100 |
| gccaagagcc gaacgattgt tctttccaac aatgagatcg cc | 11142 |

<210> SEQ ID NO 25
<211> LENGTH: 13879
<212> TYPE: DNA
<213> ORGANISM: Artificial sequence
<220> FEATURE:
<223> OTHER INFORMATION: Synthetic sequence

<400> SEQUENCE: 25

| | |
|---|---:|
| tttccaccgc cgctcaatca gtctagacat acaggtggaa aggtgagagt aaagacgtga | 60 |
| caaccttctc atcctcttca aagtctagac atacaggtgg aaaggtgaga gtaaagacaa | 120 |
| accgtgccac actaaaccga tgagtctaga catacaggtg gaaaggtgag agtaaagact | 180 |
| caagtaacta cctgttcttt cacaagtcta gacctgcagg tggtaaggtg agagtaaaga | 240 |
| cttttatcct cctctctatg cttctgagtc tagacattta ggtggaaagg tgagagtaaa | 300 |
| gacttgtgga gatccatgaa cttcggcagt ctagacctgc aggtggaaag gtgagagtaa | 360 |
| agacgtcctt cacacgatct tcctctgtta gtctaggcct gcaggtggaa aggtgagagt | 420 |
| aaagacgcat aagcgtaatt gaagctctct ccggtccaga ccttgtcgcg cttgtgttgc | 480 |
| gacaaaggcg gagtccgcaa taagttcttt ttacaatgtt ttttccataa aaccgataca | 540 |
| atcaagtatc ggttttgctt tttttatgaa aatatgttat gctatgtgct caaataaaaa | 600 |
| tatcaataaa atagcgtttt tttgataatt tatcgctaaa attatacata atcacgcaac | 660 |
| attgccattc tcacacagga gaaagtcatg gcagaaagc aagcagatgc aatgccgcaa | 720 |
| gtgcggcgca agcatgaagt atgaagtaat tggattgggc aagaagtcat gcagatatat | 780 |
| gtgcccagat tgcggcaatc acaccagcgc gcgcaagatt cagaacaaga aaaagcgcga | 840 |
| caaaaagtat ggatccgcaa gcaaagcgca gagccagagg atagctgtgg ctggcgcgct | 900 |
| ttatccagac aaaaaagtgc agaccataaa gacctacaaa tacccagcgg atcttaatgg | 960 |
| cgaagttcat gacagcggcg tcgcagagaa gattgcgcag gcgattcagg aagatgagat | 1020 |
| cggcctgctt ggcccgtcca gcgaatacgc ttgctggatt gcttcacaaa aacagagcga | 1080 |
| gccgtattca gttgtagatt tttggtttga cgcggtgtgc gcaggcggag tattcgcgta | 1140 |
| ttctggcgcg cgcctgcttt ccacagtcct ccagttgagt ggcgaggaaa gcgttttgcg | 1200 |
| cgctgcttta gcatctagcc cgtttgtaga tgacattaat ttggcgcaag cggaaaagtt | 1260 |
| cctagccgtt agccggcgca caggccaaga taagctaggc aagcgcattg gagaatgttt | 1320 |
| tgcggaaggc cggcttgaag cgcttggcat caaagatcgc atgcgcgaat tcgtgcaagc | 1380 |
| gattgatgtg gcccaaaccg cgggccagcg gttcgcggcc aagctaaaga tattcggcat | 1440 |
| cagtcagatg cctgaagcca agcaatggaa caatgattcc gggctcactg tatgtatttt | 1500 |
| gccggattat tatgtcccgg aagaaaaccg cgcggaccag ctggttgttt tgcttcggcg | 1560 |
| cttacgcgag atcgcgtatt gcatgggaat tgaggatgaa gcaggatttg agcatctagg | 1620 |
| cattgacccct ggtgctcttt ccaatttttc caatggcaat ccaaagcgag gatttctcgg | 1680 |
| ccgcctgctc aataatgaca ttatagcgct ggcaaacaac atgtcagcca tgacgccgta | 1740 |
| ttgggaaggc agaaaaggcg agttgattga gcgccttgca tggcttaaac atcgcgctga | 1800 |

-continued

```
aggattgtat ttgaaagagc cacatttcgg caactcctgg gcagaccacc gcagcaggat    1860
tttcagtcgc attgcgggct ggcttccgg atgcgcgggc aagctcaaga ttgccaagga    1920
tcagatttca ggcgtgcgta cggatttgtt tctgctcaag cgccttctgg atgcggtacc    1980
gcaaagcgcg ccgtcgccgg actttattgc ttccatcagc gcgctggatc ggttttgga    2040 agcggcagaa agcagccagg atccggcaga acaggtacgc gctttgtacg cgtttcatct    2100
gaacgcgcct gcgtccgat ccatcgccaa caaggcggta cagaggtctg attcccagga    2160
gtggcttatc aaggaactgg atgctgtaga tcaccttgaa ttcaacaaag catttccgtt    2220 ttttcggat acaggaaaga aaagaagaa aggagcgaat agcaacggag cgccttctga    2280
agaagaatac acggaaacag aatccattca acaaccagaa gatgcagagc aggaagtgaa    2340
tggtcaagaa ggaaatggcg cttcaaagaa ccagaaaaag tttcagcgca ttcctcgatt    2400
tttcggggaa gggtcaagga gtgagtatcg aatttaaca gaagcgccgc aatattttga    2460
catgttctgc aataatatgc gcgcgatctt tatgcagcta gagagtcagc cgcgcaaggc    2520
gcctcgtgat ttcaaatgct ttctgcagaa tcgtttgcag aagctttaca agcaaacctt    2580
tctcaatgct cgcagtaata aatgccgcgc gcttctggaa tccgtcctta tttcatgggg    2640
agaattttat acttatggcg cgaatgaaaa aagtttcgt ctgcgccatg aagcgagcga    2700
gcgcagctcg gatccggact atgtggttca gcaggcattg gaaatcgcgc gccggctttt    2760
cttgttcgga tttgagtggc gcgattgctc tgctggagag cgcgtggatt tggttgaaat    2820
ccacaaaaaa gcaatctcat ttttgcttgc aatcactcag gccgaggttt cagttggttc    2880
ctataactgg cttgggaata gcaccgtgag ccggtatctt tcggttgctg gcacagacac    2940
attgtacggc actcaactgg aggagttttt gaacgccaca gtgctttcac agatgcgtgg    3000
gctggcgatt cggctttcat ctcaggagtt aaaagacgga tttgatgttc agttggagag    3060
ttcgtgccag gacaatctcc agcatctgct ggtgtatcgc gcttcgcgcg acttggctgc    3120
gtgcaaacgc gctacatgcc cggctgaatt ggatccgaaa attcttgttc tgccggttgg    3180
tgcgtttatc gcgagcgtaa tgaaaatgat tgagcgtggc gatgaaccat tagcaggcgc    3240
gtatttgcgt catcggccgc attcattcgg ctggcagata cgggttcgtg gagtggcgga    3300
agtaggcatg gatcagggca cagcgctagc attccagaag ccgactgaat cagagccgtt    3360
taaaataaag ccgttttccg ctcaatacgg cccagtactt tggcttaatt cttcatccta    3420
tagccagagc cagtatctgg atggattttt aagccagcca aagaattggt ctatgcgggt    3480
gctacctcaa gccggatcag tgcgcgtgga acagcgcgtt gctctgatat ggaatttgca    3540
ggcaggcaag atgcggctgg agcgctctgg agcgcgcgcg tttttcatgc cagtgccatt    3600
cagcttcagg ccgtctggtt caggagatga agcagtattg gcgccgaatc ggtacttggg    3660 acttttccg cattccggag gaatagaata cgcggtggtg gatgtattag attccgcggg    3720
tttcaaaatt cttgagcgcg gtacgattgc ggtaaatggc ttttcccaga agcgcggcga    3780
acgccaagag gaggcacaca gagaaaaaca gagacgcgga atttctgata taggccgcaa    3840
gaagccggtg caagctgaag ttgacgcagc caatgaattg caccgcaaat acaccgatgt    3900
tgccactcgt ttagggtgca gaattgtggt tcagtgggcg ccccagccaa agccgggcac    3960
agcgccgacc gcgcaaacag tatacgcgcg cgcagtgcgg accgaagcgc cgcgatctgg    4020
aaatcaagag gatcatgctc gtatgaaatc ctcttgggga tatacctggg gcacctattg    4080
ggagaagcgc aaaccagagg atattttggg catctcaacc caagtatact ggaccggcgg    4140
```

```
tataggcgag tcatgtcccg cagtcgcggt tgcgcttttg gggcacatta gggcaacatc    4200
cactcaaact gaatgggaaa agaggaggt  tgtattcggt cgactgaaga agttctttcc    4260
aagctagacg atcttttta  aaactgggct gctggctatc gtatggtcag tagctcttat    4320 tttttactt  gatatatggt attatctcaa taatatgcat ctcttcatag atacaacaga    4380 aaagaatca  tttgatattg ctttgattga tgatgagcgc gttatcaaaa agaagcgaat    4440
caaatcaatc cgccaacatt cggaaaagct tttgaaatca attgacgcgc ttttgttgtc    4500
cgcaaaatca tctctgaaag atatacaagg catcatcgcg gtaaaaggcc ctgggtcatt    4560
tacctcattg cgcattggaa tcgcgacagc caacgcgttg gcattcgctt tgggagtggg    4620
gattgctgga gttgacaaaa cagatgagtg gagtaagatt gtttcttcag cagatttgat    4680
ctttaaaaag caaaaaaaga acttaaatat cgtcataccc gaatacggca gagagccgga    4740
cattacctaa ataggagggt ttagaaatgt tattgctcat tttgattctc acaatagttt    4800
tgagcatcat tcttttgtgc ttttgcgcgt ttattctctg cataatcaca gaagatggca    4860
gggaaatgct tttgatgttt ggaataggca aatgccactt gaattattaa agtggctttt    4920
ttatttgtac aaaaacagtg tcagagcgcc gattcggcgc tctgacactg ttttacaaac    4980 cctcaccca  accctctccc gaatacagga gagggaattt ttatactgtg cataacttgt    5040
gcgcaaatag tgcctagata agggttgcgt aaaattacaa gagtggtgta taatatcatc    5100
atagtggtga ggagtgggga taagtggtgg agaacctcat caataataga taccaatgtt    5160
cataggagaa tacaaacata ctattgatac caaaggaaga atggcaatac ctgccaaatt    5220
tcggcaggat ttgaaaaagg gcgcaatcgt aacaaaagga ttggataatt gccttttgt     5280 atacactcaa gatgaatgga aaaaactcgt ggacaagcta tctaatcttc caatctcaca    5340
gcagaaaagc cgggcatttg ccagattaat gctagcagga gcaatggacg tgcaaattga    5400
ctcccaaggc agaattctta taccagaata tcttcgcaaa ttcgcgtcaa tcaagaaaga    5460
caccataata gcagggcttt acagtcggct tgaaatatgg gattcaaaag aatgggaaaa    5520
atacaaatca gccactgaaa agataagcac aaaaatagct gaagagctca cgctctaggc    5580
caaaaacaaa aataaaattc aaaacaatca cgagatcctt cgactccgcg agtacgcttc    5640
gctcagagcc tgccccgagt attccgaggg gatgacggtt gaaattcgga tggcataata    5700
attttatttt tggagctggt cttttagtag ctccattttt tatcccatga gcaaatcaga    5760
acacatacca gtattattaa acgaagtaat tgaaggtctt gacttgtcct ctaatgatac    5820
agtaatagac gccacagtag gcggagcagg acacgcgcaa gctattttag aaaaaaccgc    5880
gccatcaggc aagcttcttg gaattgattg ggacgcgaaa gcaatcgagc gcgcgcgaga    5940
acatctaaaa agatttagca accgaattat attaaaaaca ggaaattaca cagatataaa    6000
acaacttctc tatgaatcag gaattaataa ggttaatgct atattattgg acttgggctt    6060
atctcttgat caactcaaag attcctctag aggatttagc ttccaatctg aaggaccatt    6120
ggacatgagg ttttctgacc agatggacac aacagctttt gatattgtga cacctggcc     6180 agagaatgat ctggtacaaa tctttcaaga atacggtgaa gagaggcgcg ctgcacgtgc    6240
agcacgcaat atcgccactg cgcgcagtca cgcgccaatc aacaccgcaa aagatctggc    6300
agaattagtt atgcgcgggg ccggaaggcg aggcaaggtt catcccgcta cccgcatatt    6360
ccaggccctg cgcattgcta caaatcatga attagacaat gtcaaacaag cattgcctaa    6420
tatgattgat atgctttctt cagaaggaag attagcagtt atcacattcc attccttaga    6480
agaccgcatt gtgaagcagt atttcaagcc attggctaaa gaggaaaatc cgcgcattaa    6540
```

```
gctcatcaat aagaaagtaa taaagccaag ccgagaggag caagtgaaaa atccagcatc   6600
cagaagcgcg aaattgagaa tcgtggaaaa gatttaatca ttccaaaaac aaaaatagca   6660
tcacatgaca acatattcgc acaaaaaaac gccgtatctg tggcacgcat tttcaatatt   6720
gctgatttta gtattagtgg ttacttattt agtacagata aacagccaag cagaaacatc   6780
ttactctatt aaaggattag aagaaaaaaa gcaagaattg aatagtatta tagaagataa   6840
agaacttgaa gcagtttcag cgcgatcttt aaatggaatc gcgcttaagg caaagaaat    6900 gaatttgcag gatccaaagg atgttacatt cataaaaata ggattaagca cagttgccgt   6960
gagcgaagag ctttctccat aacatgactt catattcatc atcaaaaaag agcaattcag   7020
ctacgcgcgc gaaattcata attggcgcgg ttttttatttt tggcgttatt ttgatttacc   7080
gcttagctga tttacagctt atcaatactc aagaaattca ggcatctgcc gcgcgccagc   7140
agtcaacagt gcgcatcctt ccagctgaac gaggcaagat tttttacaag gagagaatag   7200
gtgatgaaga atttccagtc gcgactaata gatcatataa ccaggtattc attattccaa   7260
aagacataca ggatccaatc aaagccgcgg aaaagctatt gcctttggtt gagccatatg   7320
ggcttgatga agaaacatta ttattccgat taagcaagca aaatgacatt tacgagccat   7380
tagcgcataa attaacagat gaagagcttg agccatttat tgggcttgat ttaattgggc   7440
ttgaatcaga agatgaaaaa gctaggtttt acccggacgc tgatttgctc gcgcatataa   7500
ctgggtttgt cggggtttca gaacaaggca aggttggtca atatgggctt gagggatttt   7560
ttgaaaatga gctcaaagga aaggacgggc ttattgaggg caaaacagat atatttggca   7620
ggcttataca aacaggaact ttaaaacgca cccaaggcga gccaggagat gatttattat   7680
taaccataca gcgcactttg caggcatatg tgtgcagaaa attagatgaa aaaattgagc   7740
aaataagagc tgctggcgga tcagtaataa ttgtgaaccc agatactggc gctattctcg   7800
cgatgtgctc ttcaccatca tttgatccga ataattataa tcaagttgaa gatattagcg   7860
tatacatgaa tccagcagtg agctcaagct atgagccagg atcaattttc aagccattta   7920
caatggccgc ggcaattaat gagaaagcag ttactagcga tacaacatat attgatgagg   7980
gagtggaaga gatcggcaaa tacaaaatcc gcaattctga caacaaagcg cacggggaag   8040
ttaatatggt aactgtttta gatgaatcat tgaatactgg cgcgatttt tgtccagcgtc   8100 agattggaaa tgagaagttc aaagattatg ttgaaaaatt cggatttggc agaacaacag   8160
atattgaatt aggaaatgag gtttctggaa atatttcttc attgtataag gatggagata   8220
tttacgcggc aactggctcg tttggccaag gaattactgt tacgcctatt cagatggtaa   8280
tggcatatgc ggcgattgct aatggaggaa aattaatgca gccatatctt attgctcagc   8340
gacaaagaca ggataaaaact attgtaactg agccagttca aattgatgag ccgatttcag   8400
tgcaggcctc aactattata tctggaatgt tggtgagcgt ggtgcgtgct gggcacgcta   8460
tatctgctgg agtggaagga tattatattg ccggcaaaac tggaaccgcg caggtcgcgg   8520
aaggcggagg gtatggaagc aagaccattc attcatttgc cgggtttggg cctgttgatg   8580
agccagtgtt tgcaatgctt gtgaaattag attatcctca atacggcgca tgggcagcta   8640
atactgcggc tcctttgttt ggcgaattag ccaaatttat actacaatac tatgaaatac   8700
ctcctgatga ggcgatataa ataaaatatg aaaaaaataa taattacaat tttacaaact   8760
ctggccaaaa gagttatttta caaatataag cccaaagtgg tggctattac tggctcagtc   8820
ggaaaaaccg cgactaagga ggcagtgttt gctgtattga ataagaaatt gcaagtgcgc   8880
```

```
aagaatgaag gcaattttaa cacggaaatc gggttgcctt tgacaatcat ggcttgcaa    8940 aaatcaccag gcaaaaatcc attcaaatgg cttgcagtgt acgcgcgcgc tattggcctt    9000
ttaatcttta ggattgatta tccaaaagtt ttggttcttg aaatgggcgc tgataagcca    9060
ggagatattg ctgaattaat aagtattgct aagccagaca ttggcataat taccgcgatt    9120
agcgctgttc atacagagca gtttaatagt attgctggcg ttgtgcgtga aaaaggaaag    9180
ctctttcgcg ttgttgaaaa ggatggttgg attatcgtga ataacgaccg atctgaagtt    9240
tatgatatcg cgcaaaagtg cgacgcgaaa aaagtatata ttgggcagtg cgctgaatta    9300
tctgataaca ccccttttc agtatgcgcg tccgagattt cagtgagcat gtcagaagct    9360
caagaaaccg gcattgctgg cacttcattt aagcttcata ctgatggaaa ggttattccg    9420
gttttgatga aaggaattat tggggagcat tggacatatc ctgccatgta cgcggcagct    9480
gttgcgcgca ttcttggggt tcatatggtt gatgttactg agggtttgcg cgagattaat    9540
cctcaatcag gaaggatgcg agttttagct ggcattaaaa aaacaatttt aattgatgat    9600
acttataatt cttcgccaaa cgcggctaag agcgcggttg atactttagc gttattgcgt    9660
attggaaggg agaaatattg cgtgtttggg gatatgttgg agcttggttc tatatctgaa    9720
gaagagcatc aaaaattagg catgcttgtc gcgcgcgagg ggattgatta tctgatttgc    9780
gttggcgagc gcgcgcgcga cattgcgcgg ggcgctataa aagcaaagat gccgaaggat    9840
catgtgtttg aatttgataa tactaaagat gctgggctct ttatccaaaa gcgtttggag    9900
caaggggata tggttctgat taaaggttcg caaggcgtgc gcatggagcg cgtgaccaaa    9960
gagattatgg cgcatccgga aaaatcaaaa gaacttcttg tgcggcaaag taagaatgg    10020 ttgagtaagg cctagtgcgt atttttgata atttcctcca cttcttccgc attttctgca    10080
tccatcaatt tcacgcgcaa ttgctttgcc ccatcccagc cagaaacata ggccttgaaa    10140
tgttttttca ttacagcgaa tgatttgtgt ttgataagtt tttcgtagag tttggcgtgc    10200
tctattaaaa cgcgcaattt gttatctttg ctgggataga aaacggagaa aacggtgtca    10260
agagtcgttt tctgtaaaaa acgactcctg acaccgtttt ctttgaagaa ccacggattg    10320
ccgaaaattg cgcggccgat cataacgcca tcaacaccgg tctcccgggc ttttttgatgc    10380 gcatcgtcta aatacgaaac atctccattc ccgataataa gcgtcttggg gcgcgattttg    10440 tctcgcatct gaataacgct tttagccaaa tgccatttag caggaacgcg ggacattct    10500 tttctagtgc gccagtgaat cgtcaaagcc gcaatgtctg tcttcagaag aataggaatc    10560
caggtatcaa tttcattttt cgtatatcca atgcgcgttt taacagaaat tggcaatttt    10620
ggcgcgcctt ttttggctgc agcaatcaaa gcgcgcgcta atcagggtt tttcatcaaa    10680 ccagccccag cgccttgctt ttcaactttc cggtccgggc atcccatgtt aatatctaat    10740
ccatcaaaac ccaaatcctg aattatgcga gctgttttt tcatattatc tggatttgct    10800
gtaaatactt gcgcgacaat aggccgctct tcgcggaaaa atttaagatt tttaagaatt    10860
tcatctttgt cgccaagagc aatgccatcc gcggacacga attcagtcca cattacatct    10920
ggcttgccat actttgcgat aatccgccta aaagccgcgt ctgtcacgtc agacatagga    10980
gccaaacaga gaatggttt tttgagttgt tgccaaaaat tattcatgtc atcttgcgct    11040
tatttgtcat cccgaggctt aattatatat ttttagaaaa taggatgtgg taaacggatt    11100
atataagtgt aatagtaatg ccacacaagc cgagaggatc tcgtctttaa gagctcgaga    11160
tgacaataca aggcgagaga atctcgcgac taataactat gcttattatc aaataaatcc    11220
ttccaatcag aattgaattt gtttataagc aacaccttat ttctgtggct tagttttttt    11280
```

-continued

```
agcttctttt cgcgctcaat agcatacgag atattgtcaa agtgttcata atacaccagt    11340
ttatcagtat tgtattttga agtaaaccct ggtattttt tatttttatg ttcccaaatt    11400
cttctggata atgaattgca tactccggta taaaataccg tatgtcgtat gtttgttgtt    11460
atatatacat aaaagttata ttgattttgt cttggcatgt ttttgtttca taagatcctc    11520
tcggcctgca aggattttg ttttggactc catgattcgt ttaccacata ttcgatatta    11580
tgtagtattg taaggtctcg ggatgacagg taaaaggcat gggaatggca tctaaatctc    11640
ctccttttc tcatgcacat aattcatcca ttcctcaatc acttttataa acgccttgaa    11700
cggagcctct ataataaaat ccaacgcaaa atgaaaatg ttaatttgcg cgaaccgcgt    11760
ggacatccat ttgccagcat gcagaatcgg aattgtaaaa aacgcccata agccccggat    11820
aaatccttgc tttgggggca ggacaatcat ttcctgattt gactggcgga tgcggtacgc    11880
gaataaggaa acaaacgaga ggaacaagag aaagataaaa atgccgataa acgtgaaatt    11940
cagcgcgatc aaaatataaa tcatcaaacc gaacgaaatg ccaaatagca ttccgtacaa    12000
caaagtaaac accgcgcgca ggaaaaagct acgcttgcta gatttgcgca tctgaataat    12060
ttcgccttga ttttgataa tatgattat gccacttatc atttgattgg tgttttcttc     12120
atcaggcagt ttagttgaga gtgcgataag cgcgagcaag gcaggcggaa aaattaaatt    12180
aatagccaaa ggcatataat caattttgtg aatcaataaa taatcaacag gaatttccag    12240
aaccacggct aataaaaatt tagtaattac caaataaata atacttcgct taatgcctcg    12300
gtgtaaagaa gcgcgggatt tttcgtactg cttttggcag atggcgcgca ccctttgctc    12360
aaattcatgc ccggtgttca tatcagacca ggcttttcct ggatcctgcg caatcgcgtc    12420
ttgcaaaata gtgaaatatc caacgtattt cctgaacaaa ggagcgagtt tttcttttat    12480
aggcgagttt aaatcttgcg ttattgtaga gtgtatttca ttcaaatgct ctcctatttc    12540
ccgtataaga tcgtgatttg cgcgcgtcca ttctggataa taggtcaata gcaaatgata    12600
tccaatagtg tcattgtcgt ttttatatag aattcggcta gtggctatat aaatctgctt    12660
caaacgttct cgatcattaa tttcatcctc aattctaacg cgctcctgaa gatattcata    12720
catggcattg attgacgcgt gcattacata tggtggcata aggaattcgt caatttccgt    12780
tgctgctatg ccagagagcc aaaatgaaag agaagaagaa tcattgatat cttttatagg    12840
agcgtgacca agcaaggtga aatattttc aaatataata tcaagttctt ttattttcg     12900
ttcagggata gtattgttcg gaaggtaccg cgcgtggata agttctgaaa ttagattttc    12960
tgagatatta tttttatggc ctgatgaaat cattctacgc aaaatgcgct caatcgcgtt    13020
tctgcggatt aaatgttctt ctttatattc aaccgcgttg cgcatgcgct cgtatataaa    13080
agttgcctgt ccagcgcggg tggttatgga gattttggt tcggtcgggt ctgtatcttt    13140
tgagcgcgct tcttccctgg ccgcgcgcac gattcgctgg attgtttctg gtatttgcat    13200
ttctttatac tagctgattt tgcttgtttt ttcaattgtt ttataaaaaa agtgcccgga    13260
atgcaaattg cgcattccgg gcttggggag acagggcagg ggatgccctg tttggggctt    13320
actgccggtc ggtcagatca cgggctacta ccgccgcaat cctcgccacc gcccaggcag    13380
taacgagacg actctttttt tacctgattg acgaccgtac cgtcgagcag gacgttatcg    13440
ccgagcagat tcgctgtatt gatgtccgta gccgcggtag ccgcgatagt cgtggtcgtc    13500
gtcgtggttt ccgtagtggc tgtgccgacc gcgctgtttt cgccgccctc ttttgtcatc    13560
cgaatgacat catcgccatt cagagtcgtt tcctcgctga ccgggttgtt ggtcccgcag    13620
```

-continued

```
ccgatcattc cgatcagggc gaccagcgcg atacagaaga aaatcatgaa atacttcatc    13680
gggtgctcct ttttatgagg tttttggaaa acgatatcac gctttgtatt attcacctcc    13740
cttccaaagc aagcgcaata tcggtctttt ttactatttt aagaacggac gagcatctta    13800
tactatttta aaataatgt caagagtgtt aacaaataca aaaaattgac tcatataaaa     13860
acggtgtcag gagtcgttt                                                 13879
```

<210> SEQ ID NO 26
<211> LENGTH: 7532
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2669)..(2692)
<223> OTHER INFORMATION: n is a, c, g, or t

<400> SEQUENCE: 26

```
tacctaatcc tgggcgtctt tggtgtatta tgcacttgcg gttagaatac acccgaacat      60
aattgacaaa gaccataaaa tgtcttatta tcctttaga aaaatcgtgt tcatttataa      120
tatatacata ccccaattcc aaggatttct tgactggcag cgggcttggt atcctgcgaa     180
acacagccag tttgggaaac ctgggtcttt attttttaaag acacaggaat tcccgcgtct    240
tttgccttgg aacaccaacc acctattgcg ccttttttct catttttagca aaagtggctg    300 tctagacctt caggtggaaa ggtgagagta agacattgg gcctgcacga ttcatgggcc      360
ggtctagacc ttcaggtgga aaggtgagag taaagactct accgcgtcca gcactatctt    420
ggtccgtcta gacatttaga tggaaaggcg agagtaaaga tgcgcgaaaag acggctacat   480 tgttccacaa gcagaaaagg attagccgcc tactgcttga acatccgcag tatttaaccc    540 atttttcccaa aggaggaaaa tcatgggtac gcagattatc aagcggatag accttgactg   600
gcagtcaagt tttccgcacg ccaagatgct ggtgaatcag gaagcatcat ttaaccacat    660
tgcagagtcc ggactcacgg cgctcataga agcgccgacc ggatccggaa aaaccgcgac    720
tggctatacc tttctttcgg ccatagcccct tcgcgcgcgc aagagtccgc aatttaaggg   780
ccggctcgtg tatgttgctc cgaataaagc attagtcggg caggtgcaga acatgcatcc    840
agatgtgaaa gtcgcgcttg gtcgcaacga gcatacatgc tcgtattacg atggaattca    900
tcaagcagac gaagtgccgt gttcgttttt ggttcgctcc ggccggtgtg gccactatgt    960
gaatcaagaa accggcgcaa cacttgaatt tggagctgaa ccatgttcgt attatcagca   1020
aatctatgag gcaaagcgcg gcatcggaat tctggcatgc actgacgcgt tttggctgtt   1080
cacgcatttg tttaatccaa agcagtggcc tcagcccatg ggtttggtat tggacgaggt   1140
tgaccgcttg gctgatattg ttcgcaggtg cttgtcatac gaaatttctg attggcgcat   1200
tgagcgcgcc attaatttgc ttgaaaaagt cggttcagtt caggtgcagt atctctcgtc   1260 tttttttgcgc accttgaatc gggtggtatc aaaaaagccg ccctggagc ccatttttgct   1320 ggatgatgag gagattcgcc aactgtttga aaaagtgggg cgcatcagcg cggatgtcat    1380
caaatccgat ttggacgccg cgattgcgag caacaaggtt gacccctatgg ctgagcgcga    1440 aatccttaag cagatagaaa cactttgctt tgacatcagc cggtatgtgc ggagtttggg    1500
atacgcgctt ccgaatcgca gaggcaaggg tgatgaacgc aagcgcgatg ctcctctttc    1560
gtacgcgtac gcgtatcata atccgagcg cgacgctggg gcgcatgtgc agaacaaagt    1620
tgtggtgtgt tcctattggg tgcggcctct tatccgcaag ctcttggaa agaacacgct     1680
```

```
cgcgtattca gcgtttgtcg gggataaaac gattttggat tatgaggctg gagttgattt    1740
tccattaatc tctctgcggt cccaatttcc ggcgagcaat gcgcgattgt atgtgccgag    1800
cgattctcca aatttggcat ataatgagca ggatgtcggt gacatggcta agactttgcg    1860
ccatattgcc atatcaactc ggcggtttgc cgagcgcggc tttcgttctc tcttgctgac    1920
tgtttcaaat agagagcgtg aattgctgta cgtcgcgtgc gcggaactga aagggctgga    1980
tgctataagt tatggcagtg gcgttactgc gcgcgcggcc gcggatagat tcaaagaagg    2040
agaaggggac gctcttattg gcgttttgtc gcattatggc actgggctgg atttgccagg    2100
caagattgct aacattgttt ttctcctgcg gccgaatttt cctccaccaa aagatcctat    2160
ggcacagttt gagattcgcc gggccgagcg catcaaaaag tcgcattggc ccgtgtggta    2220
ctggcgcgcg taccgagagg ctctgaatgc ccagggacgc ccgatacgaa gcgccgatga    2280 caaagggggtc gcgttcttta tctcccagca attcaagaag cgtttattca acatttttgcc   2340 ggagcatctt gagagcgcat atcggagccg cctcacatgg gaccagtgcg agaaagacgc    2400
gctgaaactg tttgaggaat aggggtatta tttcgttgtt tttatggccc ggatggtgtt    2460
ttttatacat catccgggtt tttatgttga tttgatgcga taatcatgat ttttgcgtgg    2520
tattgacaaa cattataaaa aacgctatta ccgcgtaca aaacctataa atcgttcatt    2580
tataatatat atacccca attccaagga tttcttgact ggcagcgggc ttggtatcct    2640
gcgaaacaca gccagtttgg gaaacctgnn nnnnnnnnnn nnnnnnnnnn nngccagttt    2700
gggaaacctg ggtctttatt tttaaagaca caggaattcc cgcgtctttt gccttggaac    2760
accaaccacc tattgcgtct ttttcgctca ttttagcaaa agtggctgtc tagacataca    2820 ggtgaaagg tgagagtaaa gacatggcct gaatagcgtc ctcgtcctcg tctagacata    2880
caggtggaaa ggtgagagta aagaccggag cactcatcct ctcactctat tttgtctaga    2940
catacaggtg gaaggtgag agtaaagaca aaccgtgcca cactaaaccg atgagtctag    3000
acatacaggt ggaaaggtga gagtaaagac tcaagtaact acctgttctt tcacaagtct    3060
agacatacag gtggaaaggt gagagtaaag actcaagtaa ctacctgttc tttcacaagt    3120
ctagacctgc aggtggtaag gtgagagtaa agactcaagt aactacctgt tctttcacaa    3180
gtctagacct gcaggtggta aggtgagagt aaagactttt atcctcctct ctatgcttct    3240
gagtctagac atttaggtgg aaaggtgaga gtaaagactt gtggagatcc atgaacttcg    3300
gcagtctaga cctgcaggtg gaaaggtgag agtaaagacg tccttcacac gatcttcctc    3360
tgttagtcta ggcctgcagg tggaaaggtg agagtaaaga cgcataagcg taattgaagc    3420
tctctccggt ccagaccttg tcgcgcttgt gttgcgacaa aggcggagtc cgcaataagt    3480 tcttttaca atgttttttc cataaaaccg atacaatcaa gtatcggttt tgctttttttt   3540 atgaaaatat gttatgctat gtgctcaaat aaaaatatca ataaaatagc gttttttga    3600 taatttatcg ctaaaattat acataatcac gcaacattgc cattctcaca caggagaaaa    3660
gtcatggcag aaagcaagca gatgcaatgc cgcaagtgcg gcgcaagcat gaagtatgaa    3720
gtaattggat tgggcaagaa gtcatgcaga tatatgtgcc cagattgcgg caatcacacc    3780
agcgcgcgca agattcagaa caagaaaaag cgcgacaaaa agtatggatc cgcaagcaaa    3840
gcgcagagcc agaggatagc tgtggctggc gcgctttatc cagacaaaaa agtgcagacc    3900
ataaagacct acaaataccc agcggatctg aatggcgaag ttcatgacag aggcgtcgca    3960
gagaagattg agcaggcgat tcaggaagat gagatcggcc tgcttggccc gtccagcgaa    4020
```

```
tacgcttgct ggattgcttc acaaaaacaa agcgagccgt attcagttgt agatttttgg      4080
tttgacgcgg tgtgcgcagg cggagtattc gcgtattctg gcgcgcgcct gctttccaca      4140
gtcctccagt tgagtggcga ggaaagcgtt ttgcgcgctg ctttagcatc tagcccgttt      4200
gtagatgaca ttaatttggc gcaagcggaa aagttcctag ccgttagccg cgcacaggc       4260 caagataagc taggcaagcg cattggagaa tgtttcgcgg aaggccggct tgaagcgctt      4320
ggcatcaaag atcgcatgcg cgaattcgtg caagcgattg atgtggccca accgcgggc       4380 cagcggttcg cggccaagct aaagatattc ggcatcagtc agatgcctga agccaagcaa      4440
tggaacaatg attccgggct cactgtatgt attttgccgg attattatgt cccggaagaa      4500
aaccgcgcgg accagctggt tgttttgctt cggcgcttac gcgagatcgc gtattgcatg      4560
ggaattgagg atgaagcagg atttgagcat ctaggcattg accctggcgc tctttccaat      4620
ttttccaatg gcaatccaaa gcgaggattt ctcggccgcc tgctcaataa tgacattata      4680
gcgctggcaa acaacatgtc agccatgacg ccgtattggg aaggcagaaa aggcgagttg      4740
attgagcgcc ttgcatggct aaacatcgc gctgaaggat tgtatttgaa agagccacat       4800
ttcggcaact cctgggcaga ccaccgcagc aggattttca gtcgcattgc gggctggctt      4860
tccggatgcg cgggcaagct caagattgcc aaggatcaga tttcaggcgt gcgtacggat      4920
ttgtttctgc tcaagcgcct tctggatgcg gtaccgcaaa gcgcgccgtc gccggacttt      4980
attgcttcca tcagcgcgct ggatcggttt ttggaagcgg cagaaagcag ccaggatccg      5040
gcagaacagg tacgcgcttt gtacgcgttt catctgaacg cgcctgcggt ccgatccatc      5100
gccaacaagg cggtacagag gtctgattcc caggagtggc ttatcaagga actggatgct      5160
gtagatcacc ttgaattcaa caaagcattt ccgttttttt cggatacagg aaagaaaaag      5220
aagaaaggag cgaatagcaa cggagcgcct tctgaagaag aatacacgga aacagaatcc      5280
attcaacaac cagaagatgc agagcaggaa gtgaatggtc aagaaggaaa tggcgcttca      5340
aagaaccaga aaaagtttca gcgcattcct cgattttttcg gggaagggtc aaggagtgag     5400
tatcgaattt taacagaagc gccgcaatat tttgacatgt tctgcaataa tatgcgcgcg      5460
atctttatgc agctagagag tcagccgcgc aaggcgcctc gtgatttcaa atgctttctg      5520
cagaatcgtt tgcagaagct ttacaagcaa acctttctca atgctcgcag taataaatgc      5580
cgcgcgcttc tggaatccgt ccttatttca tggggagaat tttatactta tggcgcgaat      5640
gaaaagaagt ttcgtctgcg ccatgaagcg agcgagcgca gctcggatcc ggactatgtg      5700
gttcagcagg cattggaaat cgcgcgccgg ctttttcttgt tcggatttga gtggcgcgat      5760
tgctctgctg gagagcgcgt ggatttggtt gaaatccaca aaaaagcaat ctcatttttg      5820
cttgcaatca ctcaggccga ggtttcagtt ggttcctata actggcttgg aatagcacc       5880 gtgagccggt atctttcggt tgctggcaca gacacattgt acggcactca actggaggag      5940
tttttgaacg ccacagtgct ttcacagatg cgtgggctgg cgattcggct ttcatctcag      6000
gagttaaaag acggatttga tgttcagttg gagagttcgt gccaggacaa tctccagcat      6060
ctgctggtgt atcgcgcttc gcgcgacttg gctgcgtgca acgcgctac atgcccggct       6120 gaattggatc cgaaaattct tgttctgccg gctggtgcgt ttatcgcgag cgtaatgaaa      6180
atgattgagc gtggcgatga accattagca ggcgcgtatt tgcgtcatcg gccgcattca      6240
ttcggctggc agatacgggt tcgtggagtg gcggaagtag gcatggatca gggcacagcg      6300
ctagcattcc agaagccgac tgaatcagag ccgtttaaaa taaagccgtt ttccgctcaa      6360
tacggcccag tactttggct taattcttca tcctatagcc agagccagta tctggatgga      6420
```

```
tttttaagcc agccaaagaa ttggtctatg cgggtgctac ctcaagccgg atcagtgcgc    6480
gtggaacagc gcgttgctct gatatggaat ttgcaggcag gcaagatgcg gctggagcgc    6540
tctggagcgc gcgcgttttt catgccagtg ccattcagct tcaggccgtc tggttcagga    6600
gatgaagcag tattggcgcc gaatcggtac ttgggacttt ttccgcattc cggaggaata    6660
gaatacgcgg tggtggatgt attagattcc gcgggtttca aaattcttga gcgcggtacg    6720
attgcggtaa atggcttttc ccagaagcgc ggcgaacgcc aagaggaggc acacagagaa    6780
aaacagagac gcggaatttc tgatataggc cgcaagaagc cggtgcaagc tgaagttgac    6840
gcagccaatg aattgcaccg caaatacacc gatgttgcca ctcgtttagg gtgcagaatt    6900
gtggttcagt gggcgcccca gccaaagccg ggcacagcgc cgaccgcgca aacagtatac    6960
gcgcgcgcag tgcggaccga agcgccgcga tctggaaatc aagaggatca tgctcgtatg    7020
aaatcctctt ggggatatac ctggagcacc tattgggaga agcgcaaacc agaggatatt    7080
ttgggcatct caacccaagt atactggacc ggcggtatag gcgagtcatg tcccgcagtc    7140
gcggttgcgc ttttggggca cattagggca acatccactc aaactgaatg ggaaaaagag    7200
gaggttgtat tcggtcgact gaagaagttc tttccaagct agacgatctt tttaaaaact    7260
gggctgctgg ctatcgtatg gtcagtagct cttattttt tacttgatat atggtattat    7320
ctcaataata tgcatctctt catagataca acagaaaaag aatcatttga tattgctttg    7380
attgatgatg agcgcgttat caaaaagaag cgaatcaaat caatccgcca acattcggaa    7440
aagcttttga aatcaattga cgcgcttttg ttgtccgcaa aatcatctct gaaagatata    7500
caaggcatca tcgcggtaaa aggccctggg tc                                  7532

<210> SEQ ID NO 27
<211> LENGTH: 16262
<212> TYPE: DNA
<213> ORGANISM: Artificial sequence
<220> FEATURE:
<223> OTHER INFORMATION: Synthetic sequence

<400> SEQUENCE: 27
cggaaaggcg gcccagaaac gggttgacca aattttgtgt tcagtggtga tgatggcgat      60
gycgatgtcg ctgcttacgc gggcgttgtg caggccgatg gagtcggaaa tcagaatggc     120
ctggacgtgg gggagggtgg ccagccagcg caggtaatga tgccgtttgc gcagtttggt     180
ttcggtgagg ccgtagcggg ccaggcgcag ggggacgagg tgggagcggt ttttgaggtg     240
ataaaagcca tcggtgtgag tgatgtgtgg gtgagtggcg agggcggcag tgagttcggc     300
gggcgtggtg gtgtgttgcc acagccagcg ctggagttca ccggcggtca gcggaaattc     360
catgaggtca aagtagctca tggtggcggt gatggcgtgc tcgagttggg ggcgacaagc     420
gggtttcatg ctcctattat agcagatttt cagagttgga ttttgctgt ttttcttgg      480 ccggagtacc cgtttttta ttgtttgaaa aatcagggct taaaaatttt aggtgagagt      540 cttttttgcta tatccaagaa gaaattttgc catatttttt ggtcaattt tattttcatt    600 cttggtaggt cttttaattc ggtcactttt aatagttggc ttcccatttg tactgggtcg     660
atgtgccagt caaattttat cttggccttt tttatcagat catcgaatgt ccattctttt     720
ttttggagaa tacaatacag gtctataaaa tcccgtgaac gtggttttg atacatggta     780 aatactttgt tgacggcaat gtctaacagg ctgtcaattt tcagaccgtt tgttttcaag     840
cccttttgta taatcggaaa ggggtagtag gtaaattccg ttttgataac atccttgtcg     900
```

```
atatggataa aaaacagatt ccggttgaag ctctgctgaa atctatctt tttaaatttt    960
acctttttct gtatttttt gagtatagta aaaatatccg tagaatcgaa ttcttttttcc   1020
gaaaagaaat ccaaatcttc ggataaccga tgatgcagat aaaattctgc gagagcggtg   1080
ccaccggaaa gataaaattt ttcccggatg agttttcctt gtgatagctg ctgaaggaga   1140
gcgctttggt tggttgtcag gattgttggc cccataggag aaaagataaa aatttttct    1200
tacctgggtc gaggtccagc ctatcccagt acttttcag ttgacttcgc ttgatttttt    1260
ttccacccaa gccaaaattt accatctgtt cgagtttcca gatagtgtat ttttctttat   1320
tttttttag ctctgtgagg tcaatattcc aattgtacat ggctgtattt tagcatatag    1380
cagcttaaat ttcaatttta ttttagccaa aatagtagaa tggtggcggt gttagatgaa   1440
tatttcgtag ttgtcttttg atatcacctg gaatttgcg tcttggtagg catcgctgaa    1500
tgcctttggc gctcgggctg attttttccc ccatttgaat tcaaatgccc tgagttttcc   1560
attttttct tccaagtaat caatttctgc cttttggtgc gtgcgccaga aatatctgtt    1620
taccgaattt tcagtatttt ccaatttttt cattctttct acgaggagaa aattttccca   1680
gagcccccg acatcttcgc gtaaggagag aggattgaga ttattaatga gtgcgttgcg    1740
aatgccgaga tcatagaagt aaattttccg cagtttttg agttcgttgc gaatgtttcg    1800
actgtatggt ttcaaagtaa aaacaatgaa agccttctca agaatgccta tataattagc   1860
cacgttttt tgatcgatat tgagcaggtt ggacagttcc cggtaggaaa cttctttacc    1920
tatctggagt gccagcgcct gcaggagttt gtcgagtact tcaggattgc ggatgttctg   1980
aaatgccaga atgtctttat ataaataact tctggtgata ttgcgcagca attcctcagc   2040
ttccgatgat ttgaggacaa tttccggata cataccgaaa atcattcttt gttccagtgt   2100
tcttttttct tcctgtatat tctgtatctg cctgagttct tccagtgaaa agggatagag   2160
gataaattca tattttcttc ctgtgagcgg ctcaacgatc tgattagcga gatcaaaaga   2220
agatgatccg gtggcgataa tctgcatttc cggaaagttg tcaacaagta gtttcagtgt   2280
cagtccgata ttttttactc tttgcgcctc gtcaaggaag ataatgtttg catctcccag   2340
ataggccttg agttcggtcg aagttttgtc ggtaagagcg gtgcgaacgt ccggttcatc   2400
acagttgagg tagcgagagg tgtggctcgc aagcttttcc tcaagggctt tgaggatagt   2460
tgtcttacct acctgtctgg cgccatagat aataataacc ttttttttga aaaggtgttt   2520
ttcaataata ggctgaaggt ctctgctaat ccgcatagta tatatgattt agatgattat   2580
actcctctca ttatatatta aaatgcggat ttagtcaatg cattctacta taaatgcttt   2640
atattagcca aaatgtcaga aaattgatat ttttgaccat ttttactata tttcggacac   2700
cttattttgg ttctcgattc atgtatcact gcccgctgta ggttgcgggc caattttaa    2760
aggagaattt tatgatgcct gttgtgctct ttataaaatc gttttttttg attttccata   2820
gttctctctt gtagggactt gaaataaaat gttttttata ctactatagg cctagttcct   2880
taacaatatt ttgcttactt taaagcgaaa ataggtaagg cacacctata ccataaggat   2940
ttaaagactc tttggcgaca gctttccacc gaccctgagt agttaaagac tgacgtatca   3000
tgtcataaca ccaacatttc tagatataaa acgcgacag ctttcaggcg ataccgacgt    3060
ttctagacat aaagactttg gataaaccat aatgcaccga cgttcctcga tataaagacc   3120
cgttgtggtc ccaaaattca ccgacatttt aagaggtaaa gacaagtgca cctgagtcgc   3180
tgcaccgaca ttcccgatat aaagactgtc gctcaacccc aaaacaccga cattcccgat   3240
ataaagactc gccctagatc ttcttgcacc gactgtataa ggaataaaga cgtccgacca   3300
```

```
cgtgcaccac accgactcgt gtgaacctaa agactcaccg ccgcactacc ctcaccgact    3360
atatcaaacc taaagattgg taacttgttt gtctgacacc gactgtatca gagataaaga    3420
ctgttttcca tgcgttgcgc accgacgttc ctagatataa agactatcat tatcggggaa    3480
accgccgact gtactagata taaagacccg tcgctttgtt tgaacgccga cattcttaag    3540
aaataaagac gtggtaagag tagtgtttca ccgacattcc tttatgtaaa gacaatgaat    3600 agtcttttc acaccgactg tgaatgtatg aaatctaaag acctgaaagt gcaatgcaaa    3660
tgctgacagt gttagtctaa agacaaagta ggaatcagga tccgccgact aaataaaact    3720
taaagacaag ccagatatcc aggccacacc gacgtcccta gatgtaaaga ctagtgactc    3780
catgctatgc accgacattc cgaggcctaa agacagagag gctaacattt gtgcaccgac    3840
ccttcaagag gtaaagacat agggaacacg ctgaatcacc gacgttccta ggtatacaga    3900
cgaaatgcaa tgaaaaacgt caccgacatt tcaagacgta aagacccaag aatctttgcc    3960
cgtccccgac attccaagac gtaaagacta gccaaaacct ccagaccccc gacattccaa    4020
gacataaaga caagcgctcc aacatgtgtc accgacatta ttccgcccca gcatcgatca    4080
ttttgacttg gaaagagaca ttcttctttc caagttttta ttttgagcaa aatttgactt    4140
tttattggtt atccttattt actatgggtg cttagtgcat cgaaaggtgg gctaagcaca    4200
acaaaagtgt tcttttttatc ttaaacttga ggttttagac ctcatcaacc caaaagggt    4260 gtaacatcat gaaacatcag aaacatcaag aaaatgcagt ctctgacgaa acatctaacc    4320
cttccgccga gccatggatt tttgattttg agaaatggtg gccctacgat acgtatccca    4380
ccatgcatca taatcaatcc gaggctttca aattaattcg aagtgtccta cggaaagaag    4440
gtgtgggtaa aaccatcctt gaacttccta ccggatctgg gaagacggtc attgggatcg    4500
tgtatctcct tactttgcat cacaagatgc aggaaggcga gattcctaca gctccgctgt    4560
tttacatcgt gcctaataag gcgctggtaa agcaggtgtg tgaaatgttc ccagatatca    4620
cctttggtgt gtatggccgg aatgaatatg attgtctgta ttaccagccg aaagaaacgt    4680
ttacagccga tcagattccc tgtttggttc taccatgcaa gcatcgggtg aaccaggatg    4740
atggaactac gcaagaatct ggtgctgagc catgtccgta ttatttggtg aagtataagg    4800
cgaagcagct gactcagaag gctcgaatca ttgtctgtac cgcttctttt tatcttttca    4860
ctcaactcat tcatgagtgg ccgctgcctg gaggactggt tattgacgaa acggatgagc    4920
tggctgaaat ttttcggcgg gcgctctcca cgaaagtcag tgattggcac ctgagtcagt    4980
gcgtcacgat gatgcggcaa agtgggatgg atggtgaagc ggatctcatg cagaaatttt    5040
atgacgccgt ggttagaatt gtcggagtca agtctcctca aaagcctacg cttttgaaga    5100
aacacgaaat cagtgagctc ctcgaggtag ttcctcagtt cgacaccaga aaactgaaaa    5160
ggcgtataaa tgccctcatc aaagacggaa agattgatgc agagaattcg cgtgaagtgc    5220
tgaatcagct gactgtggtt gccaatgatc tgaaacgata cgccgtttcg cttgcctatg    5280
ccttgcctga gggtgaccgt agggccctta ttacctctac tgcatattat gaaggaccgg    5340
atgatcttcc agggaagaag aaagttcggt gtgtcattaa tatctgcaat tggtacatgc    5400
cgcctctcat taggcggatt ctctcgcctc ggaccctggc atatacagcc actatcggtg    5460
agtatagtga ctttgcctac gataccggaa ttgaaggttc gttttatacc atgaactctg    5520
attttccggt ggagaactcc cgtatcttca tgcccgatga cgttgccaac ttggctgtga    5580
aatcggtcaa accaggcgac aaagatcgga tgatgcgtct gattgctaag tcagctcgtg    5640
```

```
aatttgcgga tcaaggtcat cggagtctgg tggtggtcat ttccaatgag gagcgttcaa    5700
ggtttctgga aattgttgaa gaatacagtc tcaaaatgct cacctatgga aatggtgttt    5760
cggcgcgcga ggctattgca aggtttcagg ctggtgaagg ggaggtgttt gtgggaacgg    5820
cagccaactg ttctcatggc ctgaacttcg ataagcagac tgctccggtg attttttttc    5880
tgcggcctgg ttatccggtg cagggagatc cactcgcaga tttcgaagaa gagcggatgg    5940
gaaataagag gtggggtgtt tggacctggc gggttatgcg gcagttactt caggtgcgtg    6000
gccggaatat ccgcagtccg gaggatttgg gagttatttt cctgatgtca ggccagttta    6060
aacgtttcgc agggaaggcg attccggggt ggcttatcaa agcctatatc tccggcaaga    6120
aattcagggc ctgtgtgtca gaggccaaaa agctcctgaa aaagtcttaa ttaagccaaa    6180
aaaattgttt ttttgtctct gtccttgaca atataattga actttgctaa gttagggtcc    6240
cctgttagag gaaacagcag caaagggaag tctgagcgcg agaggcctta gtctttagag    6300
ttcttaataa gaacttttct gggcccaaag tgcgctttag tctttattcc ctgagctctg    6360
tctactttga tggggccttt ttttattcaa atttttttat tttcgctacg tcttgacaaa    6420
aatatagatg tatactatat ttcgcccgag gtaataaaga aaatagcggt aaagctataa    6480
gattttatta tttcatttat aagaactttg aaaaccgaca ttatcaaaaa ccatgcaaag    6540
ccctttagat gagggcagga ggttgaaaaa atgaagagaa ttctgaacag tctgaaagtt    6600
gctgccttga gacttctgtt tcaggcaaa ggttctgaat tagtgaagac agtcaaatat    6660
ccattggttt ccccggttca aggcgcggtt gaagaacttg ctgaagcaat tcggcacgac    6720
aacctgcacc tttttgggca gaaggaaata gtggatctta tggagaaaga cgaaggaacc    6780
caggtgtatt cggttgtgga ttttggttg ataccctgc gtttagggat gttttctca     6840
ccatcagcga atgcgttgaa aatcacgctg ggaaaattca attctgatca ggtttcacct    6900
tttcgtaagg ttttggagca gtcaccttt tttcttgcgg gtcgcttgaa ggttgaacct    6960
gcggaaagga tactttctgt tgaaatcaga aagattggta aaagagaaaa cagagttgag    7020
aactatgccg ccgatgtgga gacatgcttc attggtcagc tttcttcaga tgagaaacag    7080
agtatccaga agctggcaaa tgatatctgg gatagcaagg atcatgagga acagagaatg    7140
ttgaaggcgg attttttttgc tatacctctt ataaagacc ccaaagctgt cacagaagaa    7200
gatcctgaaa atgaaacggc gggaaaacag aaaccgcttg aattatgtgt tgtcttgtt    7260
cctgagttgt atacccgagg tttcggctcc attgctgatt ttctggttca gcgacttacc    7320
ttgctgcgtg acaaaatgag taccgacacg gcggaagatt gcctcgagta tgttggcatt    7380
gaggaagaaa aaggcaatgg aatgaattcc ttgctcggca ctttttttgaa gaacctgcag    7440
ggtgatggtt ttgaacagat ttttcagttt atgcttgggt cttatgttgg ctggcagggg    7500
aaggaagatg tactgcgcga acgattggat ttgctggccg aaaaagtcaa aagattacca    7560
aagccaaaat tgccggaga atggagtggt catcgtatgt ttctccatgg tcagctgaaa    7620
agctggtcgt cgaatttctt ccgtcttttt aatgagacgc gggaacttct ggaaagtatc    7680
aagagtgata ttcaacatgc caccatgctc attagctatg tggaagagaa aggaggctat    7740
catccacagc tgttgagtca gtatcggaag ttaatggaac aattaccggc gttgcggact    7800
aaggttttgg atcctgagat tgagatgacg catatgtccg aggctgttcg aagttacatt    7860
atgatacaca gtctgtagc gggatttctg ccggatttac tcgagtcttt ggatcgagat    7920
aaggataggg aattttttgct ttccatcttt cctcgtattc caaagataga taagaagacg    7980
aaagagatcg ttgcatggga gctaccgggc gagccagagg aaggctattt gttcacagca    8040
```

```
aacaaccttt tccggaattt tcttgagaat ccgaaacatg tgccacgatt tatggcagag   8100
aggattcccg aggattggac gcgtttgcgc tcggcccctg tgtggtttga tgggatggtg   8160
aagcaatggc agaaggtggt gaatcagttg gttgaatctc caggcgccct ttatcagttc   8220
aatgaaagtt ttttgcgtca aagactgcaa gcaatgctta cggtctataa gcgggatctc   8280
cagactgaga agtttctgaa gctgctggct gatgtctgtc gtccactcgt tgattttttc   8340
ggacttggag gaaatgatat tatcttcaag tcatgtcagg atccaagaaa gcaatggcag   8400
actgttattc cactcagtgt cccagcggat gtttatacag catgtgaagg cttggctatt   8460
cgtctccgcg aaactcttgg attcgaatgg aaaaatctga aggacacga gcgggaagat   8520 tttttacggc tgcatcagtt gctgggaaat ctgctgttct ggatcaggga tgcgaaactt   8580
gtcgtgaagc tggaagactg gatgaacaat ccttgtgttc aggagtatgt ggaagcacga   8640
aaagccattg atcttcccct tggagatttc ggatttgagg tgccgatttt tctcaatggc   8700
tatctctttt cggaactgcg ccagctgaa ttgttgctga ggcgtaagtc ggtgatgacg   8760
tcttacagcg tcaaaacgac aggctcgcca aataggctct tccagttggt ttacctacct   8820
ctaaacccct cagatccgga aaagaaaaat tccaacaact ttcaggagcg cctcgataca   8880
cctaccggtt tgtcgcgtcg ttttctggat cttacgctgg atgcatttgc tggcaaactc   8940
ttgacggatc cggtaactca ggaactgaag acgatggccg gttttacga tcatctcttt   9000 ggcttcaagt tgccgtgtaa actggcggcg atgagtaacc atccaggatc ctcttccaaa   9060
atggtggttc tggcaaaacc aaagaagggt gttgctagta acatcggctt tgaacctatt   9120
cccgatcctg ctcatcctgt gttccgggtg agaagttcct ggccggagtt gaagtacctg   9180
gaggggttgt tgtatcttcc cgaagataca ccactgacca ttgaactggc ggaaacgtcg   9240
gtcagttgtc agtctgtgag ttcagtcgct ttcgatttga agaatctgac gactatcttg   9300
ggtcgtgttg gtgaattcag ggtgacggca gatcaaccct tcaagctgac gcccattatt   9360
cctgagaaag aggaatcctt catcgggaag acctacctcg gtcttgatgc tggagagcga   9420
tctggcgttg gtttcgcgat tgtgacggtt gacggcgatg ggtatgaggt gcagaggttg   9480
ggtgtgcatg aagatactca gcttatggcg cttcagcaag tcgccagcaa gtctcttaag   9540
gagccggttt tccagccact ccgtaagggc acatttcgtc agcaggagcg cattcgcaaa   9600
agcctccgcg gttgctactg gaatttctat catgcattga tgatcaagta ccgagctaaa   9660
gttgtgcatg aggaatcggt gggttcatcc ggtctggtgg ggcagtggct gcgtgcattt   9720
cagaaggatc tcaaaaaggc tgatgttctg cccaagaagg gtggaaaaaa tggtgtagac   9780
aaaaaaaaga gagaaagcag cgctcaggat accttatggg gaggagcttt ctcgaagaag   9840
gaagagcagc agatagcctt tgaggttcag gcagctggat caagccagtt ttgtctgaag   9900
tgtggttggt ggtttcagtt ggggatgcgg gaagtaaatc gtgtgcagga gagtggcgtg   9960
gtgctggact ggaaccggtc cattgtaacc ttcctcatcg aatcctcagg agaaaaggta  10020
tatggtttca gtcctcagca actggaaaaa ggctttcgtc ctgacatcga aacgttcaaa  10080
aaaatggtaa gggattttat gagacccccc atgtttgatc gcaaaggtcg gccggccgcg  10140
gcgtatgaaa gattcgtact gggacgtcgt caccgtcgtt atcgctttga taagttttt   10200 gaagagagat ttggtcgcag tgctctttc atctgcccgc gggtcgggtg tgggaatttc  10260
gatcactcca gtgagcagtc agccgttgtc cttgcctta ttggttacat tgctgataag  10320
gaagggatga gtggtaagaa gcttgtttat gtgaggctgg ctgaacttat ggctgagtgg  10380
```

```
aagctgaaga aactggagag atcaagggtg gaagaacaga gctcggcaca ataatttgag    10440
aagtaaaata gttttttaga ttcagtttcg caaaggaggt gatttggttc tttgaagaga    10500
ggtgtcatta tatgtggcat ctcttttcat tttgagagat tttttctaaa aataaaactt    10560
ggaaagaaat agttctttcc aagtcaaaat gatcgatttt aaggaatgtc ggtgaagtga    10620
tttatgaaca aatgtcttta tatttcatat ggtcggtgta agtacgaatg cgagttgcct    10680
ttaggttttt accgtcggta atccacatta ttcacttggt ctttaggctt catagcgtcg    10740
gtattctttt tatatatgca agtctttaca ttgaggaacg tcgatgttca aaccagatgt    10800
gtttgtcttt atacctcgga atgtcggtga agtgatttat gaacaaagtc tttaatttttt    10860
acacagtcgg tggctttccg agcaagagta gtctttatat ttagaacagt cggcgtcggc    10920
agtgcttttt ataagtcttt gtatctcatg tagtcggtgc attgtctttg caactgggtc    10980
tttatctctt aatatggtcg gtggaaactc ttgtgggaat ctttatctca agaaaagtcg    11040
gtgtcgcctg aaagctgtcg cgtctttagg tctcatgcag tcggtgtcgg tcaaaagctc    11100
gcttgtcttt atattttata cagtcggtgt aaaggtgagc tggctgagtc tttatccctc    11160
ttaaagtcgg tgcaagaagt atggcggtat gtctttactt gtcgttaggt cggtgttcat    11220
ccgtctctag ggtgtcttta tctttatgaa tgtcggtgta ggtccaaacg atgtatgtct    11280
tacatcagga attcaggaat gtcggggtta ctaatatgca atggagtctt tatgtctggg    11340
aacgtcgtta ttttactctt gcgagattgt ctttactcag gaagtcggag ctcgattgat    11400
tgacattgcg tcttttagat accatactgt cggtgtggac ggctcgcctg atggtcttta    11460
cctttatac ggtcggtggg ttgctgggcg cttcagtctt tacgtttcat gcggtcggtg    11520
tcattctcat gccctacgtc tttatctcta agaatgtcgg tggagcgact taggtgcact    11580
ggtctttatg tttagaaatg tcggtgtgat tacaggtatc aaatgtcttt agctctggga    11640
aggtcggtat cgatccaaag atccgggggtt ttaaattgtt gtcaatgaac taggcacata    11700
gtaatataaa aaacatttta ttacaagccc ccctccttttt tgtttggcgc ccaacaaaaa    11760
aaatcgccca aaagagcagc ttttcgggcg cggcgcctcc atatatagcg caccaaacta    11820
tttcaacgcc ctggccaaat acctccccgt gtgactcttt tttaccttgg ccacatcacg    11880
cggcgtacct tcggccacca gcaaaccacc gtgattgcca ccttccggac ccagatcaat    11940
cacccagtcc gaagatttaa taacttccaa attgtgttca ataatcaata gactgttgcc    12000
cttatccacc agcttgctca gcacgtgcag caaccgtttc acatcatcaa aatgcaaacc    12060
cgtcgtcggc tcatccaaaa tatacaacgt ctttcccgtc gagcgccgtg acaattccgt    12120
cgccagcttc acacgctgcg cttcaccacc actcagcgtc gtcgcattct gtcccagctg    12180
aatatagccc aaacccactt caaacagcgt cttcaacttt tcatgaataa tcggaatatt    12240
gctgaaaaat ttcgtcgcat cttcgaccgt catgttcagt acctcggaaa tattttttccc    12300
cttgtaatga atttccaaag cctgctcgtt gtagcggcgg cctttgcatt cgtcgcaatc    12360
cacatacacg tccggcagga agtgcatctc aattttggtc acaccatcgc cctgacaggc    12420
ttcgcagcgg ccaccccttca cattgaaact gaaacgcccg gccttgtagc cgcgcatctt    12480
cgcttccggc acctgcgtga acagatcgcg aatgtaggta aacacgccgg tgtaggtggc    12540
ggcgttggag cggggagtac ggccgatcgg cgactgatca atatcaatca ccttatcgag    12600
atattccagt ccgcgcagct ctttgtgttt gccgggaata tccttggcat tatgaaaatg    12660
ttgtgacaac gcgcgggcga gaatatcggt catcaacgtc gatttgccgc tgccggaaac    12720
gccggtgatg cacactaatt ttcccagcgg aatgcgcacg ttgatatttt gtaggttgtg    12780
```

```
ggcggtggca ccgcggattt caatatattt gccgttgccg cggcggtact tgtgcggcgc   12840
ttcaatgaat tttttgccgc tcagatattg accggtcaat gacgctttat ttttaataat   12900
ttcctgaggt gtgccaaggg caacaatttc gccaccgtgt tgccggcac caggccccac    12960 gtcaataaca taatcagcgg agcgaatcgt tcttcatcg tgctcgacga cgatcacggt    13020
attgcctaat tcgcgcagcg ctttgagtgt gtctatgagt ttggagttgt cgcgttggtg   13080
caagccaatg ctgggttcat cgaggatata gataacgccg accaaagatg aaccgatttg   13140
cgtggccaga cgaatgcgtt gcgcttcacc gccgcttaaa gtcgaagcag cgcgatctaa   13200
agtcaaataa tccagaccta cattatgtaa aaaagtcagg cgttcgcgga tttcttcat   13260 gatctgatgc gaaattttgg cttcgcgtac ggacatgacg tagacattat tttttgccat   13320
gctgttgccg ccggagttgg caccacctt gccggccgcg tttttggcgc cagcacccct   13380
cgcgccagca cccgcaccac caaccacaaa cccctcaaaa aatgcctgcg cttcttcaat   13440
gctcaacccc gtcgtgtcag aaatggattt gccgcgaatc gttacggcca gtgcaatttt   13500
gttcaaccgt ttcccgtgac acgtcggaca atcaaagacg cgcatgtagc gttcgatttc   13560
cgagcggata tattccgact cggtttcttt gtagcgccgt tccaaattcg gtatcacgcc   13620
ttcatacgtc gtcacaaatt cacggatttt ggatgtcgag ttcatgccgc tgttgacgtc   13680
gaaagattct tcgccggtgc cgtaaaacac cagcttcagt tgcgcggcgg tcattttttt   13740
caccggttcg tccaaagaaa aaccgtattt ggccgccact gtcgccagaa tccgcagcat   13800
ccagccctga ttcgaagacg tgcgtgacca gggtctgatg gcaccctgat tgatgctcaa   13860 attttattg ggaatgatca gttcagcgtc gacttcgagc ttggtgccca atccagtgca   13920
ttccacgcag gcgccgtgcg ggctgttaaa cgaaaacagg cgcggttcaa tttccggcag   13980
gttgatgccg cagcgcggac aggcgaagtg ctgactgaac agctgatctt tttcgctggt   14040
actgtcgtgc acaatcacca taccatcacc caaatccaag gcggtttcca gagattcgtg   14100
caagcggctg cggttttgc gcagctcttt gtcaacaacc aagcgatcta caacaacatc   14160
aatggtatgt ttcttttct tatcgaggac gagatcgagt gcttcttcga tgctcatcat   14220
attcccgttg acgcgcacgc gcacaaaacc ggctttgcgc gtttcttcaa agacgtgttt   14280
gtgttcacct tttttgtcgc ggataatttg cgcgatgagc ataaatttcg tatccgcttt   14340
caggcgcaga atttgttcga ggatttgttc ggtggtttgt ttgctgactt tatcaccgca   14400
gttggggcag tgtggttggc cgatgcgggc gtagagcaaa cgcaggtaat cgtaaatttc   14460
ggtgacggtc ccgacggtgg atcggggatt gtgggatgtg gttttttgat cgatggagat   14520
ggcgggcgag aggccttcaa tgctgtcgac gtcaggcttg tccatcaggc cgaggaattg   14580
gcgggcgtag aagacaggc tttcgacgta gcggcgctga ccttcggcat agatcgtatc   14640
aaaagccagg gaagattttc ccgagccgga caggccggtg atgacgacga gctggtcacg   14700
ggggatgtcc aggctgatat ttttcaggtt gtggacgcgg gcgcctttga tgatgatcga   14760
attttcacct gccataattg atcgttatga gacaacaaaa atttttagag caaagcccgt   14820
aacctgcttt cgaggcagaa ttttcaaaat actgccgagg cgaaggaaaa aattttgagg   14880
aatactgtta gtatttcgag aaattttta caagccgcag gcggatttg aaaattatga    14940 tccggaatga ggttgcgggt tttactctag acgaacttcc gccagtctac tactttttt    15000 tgcgtaagtc aaccgtttgt gggcgggct gattcggttt tgtggtggtt tcgggagcag    15060
catagatgta gcggaaaatt caaaaaactg gtataatatt gctacaacct atacaaacaa   15120
```

```
aagcgtaaaa atcatgcatt tttcacgttt cggattttat ttccgtaacc gacgcatggt   15180
agaacgtttc ttcgttctat tttgtgctat tttttctgct gtcctggttt tgtcgcttgt   15240
tgccctggtg ctggtggctg acaaaattaa tatcaatccc attgtgcaca tcttgtttcg   15300 ttttttttcag cgacccttg tcagtgcgct gattctgtct tttttcgtca caacccttct   15360
ttacgccgtt tttgttctgg tgcatccagt gcagcatcat accgtgtatt ggcagcgtca   15420
ttcgcagcga tatatattc gcaagaaatc ccatattcac cgcagattgc gtcacattcc   15480
cgcgcagaca tcacataagc tgttggcgct cagttcactt tttgttgtgg ttaaaattgt   15540
ttttgtcagt tttgcctccg gttttttacc gcatgatgtt ttggcacaga ccgttgatcc   15600
gagcggacag aaaagtcagt cggtgttggt ggcggcgttt tatgtccagg tgcttgattc   15660
cgatgatttg tatatttgga ttttatgtt gggccttttg ccgctggcgg ttctgatttt   15720
tttcatcgtt tttcgttcgc atattttcc gcataagaat tttcattatg agagcgcaca   15780
tctggatacg aatattgtca cttttgcggc ccggaagaag gcggagcagc ggcgcaaaaa   15840
gccatcacct ccggccggta ttgtacctt gcatgatgca taacctatga attctgtttt   15900
gcagaaaaaa ttagctggtc tgccgcatca acccggcgtc tatgtgtata agacgcacg   15960 gggtgatgtt ttgtacgtgg ggaaggccaa agatttggcg aagcgcgtgc gatcgtattg   16020
gcagtcgggt cgctcgctgg tgccggacaa agctttgatg gtgagtcagg cggctgatat   16080
cgatatcacg gtggtgagtt cggaaacgga agctttttg ctcgaagcga gtttcattaa   16140
aaaataccgg ccgcggttta atattatttt gaaagatgat aaaagttttt cgtatattaa   16200
ggtgacgttg cgggaagaat ttccgagggt gctggtggtg cggcgcgtga cgcgcgatgg   16260
ca                                                                  16262
```

<210> SEQ ID NO 28
<211> LENGTH: 43
<212> TYPE: DNA
<213> ORGANISM: Artificial sequence
<220> FEATURE:
<223> OTHER INFORMATION: Synthetic sequence

<400> SEQUENCE: 28

```
ctccgaaagt atcggggata aaggcatcaa taccaaactc tgg                     43
```

<210> SEQ ID NO 29
<211> LENGTH: 411
<212> TYPE: PRT
<213> ORGANISM: Artificial Sequence
<220> FEATURE:
<223> OTHER INFORMATION: Synthetic sequence

<400> SEQUENCE: 29

```
Glu His Pro Glu Thr Pro Ile Ile Gly Ile Asp Arg Gly Glu Arg Asn
1               5                   10                  15

Leu Ile Tyr Ile Thr Val Ile Asp Ser Thr Gly Lys Ile Leu Glu Gln
            20                  25                  30

Arg Ser Leu Asn Thr Ile Gln Gln Phe Asp Tyr Gln Lys Lys Leu Asp
        35                  40                  45

Asn Arg Glu Lys Glu Arg Val Ala Ala Arg Gln Ala Trp Ser Val Val
    50                  55                  60

Gly Thr Ile Lys Asp Leu Lys Gln Gly Tyr Leu Ser Gln Val Ile His
65                  70                  75                  80

Glu Ile Val Asp Leu Met Ile His Tyr Gln Ala Val Val Val Leu Glu
                85                  90                  95
```

```
Asn Leu Asn Phe Gly Phe Lys Ser Lys Arg Thr Gly Ile Ala Glu Lys
                100                 105                 110

Ala Val Tyr Gln Gln Phe Glu Lys Val Leu Ile Asp Lys Leu Asn Cys
            115                 120                 125

Leu Val Leu Lys Asp Tyr Pro Ala Glu Lys Val Gly Val Leu Asn
    130                 135                 140

Pro Tyr Gln Leu Thr Asp Gln Phe Thr Ser Phe Ala Lys Met Gly Thr
145                 150                 155                 160

Gln Ser Gly Phe Leu Phe Tyr Val Pro Ala Pro Tyr Thr Ser Lys Ile
                165                 170                 175

Asp Pro Leu Thr Gly Phe Val Asp Pro Val Gln Lys Thr Ile Lys
            180                 185                 190

Asn His Glu Ser Arg Lys His Phe Leu Glu Gly Phe Asp Phe Leu His
            195                 200                 205

Tyr Asp Val Lys Thr Gly Asp Phe Ile Leu His Phe Lys Met Asn Arg
210                 215                 220

Asn Leu Ser Phe Gln Arg Gly Leu Pro Gly Phe Met Pro Ala Trp Asp
225                 230                 235                 240

Ile Val Phe Glu Lys Asn Glu Thr Gln Phe Asp Ala Lys Gly Thr Pro
                245                 250                 255

Phe Ile Ala Gly Lys Arg Ile Val Pro Val Ile Glu Asn His Arg Phe
            260                 265                 270

Thr Gly Arg Tyr Arg Asp Leu Tyr Pro Ala Asn Glu Leu Ile Ala Leu
            275                 280                 285

Leu Glu Glu Lys Gly Ile Val Phe Arg Asp Gly Ser Asn Ile Leu Pro
        290                 295                 300

Lys Leu Leu Glu Asn Asp Asp Ser His Ala Ile Asp Thr Met Val Ala
305                 310                 315                 320

Leu Ile Arg Ser Val Leu Gln Met Arg Asn Ile Ser Asn Ala Ala Thr
                325                 330                 335

Gly Glu Asp Tyr Ile Asn Ser Pro Val Arg Asp Leu Asn Gly Val Cys
            340                 345                 350

Phe Asp Ser Arg Phe Gln Asn Pro Glu Trp Pro Met Asp Ala Asp Ala
        355                 360                 365

Asn Gly Ala Tyr His Ile Ala Leu Lys Gly Gln Leu Leu Asn His
370                 375                 380

Leu Lys Glu Ser Lys Asp Leu Lys Leu Gln Asn Gly Ile Ser Asn Gln
385                 390                 395                 400

Asp Gln Leu Ala Tyr Ile Gln Glu Leu Arg Asn
                405                 410

<210> SEQ ID NO 30
<211> LENGTH: 406
<212> TYPE: PRT
<213> ORGANISM: Artificial Sequence
<220> FEATURE:
<223> OTHER INFORMATION: Synthetic sequence

<400> SEQUENCE: 30

His Asp Asp Asn Pro Tyr Val Ile Gly Ile Asp Arg Gly Glu Arg Asn
1               5                   10                  15

Leu Leu Tyr Ile Val Val Val Asp Gly Lys Gly Asn Ile Val Glu Gln
                20                  25                  30

Tyr Ser Leu Asn Glu Ile Ile Asn Phe Asn Gly Ile Arg Ile Lys
            35                  40                  45
```

Thr Asp Tyr His Ser Leu Leu Asp Lys Lys Glu Lys Glu Arg Phe Glu
 50                  55                  60

Ala Arg Gln Asn Trp Thr Ser Ile Glu Asn Ile Lys Glu Leu Lys Ala
 65                  70                  75                  80

Gly Tyr Ile Ser Gln Val Val His Lys Ile Cys Glu Leu Val Glu Lys
                 85                  90                  95

Tyr Asp Ala Val Ile Ala Leu Glu Asp Leu Asn Ser Gly Phe Lys Asn
                100                 105                 110

Ser Arg Val Lys Val Glu Lys Gln Val Tyr Gln Lys Phe Glu Lys Val
            115                 120                 125

Leu Ile Asp Lys Leu Asn Tyr Met Val Asp Lys Lys Ser Asn Pro Cys
130                 135                 140

Ala Thr Gly Gly Ala Leu Lys Gly Tyr Gln Ile Thr Asn Lys Phe Glu
145                 150                 155                 160

Ser Phe Lys Ser Met Ser Thr Gln Asn Gly Phe Ile Phe Tyr Ile Pro
                165                 170                 175

Ala Trp Leu Thr Ser Lys Ile Asp Pro Ser Thr Gly Phe Val Asn Leu
                180                 185                 190

Leu Lys Thr Lys Tyr Thr Ser Ile Ala Asp Ser Lys Lys Phe Ile Ser
            195                 200                 205

Ser Phe Asp Arg Ile Met Tyr Val Pro Glu Glu Asp Leu Phe Glu Phe
210                 215                 220

Ala Leu Asp Tyr Lys Asn Phe Ser Arg Thr Asp Ala Asp Tyr Ile Lys
225                 230                 235                 240

Lys Trp Lys Leu Tyr Ser Tyr Gly Asn Arg Ile Arg Ile Phe Ala Ala
                245                 250                 255

Ala Lys Lys Asn Asn Val Phe Ala Gln Glu Glu Val Cys Leu Thr Ser
                260                 265                 270

Ala Tyr Lys Glu Leu Phe Asn Lys Tyr Gly Ile Asn Tyr Gln Gln Gly
            275                 280                 285

Asp Ile Arg Ala Leu Leu Cys Glu Gln Ser Asp Lys Ala Phe Tyr Ser
290                 295                 300

Ser Phe Met Ala Leu Met Ser Leu Met Leu Gln Met Arg Asn Ile Ser
305                 310                 315                 320

Thr Gly Arg Thr Asp Val Asp Phe Leu Ile Ser Pro Val Lys Asn Ser
                325                 330                 335

Asp Gly Ile Phe Tyr Asp Ser Arg Asn Tyr Glu Ala Gln Glu Asn Ala
                340                 345                 350

Ile Leu Pro Lys Asn Ala Asp Ala Asn Gly Ala Tyr Asn Ile Ala Arg
            355                 360                 365

Lys Val Leu Trp Ala Ile Gly Gln Phe Lys Lys Ala Glu Asp Glu Lys
370                 375                 380

Leu Asp Lys Val Lys Ile Ala Ile Ser Asn Lys Glu Trp Leu Glu Tyr
385                 390                 395                 400

Ala Gln Thr Ser Val Lys
                405

<210> SEQ ID NO 31
<211> LENGTH: 25
<212> TYPE: DNA
<213> ORGANISM: Artificial sequence
<220> FEATURE:
<223> OTHER INFORMATION: Synthetic sequence

<400> SEQUENCE: 31
ctccgaaagt atcggggata aaggc                                           25

<210> SEQ ID NO 32
<211> LENGTH: 25
<212> TYPE: DNA
<213> ORGANISM: Artificial sequence
<220> FEATURE:
<223> OTHER INFORMATION: Synthetic sequence

<400> SEQUENCE: 32
caccgaaatt tggagaggat aaggc                                           25

<210> SEQ ID NO 33
<211> LENGTH: 25
<212> TYPE: DNA
<213> ORGANISM: Artificial sequence
<220> FEATURE:
<223> OTHER INFORMATION: Synthetic sequence

<400> SEQUENCE: 33
ctccgaatta tcgggaggat aaggc                                           25

<210> SEQ ID NO 34
<211> LENGTH: 25
<212> TYPE: DNA
<213> ORGANISM: Artificial sequence
<220> FEATURE:
<223> OTHER INFORMATION: Synthetic sequence

<400> SEQUENCE: 34
ccccgaatat aggggacaaa aaggc                                           25

<210> SEQ ID NO 35
<211> LENGTH: 36
<212> TYPE: DNA
<213> ORGANISM: Artificial sequence
<220> FEATURE:
<223> OTHER INFORMATION: Synthetic sequence

<400> SEQUENCE: 35
gtctagacat acaggtggaa aggtgagagt aaagac                               36

<210> SEQ ID NO 36
<211> LENGTH: 25
<212> TYPE: DNA
<213> ORGANISM: Artificial sequence
<220> FEATURE:
<223> OTHER INFORMATION: Synthetic sequence

<400> SEQUENCE: 36
ctccgtgaat acgtggggta aaggc                                           25

<210> SEQ ID NO 37
<211> LENGTH: 10
<212> TYPE: RNA
<213> ORGANISM: Artificial sequence
<220> FEATURE:
<223> OTHER INFORMATION: Synthetic sequence

<400> SEQUENCE: 37
aaaaaaaaaa                                                            10

<210> SEQ ID NO 38
<211> LENGTH: 10
<212> TYPE: RNA

```
<213> ORGANISM: Artificial sequence
<220> FEATURE:
<223> OTHER INFORMATION: Synthetic sequence

<400> SEQUENCE: 38
aaaaaaaaaa                                                                 10

<210> SEQ ID NO 39
<211> LENGTH: 10
<212> TYPE: RNA
<213> ORGANISM: Artificial sequence
<220> FEATURE:
<223> OTHER INFORMATION: Synthetic sequence

<400> SEQUENCE: 39
aaaaaaaaaa                                                                 10

<210> SEQ ID NO 40
<211> LENGTH: 10
<212> TYPE: RNA
<213> ORGANISM: Artificial sequence
<220> FEATURE:
<223> OTHER INFORMATION: Synthetic sequence

<400> SEQUENCE: 40
aaaaaaaaaa                                                                 10

<210> SEQ ID NO 41
<211> LENGTH: 76
<212> TYPE: RNA
<213> ORGANISM: Artificial sequence
<220> FEATURE:
<223> OTHER INFORMATION: Synthetic sequence

<400> SEQUENCE: 41
cuccgaaagu aucaaaauaa aaaggguuuc caguuuuuaa cuaaacuuua gccuuccacc          60
cuuuccugau uuuguu                                                          76

<210> SEQ ID NO 42
<211> LENGTH: 79
<212> TYPE: RNA
<213> ORGANISM: Artificial sequence
<220> FEATURE:
<223> OTHER INFORMATION: Synthetic sequence

<400> SEQUENCE: 42
accugccaaa auuucguuca acgaaacuua agcaggcaag aaaauuuaaa auuaaauccg          60
cuggugggcg gauaaaguc                                                       79

<210> SEQ ID NO 43
<211> LENGTH: 51
<212> TYPE: RNA
<213> ORGANISM: Artificial sequence
<220> FEATURE:
<223> OTHER INFORMATION: Synthetic sequence

<400> SEQUENCE: 43
gguauuuccg gacagcggcu ugaccgcauc guccucgccu uuuccuaaaa u                   51

<210> SEQ ID NO 44
<211> LENGTH: 10
<212> TYPE: RNA
<213> ORGANISM: Artificial sequence
<220> FEATURE:
<223> OTHER INFORMATION: Synthetic sequence
```

```
<400> SEQUENCE: 44
aaaaaaaaaa                                                              10

<210> SEQ ID NO 45
<211> LENGTH: 10
<212> TYPE: RNA
<213> ORGANISM: Artificial sequence
<220> FEATURE:
<223> OTHER INFORMATION: Synthetic sequence

<400> SEQUENCE: 45
aaaaaaaaaa                                                              10

<210> SEQ ID NO 46
<211> LENGTH: 10
<212> TYPE: RNA
<213> ORGANISM: Artificial sequence
<220> FEATURE:
<223> OTHER INFORMATION: Synthetic sequence

<400> SEQUENCE: 46
aaaaaaaaaa                                                              10

<210> SEQ ID NO 47
<211> LENGTH: 10
<212> TYPE: RNA
<213> ORGANISM: Artificial sequence
<220> FEATURE:
<223> OTHER INFORMATION: Synthetic sequence

<400> SEQUENCE: 47
aaaaaaaaaa                                                              10

<210> SEQ ID NO 48
<211> LENGTH: 10
<212> TYPE: RNA
<213> ORGANISM: Artificial sequence
<220> FEATURE:
<223> OTHER INFORMATION: Synthetic sequence

<400> SEQUENCE: 48
aaaaaaaaaa                                                              10

<210> SEQ ID NO 49
<211> LENGTH: 10
<212> TYPE: RNA
<213> ORGANISM: Artificial sequence
<220> FEATURE:
<223> OTHER INFORMATION: Synthetic sequence

<400> SEQUENCE: 49
aaaaaaaaaa                                                              10

<210> SEQ ID NO 50
<211> LENGTH: 10
<212> TYPE: RNA
<213> ORGANISM: Artificial sequence
<220> FEATURE:
<223> OTHER INFORMATION: Synthetic sequence

<400> SEQUENCE: 50
aaaaaaaaaa                                                              10

<210> SEQ ID NO 51
```

<211> LENGTH: 1224
<212> TYPE: PRT
<213> ORGANISM: Artificial Sequence
<220> FEATURE:
<223> OTHER INFORMATION: Synthetic sequence

<400> SEQUENCE: 51

```
Met Asp Lys Lys Ile Thr Gly Tyr Arg Leu His Phe Lys Arg Ile Leu
1               5                   10                  15

Phe Ser Gly Gly Glu Ile Val Arg Thr Ile Lys Phe Pro Leu Ser Ser
            20                  25                  30

Thr Ser Leu Ser Ser Gly Lys Asn Asp Leu Ile Asn Asn Phe Glu Gly
        35                  40                  45

Gln Leu Ile Asn Asp Asp Leu Lys Ile Arg Gly Asp Val Asn Leu Asn
    50                  55                  60

Asp Tyr Leu Ile Tyr Glu Phe Ser Gly Lys Pro Ile Tyr Thr Leu Phe
65                  70                  75                  80

Asn Phe Trp Ile Asp Ser Leu Lys Ser Gly Ile Ile Trp Ala Asp Lys
                85                  90                  95

Pro Ala Ser Leu Ile Asp Phe Ile Asn Glu Phe Tyr Leu Ile Lys Ser
            100                 105                 110

Pro Tyr Asp Leu Val Trp Glu Arg Ala Thr Glu Phe Lys Lys Tyr
        115                 120                 125

Phe Asp Lys Lys Ser Phe Lys Glu Ile Leu Ile Ser Gly Pro Ile Arg
    130                 135                 140

Lys Thr Lys Asn Pro Ser Lys Lys Glu Ser Phe Lys Lys Asp Asn
145                 150                 155                 160

Lys Leu Pro Asp Glu Tyr Val Ile Lys Glu Gly Asn Ser Leu Ser Val
                165                 170                 175

Glu Ser Pro Glu Val Leu Lys Phe Ile Asn Lys Ile Val Ser Ser Phe
            180                 185                 190

Phe Asp Glu Asp Gly Asn Leu Ile Leu Glu Gly Lys Lys Gln Asp Asn
        195                 200                 205

Phe Trp Leu Asn Glu Phe Gly Ile Asp Lys Ser Ile Ile Gln Lys Thr
    210                 215                 220

Lys Pro Glu Gly Glu Leu Lys Asp Ile Thr Phe Val Ile Ile Pro Glu
225                 230                 235                 240

Leu Ile Val Asp Ser Phe Asn Lys Glu Tyr Glu Val Asp Ser Leu Ile
                245                 250                 255

Glu Lys Arg Arg Val Trp Leu Lys Lys Arg Phe Asn Lys Glu Lys Glu
            260                 265                 270

Ile Glu Lys Asn Leu Gln Leu Ile Leu Gly Leu Ser Asn Asn Phe Asn
        275                 280                 285

Gly Phe Ser Asn Phe Leu Gly Lys Gly Leu Arg Ala Phe Gln Gly Gly
    290                 295                 300

Lys Ile Leu Met Ile Phe Glu Ala Met Ser Lys Ile Asn Pro Ser Ile
305                 310                 315                 320

Lys Asn Gln Glu Asn Lys Glu Lys Val Leu Glu Ala Leu Asn Phe Leu
                325                 330                 335

Ser Asp Lys Ser Lys Phe Phe Pro Leu Arg Pro Ser Leu Asn Ile Val
            340                 345                 350

Lys Ser Trp Ala Asp Tyr Arg Thr Phe Phe Gly Gly Lys Leu Gln Ser
        355                 360                 365

Trp Tyr Ser Asn Gly Ile Arg Arg Lys Asn Glu Leu Lys Val Gln Val
    370                 375                 380
```

```
Lys Glu Ile Tyr Glu Phe Leu Thr Lys Ala Gln Asp Tyr Leu Ala Ala
385                 390                 395                 400

Lys Ile Ser Phe Asn Asp Glu Asn Lys Arg Tyr Ala Arg Lys Glu Leu
            405                 410                 415

Glu Ser Ile Asn Leu Lys Ile Asn Arg Leu Lys Gln Phe Ile Glu Asn
            420                 425                 430

Glu Asn Phe Asp Ile Ser Ser Glu Asp Arg Tyr Leu Ile Phe Asp Thr
            435                 440                 445

Leu Leu Ser Ser Leu Arg Thr Gln Leu Asn Leu Tyr Tyr Gln Lys Tyr
450                 455                 460

Leu Ser Ser Glu Glu Asp Asn Ile Arg Glu Asn Lys Asp Leu Lys Gly
465                 470                 475                 480

Ile Tyr Gln Lys Ile Tyr Lys Pro Ile Ala Phe Phe Gly Lys Ala Thr
            485                 490                 495

Lys Arg Lys Asn Lys Lys Val Ile Glu Thr Val Pro Ile Ile Glu
            500                 505                 510

Ser Gly Ile Asn Asn Leu Phe Ser Leu Met Lys Lys Leu Glu Lys Thr
            515                 520                 525

Phe Leu Pro Lys Asn Thr Phe Ser Lys Val Lys Asn Lys Asn Glu Asp
530                 535                 540

Glu Glu Thr Asn Leu Arg Asn Leu Val Asp Tyr Tyr Gln Asn Lys Val
545                 550                 555                 560

Ser His Lys Met Leu Asn Ser Leu Thr Phe Val Asn Lys Leu Glu Glu
            565                 570                 575

Val Met Lys Ser Val Ile Glu Glu Asn Asp Trp Asp Lys Leu His Ser
            580                 585                 590

Asn Lys Tyr Val Phe Tyr Lys Ser Glu Tyr Gln Lys Gly Ala Leu Glu
            595                 600                 605

Leu Ile Pro Leu Lys Lys Gly Ser Trp Ile Asp Ile Phe Glu Lys Ile
610                 615                 620

Ile Leu Glu Met Thr Ser Tyr Leu Leu Thr Phe Asp Leu Thr Asp Leu
625                 630                 635                 640

Leu Lys Asp Lys Lys Ile Leu Leu Asp Trp Ile Glu Ile Ala Lys Asn
            645                 650                 655

Thr Leu Ala Lys Leu Ile Lys Phe Asn Thr Cys Asp Val Phe Thr Leu
            660                 665                 670

Asp Glu Leu Asn Leu Asp Leu Arg Asn Phe Pro Lys Ala Met Asp Tyr
            675                 680                 685

Ile Lys Ile Phe Lys Ile Thr Lys Val Asp Lys Asn Glu Leu Asn Phe
            690                 695                 700

Ile Val Gln Ser Phe Ile Leu Ser Glu Leu Lys Gly Ala Ala Thr Leu
705                 710                 715                 720

Phe Ser Lys Glu Lys Tyr Leu Ala Lys Tyr Asn Val Gln Val Ile Asn
            725                 730                 735

Ala Asp Lys Lys Phe Lys Leu Phe Tyr Lys Pro Asn Asp Gly Phe Ile
            740                 745                 750

Glu Arg Glu Val Asp Arg Lys Asn Leu Leu Lys Pro His Gln Tyr Phe
            755                 760                 765

Val Ala Leu Asp Lys Ile Glu Asp Lys Lys Ile Lys Glu Lys Ala Asn
            770                 775                 780

Phe Leu Leu Ile Thr Lys Glu Asp Ile Lys Pro Val Phe Ile Lys Glu
785                 790                 795                 800
```

-continued

```
Glu Asn Phe Ser Lys Leu Tyr Lys Ile Ser Ser Phe Tyr Gln Ile
            805                 810                 815

Gln Phe Leu Asp Lys Phe Ile Tyr Met Pro Glu Glu Phe Lys Asp Leu
            820                 825                 830

Gly Ile Arg Leu Ser Glu Trp Asn Phe Val Leu Glu Arg Glu Tyr Lys
            835                 840                 845

Ile Asp Trp Asp Leu Cys Thr Lys Arg Pro Lys Met Thr Phe Ile Glu
850                 855                 860

Asn Ser Lys Lys Asn Lys Leu Tyr Leu Ser Ile Pro Phe Asn Val Phe
865                 870                 875                 880

Tyr Lys Ser Lys Lys Lys Asp Val Ser Leu Ser Lys Val Ile Ser Asn
            885                 890                 895

Arg Leu Ser Tyr Pro Ile Leu Gly Ile Asp Val Gly Glu Tyr Gly Leu
            900                 905                 910

Ala Tyr Leu Leu Ala Glu Phe Ser Asp Lys Lys Ile Lys Ile Leu Lys
            915                 920                 925

Lys Gly Phe Ile Glu Asp Arg Asn Ile Ala Asn Ile Lys Asp Lys Phe
            930                 935                 940

Ala Glu Ile Gln Leu Lys Ala Arg Thr Gly Ile Phe Asn Glu Glu Asp
945                 950                 955                 960

Thr Thr Ile Ala Arg Val Arg Glu Asn Ala Ile Gly Asn Leu Arg Asn
                965                 970                 975

Lys Val His Tyr Ile Leu Thr Ser Asp Arg Gly Ala Ser Ile Ile Tyr
            980                 985                 990

Glu Arg Ser Ile Ser Asn Phe Glu Thr Gly Ser Gly Arg Thr Thr Lys
            995                 1000                1005

Ile Tyr Asp Ser Val Lys Arg Ala Asp Thr Glu Phe Glu Thr Glu
            1010                1015                1020

Ala Asp Lys Phe Ile His Asn His Val Trp Gly Lys Asn Thr Lys
            1025                1030                1035

Tyr Val Gly Arg Ser Leu Ser Ala Tyr Gly Ser Ser Tyr Ile Cys
            1040                1045                1050

Ser Lys Cys His Arg Ser Ile Tyr Gln Phe Lys Lys Glu Asp Leu
            1055                1060                1065

Arg Glu Ile Lys Leu Leu Met Arg Glu Gly Asn Ile Leu Thr Phe
            1070                1075                1080

Leu Thr Pro Ile Gly Lys Val Trp Gly Tyr Ser Lys Asp Glu Lys
            1085                1090                1095

Phe Lys Lys Asp Tyr Gln Phe Lys Pro Thr Glu Lys Asp Phe Lys
            1100                1105                1110

Glu Phe Ile Lys Ile Leu Lys Asp Phe Ala Arg Pro Pro Val Gly
            1115                1120                1125

Lys Asn Lys Thr Glu Val Leu Glu Lys Phe Phe Leu Lys Asp Asn
            1130                1135                1140

Asp Lys Lys Ala Lys Ile Asp Glu Phe Arg Lys Lys Arg Gly Ala
            1145                1150                1155

Ser Ala Ile Phe Ile Cys Pro Phe Cys Gly Phe Ile Ala Asp Ala
            1160                1165                1170

Asp Ile Gln Ala Ala Phe Val Met Ala Val Arg Gly Tyr Ile Arg
            1175                1180                1185

Phe Lys Glu Ser Gln Ile Lys Glu Glu Asn Lys Ser Leu Ile Leu
            1190                1195                1200

Glu Lys Thr Ile Asn Tyr Leu Lys Glu Val Gln Phe Lys Pro Glu
```

Asp Ile Phe Leu Pro Phe
        1220

<210> SEQ ID NO 52
<211> LENGTH: 1154
<212> TYPE: PRT
<213> ORGANISM: Artificial Sequence
<220> FEATURE:
<223> OTHER INFORMATION: Synthetic sequence

<400> SEQUENCE: 52

Met Lys Asp Ser Lys Ile Asn Ala Pro Ile Asn Ile Asn Ala Asn Asn
1               5                   10                  15

Val Ser Lys Asn Lys Thr Pro Lys Lys Pro Arg Arg Lys Ser Gly
            20                  25                  30

Lys Arg Gly Tyr Arg Leu His Asp Glu Arg Ile Ala Tyr Ser Gly Gly
            35                  40                  45

Thr Gly Ser Cys Arg Ser Ile Lys Tyr Glu Leu Leu Asn Pro Asp Ala
    50                  55                  60

Thr Arg Lys Asn Leu Leu Arg Gly Ser Gly Leu Gln His Glu Ile Ile
65                  70                  75                  80

Ser Ala Val Arg Gln Asp Asn Leu Leu Leu Tyr Gly Pro Leu Asn Phe
                85                  90                  95

Asn Asp Tyr Ile Phe Asp Lys Asp Ala Pro Asn Leu Leu His Phe Trp
                100                 105                 110

Thr Leu Ala Leu Ser Leu Gly Phe Val Phe Ser Asn Gln Asn Ser Ile
            115                 120                 125

Glu Arg Glu Phe Lys Asp Tyr Leu Gly Val Ser Thr Glu Glu Ala Val
    130                 135                 140

Leu Phe Gly Lys Leu Asn Glu Thr Leu Lys Ala Val Phe Asp Glu Ala
145                 150                 155                 160

Lys Phe Ile Ser Gly Phe Leu Tyr Arg Asn Phe Arg Gly Leu Ala Ser
                165                 170                 175

Lys Thr Arg Glu Gln Arg Ile Lys Leu Leu Thr Asp Thr Leu Arg Glu
            180                 185                 190

Pro Leu Asp Gly Val Asn Gly Asp Ser Val Ser Glu Ile Ile Lys Pro
        195                 200                 205

Tyr Ala Glu Lys Trp Ala Glu Tyr Asp Gly Glu Cys Asp Gln Phe Val
    210                 215                 220

Phe Lys Cys Glu Leu Phe Ser Ile Lys Ser Thr Asp Lys Pro Arg Glu
225                 230                 235                 240

Asn Thr Arg Leu Ser Phe Ala Ile Asp Pro Ala Phe Glu Val Met Lys
                245                 250                 255

Leu Asp Asp Lys Thr Val Phe Phe Asp Asp Leu Ile Thr His Tyr Lys
            260                 265                 270

Glu Asn Cys Ser Asp Glu Ala Gln Ala Lys Arg Phe Leu Gly Ile Gly
        275                 280                 285

Asp Asn Gly Asn Tyr Phe Asn Gly Ile Phe Gly Leu Phe Glu Leu
    290                 295                 300

Leu Thr Asp Gly Asp Glu Lys Ile Cys Glu Thr Thr Asp His Leu Ala
305                 310                 315                 320

Arg Ile Tyr Gly Phe Asp Glu Thr Lys Lys Thr Glu Ile Asn Lys Arg
                325                 330                 335

Leu Val Arg Leu Ala Glu Tyr Ala Arg Gln Ile Asn Arg Arg Pro Cys

```
               340             345             350
Leu Val Lys Arg Trp Ser Glu Tyr Arg Ser Asp Phe Asn Gly Thr Ile
            355             360             365
Glu Ser Trp Tyr Ser Asn Arg Gln Ser Lys Gln Asn Asp Thr Leu Lys
            370             375             380
Gln Leu Asp Glu Lys Leu Lys Leu Leu Glu Met Arg Ala Ser Phe
385             390             395             400
Pro Thr Asp Ser Asp Leu Cys Gly Ile Lys Ser Leu Ser Glu Thr Ile
            405             410             415
Glu Phe Ile Arg Ser Leu Lys Gly Glu Arg Ile Ala Arg Lys Val Thr
            420             425             430
Asp Glu Leu Glu Ser Tyr Leu Ala Val Leu Gly Ser Glu Leu Asn Gln
            435             440             445
Tyr Thr Gln Gln Asn Lys Asp His Ala Leu Pro Leu Gly Trp Gln Lys
            450             455             460
Lys Leu Ser Lys His Ile Gln Ser Ser Pro Leu Phe Phe Gly Glu Asn
465             470             475             480
Lys Ile Ala Leu Trp Glu Lys Leu Ile Asn Leu Lys Glu Leu Ile Lys
            485             490             495
Thr Glu Val Lys Glu Leu Glu Val Val Leu Ala Glu Asp Phe Asp Asp
            500             505             510
Tyr Glu Ile Thr Asp Lys Gln Val Asp Asn Leu Ala Ala Leu Ala Gly
            515             520             525
Arg Phe Ser Glu Ser Pro Asp Gly Ser Gly His Pro Leu Val Thr Glu
            530             535             540
Arg Leu Ala Lys Ile Glu Ser Thr Leu Gly Val Asp Phe Thr His Lys
545             550             555             560
Asn Asn Arg Ala Lys Phe Tyr Leu Ser Gly Phe Glu Arg Gly Lys Phe
            565             570             575
Gly Lys Leu Asp Val Pro Asn Lys Ile Lys Val Ser His Leu Phe Glu
            580             585             590
Leu Ala Asp Leu Ser Ile Leu Tyr Asn Ala Val Ala Asn Ser Pro Glu
            595             600             605
Asp Gly Tyr Ile Leu Arg Asp Thr Ala Gln Leu Ser Lys Ile Ile Leu
            610             615             620
Ser Ala Lys Leu Arg Asp Ala Asp Arg Glu Lys Gln Arg Lys Thr Val
625             630             635             640
Leu Ala His Ser Thr Leu Gln Gly Tyr Ser Ala Leu Ile Ser Lys Arg
            645             650             655
Glu Phe Val Ser Arg Tyr Pro Leu Gln Ala Val Asn Gly Ser Gln Asn
            660             665             670
Leu Met Ala Tyr Asp Ala Asn Arg Lys Tyr Tyr Ala Tyr Asn Ser
            675             680             685
Glu Lys Phe Ala Gly Thr Lys Glu Leu Thr Val Ala Leu Arg Gly Asn
            690             695             700
Asn Phe Gly Pro Glu Ala Phe Gly Gly Lys Phe Lys Lys Val Pro Ala
705             710             715             720
Leu Arg Val Gln Ser Ser Lys Tyr Gln Ile Gln Phe Leu Asp Trp Phe
            725             730             735
Phe Glu Lys Gln Lys Lys Arg Lys Thr Glu Leu Gly Ala Gly Gly Ser
            740             745             750
Phe Thr Ile Ala Glu Ile Ser Cys Lys Val Asn Trp Asp Asp Lys Thr
            755             760             765
```

```
Pro Val Ile Phe Glu Lys Pro Asp Pro Arg Leu Phe Ser Gln Pro
    770                 775                 780
Phe Thr Ile Asn Pro Pro Glu Asn Ser Ala Lys Lys Asp Tyr Ala Arg
785                 790                 795                 800
Tyr Ile Gly Ile Asp Ile Gly Glu Tyr Gly Leu Ala Trp His Leu Val
                805                 810                 815
Glu Val Phe Glu Asp Ala Asn Glu Asp Ile Gly Gly Ala Gly Lys Asn
            820                 825                 830
Ala Val Arg Ile Lys Ser Val Glu Lys Gly Phe Phe Thr Asp Pro Gln
                835                 840                 845
Gln Ile Ser Leu Lys Glu Asp Val Lys Lys Leu Arg Glu Asn Gln Val
    850                 855                 860
Arg Ala Thr Phe Thr Ser Pro Asp Thr Lys Ile Ala Arg Val Arg Glu
865                 870                 875                 880
Ser Leu Ile Gly Ser Tyr Arg Asn Leu Leu Glu Asp Leu Ala Val Arg
                885                 890                 895
Lys Asp Ala Arg Leu Cys Phe Glu Tyr Glu Val Ser Gly Phe Glu Ser
            900                 905                 910
Gly Gly Ala Arg Ile Ser Lys Val Tyr Asp Ser Ile Lys Arg Ser Ser
                915                 920                 925
Val Ala Lys Lys Glu Asn Lys Ala Glu Asn Lys Gln Ser Trp Gly Lys
930                 935                 940
Leu Phe Gly Pro Glu Phe Ser Phe Lys Ala Ile Glu Ile Thr Ala Ala
945                 950                 955                 960
Gly Thr Ser Gln Tyr Cys Thr Lys Cys Lys Arg Trp Ala Ser Leu Ala
                965                 970                 975
Ile Lys Asp Asn Asn Tyr Gln Leu Leu Glu Trp Asp Asn Gly Glu
            980                 985                 990
Thr Gly Asp Lys Arg Gly Ser Asp Gly Leu Leu Ala Val Thr Leu Asp
                995                1000                1005
Gly Glu Gly Lys Glu Thr Asn Arg Thr Val Arg Leu Phe Pro Lys
    1010                1015                1020
Asp Gly Lys Lys Ala Gly Asp Thr Ile Leu Gly Lys Asp Leu Lys
    1025                1030                1035
Ser Ala Ile Tyr Arg Ala Met Arg Pro Asn Met Arg Pro Ser Glu
    1040                1045                1050
Asp Gly Ser Ile Ser Leu Gly Ala Gly Met Glu Ala Val Arg Arg
    1055                1060                1065
Asp Leu Met Pro Glu Gln Trp Glu Lys Leu Thr Leu Glu Phe Gly
    1070                1075                1080
Gln Gly Lys Pro Arg Gly Asn Met Ala Ile Tyr Val Cys Pro Tyr
    1085                1090                1095
Cys Gly His Ile Ser Asp Ala Asp Met Gln Ala Ala Phe Asn Ile
    1100                1105                1110
Ala Val Arg Gly Tyr Leu Ala Asn Arg Asp Lys Glu Lys Lys Val
    1115                1120                1125
Lys Leu Gly Lys Glu Tyr Leu Thr Asp Glu Gln Ser Lys Leu Thr
    1130                1135                1140
Phe Asp Pro Val Gly Ile Leu Glu His Thr Thr
    1145                1150
```

<210> SEQ ID NO 53
<211> LENGTH: 1184

```
<212> TYPE: PRT
<213> ORGANISM: Artificial Sequence
<220> FEATURE:
<223> OTHER INFORMATION: Synthetic sequence

<400> SEQUENCE: 53

Met Phe Asn Gln Lys Lys Gly Tyr Arg Leu His Leu Glu Arg Ile Ile
1               5                   10                  15

Tyr Ser Gly Gly Glu Ile Thr Arg Ser Ile Lys Tyr Leu Leu Ala Ser
            20                  25                  30

His Ser Asp Ser Gln Lys Asn Lys Glu Leu Leu Asn Asn Phe Ser Gln
        35                  40                  45

Asp Leu Tyr Asn Asp Asp Leu Lys Ile Arg Gly Cys Leu Asn Leu Asn
    50                  55                  60

Asp Leu Val Asn Asn Gln Ile Tyr Asn Leu Ala Asp Phe Trp Ile
65                  70                  75                  80

Asp Ser Leu Arg Ala Gly Val Ile Trp Gln Ser Ser Ala Ser Ser Leu
                85                  90                  95

Ile Asp Phe Ile Lys Arg Leu Asn His Gln Glu Thr Ile Gly Glu Lys
            100                 105                 110

Ile Phe Asn Asn Ala Asn Glu Arg Ile Lys Arg Phe Phe Asn Ser Glu
        115                 120                 125

Lys Phe Ile Lys Glu Ile Ile Leu Ser Glu Pro Lys Arg Ile Ser Ser
130                 135                 140

Lys Lys Gln Ala Phe Tyr Asn Ser Leu Phe Asp Ile Leu Lys Asp Glu
145                 150                 155                 160

Phe Lys Lys Gln Glu Lys Asn Glu Lys Ile Ile Asp Asn Lys Ala
                165                 170                 175

Glu Gln Leu Ile Lys Glu Ile Val Asp Ala Phe Tyr Ser Asn Asp Gly
            180                 185                 190

Val Phe Leu Met Glu Gly Glu Lys Gln Asn Asn Phe Trp Gln Glu
        195                 200                 205

Lys Phe Asn Ile Asp Lys Asn Met Ile Lys Lys Glu Lys Glu Asp Ile
210                 215                 220

Leu Lys Asp Val Gly Asp Ile Thr Ala Phe Ile His Pro Pro Leu Ile
225                 230                 235                 240

Ile Leu Lys Gly Asp Val Ser Gln Leu Ile Asp Glu Arg Lys Lys Tyr
                245                 250                 255

Phe Ser Glu Lys Asp Leu Glu Glu Ile Leu Gly Leu Ser Asp Asn Phe
            260                 265                 270

Asn Ala Phe Ser His Tyr Phe Asn Lys Phe Phe Leu Leu Leu Tyr Gln
        275                 280                 285

Asp Lys Gln Glu Lys Ile Phe Glu Cys Tyr Gln Lys Ile Phe Ser Phe
290                 295                 300

Ser Gln Glu Asp Arg Lys Arg Ile Lys Asp Ala Leu Asp Phe Leu Leu
305                 310                 315                 320

Glu Lys Ser Lys Leu Leu Gly Leu Pro Lys Ile Val Asn Ser Trp Ser
                325                 330                 335

Asp Tyr Arg Ser Val Phe Gly Gly Lys Ile Lys Ser Trp Phe Ser Asn
            340                 345                 350

Tyr Leu Asn Arg Glu Asp Lys Ala Lys Lys Gln Glu Lys Lys Ile Lys
        355                 360                 365

Glu Gly Leu Glu Lys Val Asn Lys Phe Leu Leu Asp Phe Ile Gln Lys
370                 375                 380
```

```
Asn Gln Val Asp Ser Asp Leu Gln Gln Glu Ile Lys Phe Tyr Tyr Asp
385                 390                 395                 400

Lys Leu Asn Gln Phe Ile Asn Ser Tyr Gln Asn Gln Glu Phe Phe His
            405                 410                 415

Gln Gln Glu Leu Phe Leu Leu Phe Ser Asp Leu Leu Ala Glu Tyr Arg
            420                 425                 430

Glu Lys Leu Asn Arg Phe Tyr Gln Lys Tyr Leu Ser Asp Lys Glu Lys
            435                 440                 445

Glu Glu Lys Lys Val Asp Glu Phe Pro Leu Phe Lys Asp Leu Phe Glu
            450                 455                 460

Lys Tyr Glu Gly Pro Ile Ser Phe Tyr Gly Lys Thr Lys Leu Glu Asp
465                 470                 475                 480

Asn Lys Lys Ile Ile Asp Leu Thr Phe Lys Thr Ile Lys Val Gly Leu
            485                 490                 495

Asn Leu Ile Arg Arg Leu Leu Ile Asp Leu Tyr Asn Ser Ser Asp Phe
            500                 505                 510

Lys Asn Ser Asp Asn Asn Gln Glu Arg Asp Leu Arg Arg Ile Phe
            515                 520                 525

Glu Phe Leu Leu Asn Lys Ile Pro Ala Thr Lys Thr Phe Arg Glu Lys
            530                 535                 540

Tyr Leu Ser Ile Leu Lys Asp Asn Phe Asp Gln Gln Thr Tyr Lys Glu
545                 550                 555                 560

Met Thr Leu Lys Pro Ser Arg Tyr Thr Phe Val Glu Asn Ile Tyr Ser
            565                 570                 575

Arg Glu Asn Arg Lys Leu Ile Glu Leu Pro Ser Lys Asn Phe Glu Glu
            580                 585                 590

Leu Leu Ser Lys Ile Ile Lys Asp Leu Thr Asp Phe Ser Leu Ser Phe
            595                 600                 605

Lys Asn Asp Asp Leu Phe Val Asp Ile Tyr Leu Leu Ser Asp Leu Val
            610                 615                 620

Glu Leu Ala Lys Thr Leu Ile Ser Leu Val Ile Asn Tyr Ser Asn Lys
625                 630                 635                 640

Ser Gln Phe Asp Ser Tyr Lys Asn Glu Leu Ile Asp Asp Thr Tyr Gln
            645                 650                 655

Lys Ala Lys Lys Tyr Leu Glu Thr Phe Lys Ile Ser Phe Phe Asn Ser
            660                 665                 670

Lys Lys Glu Ala Asn Tyr Phe Tyr Gln Thr Arg Val Leu Ser Glu Leu
            675                 680                 685

Lys Gly Ala Val Ala Leu Phe Ser Lys Tyr Tyr Gln Ala Lys Tyr
            690                 695                 700

Asn Ile Gln Ile Leu Lys Ser Asn Glu Ile Phe Pro Leu Phe Val Lys
705                 710                 715                 720

Phe Ser Asp Leu Leu Lys Lys Glu Glu Ile Asn Asp Ile Asn Lys Leu
            725                 730                 735

Lys Leu Ile Phe Lys Lys Pro Tyr Arg Tyr Leu Ile Ala Leu Lys Lys
            740                 745                 750

Ile Lys Phe Lys Lys Gln Gln Gln Ser Ser Val Ile His Leu Asp
            755                 760                 765

Lys Lys Asn Lys Asp Leu Val Leu Ile Ser Pro Gln Asp Glu Asp Phe
            770                 775                 780

Leu Phe Lys Leu Thr Ser Ser Phe Tyr Gln Leu Gln Phe Leu Asp Arg
785                 790                 795                 800

Phe Val Tyr Pro Val Lys Lys Trp Leu Asn Val Asp Ile Thr Leu Ser
```

805                 810                 815
Glu Trp Ser Phe Ile Leu Glu Lys Lys Tyr Lys Ile Asn Trp Asp Phe
                820                 825                 830

Asn Asn Gly Lys Pro Glu Phe Ser Glu Ile Asp Ser Arg Leu Tyr Leu
        835                 840                 845

Asn Ile Pro Phe Lys Ile Lys Ala Ile Asn Gln Gln Lys Ile Leu Lys
    850                 855                 860

Pro Lys Glu Leu Phe Leu Gly Ile Asp Val Gly Glu Tyr Gly Val Gly
865                 870                 875                 880

Tyr Ala Leu Val Asn Phe Lys Asp Glu Ile Lys Ile Ile Lys Ser
                885                 890                 895

Gly Phe Ile Arg Ser Lys Asn Ile Ala Ser Ile Arg Asp Lys Tyr Arg
            900                 905                 910

Leu Leu Gln Asp Arg Ser Lys Lys Gly Val Tyr Phe Ser Ser Thr Asn
                915                 920                 925

Val Val Gln Glu Val Arg Glu Asn Ala Ile Gly Glu Ile Arg Asn Gln
930                 935                 940

Ile His Asp Ile Leu Ile Lys Asn Asn Ala Asp Leu Ile Tyr Glu Tyr
945                 950                 955                 960

Asn Ile Ser Asn Phe Glu Thr Gly Ser Gly Arg Ile Thr Lys Ile Tyr
                965                 970                 975

Asp Ser Ile Lys Lys Ser Asp Val Tyr Ala Glu Asn Glu Ala Asp Lys
            980                 985                 990

Ser Val Ile Gln His Val Trp Gly Ile Lys Lys Ser Ile Ala Ser His
                995                1000                1005

Leu Ser Ala Tyr Gly Ser Ser Tyr Thr Cys Ser Asn Cys Gly Arg
    1010                1015                1020

Ser Ile Phe Ser Phe Ser Glu Asn Asp Ile Phe Ser Ser Lys Val
    1025                1030                1035

Ile Lys Arg Asp Gly Asn Ile Ile Thr Ile Gln Thr Pro Lys Gly
    1040                1045                1050

Glu Val Phe Ala Tyr Ser Lys Asp Lys Lys Phe Asn Ile Gly Tyr
    1055                1060                1065

Ser Phe Ser Gln Glu Lys Asn Lys Glu Glu Met Lys Asn Leu Phe
    1070                1075                1080

Met Lys Ile Val Lys Ala Tyr Ala Arg Pro Pro Leu Leu Lys Ser
    1085                1090                1095

Glu Val Leu Leu Thr Gln Lys Lys Leu Asp Arg Glu Phe Leu Glu
    1100                1105                1110

Lys Phe Lys Lys Glu Arg Gly Asn Ser Ala Ile Phe Val Cys Pro
    1115                1120                1125

Phe Val Asp Cys Gln Ser Leu Ala Asp Ser Asp Ile Gln Ala Ala
    1130                1135                1140

Phe Ile Met Ala Leu Arg Gly Tyr Leu Lys Lys Lys Gly Lys
    1145                1150                1155

Asp Ile Asn Tyr Leu Glu Glu Ser Leu Asn Tyr Leu Gln Asn Phe
    1160                1165                1170

Lys Gly Lys Ile Asn Phe Ser Asn Leu Leu His
    1175                1180

<210> SEQ ID NO 54
<211> LENGTH: 1338
<212> TYPE: PRT
<213> ORGANISM: Artificial Sequence
<220> FEATURE:
<223> OTHER INFORMATION: Synthetic sequence

<400> SEQUENCE: 54

```
Met Asn Lys Lys Ser Ser Asn Ser Thr Gly Tyr Arg Leu His Lys Asp
1               5                   10                  15

Arg Ile Leu Phe Ser Gly Gly Glu Ile Met Arg Thr Ile Lys Tyr Pro
            20                  25                  30

Leu Val Val Glu Lys Asn Asn Leu Asn Ser Glu Glu Ile Val Glu Lys
        35                  40                  45

Ile Arg Gln Ala Ile Ile Asn Asp Asp Arg Val Ile Arg Ser Asp Ile
    50                  55                  60

Asn Leu Asn Asp Tyr Ile Glu Tyr Thr Lys Lys Gly Asn Arg Leu Tyr
65                  70                  75                  80

Thr Leu Ile Asp Phe Trp Gln Asp Cys Leu Arg Ala Gly Val Ile Trp
                85                  90                  95

Gln Pro Ser Thr Ser Phe Leu Leu Tyr Leu Ile Asn Lys Leu Tyr Ser
            100                 105                 110

Lys Pro Lys Ala Ile Glu Leu Ile Glu Asn Ala Lys Pro Asp Ile Ser
        115                 120                 125

Arg Phe Phe Asp Val Asp Lys Phe Ser Lys Cys Phe Ile Leu Pro Gly
    130                 135                 140

Glu Ile Arg Glu Gly Lys Ile Leu Lys Thr Phe Lys Arg Glu Leu Ile
145                 150                 155                 160

Glu Ala Leu Lys Gly Glu Phe Lys Lys Gly Lys Glu Lys Ile Lys
                165                 170                 175

Asp Glu Asp Asp Tyr Leu Glu Lys Phe Val Glu Lys Asp Ala Arg Lys
            180                 185                 190

Leu Ile Arg Glu Ile Ala Asp Cys Phe Phe Ser Asn Asp Ile Leu Val
        195                 200                 205

Thr His Asp Leu Lys Glu Gly Lys Lys Glu Tyr Gln Asp Arg Leu Trp
    210                 215                 220

Glu Glu Lys Phe Gly Ile Lys Lys Gly Lys Leu Leu Glu Asn Phe Lys
225                 230                 235                 240

Leu Pro Asp His Leu Arg Asn Phe Lys Asn Ile Ser Phe Phe Ile Ile
                245                 250                 255

Pro Glu Leu Ser Asp Lys Ser Lys Asn Phe Asp Glu Leu Ile Glu Leu
            260                 265                 270

Arg Arg Lys Trp Leu Leu Glu Arg Lys Ile Cys Val Arg Glu Asp Gly
        275                 280                 285

Asp Tyr Leu Glu Asn Glu Lys Lys Leu Asp Glu Glu Leu Arg Asn Leu
    290                 295                 300

Val Gly Leu Ser Asp Asn Cys Asn Pro Leu Ser Asn Phe Leu Gly Thr
305                 310                 315                 320

Val Phe Cys Glu Leu Leu Val Pro Asn Asn Leu Asn Glu Asp Asn Ala
                325                 330                 335

Leu Glu Lys Phe Tyr Asp Val Phe Thr Ile Val Glu Pro Lys Ile Ala
            340                 345                 350

Glu Leu Asn Ile Lys Asp Gln Ile Met Gly Ser Leu Glu Phe Leu Arg
        355                 360                 365

Leu Arg Ala Lys Gln Leu Gly Ser Pro Asn Leu Val Asn Phe Ser Lys
    370                 375                 380

Ser Gln Asn Leu Lys Ala Asn Glu Ser Ile Lys Leu Asp Gly Trp Ser
385                 390                 395                 400
```

-continued

```
Leu Tyr Arg Gln Asn Phe Gly Ser Lys Met Gln Ser Trp Phe Thr Ser
                405                 410                 415
Tyr Ile Glu Arg Asn Lys Leu Leu Glu Asp Ser Leu Lys Asn Phe Lys
            420                 425                 430
Glu Lys Ile Lys Lys Ala Gln Asn Phe Ile Lys Asn Leu Lys Asn Ile
        435                 440                 445
Ser Glu Glu Pro Gln Gln Glu Glu Ala Gln Gln Glu Lys Glu Glu
    450                 455                 460
Ile Val Glu Leu Phe Glu Lys Ile Phe Ser Ser Leu Glu Lys Val Asn
465                 470                 475                 480
Arg Glu Asn Phe Glu Val Phe Asp Ser Leu Leu Ser Ser Leu Arg Lys
                485                 490                 495
Arg Leu Asn Phe Phe Tyr Gln Gln Tyr Leu Tyr Asn Glu Ala Lys Glu
            500                 505                 510
Gly Asp Asp Val Lys Lys His Lys Ile Leu Gly Pro Ile Phe Lys Asn
        515                 520                 525
Ile Glu Lys Pro Ile Ala Phe Tyr Gly Glu Thr Gln Arg Lys Lys Asn
    530                 535                 540
Glu Lys Phe Val Glu Asp Thr Ile Pro Ile Leu Glu Glu Gly Thr Val
545                 550                 555                 560
Phe Leu Thr Thr Leu Ile Ser Asn Leu Leu Asp Ser Phe Ser Pro Lys
                565                 570                 575
Gln Val Phe Pro Asp Val Arg Lys Lys Asp Glu Thr Glu Glu Ile Ile
            580                 585                 590
Tyr Arg Lys Glu Leu Gln Phe Phe Trp Asn Lys Leu Lys Asp Leu Ala
        595                 600                 605
Val Asn Ser Lys Glu Phe Glu Lys Glu Tyr Gln Asp Ile Ile Glu Ser
    610                 615                 620
Ala Val Asp Glu Ser Glu Leu Ser Lys Leu Lys Glu Leu Phe Val Asn
625                 630                 635                 640
Lys Lys Lys Asn Gly Ser Lys Tyr Asn Lys Tyr Thr Phe Tyr Lys Ser
                645                 650                 655
Lys Tyr Thr Lys Gly Ser Ile Glu Glu Ile Lys Leu Lys Gly Ser Lys
            660                 665                 670
Glu Glu Tyr Leu Leu Arg Phe Glu Lys Leu Ile Lys Ser Leu Thr Asn
        675                 680                 685
Phe Leu Thr Gln Phe Asn Arg Asn Lys Leu Leu Gln Asp Lys Asp Leu
    690                 695                 700
Leu Leu Asp Trp Val Glu Leu Ala Lys Asn Ile Val Ser Val Leu Ile
705                 710                 715                 720
Arg Phe Ser Thr Asn Thr Glu Phe Ser Leu Asn Glu Ile Lys Ala Gln
                725                 730                 735
Ser Gln Phe Lys Lys Ala Lys Asn Tyr Leu Glu Leu Phe Lys Leu Lys
            740                 745                 750
Lys Ala Lys Lys Lys Glu Phe Gly Phe Ile Ile Gln Ser Phe Ile Leu
        755                 760                 765
Ser Glu Ile Lys Gly Ala Ala Thr Leu Tyr Ser Lys Arg Lys Tyr Ile
    770                 775                 780
Ala Ser Tyr Ser Val Gln Ile Val Gly Ser Asn Asn Lys Phe Lys Leu
785                 790                 795                 800
Phe Tyr Gln Pro Leu Asp Ser Ser Ile Asn Ile Ser Gly Gly Pro Lys
                805                 810                 815
```

```
Asp Phe Val Thr Lys Lys His Lys Tyr Leu Ile Val Phe Gln Asp Leu
            820                 825                 830

Lys Asn Val Lys Asn Lys Asp Ala Thr Glu Asn Arg Ile Asn Leu Leu
            835                 840                 845

Arg Leu Asn Lys Glu Arg Lys Ile Pro Leu Val Ala Tyr Lys Asp Asp
850                 855                 860

Leu Val Ser Lys Ser Leu Leu Leu Ser Ser Pro Tyr Gln Leu Gln
865                 870                 875                 880

Phe Leu Asp Lys Tyr Leu Tyr Arg Pro Arg Gly Trp Glu Asn Ile Asp
            885                 890                 895

Ile Lys Leu Asn Glu Trp Ser Phe Val Val Glu Glu Ala Tyr Asp Ile
            900                 905                 910

Glu Trp Asp Leu Asn Ser Lys Thr Pro Lys Leu Ile Pro Ser Pro Lys
            915                 920                 925

Ser Asn Arg Asn Lys Leu Tyr Leu Ala Ile Pro Phe Thr Leu Lys Gly
            930                 935                 940

Asn Val Lys Glu Pro Pro Leu Asp Lys Ile Val Leu Ser Glu Thr
945                 950                 955                 960

Lys Lys Asp His Ser Arg Asp Lys Asn Arg Leu Asn Tyr Pro Ile Leu
            965                 970                 975

Gly Val Asp Val Gly Glu Tyr Gly Val Ala Trp Cys Leu Thr Lys Phe
            980                 985                 990

Asp Tyr Asn Gln Asp Phe Ser Leu Arg Asp Ile Asp Ile Gln Gly Lys
            995                 1000                1005

Gly Phe Ile Glu Asp Arg Asn Ile Gly Lys Ile Lys Asp Tyr Phe
    1010                1015                1020

Ala Glu Ile Gln Gln Lys Ser Arg Lys Gly Ala Tyr Asp Glu Asp
    1025                1030                1035

Asp Thr Thr Ile Ala Lys Val Arg Glu Asn Ala Ile Gly Lys Leu
    1040                1045                1050

Arg Asn Ala Ile His Ser Ile Leu Thr Gly Ser Leu Glu Gly Ala
    1055                1060                1065

Ser Pro Val Tyr Glu Asp Ala Ile Ser Asn Phe Glu Thr Gly Ser
    1070                1075                1080

Gly Lys Thr Ile Lys Ile Tyr Asn Ser Val Lys Arg Ala Asp Thr
    1085                1090                1095

Glu Phe Lys Ser Glu Ala Asp Lys Ala Glu His Ser Leu Val Trp
    1100                1105                1110

Gly Lys Lys Asp Arg Asn Gln Glu Thr Lys Tyr Ile Gly Arg Asn
    1115                1120                1125

Val Ser Ala Tyr Ala Ser Ser Tyr Thr Cys Val Asn Cys Leu His
    1130                1135                1140

Thr Leu Phe Lys Val Lys Lys Glu Asp Leu Ser Asn Ile Lys Ile
    1145                1150                1155

Leu Glu Lys Asp Gly Arg Ile Val Thr Met Ser Ser Pro Tyr Gly
    1160                1165                1170

Pro Asp Lys Lys Val Arg Gly Tyr Leu Ser Glu Lys Glu Lys Tyr
    1175                1180                1185

Glu Ile Gly Tyr Gln Phe Lys Glu Ser Glu Glu Asp Leu Lys Ala
    1190                1195                1200

Phe Arg Lys Ile Val Arg Asp Phe Ala Arg Pro Pro Val Asn Lys
    1205                1210                1215

Asn Ser Glu Val Leu Glu Lys Tyr Ala Lys Glu Ile Leu Ala Gly
```

```
            1220                1225                1230

Asn Lys Ile Glu Glu Phe Arg Lys Lys Arg Gly Asn Ser Ala Ile
        1235                1240                1245

Phe Val Cys Pro Phe Cys Gln Phe Lys Ala Asp Ala Asp Ile Gln
    1250                1255                1260

Ala Ala Phe Met Met Ala Met Arg Gly Tyr Leu Arg Phe Ser Gly
1265                1270                1275

Ile Val Pro Ser Lys Glu Asn Ser Lys Asn Asn Pro Gln Glu Ser
        1280                1285                1290

Glu Asp Lys Ser Leu Lys Asn Ser Lys Lys Gln Ser Glu Thr Gly
    1295                1300                1305

Asp Thr Phe Leu Thr Lys Thr Ala Glu Tyr Leu Gln Gln Leu Arg
1310                1315                1320

Phe Glu Ile Lys Glu Lys Ile Lys Glu Ala Val Lys Val Asp Phe
        1325                1330                1335

<210> SEQ ID NO 55
<211> LENGTH: 1268
<212> TYPE: PRT
<213> ORGANISM: Artificial Sequence
<220> FEATURE:
<223> OTHER INFORMATION: Synthetic sequence

<400> SEQUENCE: 55

Met Thr Lys Arg Lys Ser Arg Leu Ala Gly Tyr Arg Leu His Lys Glu
1               5                   10                  15

Arg Ile Leu Phe Ala Gly Gly Gln Ile Ile Arg Thr Ile Lys Tyr Pro
            20                  25                  30

Leu Thr Pro Ser Tyr Pro Thr Glu Glu Met Thr Gln Phe Leu Lys Asp
        35                  40                  45

Phe Glu Glu Ala Val Ile Ala Asp Asp Leu Lys Ile Arg Gly Asp Leu
    50                  55                  60

Asn Ile Asn Asp Tyr Leu Thr Tyr Thr Ala Lys Gly Lys Pro Leu Tyr
65                  70                  75                  80

Thr Leu Phe Asp Phe Trp Val Asp Ser Leu Arg Asn Gly Val Ile Trp
                85                  90                  95

Met Ser Lys Gly Thr Met Leu Ile Asp Phe Leu Ala Thr Gln Tyr Asn
            100                 105                 110

Ile Asn Ser Pro Phe Asp Asn Val Trp Lys Ala Ser Pro Arg Ile
        115                 120                 125

Thr Ser Phe Phe Lys Lys Asp Glu Phe Lys Glu Ile Ile Leu Cys Asp
    130                 135                 140

Pro Val Arg Ser Ser Thr Lys Asn Ser Phe His Lys Arg Ile Thr
145                 150                 155                 160

Gly Tyr Leu Lys Asp His Leu Lys Val Lys Asn Gly Asp Ser Tyr Thr
                165                 170                 175

Ile Val Ser Asn Asp Ala Gln Lys Val Val Glu Phe Ile Val His Ser
            180                 185                 190

Phe Phe Asn Asn Glu Gly Lys Leu Ile Leu Glu Gly Glu Gln Phe
        195                 200                 205

Lys Phe Trp Lys Lys Glu Tyr Asn Leu Asp Lys Ala Ile Ile Glu Ser
    210                 215                 220

Ala Lys Pro Lys Gly Lys Tyr Ala Asp Ile Thr Phe Val Ile Pro
225                 230                 235                 240

Glu Leu Ile Ser Asn Leu Asn Pro Lys Gln Ser Leu Glu Asp Leu Ile
```

```
                    245                 250                 255
Asn Lys Arg Asp Val Trp Leu Gln Gly Arg Phe Asp Lys Glu Asp
            260                 265                 270
Lys Leu Leu Leu Ser Ile Leu Gly Leu Ser Asp Asn Phe Asn Gly Phe
            275                 280                 285
Ser Asn Phe Leu Gly Val Val Leu Arg Asp Leu Gln Lys Glu Asn Gly
            290                 295                 300
Asn Lys Glu Val Leu Tyr Asp Ala Gln Lys Thr Val Phe Pro Leu Leu
305                     310                 315                 320
Gly Asn Ser Lys Asp Glu Val Leu Glu Ala Leu Asp Phe Leu Ser Gln
                325                 330                 335
Lys Ala Lys Leu Leu Gly Val Thr Ser Leu Pro Leu Val Asn Gly Trp
            340                 345                 350
His Glu Tyr Arg Ser Ile Phe Gly Gly Lys Leu Lys Ser Trp Phe Thr
            355                 360                 365
Asn Ser Gln Asn Arg Lys Glu Glu Leu Asp Gly Gln Ile Ser Arg Phe
370                 375                 380
Lys Glu Ser Leu Phe Lys Ala Arg Asn Tyr Leu Gln Thr Glu Asn Phe
385                 390                 395                 400
Gly Glu Glu Ala Asn Lys Glu Lys Glu Asp Ile Leu Ser Phe Leu Ser
                    405                 410                 415
Leu Leu Glu Asn Phe Phe Thr Asp Glu Lys Arg Ser Ile Lys Val Glu
                420                 425                 430
Glu Asn Tyr Gln Leu Phe Glu Pro Leu Leu Ala Leu Val Lys Arg Arg
            435                 440                 445
Leu Asn Phe Phe Tyr Gln Arg Tyr Ile Gln Lys Glu Gly Asp Glu Thr
450                 455                 460
Lys Val Asn Glu Leu Gly His Phe Lys Gly Leu Tyr Glu Lys Ile Tyr
465                 470                 475                 480
Lys Pro Val Ala Phe Tyr Gly Tyr Ala Ala Lys Lys Val Asn Lys Lys
                485                 490                 495
Phe Val Asn Gln Thr Phe Pro Ile Leu Glu Asp Gly Ile Glu Asn Ile
                500                 505                 510
Glu Lys Leu Ile Ser Tyr Leu Gln Asn Ser Phe Ser Val Gln Glu Thr
            515                 520                 525
Phe Glu Glu Val Lys Gln Gly Lys Glu Ile Asp Asp Pro Tyr Arg
            530                 535                 540
Lys Leu Leu Gln Phe Phe Trp Asn Lys Tyr Leu Glu Asp Ser Ile Asn
545                 550                 555                 560
Ser His Leu Phe Ala Glu Lys Tyr Lys Asp Ile Leu Lys Gly Asn Ile
                565                 570                 575
Glu Asp Asn Glu Trp Glu Lys Val Ile Asp Lys Thr Lys Lys Gly Lys
            580                 585                 590
Tyr Val Phe Tyr Lys Ser Pro Tyr Ala Lys Gly Ser Leu Glu Glu Ile
            595                 600                 605
Pro Ile Gly Thr Ser Asn Tyr Leu Glu Gln Leu Gln Ile Ser Ile Leu
            610                 615                 620
Glu Leu Ser Lys Phe Ile Leu Ser Tyr Lys Lys Asp Ile Leu Leu Ser
625                 630                 635                 640
Asp Val Gly Leu Leu Leu Asp Trp Val Glu Leu Ser Lys Asn Val Ile
                645                 650                 655
Ser Ile Leu Leu Arg Phe Asn Thr Lys Lys Thr Tyr Arg Ile Asp Asp
                660                 665                 670
```

```
Leu Arg Leu Asp Asn Phe Ser Gln Ala Lys Arg Tyr Gln Glu Leu Phe
        675                 680                 685

Lys His Gly Asp Tyr Pro Lys Asn Glu Phe Ser Phe Ile Ile Gln Ser
    690                 695                 700

Leu Val Leu Ser Glu Ile Arg Gly Ala Ala Thr Leu Tyr Ser Lys Arg
705                 710                 715                 720

Glu Tyr Ile Ala Ser Tyr Ser Val Gln Val Gly Ser Asp Ser Lys
                725                 730                 735

Tyr Arg Ile Tyr Tyr Ile Pro Lys Glu Lys Ile Ser Ile Thr Pro Asp
            740                 745                 750

Val Val Lys Ser Arg Pro Glu Ser Ser Glu Arg Lys Gln Leu Met Gly
                755                 760                 765

Pro His Tyr Tyr Ala Val Ala Leu Gly Lys Val Leu Glu Lys Lys Lys
    770                 775                 780

Ser Glu Ile Phe Asn Ser Ile Ala Leu Phe Lys Lys Asn Ile Lys Ala
785                 790                 795                 800

Ile Phe Leu Pro Glu Ser Ser Leu Arg Gly Val Phe Arg Leu Ser Ser
                805                 810                 815

Ser Pro Tyr Gln Leu Gln Phe Leu Asp Lys Phe Ile Tyr Arg Pro Phe
        820                 825                 830

Gly Trp Glu Asn Ile Asp Val Ser Leu Ser Glu Trp Ser Phe Ile Val
    835                 840                 845

Glu Lys Arg Tyr Thr Ile Asn Trp Asp Leu Arg Ser Lys Lys Pro Lys
850                 855                 860

Leu Leu Pro Val Thr Asp Thr Glu Arg Ile Lys Lys Asn Lys Val Tyr
865                 870                 875                 880

Ile Ala Ile Pro Phe Asn Leu Ile Pro Ser Lys Glu Val Arg Gln Ala
                885                 890                 895

Ala Pro Leu Lys Thr Ile Ala Lys Gly Lys Glu Thr Arg Glu Lys Asp
        900                 905                 910

Leu Ser Arg Leu Asn Phe Pro Ile Met Gly Val Asp Val Gly Glu Tyr
    915                 920                 925

Gly Leu Ala Tyr Cys Leu Val Lys Ile Ile Phe Asp Lys Asn Thr Tyr
    930                 935                 940

Lys Ile Leu Ala Ile Glu Leu Val Ser Asp Lys Lys Glu Ala Phe Gly
945                 950                 955                 960

Phe Ile Glu Asp Arg Asn Ile Gly Asn Ile Lys Asp Lys Phe Ala Glu
                965                 970                 975

Ile Gln His Arg Ala Arg Gln Gly Ser Phe Asp Glu Asp Thr Val
        980                 985                 990

Ile Thr Arg Val Arg Glu Asn Ala  Val Gly His Leu Arg  Asn Arg Leu
        995                 1000                1005

His Val  Ile Val Thr Leu Gln  Arg Ser Ser Val  Tyr Glu Asp
    1010                1015                1020

Ser Ile  Ser Asn Phe Glu Thr  Gly Ser Gly Arg Thr  Thr Lys Ile
    1025                1030                1035

Tyr Asn  Ser Val Lys Arg Ala  Asp Thr Glu Ser Asp  Thr Asn Ala
    1040                1045                1050

Asp Lys  Met Thr His Asn  Val Trp Gly Glu Lys  Thr Lys Trp
    1055                1060                1065

Val Gly  Arg Asn Val Ser Ala  Tyr Ala Ser Ser Tyr  Thr Cys Val
    1070                1075                1080
```

```
Ser Cys Leu Lys Ser Leu Tyr Gln Val Arg Lys Glu Asp Leu Ser
    1085                1090                1095

Lys Met Arg Ile Thr Gln Arg Gly Gly Arg Ile Val Thr Ile Ser
    1100                1105                1110

Gly Pro His Gly Asp Ile Lys Gly Tyr Val Ser Lys Glu Glu Lys
    1115                1120                1125

Tyr Asn Leu Gly Tyr His Phe Arg Glu Thr Asp Asp Glu Leu Lys
    1130                1135                1140

Asn Phe Arg Lys Ile Val Gln Asp Phe Ala Arg Pro Pro Val Gly
    1145                1150                1155

Asp His Ser Glu Val Leu Lys Lys Tyr Ala Lys Gln Ile Leu Glu
    1160                1165                1170

Lys Gly Lys Ile Glu Glu Trp Arg Lys Arg Arg Gly Asn Ser Ser
    1175                1180                1185

Ile Phe Ile Cys Pro Phe Cys Gln Tyr Ile Thr Asp Ala Asp Val
    1190                1195                1200

Gln Ala Ala Phe Met Met Ala Ile Arg Gly Tyr Leu Arg Phe Ser
    1205                1210                1215

Gly Ile Val Pro Ser Arg Gly Asn Lys Lys Asp Gln Asp Gln Glu
    1220                1225                1230

Gln Glu Asp Glu Lys Thr Ala Gly Glu Ser Phe Leu Glu Gln Thr
    1235                1240                1245

Gln Arg Gln Leu Gly Asp Val Asn Leu Ser Lys Ile Leu Glu Ala
    1250                1255                1260

Phe Ser Leu Lys Ile
    1265

<210> SEQ ID NO 56
<211> LENGTH: 1212
<212> TYPE: PRT
<213> ORGANISM: Artificial Sequence
<220> FEATURE:
<223> OTHER INFORMATION: Synthetic sequence

<400> SEQUENCE: 56

Met Val Phe Pro Ala Met Leu Phe Tyr Thr Arg Pro Glu Tyr Ala Phe
1               5                   10                  15

Leu Thr Ile Leu Ile Ser Leu Glu Ser Ser Val Leu Phe Leu Pro Lys
            20                  25                  30

Lys Ile Ile Val Met Thr Ala Lys Thr Gln Lys Asn Lys Asn Ser Lys
        35                  40                  45

Lys Thr Lys His Phe Gly Gln Thr Gly Tyr Ala Leu His Lys Ser Arg
    50                  55                  60

Leu Val Tyr Thr Gly Lys Glu Ala Ile Arg Ser Ile Lys Phe Pro Leu
65                  70                  75                  80

Lys Ser Thr Ser Gln Val Lys Leu Asp Asp Phe Ala Asn Lys Val Ile
            85                  90                  95

Ser Asp Tyr Ser Leu Ile Gln Gly Ala Thr Asn Ile Asn Glu Tyr Leu
            100                 105                 110

Thr Glu Tyr Gln Asn Ala Gln His Ser Tyr Ser Leu Ile Asp Phe Trp
        115                 120                 125

Val Asp Ser Leu Arg Ala Gly Val Val Phe Ala Lys Thr Pro Ala Ala
    130                 135                 140

Leu Thr Asp Phe Leu His Val Val Tyr Gln Arg Thr Ser Pro Ser Arg
145                 150                 155                 160
```

-continued

Leu Ala Phe Asp Gln Met Tyr Lys Ser Leu Arg Ser Lys Leu Asp Tyr
            165                 170                 175

Glu Leu Phe Leu Gln Lys Ile Ile Leu Ser Thr Gly Ile Arg Lys Ser
            180                 185                 190

Ala Gly Lys His Gly Ile Leu Ser Cys Phe Lys Lys Glu Trp Gln Ser
            195                 200                 205

Asp Pro Ser Val Leu Lys Glu Val Asp Tyr Ile Phe Ser Asn Leu Ile
            210                 215                 220

Lys Asn Gly Ala Thr Leu Ser Gln Glu Glu Arg Asn Phe Trp Lys
225                 230                 235                 240

Ser Ala Tyr Asn Leu Gln Leu Pro Ala Lys Gln Lys Gly Ala Asn Leu
            245                 250                 255

Thr Phe Tyr Val Leu Pro Glu Leu Lys Phe Asp Ser Asn Met Asn Ile
            260                 265                 270

Ser Thr Cys Phe Ser Asp Arg Phe Ser Phe Lys Lys Gln Asn Asp
            275                 280                 285

Ser Lys Leu Asp Ala Ile Phe Gly Phe Asp Asn Phe Ser Ala Phe
            290                 295                 300

Ser Asn Tyr Phe Gly Glu Ile Leu Gln Leu Phe Lys Glu Gln Lys Thr
305                 310                 315                 320

Gln Lys Ile Ala Asp Tyr Leu Ile Asn Phe Phe Asp Ile Trp Arg Gly
            325                 330                 335

Met Glu Asp Glu Leu Asn Arg Arg Leu Val Phe Leu Ser Asn Gln Ala
            340                 345                 350

Gln Lys Leu Val Gln Ala Asn Ile Ala Thr Asn Tyr Ala Asp Phe Arg
            355                 360                 365

Met Ser Phe Gly Gly Lys Leu Gln Ser Trp Phe Ser Gly Tyr Gln Asn
            370                 375                 380

Gln Asn Gln Lys Ile Ile Glu Gln Leu Asn Asp His Gly Glu Asp Leu
385                 390                 395                 400

Lys Lys Ile Asn Asp Ala Val Thr Lys Gln Asn Val Lys Pro Glu Asp
            405                 410                 415

Glu Glu Arg Lys Thr Asp Leu Leu Thr Asp Leu Ala Asp Leu Gln Lys
            420                 425                 430

Tyr Gln Ser Glu Leu Ala Gly Gly Lys Glu Leu Glu Phe Ala Lys Leu
            435                 440                 445

Asp Leu Tyr Arg Asp Leu Leu Ala Phe Phe Arg Ser Asp Phe Asn Trp
            450                 455                 460

Phe Phe Gln Asn Tyr Leu Leu Glu Glu Lys Lys Ala Asp Lys
465                 470                 475                 480

Asp Ile Ser Val Asn Lys Lys Tyr Lys Lys Leu Phe Lys Asn Leu Arg
            485                 490                 495

Leu Val Pro Glu Phe Gly Leu Ala Arg Lys Lys Ala Tyr Gln Lys
            500                 505                 510

Tyr Ile Asp Ser Thr Ile Pro Ile Ile Lys Thr Gly Trp Gln Val Val
            515                 520                 525

Thr Asp Ala Leu Pro Ile Leu Arg Glu Asn Met Ser Tyr Glu Phe Leu
            530                 535                 540

Leu Asn Pro Lys Lys Lys Asp Tyr Phe Ile Ala Asn Leu Glu Lys Phe
545                 550                 555                 560

Asn Arg Lys Leu Lys Thr Lys Thr Trp Asn Arg Pro Lys Phe Ser Gln
            565                 570                 575

Leu Ser Glu Lys Ile Val Arg His Tyr Asn Asn Asn Gln Val Pro Thr

```
            580                 585                 590
Ser Asn Gln Val Phe Tyr Lys Asn Arg Phe Ser Asn Ser Arg Gln Glu
            595                 600                 605
Ile Ile Leu Ile Asp Gly Leu Asn Gln Glu Lys Glu Leu Lys Trp Leu
            610                 615                 620
Val Asn Ser Cys Leu Glu Cys Leu Ala Lys Pro Val Leu Ser Ala Asp
625                 630                 635                 640
Ala Gly Leu Met Ile Asp Gln Leu Glu Leu Thr Lys Met Val Leu Gly
                645                 650                 655
Trp Leu Ile Asn Gly Asn Asn Asp Ser Ile Ile Asn Phe Asp Lys Tyr
                660                 665                 670
Asp Leu Ala Asn Phe Ile Lys Ala Ser Lys Phe Ile Glu Val Phe Lys
                675                 680                 685
Thr Asn Gln Phe Ala Gly Arg Gln Leu Ser Arg Phe Leu Met Ser Tyr
                690                 695                 700
Ile Phe Gly Glu Leu Arg Gly Ala Val Gly Leu Phe Ser Arg Gln Ser
705                 710                 715                 720
Phe Val Asn Arg Tyr Val Val Ser Pro Met Ala Ser Leu Ser Asn Tyr
                725                 730                 735
Pro Leu Val Asn Asp Gly Ala Lys Trp Tyr Leu Ala Leu Gly Lys Ser
                740                 745                 750
Ser Lys Lys Pro Lys Glu Gly Met Lys Glu Phe Thr Glu Tyr Ala Asp
                755                 760                 765
Lys Glu Ser Asp Lys Ala Lys Ser Ala His Phe Phe Pro Asp Asp Leu
                770                 775                 780
Leu Tyr Val Ser Ser Ile Tyr Gln Met Gln Phe Leu His Ala Leu
785                 790                 795                 800
Lys Arg Gln Lys Glu Gly Lys Lys Trp His Lys Trp Gln Gln Ile Asn
                805                 810                 815
Leu Lys Leu Ser Asp His Ala Phe Ile Val Glu Asp Glu Tyr Gln Val
                820                 825                 830
Lys Trp Asp Leu Ile Thr Gly Lys Pro Asn Leu Lys Arg Val Ala Glu
                835                 840                 845
Asn Arg Arg Val Phe Val Ser Val Pro Phe Ile Leu Asn Pro Leu Ser
850                 855                 860
Glu Gln Lys Thr Gln Ser Glu Asn Ile Ala Asn Arg Tyr Arg Tyr Leu
865                 870                 875                 880
Gly Ile Asp Val Gly Glu Tyr Gly Leu Ala Tyr Ala Val Leu Asp Phe
                885                 890                 895
Ser Asn Lys Lys Arg Ala Glu Ile Ile Asp Gln Gly Phe Ile Tyr Asp
                900                 905                 910
Gly Ser Leu Arg Lys Ile Arg Asp His Phe Asp Leu Ile Lys Asp Thr
                915                 920                 925
Gln Thr Lys Gly Thr Phe Ser Val Pro Ser Thr Ala Leu Ser Arg Val
                930                 935                 940
Arg Glu Asn Ala Ile Thr Ala Leu Arg Asn Lys Ile His Asp Leu Val
945                 950                 955                 960
Leu Arg Phe Asn Ala Lys Pro Val Tyr Glu Phe Ser Ile Ser Asn Phe
                965                 970                 975
Glu Thr Gly Ser Gly Lys Val Thr Lys Ile Tyr Asn Ser Val Lys Lys
                980                 985                 990
Ala Asp Ile Tyr Pro Glu Ile Asp  Thr Asp Lys Ala Val  Gln Lys His
                995                 1000                1005
```

```
Ile Trp Gly Lys Asn Pro Lys Leu Ile Gly Gln Glu Val Ser Ala
1010                1015                1020

Tyr Ala Thr Ser Tyr Thr Cys Ser Lys Cys His Gln Ser Ile Tyr
    1025                1030                1035

Asp Gln Gly Leu Asp Lys Glu Ser Lys Ile Lys Ala Asn Gln Ile
1040                1045                1050

Ile Asn Ala Ser Pro Thr Gly Leu Ile Lys Ile Lys Leu Val Ser
    1055                1060                1065

Lys Val Glu Ala Trp Gly Phe Val Lys Gly Ser Arg Lys Leu Glu
1070                1075                1080

Ile Thr Glu Asn Glu Arg Thr Val Ser Leu Phe Lys Gly Gln Lys
    1085                1090                1095

Ile Gly Asp Glu Val Ala Gln Arg Leu Val Lys Asn Phe Ala Arg
1100                1105                1110

Pro Pro Ile Asn Glu Ala Ser Glu Ala Ile Lys Leu Ala Met Ser
    1115                1120                1125

Gln Lys Lys Leu Asn Ser Asn Met Ile Asn Phe Glu Lys Leu Ala
1130                1135                1140

Glu Asp Arg Gly Asn Met Ala Met Phe Val Cys Pro Phe Cys Leu
    1145                1150                1155

His Val Asp Ala Asp Ile Gln Ala Ala Gln Asn Ile Ala Leu
1160                1165                1170

Arg Gly Phe Leu Lys Asn Glu Phe Glu Lys Asp Asn Asn Gly Lys
    1175                1180                1185

Lys Glu Ser Phe Asn Tyr Ile Gln Ala Val Lys Asn Phe Phe Gln
1190                1195                1200

Ser Gly Gly Met Ala Asp Tyr Asn Glu
    1205                1210

<210> SEQ ID NO 57
<211> LENGTH: 1258
<212> TYPE: PRT
<213> ORGANISM: Artificial Sequence
<220> FEATURE:
<223> OTHER INFORMATION: Synthetic sequence

<400> SEQUENCE: 57

Met Asn Glu Lys Lys Thr Ala Thr Gln Arg Arg Asn Ala Arg Arg
1               5                   10                  15

Arg Gly Glu Arg Ala Arg Thr Lys Ser Gln Glu Leu Arg Gly Tyr Arg
            20                  25                  30

Leu His Asp Ala Arg Ile Glu Phe Ser Gly Leu Gly Ser Met Arg
        35                  40                  45

Thr Val Lys Val Glu Leu Leu Asn Pro Asp Ser Ser Arg Glu Asp Pro
    50                  55                  60

Gln Arg Gly Gln Gly Leu Gln Gly Lys Val Lys Ala Val Phe Asp
65                  70                  75                  80

Asp Tyr Arg Ala Leu Tyr Gly Pro Met Asn Ile Glu Asp Tyr Leu Ser
                85                  90                  95

Asp Pro Asp Cys Pro Ser Phe Leu Gly Leu Trp Val Lys Ala Val Cys
            100                 105                 110

Leu Gly Val Ile Met Ser Arg Lys Thr Ala Thr Asp Phe Gly Glu Leu
        115                 120                 125

Arg Gly Gly Ser Lys Ser Gly Gln Ala Phe Asp Ser Ile Pro Glu His
    130                 135                 140
```

```
Leu Arg Arg Gln Leu Ile Lys Leu Lys Trp Leu Asp Trp Tyr Asp Lys
145                 150                 155                 160

Gly Ile Arg Lys Ser Ser Lys Ala Ser Arg Leu Lys Ser Leu Thr
            165                 170                 175

Asp Val Phe Ala Asn Pro Lys Gln Pro Asp Gln Gly Val Met Ala Ala
            180                 185                 190

Trp Glu Gln Gly Glu Lys Leu Ala Glu Ser Ser Arg Asp Ile Ala Ala
            195                 200                 205

Leu Gly Arg Arg Glu Phe Lys Asp Lys Leu Phe Ala Ile Pro Pro Pro
210                 215                 220

Thr Ser Ser Val Val Leu Asp Asp Val Lys Ala Thr Lys Val Ser
225                 230                 235                 240

Arg Asp Trp Gln Trp Ala Val Asp Pro Gln Phe Lys Leu Pro Ser Thr
            245                 250                 255

Asp Leu Asp Ile Thr Arg Ala Leu Glu Glu Val Asp Arg Gln Trp Phe
            260                 265                 270

Glu Arg Leu Gly Asn Asn Arg Gly Met Val Gln Gln Phe Ala Ile
        275                 280                 285

Gly Asp Asn Gly Asn His Leu Asn Asn Gly Leu Phe Gly His Phe Phe
290                 295                 300

Ala Ser Ile Arg Ser Ala Asn Leu Ala Asp Ile Val Ala Glu Met Gly
305                 310                 315                 320

Thr Ala Phe Gly Phe Ser Ala Glu Glu Arg Asp Ile Val Arg Gln Arg
            325                 330                 335

Leu Glu Thr Leu His Glu Tyr Ala Gln Gly Leu Pro Glu Lys Pro Val
            340                 345                 350

Leu Ala Ser Arg Trp Ala Glu Tyr Arg Thr Asp Met Thr Ala Lys Leu
            355                 360                 365

Gly Ser Trp Tyr Ser Asn Arg Thr Ser Lys Gly Ala Ala Ser Ile Thr
370                 375                 380

Gln Val Trp Gly Thr Ile Asn Thr Glu Thr Gly Glu Val Lys Asp Asp
385                 390                 395                 400

Gly Leu Val Arg Thr Leu Glu Asn Ile Gln Ser Asp Leu Pro Asp Ser
            405                 410                 415

Cys Ser Ile Lys Glu Gly Ile Leu Gln Glu Thr Leu Asp Phe Ile Gly
            420                 425                 430

Asp Arg Arg Ser Ser Thr Asp Arg Ala Phe Thr Asp Glu Leu Glu Leu
        435                 440                 445

Tyr Leu Ala Thr Leu Arg Ser Asp Leu Asn Thr Trp Cys Gln Glu Gln
            450                 455                 460

Ser Ala Leu Trp Glu Glu Lys Gln Arg Gln Val Ala Thr Pro Ala Ser
465                 470                 475                 480

Asp Glu Lys Ser Lys Lys Ala Asp Asn Pro Trp Ala Gly Lys Gly Ser
            485                 490                 495

Lys Thr Asp Lys Trp Leu Gly Ala Leu His Thr Arg Ile Gln Ser Ser
            500                 505                 510

Pro Leu Phe Trp Gly Val Asp Lys Leu Glu Leu Trp Lys Thr Leu Ala
            515                 520                 525

Asn Leu Lys Gln Ala Ile Arg Asp Glu Ile Asp Lys Leu Asn Glu Gln
            530                 535                 540

Val Glu Val Phe Gly Arg Ser Ala Tyr Asp Glu Pro Val Gly Lys Asp
545                 550                 555                 560
```

Ala Asp Ser Gly Glu Gly Asp Arg Arg Val Asp Gln Leu Ser Tyr Leu
                565                 570                 575

Ser Ala Arg Leu Gly Asp Gln Ala His Glu Glu Val Arg Gln Arg Leu
            580                 585                 590

Asp Ala Ile Ala Leu Ala Leu Gly Val Lys Phe Ser Glu Arg Asp Asp
        595                 600                 605

Leu His Arg Phe Phe Val Ser Ser Arg Ala Arg Arg Arg Ala Ala Leu
    610                 615                 620

Leu Ala Met Pro Asn Thr Ile Thr Val Gly Lys Leu Arg Glu Leu Ala
625                 630                 635                 640

Asp Leu Thr Pro Leu Trp Glu Arg Ile Lys Lys Lys Pro Glu Glu Pro
                645                 650                 655

Arg Leu Leu Ala Asp Thr Val Ala Leu Ser Lys Val Val Asn Ser Ala
            660                 665                 670

Cys Ala Ser Arg Ala Asn Pro Ser Asp Gln Ile Glu Leu Thr Thr Ile
        675                 680                 685

His Ser Arg Leu Asp Gly Tyr Ser Lys Asn Ile Gly His Thr Glu Phe
    690                 695                 700

Ile Ser Arg Ala Thr Val Gln Ser Thr Asn Gly Ala Gln Asn Thr Val
705                 710                 715                 720

Ala Leu Asp Ser Leu Val Ser Pro Arg Leu Phe Tyr Tyr Asn Phe Pro
                725                 730                 735

Asn Ile Val Glu Ser Ala Glu Pro His Val Ser His Leu Glu Val Ala
            740                 745                 750

Thr Arg Gly Asn Leu Gly Ser Phe Glu Glu Phe Ala Ala Lys Glu His
        755                 760                 765

Arg Thr Phe Asp Arg Glu Asn Pro Gln Lys Asp Ser Arg Asn Arg Ile
    770                 775                 780

Asp Ser Val Asn Pro Leu Ala Val Ala Ser Ser Arg Tyr Gln Ile Gln
785                 790                 795                 800

Phe Phe Thr Trp Trp Ala Gly Leu His Arg Ser Lys Glu Thr Ala Leu
                805                 810                 815

Glu Val Gly Gly Ser Phe Thr Ile Ala Glu Arg Gln Val Arg Leu Asp
            820                 825                 830

Trp Ser Gln Glu Lys Pro Gln Ala Val Val Ser Glu Glu Leu Arg Val
        835                 840                 845

Phe Val Ser Gln Pro Phe Thr Ile Val Pro Asp Asp Lys Lys Arg Pro
    850                 855                 860

Ala Thr Ser Gly Thr Arg Tyr Ile Gly Val Asp Ile Gly Glu Tyr Gly
865                 870                 875                 880

Leu Ala Trp Ser Cys Trp Glu Phe Ala Pro Gly Tyr Trp Asn Gly Ser
                885                 890                 895

Val Val Asn Pro Ser Lys Val Thr Cys Leu Asp Tyr Gly Phe Leu Ala
            900                 905                 910

Glu Pro Gly Gln Arg Arg Ile Val Glu Arg Val Lys Lys Leu Arg Glu
        915                 920                 925

Ser Gln Ala Thr Lys Thr Phe Thr Ser Pro Asp Thr Tyr Ile Ala Arg
    930                 935                 940

Leu Arg Glu Asn Val Val Ala Thr Tyr Gln Ala Gln Leu Glu Ala Leu
945                 950                 955                 960

Met Met Ala Tyr Asn Ala Gln Leu Val Phe Glu Ser Glu Ile Ser Ala
                965                 970                 975

Phe Glu Thr Gly Gly Asn Arg Val Lys Lys Ile Tyr Asp Ala Ile Lys

```
                 980              985              990
Arg Ser Ser Val Phe Gly Arg Ser Asp Ala Glu Ala Thr Asp Asn Asn
                995             1000            1005

Gln His Trp Gly Lys Asn Gly Asn Arg Ser Ser Val Lys Asp Pro
   1010            1015            1020

Asp Lys Leu Arg Leu Asn Glu Ala Gly Gln Val Ala Ala Arg Val
   1025            1030            1035

Pro Trp Ala Glu Pro Val Ser Ala Trp Met Thr Ser Gln Thr Cys
   1040            1045            1050

Ser Ala Cys Gly Arg Val Tyr Val Arg Ala Tyr Arg Gly Lys Asn
   1055            1060            1065

Ser Asn Glu Pro Asp Ser Gly Ala Thr Gly Glu Val Arg Tyr Phe
   1070            1075            1080

Asp Asn Lys Gln Gln Lys Ile Leu Thr Lys Thr Ile Gly Ala Asp
   1085            1090            1095

Thr Val Trp Val Thr Asp Gln Glu Arg Lys Glu Phe Glu Arg Gly
   1100            1105            1110

Val Tyr Asn Ala Met Arg Pro Asn Ala Phe Met Pro Asp Gly Arg
   1115            1120            1125

Trp Thr Ala Ala Gly Glu Ile Leu Glu Ala Ala Leu Lys Ser Arg
   1130            1135            1140

Gly Thr Leu Asp Gly Gly Arg Gly Phe Ala Gly Leu His Leu Thr
   1145            1150            1155

Ser Lys Ala Gln Val His Glu Tyr Ile Glu Gly Thr Gly Lys Ser
   1160            1165            1170

His Arg Asp Ala His Gly Asn Ser Ala Ile Phe Ile Cys Pro Tyr
   1175            1180            1185

Thr Asp Cys Gly His Ile Ala Asp Ala Asp Leu Gln Ala Ser Tyr
   1190            1195            1200

Asn Ile Ala Leu Arg Gly Phe Ala Tyr Ala Ile Val Arg Lys Lys
   1205            1210            1215

His Pro Glu Leu Phe Ala Gly Ser Gly Ser Ser Thr Asp Gly Asp
   1220            1225            1230

Glu Gly Gly Gly Lys Lys Pro Gln Gln Lys Gln Ala Phe Ile Asp
   1235            1240            1245

Glu Ile Val Arg Ala Ala Gly Arg Ala Ser
   1250            1255

<210> SEQ ID NO 58
<211> LENGTH: 724
<212> TYPE: PRT
<213> ORGANISM: Artificial Sequence
<220> FEATURE:
<223> OTHER INFORMATION: Synthetic sequence

<400> SEQUENCE: 58

Met Ala Asn Arg Gln Ile Ser Pro Val Asp Ser Thr Asn Asn Phe Ile
1               5                   10                  15

Phe Thr Leu Tyr Val Ser Phe Asp Thr Val Leu Tyr Ala Arg Ile Leu
                20                  25                  30

Ala Phe Leu Thr Leu Ser Cys Leu Leu Val Gly Phe Leu Glu Tyr Ile
            35                  40                  45

Tyr Pro Leu Gly Val Ile Tyr Leu Ile Met Pro Thr Asn Gln Gln Tyr
        50                  55                  60

Asp Gly Leu Thr Gly Tyr Gln Leu His Thr Glu Arg Leu Arg His Thr
```

-continued

```
                65                  70                  75                  80
        Gly Lys Ser Gly Ile Arg Thr Phe Lys Leu Pro Leu Lys Thr Asn Asp
                            85                  90                  95
        Gln Glu Leu Phe Gly Asn Phe Glu Asn Ile Lys His Asp His Glu
                        100                 105                 110
        Gly Gln Ile Gly Ala Thr Asn Ile Thr Thr Trp Thr Glu Gln Lys
                        115                 120                 125
        Ser Ser Arg Gln Ile Tyr Ser Leu Leu Asp Phe Trp Leu Asp Ser Val
        130                 135                 140
        Arg Ala Gly Val Val Phe Ala Ser Ser Ala Glu Leu Asn Glu Leu
        145                 150                 155                 160
        Leu Ser Val Cys Gly Asp Glu Asp Ala Val Asp Glu Gln Val Lys Thr
                        165                 170                 175
        Ala Met Arg Ala Ile Asn Pro Thr Phe Phe Lys His Leu Lys Phe Asn
                        180                 185                 190
        Asp Phe Lys Glu Glu Ile Ala Leu Lys Glu Gly Met Arg Ser Ser Ser
                        195                 200                 205
        Thr Lys Asn Ser Val Thr Arg Arg Leu Tyr Lys Cys Leu Asp Cys Thr
        210                 215                 220
        Glu Glu Asp Ala Pro Glu Glu Ile Gln Gln Ala Val Ala Asp Leu Ile
        225                 230                 235                 240
        Lys Thr Phe Phe Thr Thr Asp Gly Lys Ile Ile Ser Arg Asn Asp Gln
                        245                 250                 255
        Asp Asp Tyr Trp Gln Val His Phe Gly Leu Asp Lys Ser Leu Tyr Lys
                        260                 265                 270
        Leu Asp Ser Asp Ile Lys Leu Thr Phe Ser Phe Leu Pro Asp Ile Pro
                        275                 280                 285
        Phe Thr Pro Glu Ala Asp Ala His Met Cys Leu Asp Lys Tyr Arg Cys
                        290                 295                 300
        Trp Ile Asp Glu Asn Ala Glu Lys Phe Gln Leu Glu Ser Lys Glu Asp
        305                 310                 315                 320
        Lys Thr Asn Phe Leu Gln Ile His Trp Gly Ile Glu Gly Asn Tyr Asn
                        325                 330                 335
        Ala Phe Ser Asn Tyr Phe Asn Gln Ile Ile Asp Leu Leu Arg Glu Glu
                        340                 345                 350
        Glu Gly Arg Gln Lys Leu Leu Asp Ala Leu Leu Asn Thr Ser Asp Leu
                        355                 360                 365
        Trp Glu Gly Ala Glu Thr Glu Leu Gln Lys Arg Phe Asp Phe Leu Val
        370                 375                 380
        Asp Lys Ala Lys Gln Leu Pro Lys Ala Lys Cys Val Asp Ser Trp Ser
        385                 390                 395                 400
        Asp Tyr Arg Thr Thr Phe Gly Gly Arg Leu Ser Ser Trp Leu Ser Asn
                        405                 410                 415
        Thr Leu Asn Gln Glu Glu Phe Ile Lys Asp Thr Val Ser Asp Gln Lys
                        420                 425                 430
        Glu Glu Leu Lys Gln Ile Ile Lys Asn Ser Glu Lys Asn Leu Tyr Lys
                        435                 440                 445
        Lys Ala Phe Ser Ala Ala Asp Asp Asn Arg Ala Val Glu Leu Ser His
        450                 455                 460
        Glu Ala Val Ile Ala Gln Lys Thr Leu Glu Lys Leu Gln Lys Ser Ser
        465                 470                 475                 480
        Ser Phe Glu Pro Gln Leu Leu Gly Val Tyr Arg Asp Asn Leu Gly Arg
                        485                 490                 495
```

```
Leu Arg Ser Leu Leu Asn Lys Ala His Gln Leu Pro Asp Glu Ile
            500                 505                 510

Glu Asn Lys Ser Ala His Glu Val Tyr Ser Ala Leu His Glu Arg Ile
            515                 520                 525

Arg Leu Met Pro Lys Phe Ile Gly Gly Ala Lys Ala Ala Arg Phe Glu
            530                 535                 540

Lys Tyr Val Lys Ser Leu Gln Ile Leu Lys Gln Gly Ala Ser Phe Leu
545                 550                 555                 560

Glu Asn Phe Glu Glu Lys Val Lys Glu Ala Met Lys Ser Ser Val Ser
                565                 570                 575

Val Glu Val Glu Glu Ile Ser Glu Gly Tyr Phe Leu Arg Gln Leu Asn
            580                 585                 590

Thr Leu Lys Arg Phe Tyr Asp Asn Ala Asn Asp Ser Arg Phe Lys Gly
            595                 600                 605

Lys Leu Ser Ser Leu Phe Asp Lys Asp Leu Gly Val Asn Ile Glu Ala
            610                 615                 620

Val Ser Asn Arg Glu Thr Phe Tyr Ile Ser Pro Tyr Ser Lys His Asp
625                 630                 635                 640

Asn Arg Ala Val Ile Ser Val Glu Val Ala Asn Tyr Gln Gln Leu Leu
                645                 650                 655

Lys Ser Trp Val Asn Glu Leu Lys Pro Tyr Trp Gly Asn Ile Ile Ala
            660                 665                 670

Thr Glu Asn Trp Gly Glu Ile Ile Asp Ala Met Gln Leu Glu Arg Ile
            675                 680                 685

Arg Ile Gly Trp Ile Tyr Lys Leu Tyr Pro Lys Leu Thr Phe Ala Ile
            690                 695                 700

Ser Asp Asp Leu Asp Glu Leu Phe Ala Lys Ala Thr Tyr Arg Asp
705                 710                 715                 720

Leu His Gly His

<210> SEQ ID NO 59
<211> LENGTH: 4
<212> TYPE: PRT
<213> ORGANISM: Artificial Sequence
<220> FEATURE:
<223> OTHER INFORMATION: Synthetic sequence

<400> SEQUENCE: 59

Ala Ala Ala Ala
1

<210> SEQ ID NO 60
<211> LENGTH: 4
<212> TYPE: PRT
<213> ORGANISM: Artificial Sequence
<220> FEATURE:
<223> OTHER INFORMATION: Synthetic sequence

<400> SEQUENCE: 60

Ala Ala Ala Ala
1

<210> SEQ ID NO 61
<211> LENGTH: 25
<212> TYPE: DNA
<213> ORGANISM: Artificial sequence
<220> FEATURE:
<223> OTHER INFORMATION: Synthetic sequence
```

```
<400> SEQUENCE: 61
aatcgagggt tagtaaccaa aaggc                                       25

<210> SEQ ID NO 62
<211> LENGTH: 25
<212> TYPE: DNA
<213> ORGANISM: Unknown
<220> FEATURE:
<223> OTHER INFORMATION: Synthetic sequence

<400> SEQUENCE: 62
ccccgaagat tagagggaaa aaggc                                       25

<210> SEQ ID NO 63
<211> LENGTH: 25
<212> TYPE: DNA
<213> ORGANISM: Unknown
<220> FEATURE:
<223> OTHER INFORMATION: Synthetic sequence

<400> SEQUENCE: 63
cgccgaaagt taggaactaa aaggc                                       25

<210> SEQ ID NO 64
<211> LENGTH: 23
<212> TYPE: DNA
<213> ORGANISM: Artificial sequence
<220> FEATURE:
<223> OTHER INFORMATION: Synthetic sequence

<400> SEQUENCE: 64
tcgaaggtta ggaaccaaaa ggc                                         23

<210> SEQ ID NO 65
<211> LENGTH: 25
<212> TYPE: DNA
<213> ORGANISM: Unknown
<220> FEATURE:
<223> OTHER INFORMATION: Synthetic sequence

<400> SEQUENCE: 65
ccccgaaact acagggagata aaggc                                      25

<210> SEQ ID NO 66
<211> LENGTH: 25
<212> TYPE: DNA
<213> ORGANISM: Unknown
<220> FEATURE:
<223> OTHER INFORMATION: Synthetic sequence

<400> SEQUENCE: 66
acccgtaaag cagagcgatg aaggc                                       25

<210> SEQ ID NO 67
<211> LENGTH: 25
<212> TYPE: DNA
<213> ORGANISM: Artificial sequence
<220> FEATURE:
<223> OTHER INFORMATION: Synthetic sequence

<400> SEQUENCE: 67
cctcggatgt aacggggata aaggc                                       25

<210> SEQ ID NO 68
<211> LENGTH: 10
```

```
<212> TYPE: RNA
<213> ORGANISM: Unknown
<220> FEATURE:
<223> OTHER INFORMATION: Synthetic sequence

<400> SEQUENCE: 68
aaaaaaaaaa                                                          10

<210> SEQ ID NO 69
<211> LENGTH: 10
<212> TYPE: RNA
<213> ORGANISM: Unknown
<220> FEATURE:
<223> OTHER INFORMATION: Synthetic sequence

<400> SEQUENCE: 69
aaaaaaaaaa                                                          10

<210> SEQ ID NO 70
<211> LENGTH: 10
<212> TYPE: RNA
<213> ORGANISM: Artificial sequence
<220> FEATURE:
<223> OTHER INFORMATION: Synthetic sequence

<400> SEQUENCE: 70
aaaaaaaaaa                                                          10

<210> SEQ ID NO 71
<211> LENGTH: 10
<212> TYPE: RNA
<213> ORGANISM: Unknown
<220> FEATURE:
<223> OTHER INFORMATION: Synthetic sequence

<400> SEQUENCE: 71
aaaaaaaaaa                                                          10

<210> SEQ ID NO 72
<211> LENGTH: 10
<212> TYPE: RNA
<213> ORGANISM: Unknown
<220> FEATURE:
<223> OTHER INFORMATION: Synthetic sequence

<400> SEQUENCE: 72
aaaaaaaaaa                                                          10

<210> SEQ ID NO 73
<211> LENGTH: 10
<212> TYPE: RNA
<213> ORGANISM: Artificial sequence
<220> FEATURE:
<223> OTHER INFORMATION: Synthetic sequence

<400> SEQUENCE: 73
aaaaaaaaaa                                                          10

<210> SEQ ID NO 74
<211> LENGTH: 10
<212> TYPE: RNA
<213> ORGANISM: Artificial sequence
<220> FEATURE:
<223> OTHER INFORMATION: Synthetic sequence

<400> SEQUENCE: 74
```

-continued aaaaaaaaaa                                                                10

<210> SEQ ID NO 75
<211> LENGTH: 10
<212> TYPE: RNA
<213> ORGANISM: Artificial sequence
<220> FEATURE:
<223> OTHER INFORMATION: Synthetic sequence

<400> SEQUENCE: 75
aaaaaaaaaa                                                                10

<210> SEQ ID NO 76
<211> LENGTH: 10
<212> TYPE: RNA
<213> ORGANISM: Artificial sequence
<220> FEATURE:
<223> OTHER INFORMATION: Synthetic sequence

<400> SEQUENCE: 76
aaaaaaaaaa                                                                10

<210> SEQ ID NO 77
<211> LENGTH: 10
<212> TYPE: RNA
<213> ORGANISM: Artificial sequence
<220> FEATURE:
<223> OTHER INFORMATION: Synthetic sequence

<400> SEQUENCE: 77
aaaaaaaaaa                                                                10

<210> SEQ ID NO 78
<211> LENGTH: 10
<212> TYPE: RNA
<213> ORGANISM: Artificial sequence
<220> FEATURE:
<223> OTHER INFORMATION: Synthetic sequence

<400> SEQUENCE: 78
aaaaaaaaaa                                                                10

<210> SEQ ID NO 79
<211> LENGTH: 10
<212> TYPE: RNA
<213> ORGANISM: Artificial sequence
<220> FEATURE:
<223> OTHER INFORMATION: Synthetic sequence

<400> SEQUENCE: 79
aaaaaaaaaa                                                                10

<210> SEQ ID NO 80
<211> LENGTH: 10
<212> TYPE: RNA
<213> ORGANISM: Artificial sequence
<220> FEATURE:
<223> OTHER INFORMATION: Synthetic sequence

<400> SEQUENCE: 80
aaaaaaaaaa                                                                10

<210> SEQ ID NO 81
<211> LENGTH: 10
<212> TYPE: RNA
<213> ORGANISM: Artificial sequence

```
<220> FEATURE:
<223> OTHER INFORMATION: Synthetic sequence

<400> SEQUENCE: 81
aaaaaaaaaa                                                              10

<210> SEQ ID NO 82
<211> LENGTH: 10
<212> TYPE: RNA
<213> ORGANISM: Artificial sequence
<220> FEATURE:
<223> OTHER INFORMATION: Synthetic sequence

<400> SEQUENCE: 82
aaaaaaaaaa                                                              10

<210> SEQ ID NO 83
<211> LENGTH: 84
<212> TYPE: PRT
<213> ORGANISM: Artificial Sequence
<220> FEATURE:
<223> OTHER INFORMATION: Synthetic sequence

<400> SEQUENCE: 83

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 84
<211> LENGTH: 57
<212> TYPE: PRT
<213> ORGANISM: Artificial Sequence
<220> FEATURE:
<223> OTHER INFORMATION: Synthetic sequence

<400> SEQUENCE: 84

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 85
<211> LENGTH: 85
<212> TYPE: PRT
<213> ORGANISM: Artificial Sequence
<220> FEATURE:
<223> OTHER INFORMATION: Synthetic sequence

<400> SEQUENCE: 85

Met Ala Ser Ser Met Leu Ser Ser Ala Thr Met Val Ala Ser Pro Ala
```

```
1               5                   10                  15
Gln Ala Thr Met Val Ala Pro Phe Asn Gly Leu Lys Ser Ser Ala Ala
                20                  25                  30

Phe Pro Ala Thr Arg Lys Ala Asn Asn Asp Ile Thr Ser Ile Thr Ser
                35                  40                  45

Asn Gly Gly Arg Val Asn Cys Met Gln Val Trp Pro Pro Ile Glu Lys
            50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 86
<211> LENGTH: 76
<212> TYPE: PRT
<213> ORGANISM: Artificial Sequence
<220> FEATURE:
<223> OTHER INFORMATION: Synthetic sequence

<400> SEQUENCE: 86

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
                35                  40                  45

Trp Gly Leu Lys Lys Ser Gly Met Thr Leu Ile Gly Ser Glu Leu Arg
            50                  55                  60

Pro Leu Lys Val Met Ser Ser Val Ser Thr Ala Cys
65                  70                  75

<210> SEQ ID NO 87
<211> LENGTH: 76
<212> TYPE: PRT
<213> ORGANISM: Artificial Sequence
<220> FEATURE:
<223> OTHER INFORMATION: Synthetic sequence

<400> SEQUENCE: 87

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
                35                  40                  45

Trp Gly Leu Lys Lys Ser Gly Met Thr Leu Ile Gly Ser Glu Leu Arg
            50                  55                  60

Pro Leu Lys Val Met Ser Ser Val Ser Thr Ala Cys
65                  70                  75

<210> SEQ ID NO 88
<211> LENGTH: 72
<212> TYPE: PRT
<213> ORGANISM: Artificial Sequence
<220> FEATURE:
<223> OTHER INFORMATION: Synthetic sequence

<400> SEQUENCE: 88

Met Ala Gln Ile Asn Asn Met Ala Gln Gly Ile Gln Thr Leu Asn Pro
1               5                   10                  15
```

Asn Ser Asn Phe His Lys Pro Gln Val Pro Lys Ser Ser Phe Leu
            20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Leu Phe Cys Ser Phe Arg Ile
50                      55                  60

Ser Ala Ser Val Ala Thr Ala Cys
65                  70

<210> SEQ ID NO 89
<211> LENGTH: 69
<212> TYPE: PRT
<213> ORGANISM: Artificial Sequence
<220> FEATURE:
<223> OTHER INFORMATION: Synthetic sequence

<400> SEQUENCE: 89

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
            35                  40                  45

Ala Ala Pro Lys Gln Ser Arg Lys Pro His Arg Phe Asp Arg Arg Cys
50                      55                  60

Leu Ser Met Val Val
65

<210> SEQ ID NO 90
<211> LENGTH: 77
<212> TYPE: PRT
<213> ORGANISM: Artificial Sequence
<220> FEATURE:
<223> OTHER INFORMATION: Synthetic sequence

<400> SEQUENCE: 90

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
50                      55                  60

Gln Arg Gly Ser Arg Arg Phe Pro Ser Val Val Val Cys
65                  70                  75

<210> SEQ ID NO 91
<211> LENGTH: 57
<212> TYPE: PRT
<213> ORGANISM: Artificial Sequence
<220> FEATURE:
<223> OTHER INFORMATION: Synthetic sequence

<400> SEQUENCE: 91

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

```
Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 92
<211> LENGTH: 65
<212> TYPE: PRT
<213> ORGANISM: Artificial Sequence
<220> FEATURE:
<223> OTHER INFORMATION: Synthetic sequence

<400> SEQUENCE: 92

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65

<210> SEQ ID NO 93
<211> LENGTH: 72
<212> TYPE: PRT
<213> ORGANISM: Artificial Sequence
<220> FEATURE:
<223> OTHER INFORMATION: Synthetic sequence

<400> SEQUENCE: 93

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 94
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
```

```
<220> FEATURE:
<221> NAME/KEY: misc_feature
<222> LOCATION: (19)..(19)
<223> OTHER INFORMATION: Xaa can be any naturally occurring amino acid

<400> SEQUENCE: 94

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic sequence

<400> SEQUENCE: 95

Gly Leu Phe His Ala Leu Leu His Leu Leu His Ser Leu Trp His Leu
1               5                   10                  15

Leu Leu His Ala
            20

<210> SEQ ID NO 96
<211> LENGTH: 7
<212> TYPE: PRT
<213> ORGANISM: Artificial Sequence
<220> FEATURE:
<223> OTHER INFORMATION: Synthetic sequence

<400> SEQUENCE: 96

Pro Lys Lys Lys Arg Lys Val
1               5

<210> SEQ ID NO 97
<211> LENGTH: 16
<212> TYPE: PRT
<213> ORGANISM: Artificial Sequence
<220> FEATURE:
<223> OTHER INFORMATION: Synthetic sequence

<400> SEQUENCE: 97

Lys Arg Pro Ala Ala Thr Lys Lys Ala Gly Gln Ala Lys Lys Lys Lys
1               5                   10                  15

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence

<400> SEQUENCE: 98

Pro Ala Ala Lys Arg Val Lys Leu Asp
1               5

<210> SEQ ID NO 99
<211> LENGTH: 11
<212> TYPE: PRT
<213> ORGANISM: Artificial Sequence
<220> FEATURE:
<223> OTHER INFORMATION: Synthetic sequence

<400> SEQUENCE: 99

Arg Gln Arg Arg Asn Glu Leu Lys Arg Ser Pro
```

```
1               5                   10

<210> SEQ ID NO 100
<211> LENGTH: 38
<212> TYPE: PRT
<213> ORGANISM: Artificial Sequence
<220> FEATURE:
<223> OTHER INFORMATION: Synthetic sequence

<400> SEQUENCE: 100

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 101
<211> LENGTH: 42
<212> TYPE: PRT
<213> ORGANISM: Artificial Sequence
<220> FEATURE:
<223> OTHER INFORMATION: Synthetic sequence

<400> SEQUENCE: 101

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 102
<211> LENGTH: 8
<212> TYPE: PRT
<213> ORGANISM: Artificial Sequence
<220> FEATURE:
<223> OTHER INFORMATION: Synthetic sequence

<400> SEQUENCE: 102

Val Ser Arg Lys Arg Pro Arg Pro
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic sequence

<400> SEQUENCE: 103

Pro Pro Lys Lys Ala Arg Glu Asp
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic sequence

<400> SEQUENCE: 104

Pro Gln Pro Lys Lys Lys Pro Leu
1               5
```

<210> SEQ ID NO 105
<211> LENGTH: 12
<212> TYPE: PRT
<213> ORGANISM: Artificial Sequence
<220> FEATURE:
<223> OTHER INFORMATION: Synthetic sequence

<400> SEQUENCE: 105

Ser Ala Leu Ile Lys Lys Lys Lys Lys Met Ala Pro
1               5                   10

<210> SEQ ID NO 106
<211> LENGTH: 5
<212> TYPE: PRT
<213> ORGANISM: Artificial Sequence
<220> FEATURE:
<223> OTHER INFORMATION: Synthetic sequence

<400> SEQUENCE: 106

Asp Arg Leu Arg Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic sequence

<400> SEQUENCE: 107

Pro Lys Gln Lys Lys Arg Lys
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic sequence

<400> SEQUENCE: 108

Arg Lys Leu Lys Lys Lys Ile Lys Lys Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic sequence

<400> SEQUENCE: 109

Arg Glu Lys Lys Lys Phe Leu Lys Arg Arg
1               5                   10

<210> SEQ ID NO 110
<211> LENGTH: 20
<212> TYPE: PRT
<213> ORGANISM: Artificial Sequence
<220> FEATURE:
<223> OTHER INFORMATION: Synthetic sequence

<400> SEQUENCE: 110

Lys Arg Lys Gly Asp Glu Val Asp Gly Val Asp Glu Val Ala Lys Lys
1               5                   10                  15

Lys Ser Lys Lys

```
<210> SEQ ID NO 111
<211> LENGTH: 17
<212> TYPE: PRT
<213> ORGANISM: Artificial Sequence
<220> FEATURE:
<223> OTHER INFORMATION: Synthetic sequence

<400> SEQUENCE: 111

Arg Lys Cys Leu Gln Ala Gly Met Asn Leu Glu Ala Arg Lys Thr Lys
1               5                   10                  15

Lys

<210> SEQ ID NO 112
<211> LENGTH: 11
<212> TYPE: PRT
<213> ORGANISM: Artificial Sequence
<220> FEATURE:
<223> OTHER INFORMATION: Synthetic sequence

<400> SEQUENCE: 112

Tyr Gly Arg Lys Lys Arg Arg Gln Arg Arg Arg
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic sequence

<400> SEQUENCE: 113

Arg Arg Gln Arg Arg Thr Ser Lys Leu Met Lys Arg
1               5                   10

<210> SEQ ID NO 114
<211> LENGTH: 27
<212> TYPE: PRT
<213> ORGANISM: Artificial Sequence
<220> FEATURE:
<223> OTHER INFORMATION: Synthetic sequence

<400> SEQUENCE: 114

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 115
<211> LENGTH: 33
<212> TYPE: PRT
<213> ORGANISM: Artificial Sequence
<220> FEATURE:
<223> OTHER INFORMATION: Synthetic sequence

<400> SEQUENCE: 115

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 116
```

```
<211> LENGTH: 16
<212> TYPE: PRT
<213> ORGANISM: Artificial Sequence
<220> FEATURE:
<223> OTHER INFORMATION: Synthetic sequence

<400> SEQUENCE: 116

Arg Gln Ile Lys Ile Trp Phe Gln Asn Arg Arg Met Lys Trp Lys Lys
1               5                   10                  15

<210> SEQ ID NO 117
<211> LENGTH: 11
<212> TYPE: PRT
<213> ORGANISM: Artificial Sequence
<220> FEATURE:
<223> OTHER INFORMATION: Synthetic sequence

<400> SEQUENCE: 117

Tyr Gly Arg Lys Lys Arg Arg Gln Arg Arg Arg
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic sequence

<400> SEQUENCE: 118

Arg Lys Lys Arg Arg Gln Arg Arg Arg
1               5

<210> SEQ ID NO 119
<211> LENGTH: 11
<212> TYPE: PRT
<213> ORGANISM: Artificial Sequence
<220> FEATURE:
<223> OTHER INFORMATION: Synthetic sequence

<400> SEQUENCE: 119

Tyr Gly Arg Lys Lys Arg Arg Gln Arg Arg Arg
1               5                   10

<210> SEQ ID NO 120
<211> LENGTH: 8
<212> TYPE: PRT
<213> ORGANISM: Artificial Sequence
<220> FEATURE:
<223> OTHER INFORMATION: Synthetic sequence

<400> SEQUENCE: 120

Arg Lys Lys Arg Arg Gln Arg Arg
1               5

<210> SEQ ID NO 121
<211> LENGTH: 11
<212> TYPE: PRT
<213> ORGANISM: Artificial Sequence
<220> FEATURE:
<223> OTHER INFORMATION: Synthetic sequence

<400> SEQUENCE: 121

Tyr Ala Arg Ala Ala Ala Arg Gln Ala Arg Ala
1               5                   10

<210> SEQ ID NO 122
<211> LENGTH: 11
```

```
<212> TYPE: PRT
<213> ORGANISM: Artificial Sequence
<220> FEATURE:
<223> OTHER INFORMATION: Synthetic sequence

<400> SEQUENCE: 122

Thr His Arg Leu Pro Arg Arg Arg Arg Arg
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic sequence

<400> SEQUENCE: 123

Gly Gly Arg Arg Ala Arg Arg Arg Arg Arg
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Synthetic sequence

<400> SEQUENCE: 124

Gly Ser Gly Gly Ser
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic sequence

<400> SEQUENCE: 125

Gly Gly Ser Gly Gly Ser
1               5

<210> SEQ ID NO 126
<211> LENGTH: 4
<212> TYPE: PRT
<213> ORGANISM: Artificial Sequence
<220> FEATURE:
<223> OTHER INFORMATION: Synthetic sequence

<400> SEQUENCE: 126

Gly Gly Gly Ser
1

<210> SEQ ID NO 127
<211> LENGTH: 4
<212> TYPE: PRT
<213> ORGANISM: Artificial Sequence
<220> FEATURE:
<223> OTHER INFORMATION: Synthetic sequence

<400> SEQUENCE: 127

Gly Gly Ser Gly
1

<210> SEQ ID NO 128
<211> LENGTH: 5
<212> TYPE: PRT
```

```
<213> ORGANISM: Artificial Sequence
<220> FEATURE:
<223> OTHER INFORMATION: Synthetic sequence

<400> SEQUENCE: 128

Gly Gly Ser Gly Gly
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic sequence

<400> SEQUENCE: 129

Gly Ser Gly Ser Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Synthetic sequence

<400> SEQUENCE: 130

Gly Ser Gly Gly Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Synthetic sequence

<400> SEQUENCE: 131

Gly Gly Gly Ser Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic sequence

<400> SEQUENCE: 132

Gly Ser Ser Ser Gly
1               5

<210> SEQ ID NO 133
<211> LENGTH: 16
<212> TYPE: PRT
<213> ORGANISM: Artificial Sequence
<220> FEATURE:
<223> OTHER INFORMATION: Synthetic sequence

<400> SEQUENCE: 133

Arg Gln Ile Lys Ile Trp Phe Gln Asn Arg Arg Met Lys Trp Lys Lys
1               5                   10                  15

<210> SEQ ID NO 134
<211> LENGTH: 11
<212> TYPE: PRT
<213> ORGANISM: Artificial Sequence
```

```
<220> FEATURE:
<223> OTHER INFORMATION: Synthetic sequence

<400> SEQUENCE: 134

Tyr Gly Arg Lys Lys Arg Arg Gln Arg Arg
1               5                   10

<210> SEQ ID NO 135
<211> LENGTH: 18
<212> TYPE: DNA
<213> ORGANISM: Artificial Sequence
<220> FEATURE:
<223> OTHER INFORMATION: Synthetic sequence

<400> SEQUENCE: 135
atcaatacca aactctgg                                                 18

<210> SEQ ID NO 136
<211> LENGTH: 23
<212> TYPE: DNA
<213> ORGANISM: Artificial Sequence
<220> FEATURE:
<223> OTHER INFORMATION: Synthetic sequence

<400> SEQUENCE: 136
aaggcatcaa taccaaactc tgg                                           23

<210> SEQ ID NO 137
<211> LENGTH: 29
<212> TYPE: DNA
<213> ORGANISM: Artificial Sequence
<220> FEATURE:
<223> OTHER INFORMATION: Synthetic sequence

<400> SEQUENCE: 137
gcgatgaagg catcaatacc aaactctgg                                     29

<210> SEQ ID NO 138
<211> LENGTH: 33
<212> TYPE: DNA
<213> ORGANISM: Artificial Sequence
<220> FEATURE:
<223> OTHER INFORMATION: Synthetic sequence

<400> SEQUENCE: 138
cagagcgatg aaggcatcaa taccaaactc tgg                                33

<210> SEQ ID NO 139
<211> LENGTH: 43
<212> TYPE: DNA
<213> ORGANISM: Artificial Sequence
<220> FEATURE:
<223> OTHER INFORMATION: Synthetic sequence

<400> SEQUENCE: 139
acccgtaaag cagagcgatg aaggcatcaa taccaaactc tgg                     43

<210> SEQ ID NO 140
<211> LENGTH: 32
<212> TYPE: DNA
<213> ORGANISM: Artificial Sequence
<220> FEATURE:
<223> OTHER INFORMATION: Synthetic sequence

<400> SEQUENCE: 140
gcgatgaagg catcaatacc aaactctggc gg                                 32
```

<210> SEQ ID NO 141
<211> LENGTH: 31
<212> TYPE: DNA
<213> ORGANISM: Artificial Sequence
<220> FEATURE:
<223> OTHER INFORMATION: Synthetic sequence

<400> SEQUENCE: 141
gcgatgaagg catcaatacc aaactctggc g                            31

<210> SEQ ID NO 142
<211> LENGTH: 30
<212> TYPE: DNA
<213> ORGANISM: Artificial Sequence
<220> FEATURE:
<223> OTHER INFORMATION: Synthetic sequence

<400> SEQUENCE: 142
gcgatgaagg catcaatacc aaactctggc                              30

<210> SEQ ID NO 143
<211> LENGTH: 29
<212> TYPE: DNA
<213> ORGANISM: Artificial Sequence
<220> FEATURE:
<223> OTHER INFORMATION: Synthetic sequence

<400> SEQUENCE: 143
gcgatgaagg catcaatacc aaactctgg                               29

<210> SEQ ID NO 144
<211> LENGTH: 28
<212> TYPE: DNA
<213> ORGANISM: Artificial Sequence
<220> FEATURE:
<223> OTHER INFORMATION: Synthetic sequence

<400> SEQUENCE: 144
gcgatgaagg catcaatacc aaactctg                                28

<210> SEQ ID NO 145
<211> LENGTH: 27
<212> TYPE: DNA
<213> ORGANISM: Artificial Sequence
<220> FEATURE:
<223> OTHER INFORMATION: Synthetic sequence

<400> SEQUENCE: 145
gcgatgaagg catcaatacc aaactct                                 27

<210> SEQ ID NO 146
<211> LENGTH: 43
<212> TYPE: DNA
<213> ORGANISM: Artificial Sequence
<220> FEATURE:
<223> OTHER INFORMATION: Synthetic sequence

<400> SEQUENCE: 146
atcaatacca aactctggac ccgtaaagca gagcgatgaa ggc                43

<210> SEQ ID NO 147
<211> LENGTH: 43
<212> TYPE: DNA
<213> ORGANISM: Artificial Sequence
<220> FEATURE:

<223> OTHER INFORMATION: Synthetic sequence

<400> SEQUENCE: 147
acccgtaaag cagagcgatg ggcgtatcaa taccaaactc tgg                          43

<210> SEQ ID NO 148
<211> LENGTH: 29
<212> TYPE: DNA
<213> ORGANISM: Artificial Sequence
<220> FEATURE:
<223> OTHER INFORMATION: Synthetic sequence

<400> SEQUENCE: 148
gcgatgggcg tatcaatacc aaactctgg                                         29

<210> SEQ ID NO 149
<211> LENGTH: 68
<212> TYPE: DNA
<213> ORGANISM: Artificial Sequence
<220> FEATURE:
<223> OTHER INFORMATION: Synthetic sequence

<400> SEQUENCE: 149
acccgtaaag cagagcgatg aaggcatcaa taccaaactc tggacccgta aagcagagcg       60
atgaaggc                                                                68

<210> SEQ ID NO 150
<211> LENGTH: 68
<212> TYPE: DNA
<213> ORGANISM: Artificial Sequence
<220> FEATURE:
<223> OTHER INFORMATION: Synthetic sequence

<400> SEQUENCE: 150
gccttcatcg ctctgcttta cgggtccaga gtttggtatt gatgccttca tcgctctgct       60
ttacgggt                                                                68

<210> SEQ ID NO 151
<211> LENGTH: 50
<212> TYPE: DNA
<213> ORGANISM: Artificial Sequence
<220> FEATURE:
<223> OTHER INFORMATION: Synthetic sequence

<400> SEQUENCE: 151
cttagttaag gatgttccag gttctttcgg gagccttggc cttctccctt                  50

<210> SEQ ID NO 152
<211> LENGTH: 70
<212> TYPE: DNA
<213> ORGANISM: Artificial Sequence
<220> FEATURE:
<223> OTHER INFORMATION: Synthetic sequence

<400> SEQUENCE: 152
ccgacttcgc tgataaaaat cttagttaag gatgttccag gttctttcgg gagccttggc       60
cttctccctt                                                              70

<210> SEQ ID NO 153
<211> LENGTH: 70
<212> TYPE: DNA
<213> ORGANISM: Artificial Sequence
<220> FEATURE:
<223> OTHER INFORMATION: Synthetic sequence

<400> SEQUENCE: 153
cttagttaag gatgttccag gttctttcgg gagccttggc cttctccctt aacctatgcc    60
actaatgatt    70

<210> SEQ ID NO 154
<211> LENGTH: 101
<212> TYPE: DNA
<213> ORGANISM: Artificial Sequence
<220> FEATURE:
<223> OTHER INFORMATION: Synthetic sequence

<400> SEQUENCE: 154
cttagttaag gatgttccag gttctttcgg gagccttggc cttctccctt aacctatgcc    60
actaatgatt aggaacacga tgaatgaaaa gaagacggcg a    101

<210> SEQ ID NO 155
<211> LENGTH: 50
<212> TYPE: DNA
<213> ORGANISM: Artificial Sequence
<220> FEATURE:
<223> OTHER INFORMATION: Synthetic sequence

<400> SEQUENCE: 155
cttagttaag gatgttccag gttctttcgg gaacgccggc cttctccctt    50

<210> SEQ ID NO 156
<211> LENGTH: 50
<212> TYPE: DNA
<213> ORGANISM: Artificial Sequence
<220> FEATURE:
<223> OTHER INFORMATION: Synthetic sequence

<400> SEQUENCE: 156
cttagttaag gatgttccag gttctttcgg gagccttgac gccctccctt    50

<210> SEQ ID NO 157
<211> LENGTH: 50
<212> TYPE: DNA
<213> ORGANISM: Artificial Sequence
<220> FEATURE:
<223> OTHER INFORMATION: Synthetic sequence

<400> SEQUENCE: 157
cttagttaag gatgttccag gttctttcgg gaacgccgac gccctccctt    50

<210> SEQ ID NO 158
<211> LENGTH: 204
<212> TYPE: DNA
<213> ORGANISM: Artificial Sequence
<220> FEATURE:
<223> OTHER INFORMATION: Synthetic sequence

<400> SEQUENCE: 158
ggagagcaac tacccgtaaa gcagagcgat gaaggcatca ataccaaact ctggacccgt    60
aaagcagagc gatgaaggct tgtcgtgtga gcagcttacc cgtaaagcag agcgatgaag    120
gcacattggc cgacttcgct gataaaaatc ttagttaagg atgttccagg ttctttcggg    180
agccttggcc ttctccctta acct    204

<210> SEQ ID NO 159
<211> LENGTH: 103
<212> TYPE: DNA

```
<213> ORGANISM: Artificial Sequence
<220> FEATURE:
<223> OTHER INFORMATION: Synthetic sequence

<400> SEQUENCE: 159
cttagttaag gatgttccag gttctttcgg gagccttggc cttctccctt aacctatgcc      60
actaatgatt gaaagcgatg aaggcatcaa taccaaactc tgg                       103

<210> SEQ ID NO 160
<211> LENGTH: 111
<212> TYPE: DNA
<213> ORGANISM: Artificial Sequence
<220> FEATURE:
<223> OTHER INFORMATION: Synthetic sequence

<400> SEQUENCE: 160
cttagttaag gatgttccag gttctttcgg gagccttggc cttctccctt aacctatgcc      60
actaatgatt gaaaaaaaaa aagcgatgaa ggcatcaata ccaaactctg g              111

<210> SEQ ID NO 161
<211> LENGTH: 123
<212> TYPE: DNA
<213> ORGANISM: Artificial Sequence
<220> FEATURE:
<223> OTHER INFORMATION: Synthetic sequence

<400> SEQUENCE: 161
ggagagcaac tacccgtaaa gcagagcgat gaaggcatca ataccaaact ctggacccgt      60
aaagcagagc gatgaaggct tgtcgtgtga gcagcttacc cgtaaagcag agcgatgaag     120
gca                                                                  123

<210> SEQ ID NO 162
<211> LENGTH: 53
<212> TYPE: DNA
<213> ORGANISM: Artificial Sequence
<220> FEATURE:
<223> OTHER INFORMATION: Synthetic sequence

<400> SEQUENCE: 162
gcctgcccgc agactaatca ataccaaact ctggcggcgt aaactttcca gtc             53

<210> SEQ ID NO 163
<211> LENGTH: 53
<212> TYPE: DNA
<213> ORGANISM: Artificial Sequence
<220> FEATURE:
<223> OTHER INFORMATION: Synthetic sequence

<400> SEQUENCE: 163
gcctgcccgc agactatact gttattgttg tactcggcgt aaactttcca gtc             53

<210> SEQ ID NO 164
<211> LENGTH: 53
<212> TYPE: DNA
<213> ORGANISM: Artificial Sequence
<220> FEATURE:
<223> OTHER INFORMATION: Synthetic sequence

<400> SEQUENCE: 164
gcctgcccgc agactgatca ataccaaact ctggcggcgt aaactttcca gtc             53

<210> SEQ ID NO 165
<211> LENGTH: 53
```

```
<212> TYPE: DNA
<213> ORGANISM: Artificial Sequence
<220> FEATURE:
<223> OTHER INFORMATION: Synthetic sequence

<400> SEQUENCE: 165
gcctgcccgc agactcatca ataccaaact ctggcggcgt aaactttcca gtc    53

<210> SEQ ID NO 166
<211> LENGTH: 53
<212> TYPE: DNA
<213> ORGANISM: Artificial Sequence
<220> FEATURE:
<223> OTHER INFORMATION: Synthetic sequence

<400> SEQUENCE: 166
gcctgcccgc agacttatca ataccaaact ctggcggcgt aaactttcca gtc    53

<210> SEQ ID NO 167
<211> LENGTH: 53
<212> TYPE: DNA
<213> ORGANISM: Artificial Sequence
<220> FEATURE:
<223> OTHER INFORMATION: Synthetic sequence

<400> SEQUENCE: 167
gcctgcccgc agacaaatca ataccaaact ctggcggcgt aaactttcca gtc    53

<210> SEQ ID NO 168
<211> LENGTH: 53
<212> TYPE: DNA
<213> ORGANISM: Artificial Sequence
<220> FEATURE:
<223> OTHER INFORMATION: Synthetic sequence

<400> SEQUENCE: 168
gcctgcccgc agacgaatca ataccaaact ctggcggcgt aaactttcca gtc    53

<210> SEQ ID NO 169
<211> LENGTH: 53
<212> TYPE: DNA
<213> ORGANISM: Artificial Sequence
<220> FEATURE:
<223> OTHER INFORMATION: Synthetic sequence

<400> SEQUENCE: 169
gcctgcccgc agaccaatca ataccaaact ctggcggcgt aaactttcca gtc    53

<210> SEQ ID NO 170
<211> LENGTH: 53
<212> TYPE: DNA
<213> ORGANISM: Artificial Sequence
<220> FEATURE:
<223> OTHER INFORMATION: Synthetic sequence

<400> SEQUENCE: 170
gcctgcccgc agacccatca ataccaaact ctggcggcgt aaactttcca gtc    53

<210> SEQ ID NO 171
<211> LENGTH: 53
<212> TYPE: DNA
<213> ORGANISM: Artificial Sequence
<220> FEATURE:
<223> OTHER INFORMATION: Synthetic sequence

<400> SEQUENCE: 171
```
gcctgcccgc agattgatca ataccaaact ctggcggcgt aaactttcca gtc        53

<210> SEQ ID NO 172
<211> LENGTH: 53
<212> TYPE: DNA
<213> ORGANISM: Artificial Sequence
<220> FEATURE:
<223> OTHER INFORMATION: Synthetic sequence

<400> SEQUENCE: 172
gcctgcccgc agagtaatca ataccaaact ctggcggcgt aaactttcca gtc        53

<210> SEQ ID NO 173
<211> LENGTH: 53
<212> TYPE: DNA
<213> ORGANISM: Artificial Sequence
<220> FEATURE:
<223> OTHER INFORMATION: Synthetic sequence

<400> SEQUENCE: 173
gcctgcccgc agaataatca ataccaaact ctggcggcgt aaactttcca gtc        53

<210> SEQ ID NO 174
<211> LENGTH: 53
<212> TYPE: DNA
<213> ORGANISM: Artificial Sequence
<220> FEATURE:
<223> OTHER INFORMATION: Synthetic sequence

<400> SEQUENCE: 174
gcctgcccgc agactagcca ataccaaact ctggcggcgt aaactttcca gtc        53

<210> SEQ ID NO 175
<211> LENGTH: 53
<212> TYPE: DNA
<213> ORGANISM: Artificial Sequence
<220> FEATURE:
<223> OTHER INFORMATION: Synthetic sequence

<400> SEQUENCE: 175
gcctgcccgc agactaattg ataccaaact ctggcggcgt aaactttcca gtc        53

<210> SEQ ID NO 176
<211> LENGTH: 53
<212> TYPE: DNA
<213> ORGANISM: Artificial Sequence
<220> FEATURE:
<223> OTHER INFORMATION: Synthetic sequence

<400> SEQUENCE: 176
gcctgcccgc agactaatca gcaccaaact ctggcggcgt aaactttcca gtc        53

<210> SEQ ID NO 177
<211> LENGTH: 53
<212> TYPE: DNA
<213> ORGANISM: Artificial Sequence
<220> FEATURE:
<223> OTHER INFORMATION: Synthetic sequence

<400> SEQUENCE: 177
gcctgcccgc agactaatca atgtcaaact ctggcggcgt aaactttcca gtc        53

<210> SEQ ID NO 178
<211> LENGTH: 53
<212> TYPE: DNA
<213> ORGANISM: Artificial Sequence -continued

```
<220> FEATURE:
<223> OTHER INFORMATION: Synthetic sequence

<400> SEQUENCE: 178
gcctgcccgc agactaatca atactgaact ctggcggcgt aaactttcca gtc       53

<210> SEQ ID NO 179
<211> LENGTH: 53
<212> TYPE: DNA
<213> ORGANISM: Artificial Sequence
<220> FEATURE:
<223> OTHER INFORMATION: Synthetic sequence

<400> SEQUENCE: 179
gcctgcccgc agactaatca ataccaggct ctggcggcgt aaactttcca gtc       53

<210> SEQ ID NO 180
<211> LENGTH: 53
<212> TYPE: DNA
<213> ORGANISM: Artificial Sequence
<220> FEATURE:
<223> OTHER INFORMATION: Synthetic sequence

<400> SEQUENCE: 180
gcctgcccgc agactaatca ataccaaatc ctggcggcgt aaactttcca gtc       53

<210> SEQ ID NO 181
<211> LENGTH: 53
<212> TYPE: DNA
<213> ORGANISM: Artificial Sequence
<220> FEATURE:
<223> OTHER INFORMATION: Synthetic sequence

<400> SEQUENCE: 181
gcctgcccgc agactaatca ataccaaact tcggcggcgt aaactttcca gtc       53

<210> SEQ ID NO 182
<211> LENGTH: 53
<212> TYPE: DNA
<213> ORGANISM: Artificial Sequence
<220> FEATURE:
<223> OTHER INFORMATION: Synthetic sequence

<400> SEQUENCE: 182
gcctgcccgc agactaatca ataccaaact ctaacggcgt aaactttcca gtc       53

<210> SEQ ID NO 183
<211> LENGTH: 53
<212> TYPE: DNA
<213> ORGANISM: Artificial Sequence
<220> FEATURE:
<223> OTHER INFORMATION: Synthetic sequence

<400> SEQUENCE: 183
gcctgcccgc agactaatca ataccaaact ctggtagcgt aaactttcca gtc       53

<210> SEQ ID NO 184
<211> LENGTH: 53
<212> TYPE: DNA
<213> ORGANISM: Artificial Sequence
<220> FEATURE:
<223> OTHER INFORMATION: Synthetic sequence

<400> SEQUENCE: 184
gactggaaag tttacgccgc cagagtttgg tattgattag tctgcgggca ggc       53
```

<210> SEQ ID NO 185
<211> LENGTH: 53
<212> TYPE: DNA
<213> ORGANISM: Artificial Sequence
<220> FEATURE:
<223> OTHER INFORMATION: Synthetic sequence

<400> SEQUENCE: 185
gactggaaag tttacgccga gtacaacaat aacagtatag tctgcgggca ggc        53

<210> SEQ ID NO 186
<211> LENGTH: 53
<212> TYPE: DNA
<213> ORGANISM: Artificial Sequence
<220> FEATURE:
<223> OTHER INFORMATION: Synthetic sequence

<400> SEQUENCE: 186
gactggaaag tttacgccgc cagagtttgg tattgatcag tctgcgggca ggc        53

<210> SEQ ID NO 187
<211> LENGTH: 53
<212> TYPE: DNA
<213> ORGANISM: Artificial Sequence
<220> FEATURE:
<223> OTHER INFORMATION: Synthetic sequence

<400> SEQUENCE: 187
gactggaaag tttacgccgc cagagtttgg tattgatgag tctgcgggca ggc        53

<210> SEQ ID NO 188
<211> LENGTH: 53
<212> TYPE: DNA
<213> ORGANISM: Artificial Sequence
<220> FEATURE:
<223> OTHER INFORMATION: Synthetic sequence

<400> SEQUENCE: 188
gactggaaag tttacgccgc cagagtttgg tattgataag tctgcgggca ggc        53

<210> SEQ ID NO 189
<211> LENGTH: 53
<212> TYPE: DNA
<213> ORGANISM: Artificial Sequence
<220> FEATURE:
<223> OTHER INFORMATION: Synthetic sequence

<400> SEQUENCE: 189
gactggaaag tttacgccgc cagagtttgg tattgatttg tctgcgggca ggc        53

<210> SEQ ID NO 190
<211> LENGTH: 53
<212> TYPE: DNA
<213> ORGANISM: Artificial Sequence
<220> FEATURE:
<223> OTHER INFORMATION: Synthetic sequence

<400> SEQUENCE: 190
gactggaaag tttacgccgc cagagtttgg tattgattcg tctgcgggca ggc        53

<210> SEQ ID NO 191
<211> LENGTH: 53
<212> TYPE: DNA
<213> ORGANISM: Artificial Sequence
<220> FEATURE:
<223> OTHER INFORMATION: Synthetic sequence

<400> SEQUENCE: 191
gactggaaag tttacgccgc cagagtttgg tattgattgg tctgcgggca ggc             53

<210> SEQ ID NO 192
<211> LENGTH: 53
<212> TYPE: DNA
<213> ORGANISM: Artificial Sequence
<220> FEATURE:
<223> OTHER INFORMATION: Synthetic sequence

<400> SEQUENCE: 192
gactggaaag tttacgccgc cagagtttgg tattgatggg tctgcgggca ggc             53

<210> SEQ ID NO 193
<211> LENGTH: 53
<212> TYPE: DNA
<213> ORGANISM: Artificial Sequence
<220> FEATURE:
<223> OTHER INFORMATION: Synthetic sequence

<400> SEQUENCE: 193
gactggaaag tttacgccgc cagagtttgg tattgatcaa tctgcgggca ggc             53

<210> SEQ ID NO 194
<211> LENGTH: 53
<212> TYPE: DNA
<213> ORGANISM: Artificial Sequence
<220> FEATURE:
<223> OTHER INFORMATION: Synthetic sequence

<400> SEQUENCE: 194
gactggaaag tttacgccgc cagagtttgg tattgattac tctgcgggca ggc             53

<210> SEQ ID NO 195
<211> LENGTH: 53
<212> TYPE: DNA
<213> ORGANISM: Artificial Sequence
<220> FEATURE:
<223> OTHER INFORMATION: Synthetic sequence

<400> SEQUENCE: 195
gactggaaag tttacgccgc cagagtttgg tattgattat tctgcgggca ggc             53

<210> SEQ ID NO 196
<211> LENGTH: 53
<212> TYPE: DNA
<213> ORGANISM: Artificial Sequence
<220> FEATURE:
<223> OTHER INFORMATION: Synthetic sequence

<400> SEQUENCE: 196
gactggaaag tttacgccgc cagagtttgg tattggctag tctgcgggca ggc             53

<210> SEQ ID NO 197
<211> LENGTH: 53
<212> TYPE: DNA
<213> ORGANISM: Artificial Sequence
<220> FEATURE:
<223> OTHER INFORMATION: Synthetic sequence

<400> SEQUENCE: 197
gactggaaag tttacgccgc cagagtttgg tatcaattag tctgcgggca ggc             53

<210> SEQ ID NO 198

<211> LENGTH: 53
<212> TYPE: DNA
<213> ORGANISM: Artificial Sequence
<220> FEATURE:
<223> OTHER INFORMATION: Synthetic sequence

<400> SEQUENCE: 198
gactggaaag tttacgccgc cagagtttgg tgctgattag tctgcgggca ggc    53

<210> SEQ ID NO 199
<211> LENGTH: 53
<212> TYPE: DNA
<213> ORGANISM: Artificial Sequence
<220> FEATURE:
<223> OTHER INFORMATION: Synthetic sequence

<400> SEQUENCE: 199
gactggaaag tttacgccgc cagagtttga cattgattag tctgcgggca ggc    53

<210> SEQ ID NO 200
<211> LENGTH: 53
<212> TYPE: DNA
<213> ORGANISM: Artificial Sequence
<220> FEATURE:
<223> OTHER INFORMATION: Synthetic sequence

<400> SEQUENCE: 200
gactggaaag tttacgccgc cagagttcag tattgattag tctgcgggca ggc    53

<210> SEQ ID NO 201
<211> LENGTH: 53
<212> TYPE: DNA
<213> ORGANISM: Artificial Sequence
<220> FEATURE:
<223> OTHER INFORMATION: Synthetic sequence

<400> SEQUENCE: 201
gactggaaag tttacgccgc cagagcctgg tattgattag tctgcgggca ggc    53

<210> SEQ ID NO 202
<211> LENGTH: 53
<212> TYPE: DNA
<213> ORGANISM: Artificial Sequence
<220> FEATURE:
<223> OTHER INFORMATION: Synthetic sequence

<400> SEQUENCE: 202
gactggaaag tttacgccgc caggatttgg tattgattag tctgcgggca ggc    53

<210> SEQ ID NO 203
<211> LENGTH: 53
<212> TYPE: DNA
<213> ORGANISM: Artificial Sequence
<220> FEATURE:
<223> OTHER INFORMATION: Synthetic sequence

<400> SEQUENCE: 203
gactggaaag tttacgccgc cgaagtttgg tattgattag tctgcgggca ggc    53

<210> SEQ ID NO 204
<211> LENGTH: 53
<212> TYPE: DNA
<213> ORGANISM: Artificial Sequence
<220> FEATURE:
<223> OTHER INFORMATION: Synthetic sequence

<400> SEQUENCE: 204
gactggaaag tttacgccgt tagagtttgg tattgattag tctgcgggca ggc       53

<210> SEQ ID NO 205
<211> LENGTH: 53
<212> TYPE: DNA
<213> ORGANISM: Artificial Sequence
<220> FEATURE:
<223> OTHER INFORMATION: Synthetic sequence

<400> SEQUENCE: 205
gactggaaag tttacgctac cagagtttgg tattgattag tctgcgggca ggc       53

<210> SEQ ID NO 206
<211> LENGTH: 5
<212> TYPE: DNA
<213> ORGANISM: Artificial Sequence
<220> FEATURE:
<223> OTHER INFORMATION: Synthetic sequence

<400> SEQUENCE: 206 ttttt       5

<210> SEQ ID NO 207
<211> LENGTH: 6
<212> TYPE: DNA
<213> ORGANISM: Artificial Sequence
<220> FEATURE:
<223> OTHER INFORMATION: Synthetic sequence

<400> SEQUENCE: 207 tttttt       6

<210> SEQ ID NO 208
<211> LENGTH: 7
<212> TYPE: DNA
<213> ORGANISM: Artificial Sequence
<220> FEATURE:
<223> OTHER INFORMATION: Synthetic sequence

<400> SEQUENCE: 208 ttttttt       7

<210> SEQ ID NO 209
<211> LENGTH: 8
<212> TYPE: DNA
<213> ORGANISM: Artificial Sequence
<220> FEATURE:
<223> OTHER INFORMATION: Synthetic sequence

<400> SEQUENCE: 209 tttttttt       8

<210> SEQ ID NO 210
<211> LENGTH: 9
<212> TYPE: DNA
<213> ORGANISM: Artificial Sequence
<220> FEATURE:
<223> OTHER INFORMATION: Synthetic sequence

<400> SEQUENCE: 210 ttttttttt       9

<210> SEQ ID NO 211
<211> LENGTH: 10
<212> TYPE: DNA

```
<213> ORGANISM: Artificial Sequence
<220> FEATURE:
<223> OTHER INFORMATION: Synthetic sequence

<400> SEQUENCE: 211
tttttttttt                                                               10

<210> SEQ ID NO 212
<211> LENGTH: 11
<212> TYPE: DNA
<213> ORGANISM: Artificial Sequence
<220> FEATURE:
<223> OTHER INFORMATION: Synthetic sequence

<400> SEQUENCE: 212
tttttttttt t                                                             11

<210> SEQ ID NO 213
<211> LENGTH: 12
<212> TYPE: DNA
<213> ORGANISM: Artificial Sequence
<220> FEATURE:
<223> OTHER INFORMATION: Synthetic sequence

<400> SEQUENCE: 213
tttttttttt tt                                                            12

<210> SEQ ID NO 214
<211> LENGTH: 10
<212> TYPE: DNA
<213> ORGANISM: Artificial Sequence
<220> FEATURE:
<223> OTHER INFORMATION: Synthetic sequence

<400> SEQUENCE: 214
tatatatata                                                               10

<210> SEQ ID NO 215
<211> LENGTH: 6
<212> TYPE: DNA
<213> ORGANISM: Artificial Sequence
<220> FEATURE:
<223> OTHER INFORMATION: Synthetic sequence

<400> SEQUENCE: 215 tatata                                                                    6

<210> SEQ ID NO 216
<211> LENGTH: 5
<212> TYPE: DNA
<213> ORGANISM: Artificial Sequence
<220> FEATURE:
<223> OTHER INFORMATION: Synthetic sequence

<400> SEQUENCE: 216 tatat                                                                     5
```

CASY COMPOSITIONS AND METHODS OF USE

CROSS-REFERENCE

This application claims the benefit of U.S. Provisional Patent Application No. 62/580,393, filed Nov. 1, 2017, which application is incorporated herein by reference in its entirety.

STATEMENT REGARDING FEDERALLY SPONSORED RESEARCH

This invention was made with government support under NSF Grant MCB0950971 (through UCB) and DOE Contract DE-AC02-05CH11231 (through LBNL). The invention was made with government support under Contract Nos. DE-AC02-05CH11231 awarded by the U.S. Department of Energy. The government has certain rights in the invention.

INCORPORATION BY REFERENCE OF SEQUENCE LISTING PROVIDED AS A TEXT FILE

A Sequence Listing is provided herewith as a text file, "BERK-372WO_SEQ_LISTING_ST25.txt" created on Oct. 30, 2018 and having a size of 345 KB. The contents of the text file are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

SUMMARY

The present disclosure provides compositions and methods that include a CasY transactivating noncoding RNA (trancRNA) (referred to herein as a "CasY trancRNA" or a "Cas12d trancRNA"), nucleic acids encoding the CasY trancRNA, and/or a modified host cell comprising the CasY trancRNA (and/or a nucleic acid encoding the same). Subject compositions and methods can also include one or more of: (a) a "CasY" protein (also referred to as a CasY polypeptide, a Cas12d protein, and a Cas12d polypeptide), a nucleic acid encoding the CasY protein, and/or a modified host cell comprising the CasY protein (and/or a nucleic acid encoding the same); and (b) a CasY guide RNA (also referred to herein as a "Cas12d guide RNA") that binds to and provides sequence specificity to the CasY protein, a nucleic acid encoding the CasY guide RNA, and/or a modified host cell comprising the CasY guide RNA (and/or a nucleic acid encoding the same).

BRIEF DESCRIPTION OF THE DRAWINGS

FIG. 1 depicts examples of naturally occurring CasY protein sequences.

FIG. 5 (panels a-d) depicts experiments performed (PAM dependent plasmid interference) to determine a PAM sequence for CasY, as well as data that were acquired.

FIG. 6 (panels a-c) presents 'repeat' sequences of naturally occurring CasY guide RNAs (the non-guide sequence portion of CasY guide RNAs), an example of a CasY guide RNA hybridizing to target DNA, and trancRNAs for three different CasY proteins.

FIG. 7 (panels a-c) presents data showing expression of a CasY locus in E. coli is sufficient for DNA interference. (panel a) Diagrams of CasY loci and neighboring proteins. (panel b) WebLogo of 5' PAM sequences depleted greater than 3-fold by CasY relative to a control library. (panel c) Plasmid interference by E. coli expressing CasY.1 and transformed with targets containing the indicated PAM. Experiments were conducted in triplicate and mean±s.d is shown.

FIG. 13, Panel B:CasY15; FIG. 13, Panel C: CasY10; FIG. 13, Panel D: CasY3; FIG. 13, Panel E: CasY11). Plasmid libraries containing randomized PAM sequences were assembled by annealing a DNA oligonucleotide containing a target with a 7-nucleotide randomized PAM region with a primer and extended with Klenow Fragment (NEB). The double-stranded DNA was digested with EcoRI and NcoI and ligated into a pUC19 backbone. The ligated library was transformed into $E.\ coli$ DH5a and >$10^8$ cells were harvested and the plasmids extracted and purified. 200 ng of the pooled library was transformed into electrocompetent $E.\ coli$ harboring a CRISPR locus or a control plasmid with no locus. The transformed cells were plated on selective medium containing carbeni-cillin (100 mg 1-1) and chloramphenicol (30 mg 1-1) for 30 h at 25° C. Plasmid DNA was extracted and the PAM sequence was amplified with adapters for Illumina sequencing. The 7-nucleotide PAM region was extracted and PAM frequencies calculated for each 7-nucleotide sequence. PAM sequences depleted above the specified threshold were used to generate a sequence logo with WebLogo.

FIG. 15 depicts Table 2 of CasY15 RNA sequences.

FIG. 16 depicts Table 3 of CasY15 DNA sequences.

FIG. 18 shows emitted fluorescence signal of "On targets" and "Off target" CasY trans substrates using FQ-ssDNA probes of different nucleotide lengths.

DEFINITIONS

Figure 2:
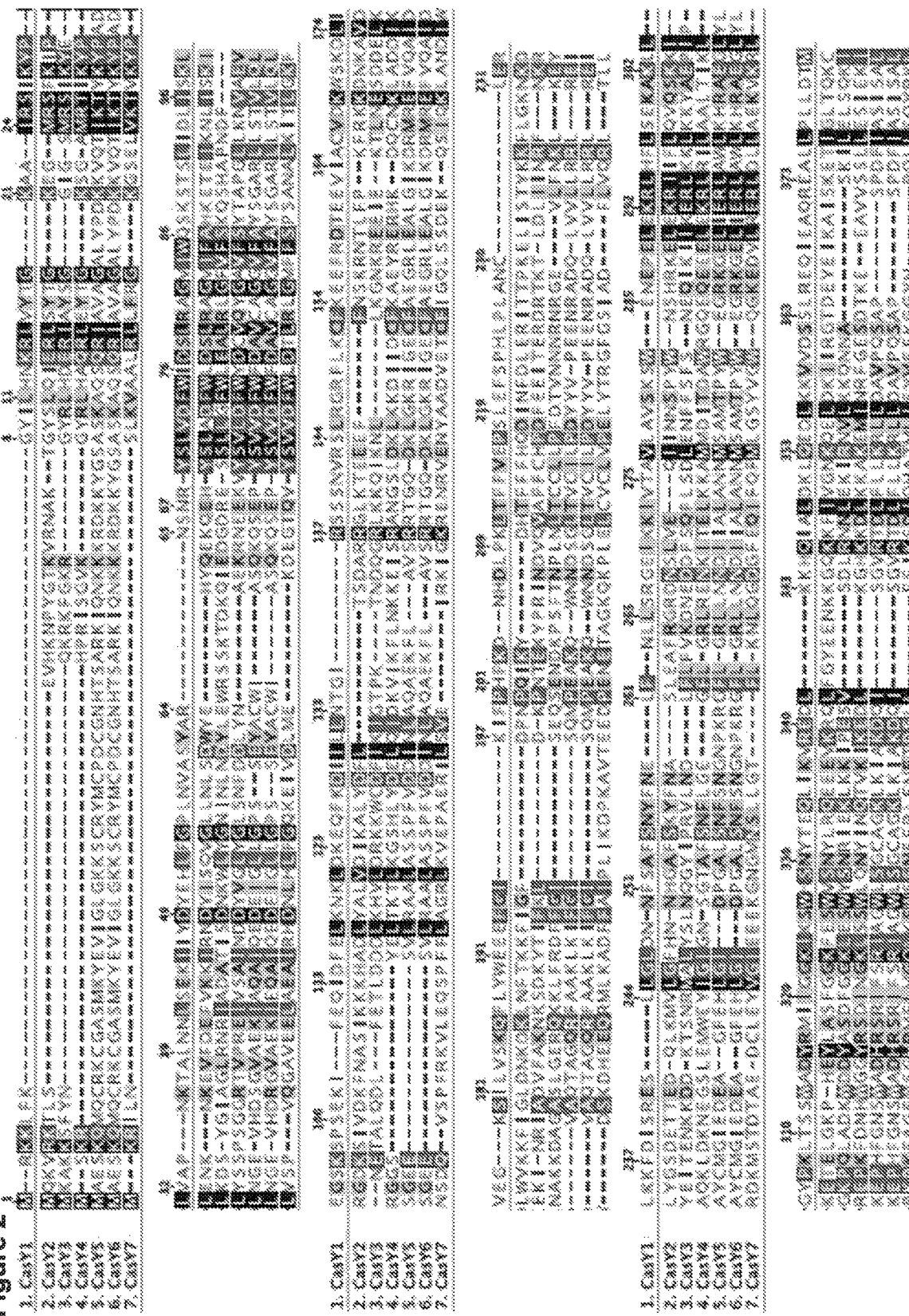
FIG. 2 depicts an alignment of naturally occurring CasY protein sequences and a zoom in of catalytic amino acids. Nucleotide sequences from top to bottom: CasY1: (SEQ ID NO: 1); CasY2: (SEQ ID NO:2); CasY3: (SEQ ID NO:3); CasY4: (SEQ ID NO:4); CasY5: (SEQ ID NO:6); CasY6: (SEQ ID NO:7); CasY7: (SEQ ID NO:5); AsCpF1_5B43: (SEQ ID NO:29); LbCpf1_5ID6: (SEQ ID NO:30).

"Heterologous," as used herein, means a nucleotide or polypeptide sequence that is not found in the native nucleic acid or protein, respectively. For example, relative to a CasY polypeptide, a heterologous polypeptide comprises an amino acid sequence from a protein other than the CasY polypeptide. In some cases, a portion of a CasY protein from one species is fused to a portion of a CasY protein from a different species. The CasY sequence from each species could therefore be considered to be heterologous relative to one another. As another example, a CasY protein (e.g., a dCasY protein) can be fused to an active domain from a non-CasY protein (e.g., a histone deacetylase), and the sequence of the active domain could be considered a heterologous polypeptide (it is heterologous to the CasY protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasY polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods that include a CasY transactivating noncoding RNA (trancRNA) (referred to herein as a "CasY trancRNA" or a "Cas12d trancRNA"), nucleic acids encoding the CasY trancRNA, and/or a modified host cell comprising the CasY trancRNA (and/or a nucleic acid encoding the same). Subject compositions and methods can also include one or more of: (a) a "CasY" protein (also referred to as a CasY polypeptide, a Cas12d protein, and a Cas12d polypeptide), a nucleic acid encoding the CasY protein, and/or a modified host cell comprising the CasY protein (and/or a nucleic acid encoding the same); and (b) a CasY guide RNA (also referred to herein as a "Cas12d guide RNA") that binds to and provides sequence specificity to the CasY protein, a nucleic acid encoding the CasY guide RNA, and/or a modified host cell comprising the CasY guide RNA (and/or a nucleic acid encoding the same).

Compositions

CRISPR/CasY Proteins, Guide RNAs, and TrancRNAs

Class 2 CRISPR-Cas systems are characterized by effector modules that include a single multidomain protein. In the CasY system, a CRISPR/Cas endonuclease (e.g., a CasY protein) interacts with (binds to) a corresponding guide RNA (e.g., a CasY guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasY protein forms a complex with a CasY guide RNA and the guide RNA provides sequence specificity to the RNP complex via the guide sequence. The CasY protein of the complex provides the site-specific activity. In other words, the CasY protein is guided to a target site (e.g., stabilized at a target site) within a target nucleic acid (e.g. a target nucleotide sequence within a target chromosomal nucleic acid; or a target nucleotide sequence within a target extrachromosomal nucleic acid, e.g., an episomal nucleic acid, a minicircle nucleic acid, a mitochondrial nucleic acid, a chloroplast nucleic acid, etc.) by virtue of its association with the guide RNA.

The present disclosure provides compositions comprising a CasY trancRNA and one ore more of: (a) CasY polypeptide (and/or a nucleic acid encoding the CasY polypeptide) (e.g., where the CasY polypeptide can be a naturally existing protein, a nickase CasY protein, a dCasY protein, a chimeric CasY protein, etc.); and (b) a CasY guide RNA (and/or a nucleic acid encoding the CasY guide RNA). The present disclosure provides compositions comprising (a) a CasY trancRNA; (b) a CasY polypeptide (and/or a nucleic acid encoding the CasY polypeptide) (e.g., where the CasY polypeptide can be a naturally existing protein, a nickase CasY protein, a dCasY protein, a chimeric CasY protein, etc.); and (c) a CasY guide RNA (and/or a nucleic acid encoding the CasY guide RNA). The present disclosure provides a nucleic acid/protein complex (RNP complex) comprising: (a) a Casy trancRNA; (b) a CasY polypeptide of the present disclosure (e.g., where the CasY polypeptide can be a naturally existing protein, a nickase CasY protein, a dCasY protein, a chimeric CasY protein, etc.); and (c) a CasY guide RNA.

CasY Protein

A CasY polypeptide (this term is used interchangeably with the term "CasY protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasY protein includes a fusion partner with an activity, and in some cases the CasY protein provides nuclease activity). In some cases, the CasY protein is a naturally-occurring protein (e.g., naturally occurs in prokaryotic cells). In other cases, the CasY protein is not a naturally-occurring polypeptide (e.g., the CasY protein is a variant CasY protein, a chimeric protein, and the like).

Assays to determine whether given protein interacts with a CasY guide RNA can be any convenient binding assay that tests for binding between a protein and a nucleic acid. Suitable binding assays (e.g., gel shift assays) will be known to one of ordinary skill in the art (e.g., assays that include adding a CasY guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CasY protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring CasY guide RNA is a crRNA, where the crRNA includes (i) a guide sequence that hybridizes to a target sequence in the target DNA and (ii) a protein binding segment which includes a stem-loop (hairpin-dsRNA duplex) that binds to the CasY protein.

In some embodiments, the CasY protein of the subject methods and/or compositions is (or is derived from) a naturally occurring (wild type) protein. Examples of naturally occurring CasY proteins are depicted in FIG. 1 and are set forth as SEQ ID NOs: 1-8 and 51-58. An alignment of example naturally occurring CasY proteins is presented in FIG. 2 (the proteins are labeled as "Y1.", "Y2.", "Y3.", etc.). Partial DNA scaffolds of 7 naturally occurring CasY CRISPR loci (assembled from sequencing data) are set forth as SEQ ID NOs: 21-27. It is important to note that this newly discovered protein (CasY) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasY protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. It is also noted herein that bacteria harboring CasY CRISPR loci were present in environmental samples that were collected at low temperature (e.g., 10-17° C.). Thus, CasY is expected to be able to function well at low temperatures (e.g., 10-14° C., 10-17° C., 10-20° C.) (e.g., better than other Cas endoconucleases discovered to date).

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 1. In some cases, a CasY protein includes an amino acid sequence having the CasY protein sequence set forth as SEQ ID NO: 1. In some cases, a CasY protein includes an amino acid sequence having the CasY protein sequence set forth as SEQ ID NO: 1, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 2. In some cases, a CasY protein includes an amino acid sequence having the CasY protein sequence set forth as SEQ ID NO: 2. In some cases, a CasY protein includes an amino acid sequence having the CasY protein sequence set forth as SEQ ID NO: 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 3. In some cases, a CasY protein includes an amino acid sequence having the CasY protein sequence set forth as SEQ ID NO: 3. In some cases, a CasY protein includes an amino acid sequence having the CasY protein sequence set forth as SEQ ID NO: 3, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 4. In some cases, a CasY protein includes an amino acid sequence having the CasY protein sequence set forth as SEQ ID NO: 4. In some cases, a CasY protein includes an amino acid sequence having the CasY protein sequence set forth as SEQ ID NO: 4, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 5. In some cases, a CasY protein includes an amino acid sequence having the CasY protein sequence set forth as SEQ ID NO: 5. In some cases, a CasY protein includes an amino acid sequence having the CasY protein sequence set forth as SEQ ID NO: 5, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 6. In some cases, a CasY protein includes an amino acid sequence having the CasY protein sequence set forth as SEQ ID NO: 6. In some cases, a CasY protein includes an amino acid sequence having the CasY protein sequence set forth as SEQ ID NO: 6, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 7. In some cases, a CasY protein includes an amino acid sequence having the CasY protein sequence set forth as SEQ ID NO: 7. In some cases, a CasY protein includes an amino acid sequence having the CasY protein sequence set forth as SEQ ID NO: 7, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 8. In some cases, a CasY protein includes an amino acid sequence having the CasY protein sequence set forth as SEQ ID NO: 8. In some cases, a CasY protein includes an amino acid sequence having the CasY protein sequence set forth as SEQ ID NO: 8, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-4. In some cases, a CasY protein includes an amino acid sequence having the CasY protein sequence set forth in any one of SEQ ID NOs: 1-4. In some cases, a CasY protein includes an amino acid sequence having the CasY protein sequence set forth in any one of SEQ ID NOs: 1-4, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-5. In some cases, a CasY protein includes an amino acid sequence having the CasY protein sequence set forth in any one of SEQ ID NOs: 1-5. In some cases, a CasY protein includes an amino acid sequence having the CasY protein sequence set forth in any one of SEQ ID NOs: 1-5, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-7. In some cases, a CasY protein includes an amino acid sequence having the CasY protein sequence set forth in any one of SEQ ID NOs: 1-7. In some cases, a CasY protein includes an amino acid sequence having the CasY protein sequence set forth in any one of SEQ ID NOs: 1-7, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-8. In some cases, a CasY protein includes an amino acid sequence having the CasY protein sequence set forth in any one of SEQ ID NOs: 1-8. In some cases, a CasY protein includes an amino acid sequence having the CasY protein sequence set forth in any one of SEQ ID NOs: 1-8, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 51-58. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 51-58. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 51-58. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 51-58. In some cases, a CasY protein includes an amino acid sequence having the CasY protein sequence set forth in any one of SEQ ID NOs: 51-58. In some cases, a CasY protein includes an amino acid sequence having the CasY protein sequence set forth in any one of SEQ ID NOs: 51-58, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8 and 51-58. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8 and 51-58. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-8 and 51-58. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-8 and 51-58. In some cases, a CasY protein includes an amino acid sequence having the CasY protein sequence set forth in any one of SEQ ID NOs: 1-8 and 51-58. In some cases, a CasY protein includes an amino acid sequence having the CasY protein sequence set forth in any one of SEQ ID NOs: 1-8 and 51-58, with the exception that the sequence includes an amino acid substitution (e.g., 1, 2, or 3 amino acid substitutions) that reduces the naturally occurring catalytic activity of the protein (e.g., such as at amino acid positions described below).

CasY Protein Domains

Figure 3:
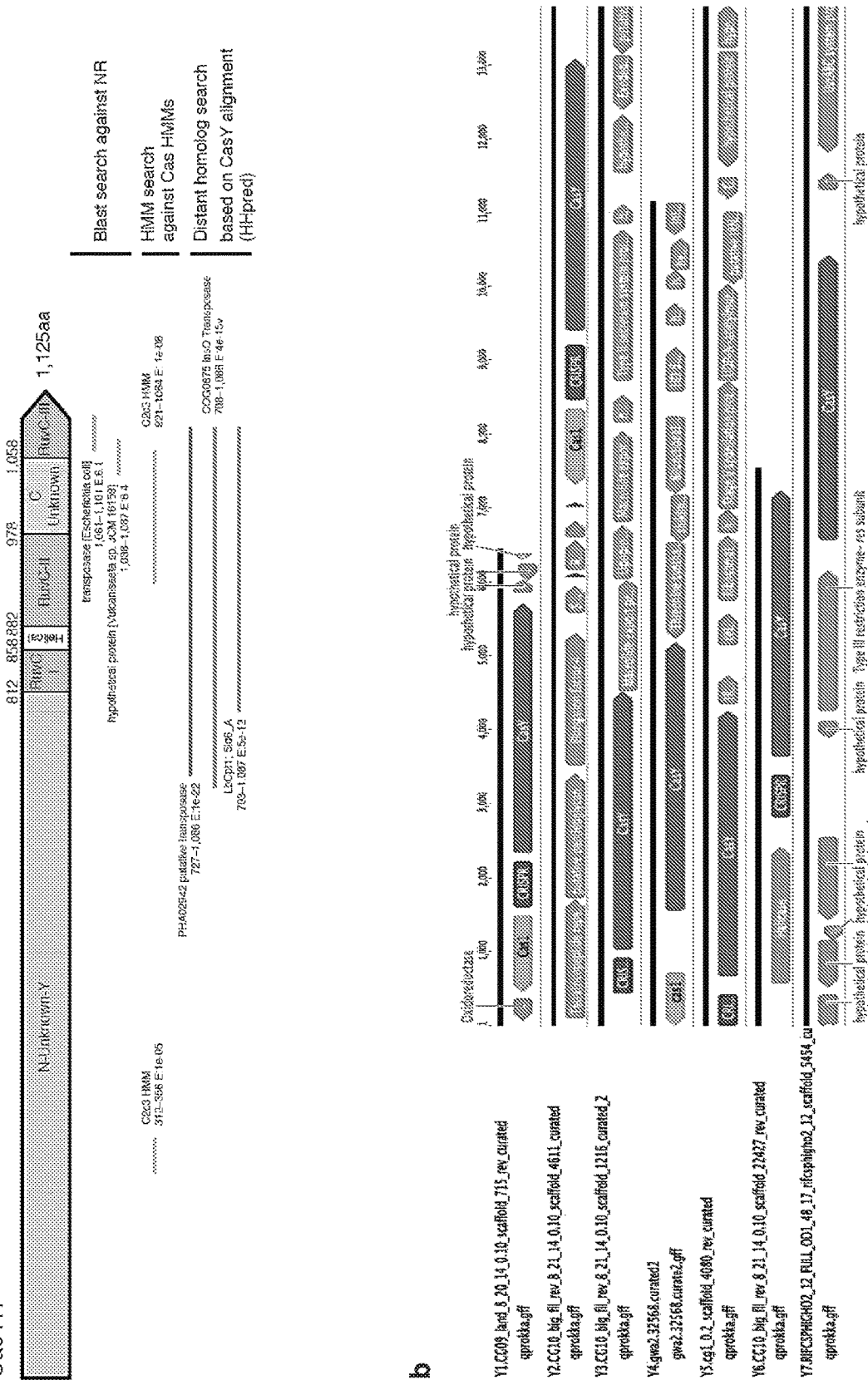
FIG. 3 (panels a-b): (panel a) depicts a schematic domain representation for CasY. Also shown are results from various searches attempting to identify homologs of CasY. (panel b) depicts portions of CasY-containing CRISPR loci.

The domains of a CasY protein are depicted in FIG. 3. As can be seen in the schematic representation of FIG. 3 (amino acids are numbered based on the CasY1 protein (SEQ ID NO: 1)), a CasY protein includes an N-terminal domain roughly 800-1000 amino acids in length (e.g., about 815 for CasY1 and about 980 for CasY5), and a C-terminal domain that includes 3 partial RuvC domains (RuvC-I, RuvC-II, and RuvC-III, also referred to herein as subdomains) that are not contiguous with respect to the primary amino acid sequence of the CasY protein, but form a RuvC domain once the protein is produced and folds. Thus, in some cases, a CasY protein (of the subject compositions and/or methods) includes an amino acid sequence with an N-terminal domain (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids). In some cases, a CasY protein (of the subject compositions and/or methods) includes an amino acid sequence having a length (e.g., not including any fused heterologous sequence such as an NLS and/or a domain with a catalytic activity) in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids) that is N-terminal to a split Ruv C domain (e.g., 3 partial RuvC domains—RuvC-I, RuvC-II, and RuvC-III).

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes a fragment of the amino acid sequence of any one of SEQ ID NOs: 1-4 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes a fragment of the amino acid sequence of any one of SEQ ID NOs: 1-5 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes a fragment of the amino acid sequence of any one of SEQ ID NOs: 1-8 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8 and 51-58. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8 and 51-58. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8 and 51-58. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8 and 51-58. In some cases, a CasY protein includes a fragment of the amino acid sequence of any one of SEQ ID NOs: 1-8 and 51-58 that corresponds to amino acids 1-812 of the CasY protein sequence set forth as SEQ ID NO: 1.

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first aminio acid sequence, that includes a split Ruv C domain (e.g., 3 partial RuvC domains—RuvC-I, RuvC-II, and RuvC-III).

In some embodiments, the split RuvC domain of a CasY protein (of the subject compositions and/or methods) includes a region between the RuvC-II and RuvC-III subdomains that is larger than the RuvC-III subdomain. For example, in some cases, the ratio of the length of the region between the RuvC-II and RuvC-III subdomains over the length of the RuvC-III subdomain is 1.1 or greater (e.g., 1.2). In some cases, the ratio of the length of the region between the RuvC-II and RuvC-III subdomains over the length of the RuvC-III subdomain is greater than 1). In some cases, the ratio of the length of the region between the RuvC-II and RuvC-III subdomains over the length of the RuvC-III subdomain is greater than 1and between 1 and 1.5 (e.g., 1 and 1.4, 1 and 1.3, or 1 and 1.2).

In some embodiments (for a CasY protein of the subject compositions and/or methods), the ratio of the length of the RuvC-II subdomain over the length of the RuvC-III subdomain is 2 or less (e.g., 1.8 or less, 1.7 or less, 1.6 or less, 1.5 or less, or 1.4 or less). For example, in some cases, the ratio of the length of the RuvC-II subdomain over the length of the RuvC-III subdomain is 1.5 or less (e.g., 1.4 or less). In some embodiments, the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4).

In some cases (for a CasY protein of the subject compositions and/or methods), the ratio of the length of the region between the RuvC-II and RuvC-III subdomains over the length of the RuvC-III subdomain is greater than 1. In some cases, the ratio of the length of the region between the RuvC-II and RuvC-III subdomains over the length of the RuvC-III subdomain is greater than 1 and between 1 and 1.3 (e.g., 1 and 1.2).

In some cases (for a CasY protein of the subject compositions and/or methods), the region between the RuvC-II and RuvC-III subdomains is at least 60 amino acids in length (e.g., at least 65, 68, or 70 amino acids in length). In some cases, the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids).

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains—RuvC-I, RuvC-II, and RuvC-III— where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains— RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains—RuvC-I, RuvC-II, and RuvC-III— where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8 and 51-58; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence with an N-terminal domain (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence (C-terminal to the first) having a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a fragment of the amino acid sequence of any one of the CasY protein sequences set forth as SEQ ID NOs: 1-4 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a fragment of the amino acid sequence of any one of the CasY protein sequences set forth as SEQ ID NOs: 1-5 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a fragment of the amino acid sequence of any one of the CasY protein sequences set forth as SEQ ID NOs: 1-8 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes a fragment of the amino acid sequence of any one of the CasY protein sequences set forth as SEQ ID NOs: 1-8 and 51-58 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-4 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-5 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-8 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8 and 51-58. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-8 and 51-58 that corresponds to amino acids 812-1125 of the CasY protein sequence set forth as SEQ ID NO: 1.

CasY Variants

A variant CasY protein has an amino acid sequence that is different by at least one amino acid (e.g., has a deletion, insertion, substitution, fusion) when compared to the amino acid sequence of the corresponding wild type CasY protein. A CasY protein that cleaves one strand but not the other of a double stranded target nucleic acid is referred to herein as a "nickase" (e.g., a "nickase CasY"). A CasY protein that has substantially no nuclease activity is referred to herein as a dead CasY protein ("dCasY") (with the caveat that nuclease activity can be provided by a heterologous polypeptide—a fusion partner—in the case of a chimeric CasY protein, which is described in more detail below). For any of the CasY variant proteins described herein (e.g., nickase CasY, dCasY, chimeric CasY), the CasY variant can include a CasY protein sequence with the same parameters described above (e.g., domains that are present, percent identity, and the like).

Variants—Catalytic Activity

In some cases, the CasY protein is a variant CasY protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasY protein is a catalytically 'dead' protein (has substantially no cleavage activity) and can be referred to as a 'dCasY.' In some cases, the variant CasY protein is a nickase (cleaves only one strand of a double stranded target nucleic acid, e.g., a double stranded target DNA). As described in more detail herein, in some cases, a CasY protein (in some case a CasY protein with wild type cleavage activity and in some cases a variant CasY with reduced cleavage activity, e.g., a dCasY or a nickase CasY) is fused (conjugated) to a heterologous polypeptide that has an activity of interest (e.g., a catalytic activity of interest) to form a fusion protein (a chimeric CasY protein).

Catalytic residues of CasY include D828, E914, D1074 when numbered according to CasY1 (e.g., see FIG. 1) (these residues are underlined in FIG. 1 for CasY1). (also see, e.g., the alignments of FIG. 2, panels a and b). Thus, in some cases, the CasY protein has reduced activity and one or more of the above described amino acids (or one or more corresponding amino acids of any CasY protein) are mutated (e.g., substituted with an alanine). In some cases, the variant CasY protein is a catalytically 'dead' protein (is catalytically inactive) and is referred to as 'dCasY.' A dCasY protein can be fused to a fusion partner that provides an activity, and in some cases, the dCasY (e.g., one without a fusion partner that provides catalytic activity—but which can have an NLS when expressed in a eukaryotic cell) can bind to target DNA and can be used for imaging (e.g., the protein can be tagged/labeled) and/or can block RNA polymerase from transcribing from a target DNA. In some cases, the variant CasY protein is a nickase (cleaves only one strand of a double stranded target nucleic acid, e.g., a double stranded target DNA).

Variants—Chimeric CasY (i.e., Fusion Proteins)

As noted above, in some cases, a CasY protein (in some cases a CasY protein with wild type cleavage activity and in some cases a variant CasY with reduced cleavage activity, e.g., a dCasY or a nickase CasY) is fused (conjugated) to a heterologous polypeptide that has an activity of interest (e.g., a catalytic activity of interest) to form a fusion protein (a chimeric CasY protein). A heterologous polypeptide to which a CasY protein can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasY protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasY protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krtippel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like;

histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (1N); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners are dihydrofolate reductase (DHFR) destabilization domain (e.g., to generate a chemically controllable chimeric CasY protein), and a chloroplast transit peptide. Suitable chloroplast transit peptides include, but are not limited to:

```
                                    (SEQ ID NO: 83)
MASMISSSAVTTVSRASRGQSAAMAPFGGLKSMTGFPVRKVNTDITSITS

NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS

NGGRVKS;

(SEQ ID NO: 85)
MASSMLSSATMVASPAQATMVAPFNGLKSSAAFPATRKANNDITSITSNG

GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG

LKKSGMTLIGSELRPLKVMSSVSTAC;

(SEQ ID NO: 87)
MAQVSRICNGVWNPSLISNLSKSSQRKSPLSVSLKTQQHPRAYPISSSWG

LKKSGMTLIGSELRPLKVMSSVSTAC;

(SEQ ID NO: 88)
MAQINNMAQGIQTLNPNSNFHKPQVPKSSSFLVFGSKKLKNSANSMLVLK

KDSIFMQLFCSFRISASVATAC;

(SEQ ID NO: 89)
MAALVTSQLATSGTVLSVTDRFRRPGFQGLRPRNPADAALGMRTVGASAA

PKQSRKPHRFDRRCLSMVV;

(SEQ ID NO: 90)
MAALTTSQLATSATGFGIADRSAPSSLLRHGFQGLKPRSPAGGDATSLSV

TTSARATPKQQRSVQRGSRRFPSVVVC;

(SEQ ID NO: 91)
MASSVLSSAAVATRSNVAQANMVAPFTGLKSAASFPVSRKQNLDITSIAS

NGGRVQC;

(SEQ ID NO: 92)
MESLAATSVFAPSRVAVPAARALVRAGTVVPTRRTSSTSGTSGVKCSAAV

TPQASPVISRSAAAA;
and
                                    (SEQ ID NO: 93)
MGAAATSMQSLKFSNRLVPPSRRLSPVPNNVTCNNLPKSAAPVRTVKCCA

SSWNSTINGAAATTNGASAASS.
```

In some case, a CasY fusion polypeptide of the present disclosure comprises: a) a CasY polypeptide of the present disclosure; and b) a chloroplast transit peptide. Thus, for example, a CRISPR-CasY complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasY fusion polypeptide of the present disclosure can comprise: a) a CasY polypeptide of the present disclosure; and b) an endosomal escape peptide. In some cases, an endosomal escape polypeptide comprises the amino acid sequence GLFXALLXLLXSLWXLLLXA (SEQ ID NO:94), wherein each X is independently selected from lysine, histidine, and arginine. In some cases, an endosomal escape polypeptide comprises the amino acid sequence GLFHALLHLLHSLWHLLLHA (SEQ ID NO:95).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et. al., J Virol. 2006 February; 80(4):1939-48; Tan et al., Proc Natl Acad Sci USA. 2003 Oct. 14; 100(21): 11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20; 533(7603):420-4; Chaikind et al., Nucleic Acids Res. 2016 Aug. 11; Choudhury et. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasY polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasY polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasY polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cis-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Abyl, etc.).

Examples of various additional suitable heterologous polypeptide (or fragments thereof) for a subject chimeric CasY polypeptide include, but are not limited to those described in the following applications (which publications are related to other CRISPR endonucleases such as Cas9, but the described fusion partners can also be used with CasY instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasY fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) a nuclear localization signal (NLS) (e.g, in some cases 2 or more, 3 or more, 4 or more, or 5 or more NLSs). Thus, in some cases, a CasY polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 96); the NLS from nucleoplasmin (e.g., the nucleoplasmin bipartite NLS with the sequence KRPAATKKAGQAKKKK (SEQ ID NO: 97)); the c-myc NLS having the amino acid sequence PAAKRVKLD (SEQ ID NO: 98) or RQRRNELKRSP (SEQ ID NO: 99); the hRNPA1 M9 NLS having the sequence NQSSNFGPMKGGNFGGRSSGPYGGGGQYFAKPRNQGGY (SEQ ID NO: 100); the sequence RMRIZFKNKGKDTAELRRRRVEVSVELRKAKKDEQILKRRNV (SEQ ID NO: 101) of the IBB domain from importin-alpha; the sequences VSRKRPRP (SEQ ID NO: 102) and PPKKARED (SEQ ID NO: 103) of the myoma T protein; the sequence PQPKKKPL (SEQ ID NO: 104) of human p53; the sequence SALIKKKKKMAP (SEQ ID NO: 105) of mouse c-abl IV; the sequences DRLRR (SEQ ID NO: 106) and PKQKKRK (SEQ ID NO: 107) of the influenza virus NS1; the sequence RKLKKKIKKL (SEQ ID NO: 108) of the Hepatitis virus delta antigen; the sequence REKKKFLKRR (SEQ ID NO: 109) of the mouse Mx1 protein; the sequence KRKGDEVDGVDEVAKKKSKK (SEQ ID NO: 110) of the human poly(ADP-ribose) polymerase; and the sequence RKCLQAGMNLEARKTKK (SEQ ID NO: 111) of the steroid hormone receptors (human) glucocorticoid. In general, NLS (or multiple NLSs) are of sufficient strength to drive accumulation of the CasY protein in a detectable amount in the nucleus of a eukaryotic cell. Detection of accumulation in the nucleus may be performed by any suitable technique. For example, a detectable marker may be fused to the CasY protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasY fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasY to generate a fusino protein, or linked to a variant CasY protein such as a dCasY, nickase CasY, or chimeric CasY protein to generate a fusion protein). In some embodiments, a PTD is covalently linked to the carboxyl terminus of a polypeptide (e.g., linked to a wild type CasY to generate a fusino protein, or linked to a variant CasY protein such as a dCasY, nickase CasY, or chimeric CasY protein to generate a fusion protein). In some cases, the PTD is inserted interally in the CasY fusion polypeptide (i.e., is not at the N- or C-terminus of the CasY fusion polypeptide) at a suitable insertion site. In some cases, a subject CasY fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasY fusion polypeptide includes one or more NLSs (e.g., 2 or more, 3 or more, 4 or more, or 5 or more NLSs). In some embodiments, a PTD is covalently linked to a nucleic acid (e.g., a CasY guide nucleic acid, a polynucleotide encoding a CasY guide nucleic acid, a polynucleotide encoding a CasY fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO: 113); Transportan GWTLNSAGYLLGKINLKALAALAKKIL (SEQ ID NO:114); KALAWEAKLAKALAKALAKHLAKALAKALKCEA (SEQ ID NO:115); and RQIKIWFQNRRMKWKK (SEQ ID NO: 116). Exemplary PTDs include but are not limited to, YGRKKRRQRRR (SEQ ID NO:112), RKKRRQRRR (SEQ ID NO:118); an arginine homopolymer of from 3 arginine residues to 50 arginine residues; Exemplary PTD domain amino acid sequences include, but are not limited to, any of the following: YGRKKRRQRRR (SEQ ID NO: 112); RKKRRQRR (SEQ ID NO:120); YARAAARQARA (SEQ ID NO:121); THRLPRRRRRR (SEQ ID NO:122); and GGRRARRRRRR (SEQ ID NO: 123). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject CasY protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 124), $GGSGGS_n$ (SEQ ID NO: 125), and $GGGS_n$ (SEQ ID NO: 126), where n is an integer of at least one), glycine-alanine polymers, alanine-serine polymers. Exemplary linkers can comprise amino acid sequences including, but not limited to, GGSG (SEQ ID NO: 127), GGSGG (SEQ ID NO: 128), GSGSG (SEQ ID NO: 129), GSGGG (SEQ ID NO: 130), GGGSG (SEQ ID NO: 131), GSSSG (SEQ ID NO: 132), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasY polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, J3-glucuronidase, invertase, Xanthine Oxidase, firefly luciferase, glucose oxidase (GO), and the like.

Protospacer Adjacent Motif (PAM)

A CasY protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for a CasY protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some embodiments (e.g., when CasY1 as described herein is used), the PAM sequence of the non-complementary strand is 5'-TA-3' (and in some cases XTA, where X is C, A, or T). As an example, see FIG. 5 and FIG. 7 (in which the PAM is TA, or CTA if you consider the PAM to be XTA where X is C, A, or T). In some embodiments (e.g., when CasY1 as described herein is used), the PAM sequence of the non-complementary strand is 5'-TA-3' (and in some cases HTA, where H is C, A, or T). As an example, see FIG. 5 and FIG. 7 (in which the PAM is TA, or CTA if the PAM is considered to be HTA where H is C, A, or T). In some cases (e.g., when CasY2 as described herein is used), the PAM sequence of the non-complementary strand is a 5'-TA-3' flanking sequence 5' of the target. In some cases (e.g., when CasY2 as described herein is used), the PAM sequence of the non-complementary strand is a 5'-YR-3' flanking sequence 5' of the target (where Y is a T or C and R is an A or G). In some cases (e.g., when CasY2 as described herein is used), the PAM sequence of the non-complementary strand is 5'-TR-3' (e.g., 5'-DTR-3') (where R is an A or G and D is an A, G, or T). As an example, see FIG. 5d.

In some cases, different CasY proteins (i.e., CasY proteins from various species) may be advantageous to use in the various provided methods in order to capitalize on various enzymatic characteristics of the different CasY proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasY proteins from different species may require different PAM sequences in the target DNA. Thus, for a particular CasY protein of choice, the PAM sequence preference may be different than the 5'-TA-3' (or XTA, HTA) sequence described above. Various methods (including in silico and/or wet lab methods) for identification of the appropriate PAM sequence are known in the art and are routine, and any convenient method can be used. The TA (XTA, HTA) PAM sequence described herein was identified using a PAM depletion assay (e.g., see FIG. 5 of the working examples below).

CasY Guide RNA

A nucleic acid molecule that binds to a CasY protein, forming a ribonucleoprotein complex (RNP), and targets the complex to a specific location within a target nucleic acid (e.g., a target DNA) is referred to herein as a "CasY guide RNA" or simply as a "guide RNA." It is to be understood that in some cases, a hybrid DNA/RNA can be made such that a CasY guide RNA includes DNA bases in addition to RNA bases, but the term "CasY guide RNA" is still used to encompass such a molecule herein.

A CasY guide RNA can be said to include two segments, a targeting segment and a protein-binding segment. The targeting segment of a CasY guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasY polypeptide. The protein-binding segment of a subject CasY guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasY guide RNA (the guide sequence of the CasY guide RNA) and the target nucleic acid.

A CasY guide RNA and a CasY protein, e.g., a fusion CasY polypeptide, form a complex (e.g., bind via non-covalent interactions). The CasY guide RNA provides target specificity to the complex by including a targeting segment, which includes a guide sequence (a nucleotide sequence that is complementary to a sequence of a target nucleic acid). The CasY protein of the complex provides the site-specific activity (e.g., cleavage activity provided by the CasY protein and/or an activity provided by the fusion partner in the case of a chimeric CasY protein). In other words, the CasY protein is guided to a target nucleic acid sequence (e.g. a target sequence) by virtue of its association with the CasY guide RNA.

The "guide sequence" also referred to as the "targeting sequence" of a CasY guide RNA can be modified so that the CasY guide RNA can target a CasY protein (e.g., a naturally occurring CasY protein, a fusion CasY polypeptide (chimeric CasY), and the like) to any desired sequence of any desired target nucleic acid, with the exception (e.g., as described herein) that the PAM sequence can be taken into account. Thus, for example, a CasY guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a CasY guide RNA has a length of 30 nucleotides (nt) or more (e.g., 35 nt or more, 40 nt or more, 45 nt or more, 50 nt or more, 55 nt or more, or 60 nt or more). In some embodiments, a CasY guide RNA has a length of 40 nucleotides (nt) or more (e.g., 45 nt or more, 50 nt or more, 55 nt or more, or 60 nt or more). In some embodiments, a CasY guide RNA has a length of from 30 nucleotides (nt) to 100 nt (e.g., 30-90, 30-80, 30-75, 30-70, 30-65, 40-100, 40-90, 40-80, 40-75, 40-70, or 40-65 nt). In some embodiments, a CasY guide RNA has a length of from 40 nucleotides (nt) to 100 nt (e.g., 40-90, 40-80, 40-75, 40-70, or 40-65 nt).

Guide Sequence of a CasY Guide RNA

A subject CasY guide RNA includes a guide sequence (i.e., a targeting sequence), which is a nucleotide sequence that is complementary to a sequence (a target site) in a target nucleic acid. In other words, the guide sequence of a CasY guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasY guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Protein-Binding Segment of a CasY Guide RNA

The protein-binding segment of a subject CasY guide RNA interacts with a CasY protein. The CasY guide RNA guides the bound CasY protein to a specific nucleotide sequence within target nucleic acid via the above mentioned guide sequence. The protein-binding segment of a CasY guide RNA comprises two stretches of nucleotides that are complementary to one another and hybridize to form a double stranded RNA duplex (dsRNA duplex). Thus, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide or multiple nucleotides) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject CasY guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject CasY guide RNA includes more paired bases, less paired bases, a smaller bulge, a larger bulge, fewer bulges, more bulges, or any convenient combination thereof, as compared to a naturally occurring duplex region (of a naturally occurring CasY guide RNA).

Examples of various Cas9 guide RNAs and cpf1 guide RNAs can be found in the art, and in some cases variations similar to those introduced into Cas9 guide RNAs can also be introduced into CasY guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4): 910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140343458; 20140349400; 20140349405; 20140356867; 20140356956; 20140356958; 20140356959; 20140357523; 20140357530; 20140364333; and 20140377868; all of which are hereby incorporated by reference in their entirety.

A CasY guide RNA comprises both the guide sequence and two stretches ("duplex-forming segments") of nucleotides that hybridize to form the dsRNA duplex of the protein-binding segment. The particular sequence of a given CasY guide RNA can be characteristic of the species in which the a crRNA is found. Examples of suitable CasY guide RNAs are provided herein.

Single-Molecule Hybrid CasY Guide RNA/Tranc RNA

A CasY guide RNA can in some cases comprise a tranc RNA (also referred to as a "scout" RNA). In some cases, a CasY guide RNA is a single-molecule guide RNA comprising: i) a CasY guide RNA; and ii) a tranc RNA. In some cases, a CasY guide RNA comprises, in order from 5' to 3': i) a CasY guide RNA; and ii) a tranc RNA. In some cases, the CasY guide RNA is linked directly to the tranc RNA. In some cases, the CasY guide RNA is linked to the tranc RNA through a nucleotide linker (e.g., a polynucleotide linker). A nucleotide linker can comprise from 1 to 30 nucleotides (e.g., from 1 to 5 nucleotides, from 5 to 10 nucleotides, from 10 to 15 nucleotides, from 15 to 20 nucleotides, from 20 to 25 nucleotides, or from 25 to 30 nucleotides). In some cases, the CasY guide RNA is linked to the tranc RNA through a non-nucleotide linkage. For example, in some cases, a CasY guide RNA is linked to the tranc RNA through a thioether linker or a triazole linker.

Example Guide RNA Sequences

Repeat sequences (non-guide sequence portion of an example CasY guide RNA) of crRNAs for naturally existing CasY proteins (e.g., see FIG. 1) are shown in Table 1.

TABLE 1 crRNA repeat sequences for CasY proteins

| Protein | crRNA repeat | SEQ ID NO: |
|---|---|---|
| CasY1 | CUCCGAAAGUAUCGGGGAUAAAGGC | 11 |
| CasY2 | CACCGAAAUUUGGAGAGGAUAAGGC | 12 |

TABLE 1-continued crRNA repeat sequences for CasY proteins

| Protein | crRNA repeat | SEQ ID NO: |
|---|---|---|
| CasY3 | CUCCGAAUUAUCGGGAGGAUAAGGC | 13 |
| CasY4 | CCCCGAAUAUAGGGGACAAAAAGGC | 14 |
| CasY5 | GUCUAGACAUACAGGUGGAAAGGUGAGAGUAAA-GAC | 15 |
| CasY6 | GUCUAGACAUACAGGUGGAAAGGUGAGAGUAAA-GAC | 15 |
| CasY18 | CUCCGUGAAUACGUGGGGUAAAGGC | 16 |
| CasY9 | AAUCGAGGGUUAGUAACCAAAAGGC | 61 |
| CasY10 | CCCCGAAGAUUAGAGGGAAAAAGGC | 62 |
| CasY11 | CGCCGAAAGUUAGGAACUAAAAGGC | 63 |
| CasY12 | UCGAAGGUUAGGAACCAAAAGGC | 64 |
| CasY14 | CCCCGAAACUACAGGGGAUAAAGGC | 65 |
| CasY15 | ACCCGUAAAGCAGAGCGAUGAAGGC | 66 |
| CasY16 | CCUCGGAUGUAACGGGGAUAAAGGC | 67 |

The repeat sequences (non-guide sequence portion of example CasY guide RNAs) depicted in Table 1 are from natural loci. In some cases, a subject CasY guide RNA comprises (e.g., in addition to a guide sequence) the crRNA sequence CTCCGAAAGTATCGGGGATAAAGGC (SEQ ID NO: 31) [RNA is CUCCGAAAGUAUCGGG-GAUAAAGGC (SEQ ID NO: 11)] (e.g., see Table 1). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGAAAGTATCGGGGATAAAGGC (SEQ ID NO: 31) [RNA is CUCCGAAAGUAUCGGG-GAUAAAGGC (SEQ ID NO: 11)]. In some cases, a subject CasY guide RNA comprises a nucleotide sequence having 90% or more identity (e.g., 93% or more, 95% or more, 97% or more, 98% or more, or 100% identity) with the crRNA sequence CTCCGAAAGTATCGGGGATAAAGGC (SEQ ID NO: 31) [RNA is CUCCGAAAGUAUCGGG-GAUAAAGGC (SEQ ID NO: 11)].

In some cases, a subject CasY guide RNA comprises (e.g., in addition to a guide sequence) the crRNA sequence CACCGAAATTTGGAGAGGATAAGGC (SEQ ID NO: 32) [RNA is CACCGAAAUUUGGAGAGGAUAAGGC (SEQ ID NO: 12)] (e.g., see Table 1). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CACCGAAATTTGGAGAGGATAAGGC (SEQ ID NO: 32) [RNA is CACCGAAAUUUGGAGAGGAUAAGGC (SEQ ID NO: 12)]. In some cases, a subject CasY guide RNA comprises a nucleotide sequence having 90% or more identity (e.g., 93% or more, 95% or more, 97% or more, 98% or more, or 100% identity) with the crRNA sequence CACCGAAATTTGGAGAGGATAAGGC (SEQ ID NO: 32) [RNA is CACCGAAAUUUGGAGAGGAUAAGGC (SEQ ID NO: 12)].

In some cases, a subject CasY guide RNA comprises (e.g., in addition to a guide sequence) the crRNA sequence CTCCGAATTATCGGGAGGATAAGGC (SEQ ID NO: 33) [RNA is CUCCGAAUUAUCGGGAGGAUAAGGC (SEQ ID NO: 13)] (e.g., see Table 1). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGAATTATCGGGAGGATAAGGC (SEQ ID NO: 33) [RNA is CUCCGAAUUAUCGGGAGGAUAAGGC (SEQ ID NO: 13)]. In some cases, a subject CasY guide RNA comprises a nucleotide sequence having 90% or more identity (e.g., 93% or more, 95% or more, 97% or more, 98% or more, or 100% identity) with the crRNA sequence CTCCGAATTATCGGGAGGATAAGGC (SEQ ID NO: 33) [RNA is CUCCGAAUUAUCGGGAGGAUAAGGC (SEQ ID NO: 13)].

In some cases, a subject CasY guide RNA comprises (e.g., in addition to a guide sequence) the crRNA sequence CCCCGAATATAGGGGACAAAAAGGC (SEQ ID NO: 34) [RNA is CCCCGAAUAUAGGGGACAAAAAGGC (SEQ ID NO: 14)] (e.g., see Table 1). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CCCCGAATATAGGGGACAAAAAGGC (SEQ ID NO: 34) [RNA is CCCCGAAUAUAGGGGACAAAAAGGC (SEQ ID NO: 14)]. In some cases, a subject CasY guide RNA comprises a nucleotide sequence having 90% or more identity (e.g., 93% or more, 95% or more, 97% or more, 98% or more, or 100% identity) with the crRNA sequence CCCCGAATATAGGGGACAAAAAGGC (SEQ ID NO: 34) [RNA is CCCCGAAUAUAGGGGACAAAAAGGC (SEQ ID NO: 14)].

In some cases, a subject CasY guide RNA comprises (e.g., in addition to a guide sequence) the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)] (e.g., see Table 1). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)]. In some cases, a subject CasY guide RNA comprises a nucleotide sequence having 90% or more identity (e.g., 93% or more, 95% or more, 97% or more, 98% or more, or 100% identity) with the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)].

In some cases, a subject CasY guide RNA comprises (e.g., in addition to a guide sequence) the crRNA sequence set forth in any one of SEQ ID NOs: 11-15. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-15. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-15.

In some cases, a subject CasY guide RNA comprises (e.g., in addition to a guide sequence) the crRNA sequence set forth in any one of SEQ ID NOs: 11-14. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-14. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-14.

The repeat sequence (non-guide sequence portion of an example CasY guide RNA) from the natural locus for CasY18 is CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises (e.g., in addition to a guide sequence) the crRNA sequence CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises a nucleotide sequence having 90% or more identity (e.g., 93% or more, 95% or more, 97% or more, 98% or more, or 100% identity) with the crRNA sequence CTCCGTGAATACGTGGGGTAAAGGC (SEQ ID NO: 36) [RNA is CUCCGUGAAUACGUGGGGUAAAGGC (SEQ ID NO: 16)].

In some cases, a subject CasY guide RNA comprises (e.g., in addition to a guide sequence) the crRNA sequence set forth in Table 1 for any one of SEQ ID NOs: 11-16. In some cases, a subject CasY guide RNA comprises (e.g., in addition to a guide sequence) a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-16. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-16.

In some cases, a subject CasY guide RNA comprises (e.g., in addition to a guide sequence) the crRNA sequence set forth in any one of SEQ ID NOs: 61-67. In some cases, a subject CasY guide RNA comprises (e.g., in addition to a guide sequence) a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 61-67. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 61-67.

In some cases, a subject CasY guide RNA comprises (e.g., in addition to a guide sequence) the crRNA sequence set forth in any one of SEQ ID NOs: 11-16 and 61-67. In some cases, a subject CasY guide RNA comprises (e.g., in addition to a guide sequence) a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-16 and 61-67. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-16 and 61-67.

CasY Transactivating Noncoding RNA (trancRNA)

Compositions and methods of the present disclosure include a CasY transactivating noncoding RNA ("trancRNA"; also referred to herein as a "CasY trancRNA"). In some cases, a trancRNA forms a complex with a CasY polypeptide of the present disclosure and a CasY guide RNA. A trancRNA can be identified as a highly transcribed RNA encoded by a nucleotide sequence present in a CasY locus. The sequence encoding a trancRNA is usually located between the cas genes and the array of the CasY locus (the repeats) (e.g., can be located adjacent to the repeat sequences). Example 4 provides an example of detection of a CasY trancRNA. In some cases, a CasY trancRNA co-immunoprecipitates (forms a complex with) with a CasY polypeptide. In some cases, the presence of a CasY trancRNA is required for function of the system. Data related to trancRNAs (e.g., their expression and their location on naturally occurring arrays) is presented in the examples section below.

In some embodiments, a CasY trancRNA has a length of from 25 nucleotides (nt) to 200 nt (e.g., 25-150, 25-100, 25-80, 25-70, 25-65, 25-60, 25-55, 35-200, 35-150, 35-100, 35-80, 35-70, 35-65, 35-60, 35-55, 40-200, 40-150, 40-100, 40-80, 40-70, 40-65, 40-60, 40-55, 45-200, 45-150, 45-100, 45-80, 45-70, 45-65, 45-60, or 45-55 nt). In some embodiments, a CasY trancRNA has a length of from 35-80 nt (e.g., 35-70, 35-65, 35-60, 35-55, 40-80, 40-70, 40-65, 40-60, 40-55, 45-80, 45-70, 45-65, 45-60, or 45-55 nt). In some embodiments, a CasY trancRNA has a length of from 40-65 nt (e.g., 40-60, 40-55, 45-65, 45-60, or 45-55 nt). In some embodiments, a CasY trancRNA has a length of about 50 nt. In some embodiments, a CasY trancRNA has a length of from 45-55 nt.

Examples of trancRNA sequences include, but are not limited to:

(SEQ ID NO: 17)
CUCCGAAAGUAUCAAAAUAAAAAGGGUUUCCAGUUUUUAACUAAACUUUA

GCCUUCCACCCUUUCCUGAUUUUGUU (e.g., CasY1);

(SEQ ID NO: 18)
ACCUGCCAAAAUUUCGUUCAACGAAACUUAAGCAGGCAAGAAAAUUAAA

AUUAAAUCCGCUGGUGGGCGGAUAAAGUC (e.g., CasY2);
and (SEQ ID NO: 19)
GGUAUUUCCGGACAGCGGCUUGACCGCAUCGUCCUCGCCUUUUCCUAAAA U (e.g., CasY4).

In some cases, a subject CasY trancRNA comprises the CasY1 trancRNA sequence above. In some cases, a subject CasY trancRNA comprises a nucleotide sequence having 70% or more identity (e.g., 75% or more, 80% or more, 85% or more, 90% or more, 93% or more, 95% or more, 97% or more, 98% or more, or 100% identity) with the CasY1 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY1 trancRNA sequence above. In some cases, a subject CasY trancRNA comprises a nucleotide sequence having 90% or more identity (e.g., 93% or more, 95% or more, 97% or more, 98% or more, or 100% identity) with the CasY1 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY1 trancRNA sequence above, and has a length of from 35-80 nt (e.g., 35-70, 35-65, 35-60, 35-55, 40-80, 40-70, 40-65, 40-60, 40-55, 45-80, 45-70, 45-65, 45-60, or 45-55 nt).

In some cases, a subject CasY trancRNA comprises the CasY2 trancRNA sequence above. In some cases, a subject CasY trancRNA comprises a nucleotide sequence having 70% or more identity (e.g., 75% or more, 80% or more, 85% or more, 90% or more, 93% or more, 95% or more, 97% or more, 98% or more, or 100% identity) with the CasY2 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY2 trancRNA sequence above. In some cases, a subject CasY trancRNA comprises a nucleotide sequence having 90% or more identity (e.g., 93% or more, 95% or more, 97% or more, 98% or more, or 100% identity) with the CasY2 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY2 trancRNA sequence above, and has a length of from 35-80 nt (e.g., 35-70, 35-65, 35-60, 35-55, 40-80, 40-70, 40-65, 40-60, 40-55, 45-80, 45-70, 45-65, 45-60, or 45-55 nt).

In some cases, a subject CasY trancRNA comprises the CasY4 trancRNA sequence above. In some cases, a subject CasY trancRNA comprises a nucleotide sequence having 70% or more identity (e.g., 75% or more, 80% or more, 85% or more, 90% or more, 93% or more, 95% or more, 97% or more, 98% or more, or 100% identity) with the CasY4 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY4 trancRNA sequence above. In some cases, a subject CasY trancRNA comprises a nucleotide sequence having 90% or more identity (e.g., 93% or more, 95% or more, 97% or more, 98% or more, or 100% identity) with the CasY4 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY4 trancRNA sequence above, and has a length of from 35-80 nt (e.g., 35-70, 35-65, 35-60, 35-55, 40-80, 40-70, 40-65, 40-60, 40-55, 45-80, 45-70, 45-65, 45-60, or 45-55 nt).

In some cases, a subject CasY trancRNA comprises the CasY1, CasY2, or CasY4 trancRNA sequence above. In some cases, a subject CasY trancRNA comprises a nucleotide sequence having 70% or more identity (e.g., 75% or more, 80% or more, 85% or more, 90% or more, 93% or more, 95% or more, 97% or more, 98% or more, or 100% identity) with the CasY1, CasY2, or CasY4 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY1, CasY2, or CasY4 trancRNA sequence above. In some cases, a subject CasY trancRNA comprises a nucleotide sequence having 90% or more identity (e.g., 93% or more, 95% or more, 97% or more, 98% or more, or 100% identity) with the CasY1, CasY2, or CasY4 trancRNA sequence above. In some cases, a subject CasY trancRNA comprises a nucleotide sequence having 80% or more identity (e.g., 85% or more, 90% or more, 93% or more, 95% or more, 97% or more, 98% or more, or 100% identity) with the CasY1, CasY2, or CasY4 trancRNA sequence above, and has a length of from 35-80 nt (e.g., 35-70, 35-65, 35-60, 35-55, 40-80, 40-70, 40-65, 40-60, 40-55, 45-80, 45-70, 45-65, 45-60, or 45-55 nt).

In some cases, a CasY trancRNA comprises a modified nucleotide (e.g., methylated). In some cases, a CasY trancRNA comprises one or more of: i) a base modification or substitution; ii) a backbone modification; iii) a modified internucleoside linkage; and iv) a modified sugar moiety. Possible nucleic acid modifications are described below.

CasY Systems

The present disclosure provides one or more nucleic acids comprising one or more of: a CasY trancRNA sequence, a nucleotide sequence encoding a CasY trancRNA, a nucleotide sequence encoding a CasY polypeptide (e.g., a wild type CasY protein, a nickase CasY protein, a dCasY protein, chimeric CasY protein/CasY fusion protein, and the like), a CasY guide RNA sequence, a nucleotide sequence encoding a CasY guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasY trancRNA, the nucleotide sequence encoding the CasY protein, and/or the nucleotide sequence encoding the CasY guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CasY polypeptide of the present disclosure is codon optimized. This type of optimization can entail a mutation of a CasY-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasY-encoding nucleotide sequence could be used. As another non-limiting example, if the intended host cell were a mouse cell, then a mouse codon-optimized CasY-encoding nucleotide sequence could be generated. As another non-limiting example, if the intended host cell were a plant cell, then a plant codon-optimized CasY-encoding nucleotide sequence could be generated. As another non-limiting example, if the intended host cell were an insect cell, then an insect codon-optimized CasY-encoding nucleotide sequence could be generated.

The present disclosure provides one or more recombinant expression vectors that include (in different recombinant expression vectors in some cases, and in the same recombinant expression vector in some cases): a CasY trancRNA sequence, a nucleotide sequence encoding a CasY trancRNA, a nucleotide sequence encoding a CasY polypeptide (e.g., a wild type CasY protein, a nickase CasY protein, a dCasY protein, chimeric CasY protein/CasY fusion protein, and the like), a CasY guide RNA sequence, a nucleotide sequence encoding a CasY guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasY trancRNA, the nucleotide sequence encoding the CasY protein, and/or the nucleotide sequence encoding the CasY guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasY guide RNA is operably linked to a control element, e.g., a transcriptional control element, such as a promoter. In some embodiments, a nucleotide sequence encoding a CasY protein or a CasY fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasY protein, thus resulting in a chimeric CasY polypeptide.

In some embodiments, a nucleotide sequence encoding a CasY guide RNA and/or a CasY fusion polypeptide is operably linked to an inducible promoter. In some embodiments, a nucleotide sequence encoding a CasY guide RNA and/or a CasY fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasY guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a CasY protein (e.g., a wild type CasY protein, a nickase CasY protein, a dCasY protein, a chimeric CasY protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasY protein and/or a CasY guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasY protein can be provided as RNA. The RNA can be provided by direct chemical synthesis or may be transcribed in vitro from a DNA (e.g., encoding the CasY protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasY guide RNA; recombinant expression vectors encoding the CasY protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasY guide RNA and/or a CasY polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasY guide RNA and/or a CasY protein to a cell may include nucleic acid sequences that encode for selectable markers in the target cells, so as to identify cells that have taken up the CasY guide RNA and/or CasY protein.

A nucleic acid comprising a nucleotide sequence encoding a CasY polypeptide, or a CasY fusion polypeptide, is in some cases an RNA. Thus, a CasY fusion protein can be introduced into cells as RNA. Methods of introducing RNA into cells are known in the art and may include, for example, direct injection, transfection, or any other method used for the introduction of DNA. A CasY protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasY polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 116). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334;

20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasY polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasY guide RNA, encoding a CasY fusion protein, etc.) and proteins (e.g., a CasY fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasY polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasY polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasY polypeptide, or a CasY fusion polypeptide, of the present disclosure is at least 80% pure, at least 85% pure, at least 90% pure, at least 95% pure, at least 98% pure, or at least 99% pure (e.g., free of contaminants, non-CasY proteins or other macromolecules, etc.).

To induce cleavage or any desired modification to a target nucleic acid (e.g., genomic DNA), or any desired modification to a polypeptide associated with target nucleic acid, the CasY guide RNA and/or the CasY polypeptide and/or the CasY trancRNA, and/or the donor template sequence, whether they be introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasY guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasY guide RNA that does not change when the guide sequence is changed to hybrized to a desired target sequence (e.g., sequences that contribute to the CasY binding aspect of the guide RNA, e.g., the sequences that contribute to the dsRNA duplex(es) of the CasY guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasY guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasY guide RNA or trancRNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasY guide RNA and/or CasY trancRNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., Chem. Commun., 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., Tetrahedron, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_n ON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278; the disclosure of which is incor-

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci.* USA, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y Acad. Sci.*, 1992, 660, 306-309; Manoharan et al., Bioorg. *Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:113); Transportan GWTLNSAGYLLGKINLKALAALAKKIL (SEQ ID NO:114); KALAWEAKLAKALAKA-LAKHLAKALAKALKCEA (SEQ ID NO:115); and RQIKIWFQNRRMKWKK (SEQ ID NO:116). Exemplary PTDs include but are not limited to, YGRKKRRQRRR (SEQ ID NO:112), RKKRRQRRR (SEQ ID NO:118); an arginine homopolymer of from 3 arginine residues to 50 arginine residues; Exemplary PTD domain amino acid sequences include, but are not limited to, any of the following: YGRKKRRQRRR (SEQ ID NO:112); RKKRRQRRR (SEQ ID NO:120); YARAAARQARA (SEQ ID NO:121); THRLPRRRRRR (SEQ ID NO:122); and GGR-RARRRRRR (SEQ ID NO: 123). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasY guide RNA (or a nucleic acid comprising a nucleotide sequence encoding same) and/or a CasY polypeptide (or a nucleic acid comprising a nucleotide sequence encoding same) and/or a CasY trancRNA (or a nucleic acid that includes a nucleotide sequence encoding same) and/or a donor polynucleotide (donor template) can be introduced into a host cell by any of a variety of well-known methods.

Any of a variety of compounds and methods can be used to deliver to a target cell a CasY system of the present disclosure. As a non-limiting example, a CasY system of the present disclosure can be combined with a lipid. As another non-limiting example, a CasY system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et. al Adv Drug Deliv Rev. 2012 Sep. 13. pii: S0169-409X(12)00283-9. doi: 10.1016/j.addr.2012.09.023), and the like.

In some cases, a CasY polypeptide of the present disclosure (e.g., wild type protein, variant protein, chimeric/fusion protein, dCasY, etc.) is provided as a nucleic acid (e.g., an mRNA, a DNA, a plasmid, an expression vector, a viral vector, etc.) that encodes the CasY polypeptide. In some cases, the CasY polypeptide of the present disclosure is provided directly as a protein (e.g., without an associated guide RNA or with an associate guide RNA, i.e., as a ribonucleoprotein complex). A CasY polypeptide of the present disclosure can be introduced into a cell (provided to the cell) by any convenient method; such methods are known to those of ordinary skill in the art. As an illustrative example, a CasY polypeptide of the present disclosure can be injected directly into a cell (e.g., with or without a CasY guide RNA or nucleic acid encoding a CasY guide RNA, and with or without a donor polynucleotide and with or without a CasY trancRNA). As another example, a preformed complex of a CasY polypeptide of the present disclosure and a CasY guide RNA (an RNP) can be introduced into a cell (e.g, eukaryotic cell) (e.g., via injection, via nucleofection; via a protein transduction domain (PTD) conjugated to one or more components, e.g., conjugated to the CasY protein, conjugated to a guide RNA, conjugated to a CasY trancRNA, conjugated to a CasY polypeptide of the present disclosure and a guide RNA; etc.).

In some cases, a nucleic acid (e.g., a CasY guide RNA and/or a nucleic acid encoding it, a nucleic acid encoding a CasY protein, a CasY trancRNA and/or a nucleic acid encoding it, and the like) and/or a polypeptide (e.g., a CasY polypeptide; a CasY fusion polypeptide) is delivered to a cell (e.g., a target host cell) in a particle, or associated with a particle. In some cases, a CasY system of the present disclosure is delivered to a cell in a particle, or associated with a particle. The terms "particle" and nanoparticle" can be used interchangeable, as appropriate. For example, a recombinant expression vector comprising a nucleotide sequence encoding a CasY polypeptide of the present disclosure and/or a CasY guide RNA, an mRNA comprising a nucleotide sequence encoding a CasY polypeptide of the present disclosure, and guide RNA may be delivered simultaneously using particles or lipid envelopes; for instance, a CasY polypeptide and/or a CasY guide RNA and/or a trancRNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasY polypepide and a CasY guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasY polypeptide of the present disclosure (or an mRNA comprising a nucleotide sequence encoding a CasY polypeptide of the present disclosure; or a recombinant expression vector comprising a nucleotide sequence encoding a CasY polypeptide of the present disclosure) and/or CasY guide RNA (or a nucleic acid such as one or more expression vectors encoding the CasY guide RNA) may be delivered simultaneously using particles or lipid envelopes. For example, a biodegradable core-shell structured nanoparticle with a poly (p1-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasY polypeptide of the present disclosure, a CasY fusion polypeptide of the present disclosure, an RNP of the present disclosure, a nucleic acid of the present disclosure, or a CasY system of the present disclosure. In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell.

In some cases, lipid nanoparticles (LNPs) are used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasY guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of from 25 nm to 200 nm. In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of 100 nm or less In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of from 35 nm to 60 nm.

Nanoparticles suitable for use in delivering a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. A prototype nanoparticle of semi-solid nature is the liposome.

In some cases, an exosome is used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. Exosomes are endogenous nano-vesicles that transport RNAs and proteins, and which can deliver RNA to the brain and other target organs.

In some cases, a liposome is used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasY system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CasY system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasY system of the present disclosure, or a component thereof, may be delivered encapsulated in PLGA microspheres such as that further described in US published applications 20130252281 and 20130245107 and 20130244279.

Supercharged proteins can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasY polypeptide of the present disclosure, a CasY fusion polypeptide of the present disclosure, an RNP of the present disclosure, a nucleic acid of the present disclosure (e.g., a CasY guide RNA and/or a CasY trancRNA) (e.g., a CasY guide RNA, a nucleic acid encoding a CasY guide RNA, a nucleic acid encoding CasY polypeptide, a donor template, and the like), or a CasY system of the present disclosure, to a target cell (e.g., a target cell in vivo, where the target cell is a target cell in circulation, a target cell in a tissue, a target cell in an organ, etc.). An implantable device suitable for use in delivering a CasY polypeptide of the present disclosure, a CasY fusion polypeptide of the present disclosure, an RNP of the present disclosure, a nucleic acid of the present disclosure (e.g., a CasY guide RNA and/or a CasY trancRNA), or a CasY system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasY polypeptide, the CasY fusion polypeptide, the RNP, or the CasY system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasY polypeptide of the present disclosure and/or a nucleic acid comprising a nucleotide sequence encoding a CasY polypeptide of the present disclosure. The present disclosure provides a modified cell comprising a CasY polypeptide of the present disclosure, where the modified cell is a cell that does not normally comprise a CasY polypeptide of the present disclosure. The present disclosure provides a modified cell (e.g., a genetically modified cell) comprising nucleic acid comprising a nucleotide sequence encoding a CasY polypeptide of the present disclosure. The present disclosure provides a genetically modified cell that is genetically modified with an mRNA comprising a nucleotide sequence encoding a CasY polypeptide of the present disclosure. The present disclosure provides a genetically modified cell that is genetically modified with a recombinant expression vector comprising a nucleotide sequence encoding a CasY polypeptide of the present disclosure. The present disclosure provides a genetically modified cell that is genetically modified with a recombinant expression vector comprising: a) a nucleotide sequence encoding a CasY polypeptide of the present disclosure; and b) a nucleotide sequence encoding a CasY guide RNA of the present disclosure. The present disclosure provides a genetically modified cell that is genetically modified with a recombinant expression vector comprising: a) a nucleotide sequence encoding a CasY polypeptide of the present disclosure; b) a nucleotide sequence encoding a CasY guide RNA of the present disclosure; and c) a nucleotide sequence encoding a donor template.

A cell that serves as a recipient for a CasY polypeptide of the present disclosure and/or a nucleic acid comprising a nucleotide sequence encoding a CasY polypeptide of the present disclosure and/or a CasY guide RNA of the present disclosure (or a nucleic acid encoding it) and/or a CasY trancRNA (or a nucleic acid encoding it), can be any of a variety of cells, including, e.g., in vitro cells; in vivo cells; ex vivo cells; primary cells; cancer cells; animal cells; plant cells; algal cells; fungal cells; etc. A cell that serves as a recipient for a CasY polypeptide of the present disclosure and/or a nucleic acid comprising a nucleotide sequence encoding a CasY polypeptide of the present disclosure and/or a CasY guide RNA of the present disclosure is referred to as a "host cell" or a "target cell." A host cell or a target cell can be a recipient of a CasY system of the present disclosure. A host cell or a target cell can be a recipient of a CasY RNP of the present disclosure. A host cell or a target cell can be a recipient of a single component of a CasY system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., a cell in culture, e.g., an established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, *Blattaria*, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasY system of the present disclosure, or a component of a CasY system of the present disclosure.

A kit of the present disclosure can comprise any combination as listed for a CasY system (e.g., see above). A kit of the present disclosure can comprise: a) a component, as described above, of a CasY system of the present disclosure, or can comprise a CasY system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasY guide RNA; vii) a CasY trancRNA; and the like. A kit of the present disclosure can comprise: a) a component, as described above, of a CasY system of the present disclosure, or can comprise a CasY system of the present disclosure; and b) a therapeutic agent.

A kit of the present disclosure can comprise a recombinant expression vector comprising: a) an insertion site for inserting a nucleic acid comprising a nucleotide sequence encoding a portion of a CasY guide RNA that hybridizes to a target nucleotide sequence in a target nucleic acid; and b) a nucleotide sequence encoding the CasY-binding portion of a CasY guide RNA. A kit of the present disclosure can comprise a recombinant expression vector comprising: a) an insertion site for inserting a nucleic acid comprising a nucleotide sequence encoding a portion of a CasY guide RNA that hybridizes to a target nucleotide sequence in a target nucleic acid; b) a nucleotide sequence encoding the CasY-binding portion of a CasY guide RNA; and c) a nucleotide sequence encoding a CasY polypeptide of the present disclosure. A kit of the present disclosure can comprise a recombinant expression vector comprising a nucleotide sequence encoding a CasY trancRNA.

Detection of ssDNA

A CasY (Cas12c) polypeptide of the present disclosure, once activated by detection of a target DNA (double or single stranded), can promiscuously cleave non-targeted single stranded DNA (ssDNA). Once a CasY (Cas12c) polypeptide is activated by a guide RNA, which occurs when the guide RNA hybridizes to a target sequence of a target DNA (i.e., the sample includes the target DNA, e.g., target ssDNA), the protein becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA). In some cases, a CasY polypeptide requires, in addition to a CasY guide RNA, a tranc RNA for activation.

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a CasY polypeptide; (ii) a guide RNA comprising: a region that binds to the CasY polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the CasY polypeptide, thereby detecting the target DNA. In some cases, the methods include can include (a) contacting the sample with: (i) a CasY polypeptide; (ii) a guide RNA comprising: a region that binds to the CasY polypeptide, and a guide sequence that hybridizes with the target DNA; (iii) a CasY tranc RNA; and (iv) a detector DNA that is single stranded and does not hybridize with the guide sequence of the guide RNA; and (b) measuring a detectable signal produced by cleavage of the single stranded detector DNA by the CasY polypeptide, thereby detecting the target DNA. As noted above, once a subject CasY polypeptide protein is activated by a guide RNA, which occurs when the sample includes a target DNA to which the guide RNA hybridizes (i.e., the sample includes the targeted target DNA), the CasY polypeptide is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a CasY polypeptide; and (ii) a guide RNA comprising: a region that binds to the CasY polypeptide, and a guide sequence that hybridizes with the target DNA, wherein the CasY polypeptide cleaves non-target ssDNAs of said plurality. Such methods can include contacting a population of nucleic acids, wherein said population comprises a target DNA and a plurality of non-target ssDNAs, with: (i) a CasY polypeptide; (ii) a guide RNA comprising: a region that binds to the CasY polypeptide, and a guide sequence that hybridizes with the target DNA, and (iii) a CasY tranc RNA, wherein the CasY polypeptide cleaves non-target ssDNAs of said plurality. Such methods can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The tranc RNA can be provided as RNA or as a nucleic acid encoding the guide RNA (e.g., a DNA such as a recombinant expression vector). The CasY polypeptide can be provided as a protein per se or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided. In some cases, a single-molecule RNA comprising: i) a CasY guide RNA; and ii) a tranc RNA (or a nucleic acid comprising a nucleotide sequence encoding the single-molecule RNA) is used.

In some cases (e.g., when contacting a sample with a guide RNA and a CasY polypeptide; or when contacting a sample with a guide RNA, a CasY polypeptide, and a tranc RNA), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

In some cases, a method of the present disclosure for detecting a target DNA comprises: a) contacting a sample with a guide RNA, a CasY polypeptide, and a detector DNA, where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasY polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a method of the present disclosure for detecting a target DNA comprises: a) contacting a sample with a guide RNA, a tranc RNA, a CasY polypeptide, and a detector DNA (or contacting a sample with: i) a single-molecule RNA comprising a guide RNA and a tranc RNA; i) a CasY polypeptide; and iii) a detector DNA), where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasY polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a detectable signal produced by cleavage of a single-stranded detector DNA is produced for no more than 60 minutes. For example, in some cases, a detectable signal produced by cleavage of a single-stranded detector DNA is produced for no more than 60 minutes, no more than 45 minutes, no more than 30 minutes, no more than 15 minutes, no more than 10 minutes, or no more than 5 minutes. For example, in some cases, a detectable signal produced by cleavage of a single-stranded detector DNA is produced for a period of time of from 1 minute to 60 minutes, e.g., from 1 minute to 5 minutes, from 5 minutes to 10 minutes, from 10 minutes to 15 minutes, from 15 minutes to 30 minutes, from 30 minutes to 45 minutes, or from 45 minutes to 60 minutes. In some cases, after the detectable signal is produced (e.g., produced for no more than 60 minutes), production of the detectable signal can be stopped, e.g., by lowering the temperature of the sample (e.g., lowering the temperature to 10° C. or less, 5° C. or less, 4° C. or less, or 0° C.), by adding an inhibitor to the sample, by lyophilizing the sample, by heating the sample to over 40° C., and the like. The measuring step can occur at any time after production of the detectable signal has been stopped. For example, the measuring step can occur from 5 minutes to 48 hours after production of the detectable signal has been stopped. For example, the measuring step can occur from 5 minutes to 15 minutes, from 15 minutes to 30 minutes, from 30 minutes to 60 minutes, from 1 hour to 4 hours, from 4 hours to 8 hours, from 8 hours to 12 hours, from 12 hours to 24 hours, from 24 hours to 36 hours, or from 36 hours to 48 hours, after production of the detectable signal has been stopped. The measuring step can occur more than 48 hours after production of the detectable signal has been stopped.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. Thus, e.g., the target DNA can be present in the sample in a concentration of 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, a target DNA is present in a sample in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 800 aM. In some cases, a target DNA is present in a sample in a range of from 50 aM to 1 pM. In some cases, a target DNA is present in a sample in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 500 pM. In some cases, a target DNA is present in a sample in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases, the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5\times10^3$ or more, $10^4$ or more, $5\times10^4$ or more, $10^5$ or more, $5\times10^5$ or more, $10^6$ or more $5\times10^6$ or more, or $10^7$ or more, DNAs. In some cases, the sample comprises from 10 to 20, from 20 to 50, from 50 to 100, from 100 to 500, from 500 to $10^3$, from $10^3$ to $5\times10^3$, from $5\times10^3$ to $10^4$, from $10^4$ to $5\times10^4$, from $5\times10^4$ to $10^5$, from $10^5$ to $5\times10^5$, from $5\times10^5$ to $10^6$, from $10^6$ to $5\times10^6$, or from $5\times10^6$ to $10^7$, or more than $10^7$, DNAs. In some cases, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5\times10^3$ non-target DNAs, one copy per $10^4$ non-target DNAs, one copy per $5\times10^4$ non-target DNAs, one copy per $10^5$ non-target DNAs, one copy per $5\times10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5\times10^3$ non-target DNAs, from 1 copy per $5\times10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples.

Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., *Euglena*), amoeboids (e.g., amoeba), sporozoans (e.g., Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum: Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis,* and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNAviruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae,* methicillin-resistant *Staphylococcus aureus, Legionella pneumophila, Streptococcus pyogenes, Escherichia coli, Neisseria gonorrhoeae, Neisseria meningitidis,* Pneumococcus, *Cryptococcus neoformans, Histoplasma capsulatum, Hemophilus influenzae* B, *Treponema pallidum,* Lyme disease spirochetes, *Pseudomonas aeruginosa, Mycobacterium leprae, Brucella abortus,* rabies virus, influenza virus, cytomegalovirus, herpes simplex virus I, herpes simplex virus II, human serum parvolike virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum: Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae.*

Measuring a Detectable Signal

In some cases, a subject method includes a step of measuring (e.g., measuring a detectable signal produced by CasY-mediated ssDNA cleavage). Because a CasY polypeptide cleaves non-targeted ssDNA once activated, which occurs when a guide RNA hybridizes with a target DNA in the presence of a CasY polypeptide (and, in some cases, also including a tranc RNA), a detectable signal can be any signal that is produced when ssDNA is cleaved. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; $10^7(24)$: 10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of CasY polypeptide, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X'). Non-limiting examples of applications of/uses for the compositions and methods of the disclosure include single-nucleotide polymorphism (SNP) detection, cancer screening, detection of bacterial infection, detection of antibiotic resistance, detection of viral infection, and the like. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence. A method of the present disclosure in some cases does not include an amplification step. A method of the present disclosure in some cases includes an amplification step.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasY polypeptide that cleaves DNAs present in the sample, and (iii) a detector ssDNA; b) measuring a detectable signal produced by CasY polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasY polypeptide that cleaves DNAs present in the sample, (iii) a tranc RNA; (iv) a detector ssDNA; b) measuring a detectable signal produced by CasY polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a CasY polypeptide that cleaves ssDNA (e.g., amplification of nucleic acids in the sample can begin prior to contact with a CasY polypeptide). In some cases, the nucleic acids in a sample are amplified simultaneous with contact with a CasY polypeptide. For example, in some cases a subject method includes amplifying nucleic acids of a sample (e.g., by contacting the sample with amplification components) prior to contacting the amplified sample with a CasY polypeptide. In some cases, a subject method includes contacting a sample with amplification components at the same time (simultaneous with) that the sample is contacted with a CasY polypeptide. If all components are added simultaneously (amplification components and detection components such as a CasY polypeptide, a guide RNA, and a detector DNA), it is possible that the trans-cleavage activity of the CasY polypeptide, will begin to degrade the nucleic acids of the sample at the same time the nucleic acids are undergoing amplification. However, even if this is the case, amplifying and detecting simultaneously can still increase sensitivity compared to performing the method without amplification.

In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted, in some cases the nucleic acids are amplified (e.g., by contact with amplification components) prior to contacting the amplified nucleic acids with a CasY polypeptide. In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with an enzymatically active CasY polypeptide. In some cases, amplification occurs for 2 minutes or more (e.g., 3 minutes or more, 4 minutes or more, 5 minutes or more, 7.5 minutes or more, 10 minutes or more, etc.) prior to contact with an active CasY polypeptide. In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a CasY polypeptide. In some such cases, the CasY polypeptide is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium actetate, 10 mM Magnesium acetate, 2 mM DTT, 5% PEG compound (Carbowax-20M), 3 mM ATP, 30 mM Phosphocreatine, 100 ng/µl creatine kinase, 420 ng/µl gp32, 140 ng/µl UvsX, 35 ng/µl UvsY, 2000M dNTPs, 300 nM each oligonucleotide, 35 ng/µl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a CasY polypeptide; ii) a guide RNA; and iii) a detector DNA that is single stranded and does not hybridize with the guide sequence of the guide RNA.

A suitable single-stranded detector DNA has a length of from 7 nucleotides to 25 nucleotides. For example, a suitable single-stranded detector DNA has a length of from 7 nucleotides to 10 nucleotides, from 11 nucleotides to 15 nucleotides, from 15 nucleotides to 20 nucleotides, or from 20 nucleotides to 25 nucleotides. In some cases, a suitable single-stranded detector DNA has a length of from 10 nucleotides to 15 nucleotides. In some cases, a suitable single-stranded detector DNA has a length of 10 nucleotides. In some cases, a suitable single-stranded detector DNA has a length of 11 nucleotides. In some cases, a suitable single-stranded detector DNA has a length of 12 nucleotides. In some cases, a suitable single-stranded detector DNA has a length of 13 nucleotides. In some cases, a suitable single-stranded detector DNA has a length of 14 nucleotides. In some cases, a suitable single-stranded detector DNA has a length of 15 nucleotides.

In some cases, a subject method includes: a) contacting a sample with a labeled single stranded detector DNA (detector ssDNA) that includes a fluorescence-emitting dye pair; a CasY polypeptide that cleaves the labeled detector ssDNA after it is activated (by binding to the guide RNA in the context of the guide RNA hybridizing to a target DNA); and b) measuring the detectable signal that is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Firster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a CasY polypeptide).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. PLoS One. 2015 Aug. 3; 10(8):e0134436.

TABLE 6

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |

TABLE 6-continued

Examples of FRET pairs (donor and acceptor FRET moieties)

| Donor | Acceptor |
|---|---|
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a CasY polypeptide. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a CasY polypeptide), but the signal will be quenched when the partners are in close proximity (e.g., prior to cleavage of the detector ssDNA by a CasY polypeptide).

A quencher moiety can quench a signal from the signal moiety (e.g., prior to cleavage of the detector ssDNA by a CasY polypeptide) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

Kits for Detecting Target DNA

The present disclosure provides a kit for detecting a target DNA, e.g., in a sample comprising a plurality of DNAs. In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; and ii) a CasY polypeptide, and/or a nucleic acid encoding said CasY polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; ii) a tranc RNA and/or a nucleic acid encoding said guide RNA; and iii) a CasY polypeptide, and/or a nucleic acid encoding said CasY polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a single-molecule RNA comprising a guide RNA and a tranc RNA, and/or a nucleic acid encoding single-molecule RNA; and iii) a CasY polypeptide, and/or a nucleic acid encoding said CasY polypeptide. In some cases, a nucleic acid encoding a single-molecule RNA includes sequence insertion sites for the insertion of guide sequences by a user.

In some cases, a subject kit comprises: (a) a labeled detector ssDNA comprising a fluorescence-emitting dye pair, e.g., a FRET pair or a quencher/fluor pair; and (b) one or more of: (i) a guide RNA, and/or a nucleic acid encoding said guide RNA; and/or i) a CasY polypeptide.

Positive Controls

A kit of the present disclosure (e.g., one that comprises a labeled detector ssDNA and a CasY polypeptide) can also include a positive control target DNA. In some cases, the kit also includes a positive control guide RNA that comprises a nucleotide sequence that hybridizes to the control target DNA. In some cases, the positive control target DNA is provided in various amounts, in separate containers. In some cases, the positive control target DNA is provided in various known concentrations, in separate containers, along with control non-target DNAs.

Nucleic Acids

While the RNAs of the disclosure (e.g., guide RNAs, tranc RNAs, single-molecule RNAs comprising a guide RNA and a tranc RNA) can be synthesized using any convenient method (e.g., chemical synthesis, in vitro using an RNA polymerase enzyme, e.g., T7 polymerase, T3 polymerase, SP6 polymerase, etc.), nucleic acids encoding such RNAs are also envisioned. Additionally, while a CasY polypeptide of the disclosure can be provided (e.g., as part of a kit) in protein form, nucleic acids (such as mRNA and/or DNA) encoding the CasY polypeptide can also be provided.

For example, in some cases, a kit of the present disclosure comprises a nucleic acid (e.g., a DNA, e.g., a recombinant expression vector) that comprises a nucleotide sequence encoding a guide RNA. In some cases, the nucleotide sequence encodes a guide RNA without a guide sequence. For example, in some cases, the nucleic acid comprises a nucleotide sequence encoding a constant region of a guide RNA (a guide RNA without a guide sequence), and comprises an insertion site for a nucleic acid encoding a guide sequence. In some cases, a kit of the present disclosure comprises a nucleic acid (e.g., an mRNA, a DNA, e.g., a recombinant expression vector) that comprises a nucleotide sequence encoding a CasY polypeptide.

In some cases, a kit of the present disclosure comprises a nucleic acid (e.g., a DNA, e.g., a recombinant expression vector) that comprises a nucleotide sequence encoding a single-molecule RNA comprising: i) a guide RNA; and ii) a tranc RNA. In some cases, the nucleotide sequence encodes the guide RNA portion of the single-molecule RNA without a guide sequence. For example, in some cases, the nucleic acid comprises a nucleotide sequence encoding: i) a constant region of a guide RNA (a guide RNA without a guide sequence), and comprises an insertion site for a nucleic acid encoding a guide sequence; and ii) a tranc RNA.

In some cases, the guide RNA-encoding nucleotide sequence is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a CasY polypeptide is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like.

Utility

CasY compositions (e.g., expression vectors, kits, compositions, nucleic acids, and the like) find use in a variety of methods. For example, a CasY compositions of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasY polypeptide of the present disclosure; and b) one or more (e.g., two) CasY guide RNAs. In some cases, a method of the present disclosure for modifying a target nucleic acid comprises contacting the target nucleic acid with: a) a CasY polypeptide, and b) one or more (e.g., two) CasY guide RNAs, and c) a CasY trancRNA. In some cases, a method of the present disclosure for modifying a target nucleic acid comprises contacting the target nucleic acid with: a) a CasY polypeptide of the present disclosure; b) a CasY guide RNA; and c) a donor nucleic acid (e.g, a donor template). In some cases, a method of the present disclosure for modifying a target nucleic acid comprises contacting the target nucleic acid with: a) a CasY polypeptide; b) a CasY guide RNA; c) a CasY trancRNA, and d) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasY polypeptide includes binding of the CasY polypeptide to a particular region in a target nucleic acid (by virtue of being targeted there by an associated CasY guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods (e.g., that are used with CRISPR/Cas9 systems), see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et. al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasY polypeptide or with a CasY fusion polypeptide, etc., encompass all methods for contacting the target nucleic acid. For example, a CasY polypeptide can be provided to a cell as protein, RNA (encoding the CasY polypeptide), or DNA (encoding the CasY polypeptide); while a CasY guide RNA can be provided as a guide RNA or as a nucleic acid encoding the guide RNA and a CasY trancRNA can be provided as a trancRNA or as a nucleic acid encoding the trancRNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasY polypeptide; in the form of a protein for a CasY fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasY polypeptide or a CasY fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a CasY locus, e.g., a nucleic acid comprising a nucleotide sequence encoding a CasY polypeptide as well as nucleotide sequences of about 1 kilobase (kb) to 5 kb in length surrounding the CasY-encoding nucleotide sequence from a cell (e.g., in some cases a cell that in its natural state (the state in which it occurs in nature) comprises a CasY locus) comprising a CasY locus, where the target cell does not normally (in its natural state) comprise a CasY locus (e.g., in some cases the locus includes a CasY trancRNA. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a CasY locus, e.g., a nucleic acid obtained from a source cell (e.g., in some cases a cell that in its natural state (the state in which it occurs in nature) comprises a CasY locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a CasY polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a CasY locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a CasY polypeptide of the present disclosure, or with a CasY fusion polypeptide of the present disclosure. In some cases, abmethod of the present disclosure for modifying a target nucleic acid comprises contacting a target nucleic acid with a CasY polypeptide and a CasY guide RNA. In some cases, abmethod of the present disclosure for modifying a target nucleic acid comprises contacting a target nucleic acid with a CasY polypeptide, a CasY guide RNA, and a CasY trancRNA. In some cases, abmethod of the present disclosure for modifying a target nucleic acid comprises contacting a target nucleic acid with a CasY polypeptide, a first CasY guide RNA, and a second CasY guide RNA (and in some cases a CasY trancRNA). In some cases, a method of the present disclosure for modifying a target nucleic acid comprises contacting a target nucleic acid with a CasY polypeptide of the present disclosure and a CasY guide RNA and a donor DNA template. In some cases, a method of the present disclosure for modifying a target nucleic acid comprises contacting a target nucleic acid with a CasY polypeptide of the present disclosure and a CasY guide RNA and a CasY trancRNA and a donor DNA template.

In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

Target Nucleic Acids and Target Cells of Interest

A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasY guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicufia, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasY protein (and/or nucleic acid encoding the protein such as DNA and/or RNA), and/or CasY guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, *Blattaria*, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Donor Polynucleotide (Donor Template)

Guided by a CasY guide RNA, a CasY protein in some cases generates site-specific double strand breaks (DSBs) or single strand breaks (SSBs) (e.g., when the CasY protein is a nickase variant) within double-stranded DNA (dsDNA) target nucleic acids, which are repaired either by nonhomologous end joining (NHEJ) or homology-directed recombination (HDR).

In some cases, contacting a target DNA (with a CasY protein and a CasY guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, a CasY trancRNA (or nucleic acid encoding same), a CasY guide RNA (or nucleic acid encoding same), and/or a CasY protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasY guide RNA and CasY protein (or CasY guide RNA and CasY trancRNA and CasY protein) is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into the genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasY protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non disease-causing base pair). In some embodiments, the donor sequence comprises a nonhomologous sequence flanked by two regions of homology, such that homology-directed repair between the target DNA region and the two flanking sequences results in insertion of the nonhomologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasY guide RNA and/or a CasY fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasY polypeptide; a nucleic acid comprising a nucleotide sequence encoding a CasY fusion polypeptide; etc.), is used as a transgene to generate a transgenic non-human organism that produces a CasY polypeptide, or a CasY fusion polypeptide, of the present disclosure. The present disclosure provides a transgenic-non-human organism comprising a nucleotide sequence encoding a CasY polypeptide, or a CasY fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasY polypeptide or a CasY fusion polypeptide. In some embodiments, the genome of the transgenic non-human animal comprises a nucleotide sequence encoding a CasY polypeptide,e or a CasY fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasY polypeptide,e or a CasY fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasY polypeptide of the present disclosure; a nucleic acid comprising a nucleotide sequence encoding a CasY fusion polypeptide of the present disclosure; etc.), is used as a transgene to generate a transgenic plant that produces a CasY polypeptide, or a CasY fusion polypeptide, of the present disclosure. The present disclosure provides a transgenic plant comprising a nucleotide sequence encoding a CasY polypeptide, or a CasY fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasY polypeptide, or a CasY fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasY polypeptide, or a CasY fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasY polypeptide, or a CasY fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure, numbered 1-32 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspects

Aspect 1. A method of guiding a CasY polypeptide to a target sequence of a target nucleic acid, the method comprising contacting the target nucleic acid with an engineered and/or non-naturally occurring complex comprising: (a) a CasY polypeptide; (b) a CasY guide RNA that comprises a guide sequence that hybridizes to a target sequence of the target nucleic acid, and comprises a region that binds to the CasY polypeptide; and (c) a CasY transactivating noncoding RNA (trancRNA).

Aspect 2. The method of aspect 1, wherein the method results in modification of the target nucleic acid, modulation of transcription from the target nucleic acid, or modification of a polypeptide associated with a target nucleic acid.

Aspect 3. The method of aspect 2, wherein the target nucleic acid is modified by being cleaved.

Aspect 4. The method of any one of aspects 1-3, wherein the target nucleic acid is selected from: double stranded DNA, single stranded DNA, RNA, genomic DNA, and extrachromosomal DNA.

Aspect 5. The method of any one of aspects 1-4, wherein the guide sequence and the region that binds to the CasY polypeptide are heterologous to one another.

Aspect 6. The method of any one of aspects 1-5, wherein said contacting results in genome editing.

Aspect 7. The method of any one of aspects 1-5, wherein said contacting takes place outside of a bacterial cell and outside of an archaeal cell.

Aspect 8. The method of any one of aspects 1-5, wherein said contacting takes place in vitro outside of a cell.

Aspect 9. The method of any one of aspects 1-7, wherein said contacting takes place inside of a target cell.

Aspect 10. The method of aspect 9, wherein said contacting comprises: introducing into the target cell at least one of: (a) the CasY polypeptide, or a nucleic acid encoding the CasY polypeptide; (b) the CasY guide RNA, or a nucleic acid encoding the CasY guide RNA; and (c) the CasY trancRNA, or a nucleic acid encoding the CasY trancRNA.

Aspect 11. The method of aspect 10, wherein the nucleic acid encoding the CasY polypeptide is a non-naturally sequence that is codon optimized for expression in the target cell.

Aspect 12. The method of any one of aspects 9-11, wherein the target cell is a eukaryotic cell.

Aspect 13. The method of any one of aspects 9-12, wherein the target cell is in culture in vitro.

Aspect 14. The method of any one of aspects 9-12, wherein the target cell is in vivo.

Aspect 15. The method of any one of aspects 9-12, wherein the target cell is ex vivo.

Aspect 16. The method of aspect 12, wherein the eukaryotic cell is selected from the group consisting of: a plant cell, a fungal cell, a single cell eukaryotic organism, a mammalian cell, a reptile cell, an insect cell, an avian cell, a fish cell, a parasite cell, an arthropod cell, an arachnid cell, a cell of an invertebrate, a cell of a vertebrate, a rodent cell, a mouse cell, a rat cell, a primate cell, a non-human primate cell, and a human cell.

Aspect 17. The method of any one of aspects 9-16, wherein said contacting further comprises: introducing a DNA donor template into the target cell.

Aspect 18. The method of any one of aspects 1-17, wherein the trancRNA comprises a nucleotide sequence having 70% or more (at least 70%, at least 75%, at least 80%, at least 85%, at least 90%, at least 95%, at least 98%, at least 99%, or 100) nucleotide sequence identity with:

(i)
(SEQ ID NO: 17)
CUCCGAAAGUAUCAAAAUAAAAAGGGUUUCCAGUUUUUAACUAAACUUUA

GCCUUCCACCCUUUCCUGAUUUUGUU;

(ii)
(SEQ ID NO: 18)
ACCUGCCAAAAUUUCGUUCAACGAAACUUAAGCAGGCAAGAAAAUUUAA

AAUUAAAUCCGCUGGUGGGCGGAUAAAGUC;
or (iii)
(SEQ ID NO: 19)
GGUAUUUCCGGACAGCGGCUUGACCGCAUCGUCCUCGCCUUUUCCUAAAA

U.

Aspect 19. A composition comprising an engineered and/or non-naturally occurring complex comprising: (a) a CasY polypeptide, or a nucleic acid encoding said CasY polypeptide; (b) a CasY guide RNA, or a nucleic acid encoding said CasY guide RNA, wherein said CasY guide RNA comprises a guide sequence that is complementary to a target sequence of a target nucleic acid, and comprises a region that can bind to the CasY polypeptide; and (c) a CasY transactivating noncoding RNA (trancRNA), or a nucleic acid encoding said CasY trancRNA.

Aspect 20. A kit comprising an engineered and/or non-naturally occurring complex comprising: (a) a CasY polypeptide, or a nucleic acid encoding said CasY polypeptide; (b) a CasY guide RNA, or a nucleic acid encoding said CasY guide RNA, wherein said CasY guide RNA comprises a guide sequence that is complementary to a target sequence of a target nucleic acid, and comprises a region that can bind to the CasY polypeptide; and (c) a CasY transactivating noncoding RNA (trancRNA), or a nucleic acid encoding said CasY trancRNA.

Aspect 21. A genetically modified eukaryotic cell, comprising at least one of: (a) a CasY polypeptide, or a nucleic acid encoding said CasY polypeptide; (b) a CasY guide RNA, or a nucleic acid encoding said CasY guide RNA, wherein said CasY guide RNA comprises a guide sequence that is complementary to a target sequence of a target nucleic acid, and comprises a region that can bind to the CasY polypeptide; and (c) a CasY transactivating noncoding RNA (trancRNA), or a nucleic acid encoding said CasY trancRNA.

Aspect 22. The composition, kit, or eukaryotic cell of any one of the preceding aspects, characterized by at least one of: (a) the nucleic acid encoding said CasY polypeptide comprises a nucleotide sequence that: (i) encodes the CasY polypeptide and, (ii) is operably linked to a heterologous promoter; (b) the nucleic acid encoding said CasY guide RNA comprises a nucleotide sequence that: (i) encodes the CasY guide RNA and, (ii) is operably linked to a heterologous promoter; and (c) the nucleic acid encoding said CasY trancRNA comprises a nucleotide sequence that: (i) encodes the CasY trancRNA and, (ii) is operably linked to a heterologous promoter.

Aspect 23. The composition, kit, or eukaryotic cell of any one of the preceding aspects, for use in a method of therapeutic treatment of a patient.

Aspect 24. The method, composition, kit, or eukaryotic cell of any one of the preceding aspects, wherein at least one of: the nucleic acid encoding said CasY polypeptide, the nucleic acid encoding said CasY guide RNA, and the nucleic acid encoding said CasY trancRNA, is a recombinant expression vector.

Aspect 25. The method, composition, kit, or eukaryotic cell of any one of the preceding aspects, wherein the CasY guide RNA and/or the CasY trancRNA comprises one or more of: a modified nucleobase, a modified backbone or non-natural internucleoside linkage, a modified sugar moiety, a Locked Nucleic Acid, a Peptide Nucleic Acid, and a deoxyribonucleotide.

Aspect 26. The method, composition, kit, or eukaryotic cell of any one of the preceding aspects, wherein the CasY polypeptide is a variant CasY polypeptide with reduced nuclease activity compared to a corresponding wild type CasY protein.

Aspect 27. The method, composition, kit, or eukaryotic cell of any one of the preceding aspects, wherein at least one of: the CasY polypeptide, the nucleic acid encoding the CasY polypeptide, the CasY guide RNA, the nucleic acid encoding the CasY guide RNA, the CasY trancRNA, and the nucleic acid encoding the CasY trancRNA; is conjugated to a heterologous moiety.

Aspect 28. The method, composition, kit, or eukaryotic cell of aspect 27, wherein the heterologous moiety is a heterologous polypeptide.

Aspect 29. The method, composition, kit, or eukaryotic cell of any one of the preceding aspects, wherein the CasY polypeptide has reduced nuclease activity compared to a corresponding wild type CasY protein, and is fused to a heterologous polypeptide.

Aspect 30. The method, composition, kit, or eukaryotic cell of aspect 29, wherein the heterologous polypeptide: (i) has DNA modifying activity, (ii) exhibits the ability to increase or decrease transcription, and/or (iii) has enzymatic activity that modifies a polypeptide associated with DNA.

Aspect 31. The method, composition, kit, or eukaryotic cell of any one of the preceding aspects, wherein the CasY polypeptide comprises an amino acid sequence having 70% or more (at least 70%, at least 75%, at least 80%, at least 85%, at least 90%, at least 95%, at least 98%, at least 99%, or 100) amino acid sequence identity with a CasY protein of FIG. 1.

Aspect 32. The method, composition, kit, or eukaryotic cell of any one of the preceding aspects, wherein the guide sequence and the region that binds to the CasY polypeptide are heterologous to one another.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

The work described herein includes an analysis of metagenomic samples of microbial communities from groundwater, sediments, and acid mine drainage.

FIG. 3. CasY domains and similarity searches. (panel a) Schematic domain representation for CasY inferred from distant homolog alignments with AcCpf1, using HHpred. Conserved catalytic residues are marked by red bars above the proteins. CasY contains a RuvC split domain in the C-terminal region (RuvC-I, RuvC-II, and RuvC-III), and a large novel N-terminal domain. Below the schematic are displayed top hits based on the following searches: (1) BLAST search against all the proteins in NCBI (NR database, including model and environmental proteins). (2) Profile hidden markov model (HMM) search based on models built using all the Cas proteins described in Makarova et al. Nat Rev Microbiol. 2015 November; 13(11):722-36, and Shmakov et al. Mol Cell. 2015 Nov. 5; 60(3):385-97). (3) Distant homolog search based on HHpred. Hits are color-coded based on their significance, and the hit range and E-value is provided. Notably, CasY had only local hits. The 812 N-terminal amino acid of CasY had only one very minor partial hit. Combined, these finding indicate CasY is a new Cas protein. (panel b) Different CasY-contaning CRISPR loci scaffolds were constructed from sequence data.

Example 2

Figure 4:
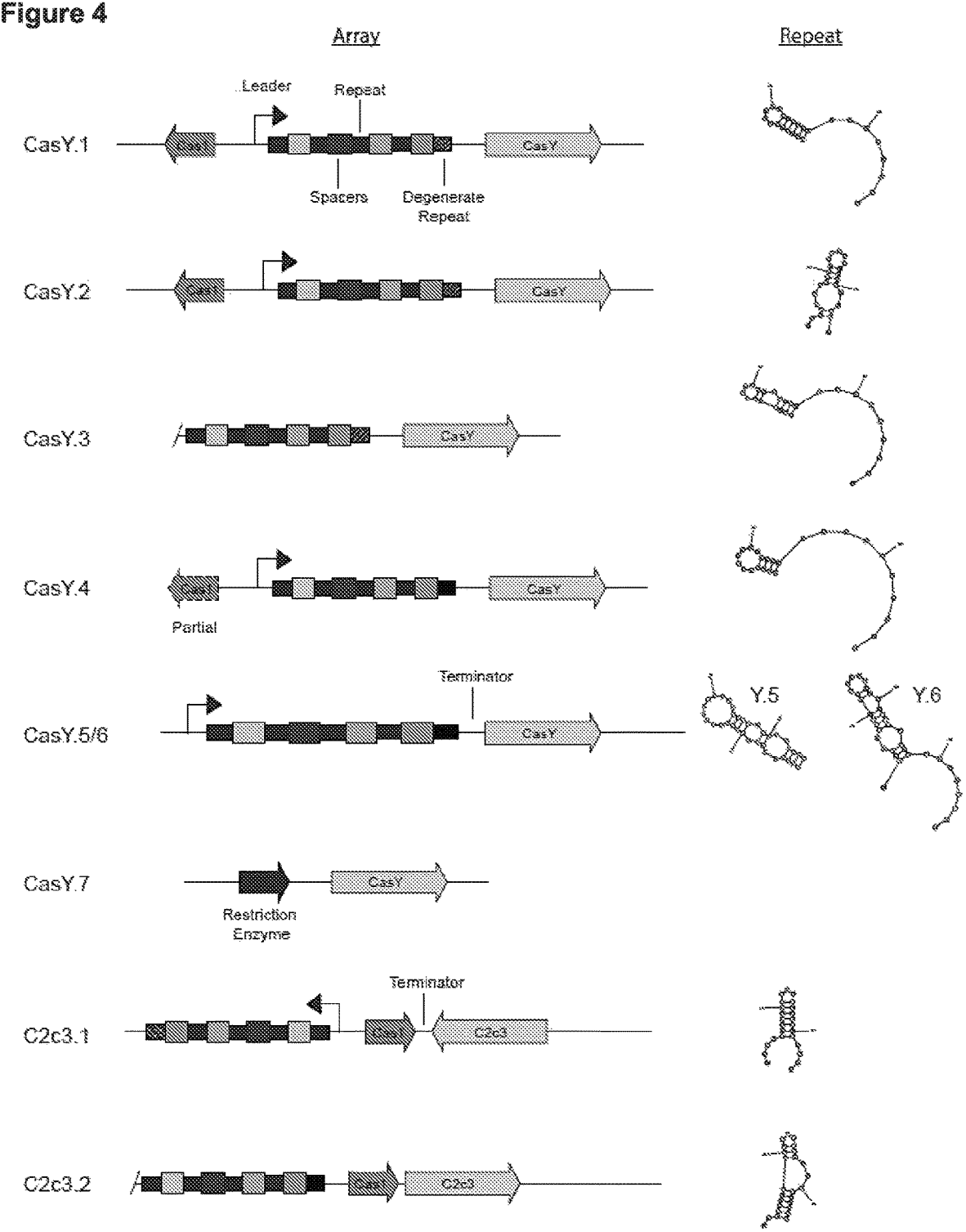
FIG. 4 depicts a schematic diagram of CasY and C2c3 loci. Interference proteins are shown in green, acquisition proteins in red. Repeats folded using RNA structure are shown to the right revealing a strong hairpin at the 5' end, suggesting self processing of the CRISPR array by CasY.

FIG. 4. Schematic diagram of Diagram of CasY and C2c3 loci. Interference proteins are shown in green, acquisition proteins in red. Repeats folded using RNA structure are shown to the right revealing a strong hairpin at the 5' end, suggesting self processing of the CRISPR array by CasY.

FIG. 5 (panels a-d) PAM dependent plasmid interference by CasY. (panel a) PAM depletion assays were conducted with CasY. E. coli containing the CasY CRISPR locus were transformed with a plasmid library with 7 nucleotides randomized 5' or 3' of the target sequence. The target plasmid was selected for and transformants were pooled. The randomized region was amplified and prepared for deep sequencing. Depleted sequences were identified and used to generate a PAM logo. (panel b) the generated PAM logo for CasY.1 showed a strong preference for sequences containing a 5'-TA-3' flanking sequence 5' of the target. A 3' PAM was not detected. (panel c) Four different PAMs were assayed directly to verify the PAM determined from the PAM depletion assay. (panel d) the generated PAM logos for CasY.2 showed a preference for sequences containing 5'-TA-3', 5'-YR-3' and/or 5'-TR-3' (e.g., 5'-DTR-3') (lower threshold and higher threshold, respectively) flanking sequence 5' of the target (where Y is a T or C; R is an A or G; and D is an A, G, or T). A 3' PAM was not detected.

FIG. 6. (panel a) 'repeat' sequences from naturally occurring CasY guide RNAs (For CasY loci Y1-Y6). (panel b) Diagram of CasY RNA guided DNA cleavage. CasY protein binds to a crRNA (the CasY guide RNA) in the repeat region (black, repeat; red, spacer). Base pairing of the guide sequence of the guide RNA to the target sequence (blue) containing the correct protospacer adjacent motif (PAM) results in double stranded cleavage of the target DNA. (panel c) examples of CasY trancRNAs.

Figure 12:
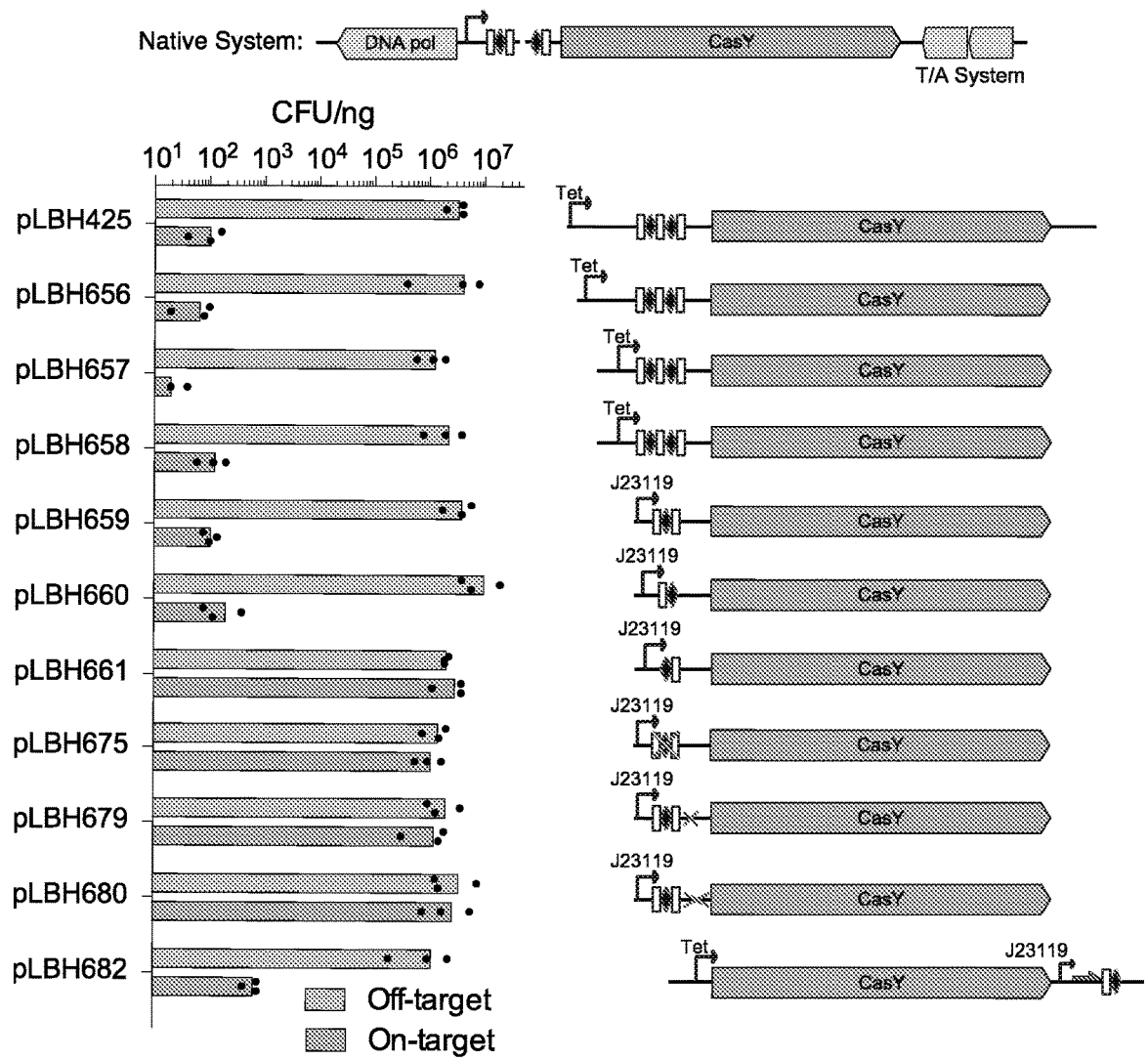
FIG. 12 depicts a plasmid interference assay containing a CRISPR loci plasmid of the present invention. 10 ng of target plasmid was transformed into electrocompetent E. coli (NEB Stable) containing the CRISPR loci plasmid. CasY15 was used for the plasmid interference assays under control of Tetracycline inducible promoter (Tet) or using a strong heterologous promoter (J23119) for sgRNA and crRNA expression. Cells were recovered for 2 h at 25° C. in super optimal broth and an appropriate dilution was plated on selective media. Plates were incubated at 25° C. and colony forming units were counted. All plasmid interference experiments were performed in triplicate and electrocompetent cells were prepared independently for each replicate. Plasmid pLBH682 included a single guide RNA and tran-cRNA was included in front of CasY15.

FIG. 12 depicts a plasmid interference assay containing a CRISPR loci plasmid of the present invention.

Figure 13:
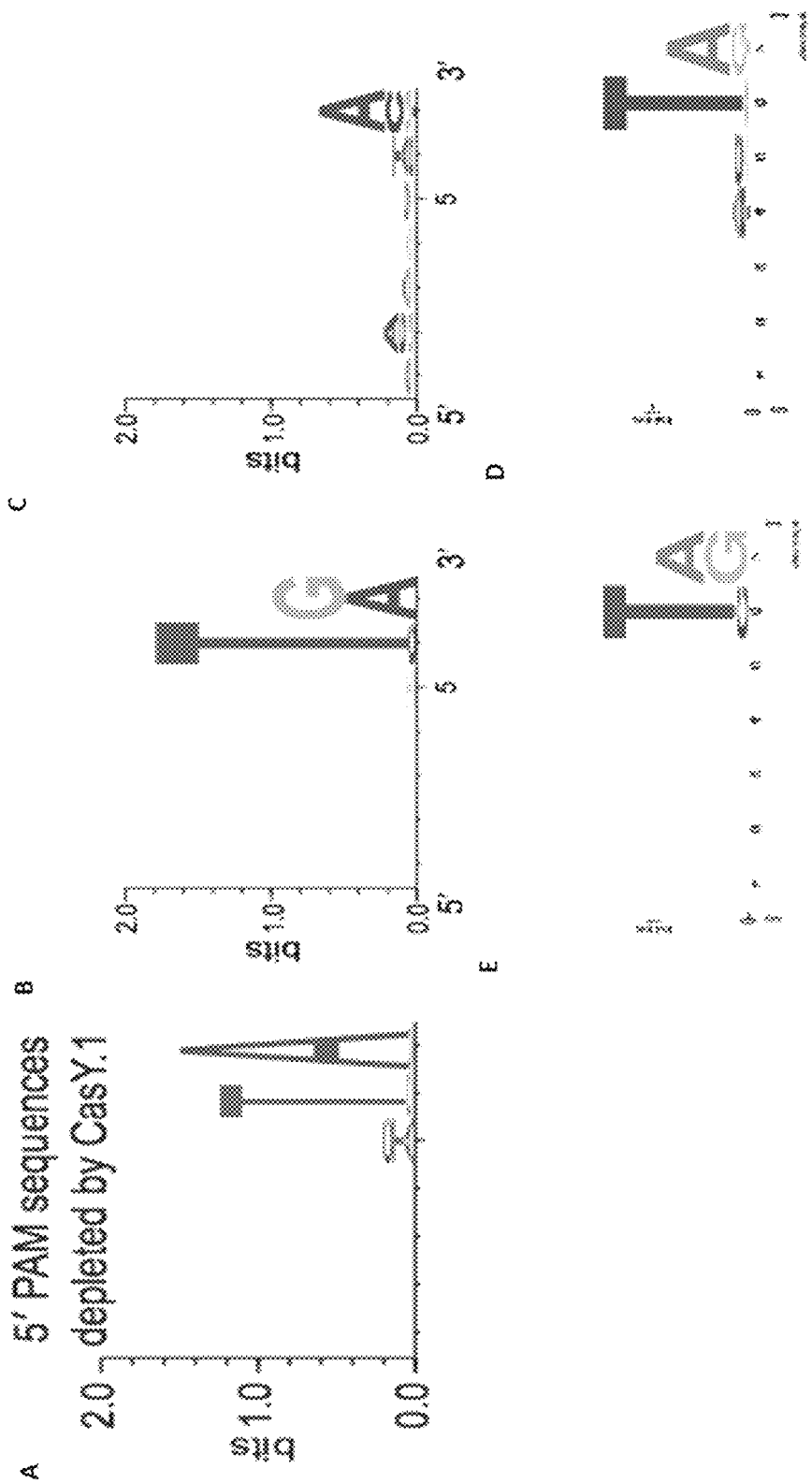
FIG. 13, Panels A-E PAM-dependent plasmid interference assays that show PAM depletion to determine a PAM sequence for CasY orthologs (FIG. 13, Panel A:CasY1.

FIG. 13, Panels A-E PAM-dependent plasmid interference assays that show PAM depletion to determine a PAM sequence for CasY orthologs (FIG. 13, Panel A:CasY1; FIG. 13, Panel B:CasY15; FIG. 13, Panel C: CasY10; FIG. 13, Panel D: CasY3; FIG. 13, Panel E: CasY11).

Figure 14:
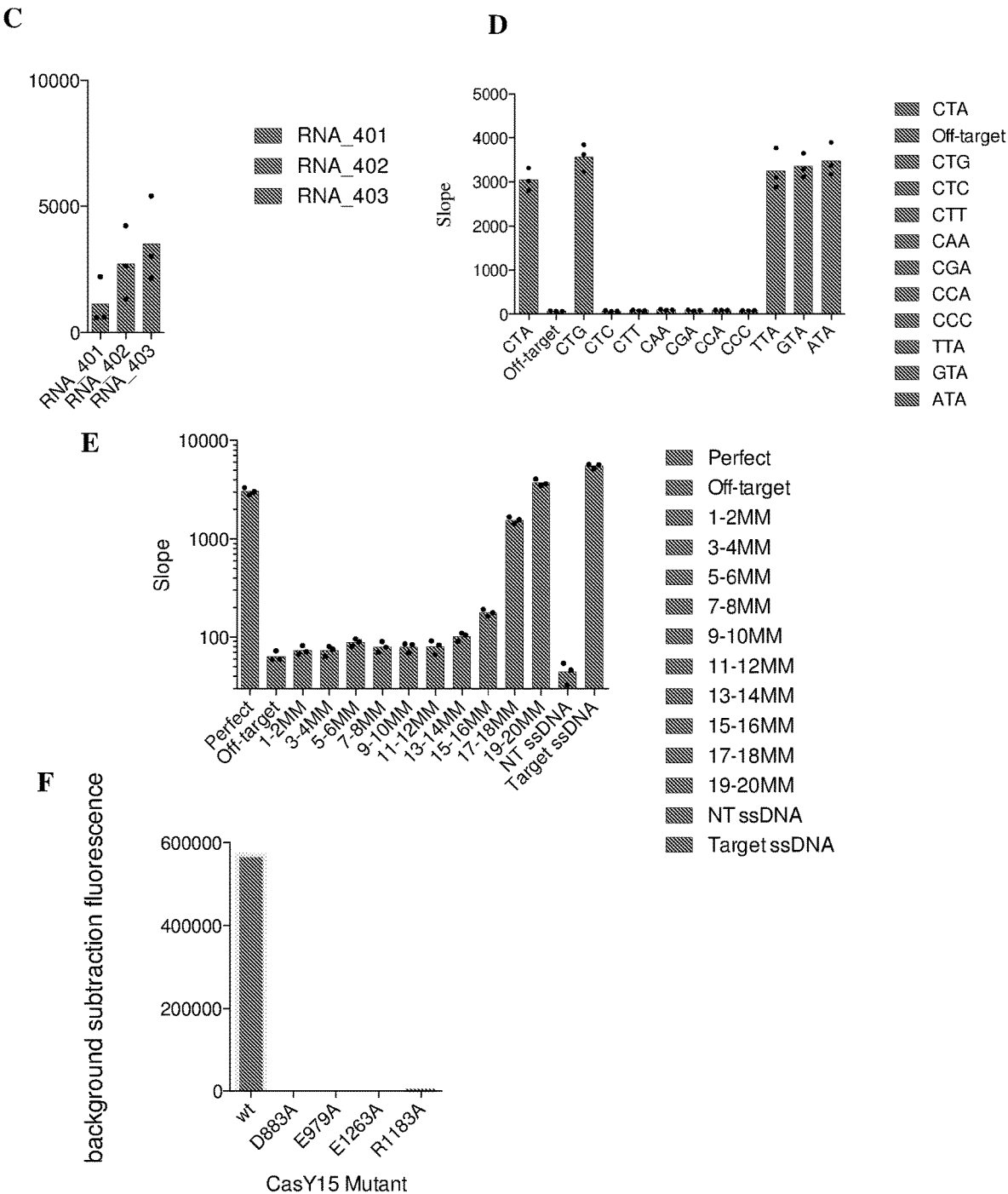
FIG. 14, Panels A-F depict CasY15 trans cleavage assays with various RNA components, PAM sequences, and mismatch tolerance. 100 nM CasY was complexed with 125 nM crRNA, 125 nM tracrRNA and 50 nM FQ probe in 1× Cleavage Buffer at 37° C. for 10 min. The reaction was then initiated by addition of 2 nM ssDNA activator for all reactions except for the RNA optimization experiments, where the variable RNA component was used to initiate. The reaction was monitored in a fluorescence plate reader for up to 120 minutes at 37° C. with fluorescence measurements taken every 1 min ($\lambda$ex: 485 nm; $\lambda$cm: 535 nm). The resulting data were background-subtracted using the readings taken in the absence of activator and fit to obtain KObs. The F-Q 8nt sequence used is shown in FIG. 18. Higher fluorescence signal indicates increased cleavage activity.

FIG. 14, Panels A-F depict CasY15 trans cleavage assays with various RNA components, PAM sequences, and mismatch tolerance.

FIG. 15 depicts Table 2 of CasY15 RNA sequences.

FIG. 16 depicts Table 3 of CasY15 DNA sequences.

Figure 17:
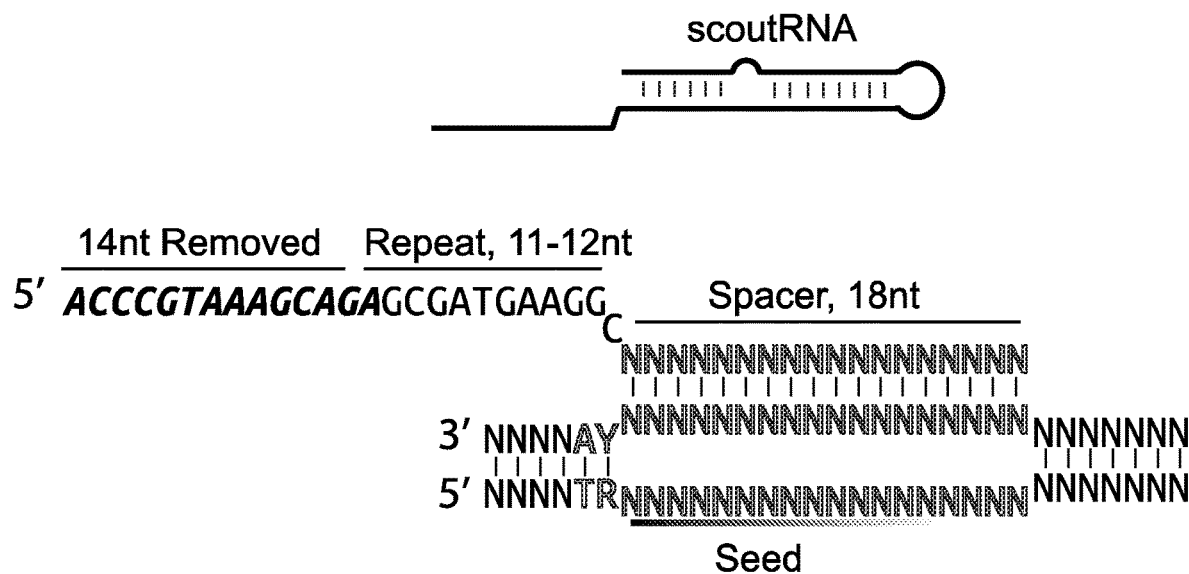
FIG. 17 depicts a model of CasY interference complex and RNA.

FIG. 17 depicts a model of CasY interference complex and RNA.

FIG. 18 shows the CasY emitted fluorescence of "On targets" and "Off target" CasY trans substrates using F-Q probes of different nucleotide lengths.

Example 2: CasY4 trancRNA

RNA mapping to the CasY locus indicated the existence of a highly transcribed noncoding RNA between the CRISPR array and CasY4

Figure 8:
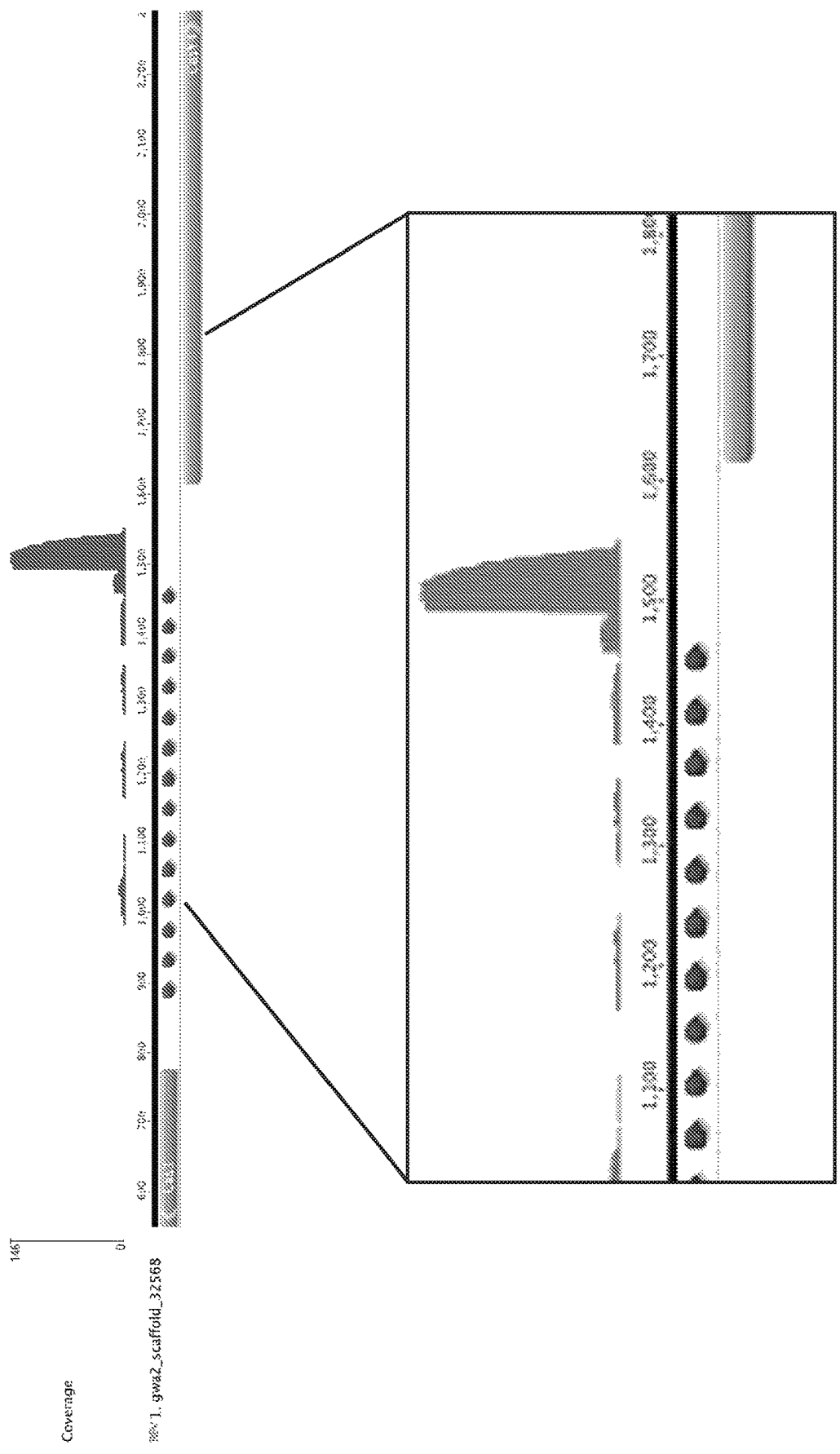
FIG. 8 presents data from environmental RNA mapping to the CasY4 locus. RNA sampled from the site in which CasY4 was found indicates the existence of a highly transcribed noncoding transcript between the CRISPR array and CasY4. Small arrows under the number-line represent the repeats of the CRISPR array; Cas1 (left) and CasY4 (right) denote the regions coding for the N' termini of these proteins; the bars above the number-line represent the coverage of RNA reads. The peak between 1,491 and 1541 represent a highly transcribed CasY4 trancRNA.

FIG. 8. Environmental RNA mapping to the CasY4 locus. RNA sampled from the site in which CasY4 was found indicates the existence of a highly transcribed noncoding transcript between the CRISPR array and CasY4. The highly transcribed noncoding RNA is not complementary to the directed repeat as are transactivating CRISPR RNAs (tracrRNA). The transactivating noncoding RNA is referred to as "trancRNA." The CasY4 trancRNA has the following nucleotide sequence: GGUAUUUCCGGACAGCGGC-UUGACCGCAUCGUCCUCGCCUUUUCCUAAAAU (SEQ ID NO: 19). Small arrows under the number-line represent the repeats of the CRISPR array; Cas1 (left) and CasY4 (right) denote the regions coding for the N' termini of these proteins; the bars above the number-line represent the coverage of RNA reads. The peak between 1,491 and 1541 represent a highly transcribed CasY4 trancRNA.

Figure 9:
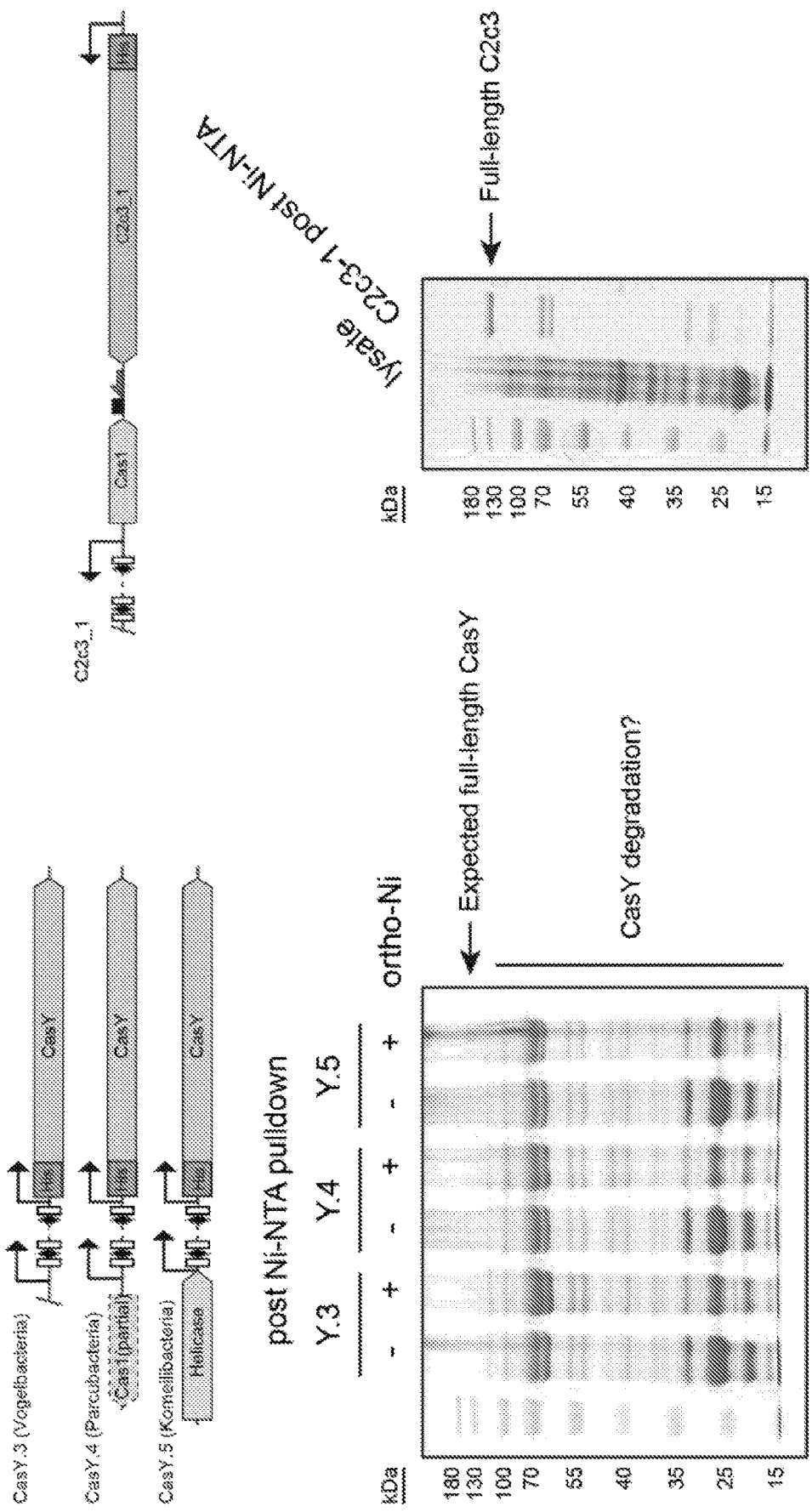
FIG. 9 depicts results from CasY pulldown experiments. A His tag was added to the N-terminus of CasY.3, CasY.4 and CasY.5 in the context of its native locus and the CasY complex was purified by Ni affinity purification. The CasYs seem to be getting degraded after the Ni column (C2c3 pulldown is included as a positive control), but the fragmented CasYs appear to be complexed with trancRNA.
Figure 9:
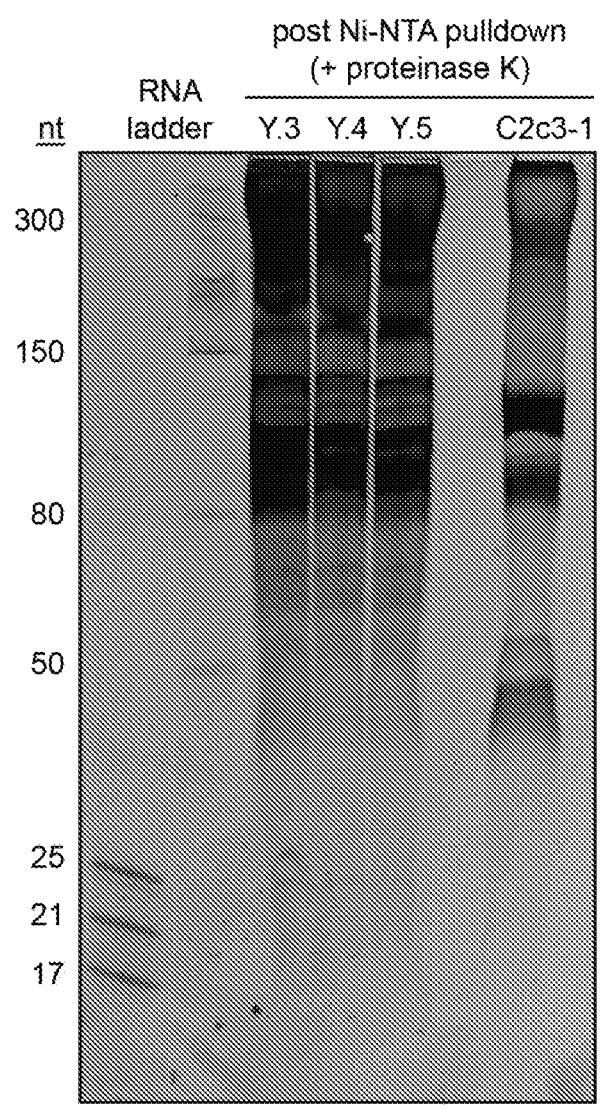

FIG. 9. CasY pulldown experiments. A His tag was added to the N-terminus of CasY.3, CasY.4 and CasY.5 in the context of its native locus and the CasY complex was purified by Ni affinity purification. The CasYs seem to be getting degraded after the Ni column (C2c3 pulldown is included as a positive control), but the fragmented CasYs appear to be complexed with trancRNA.

Figure 10:
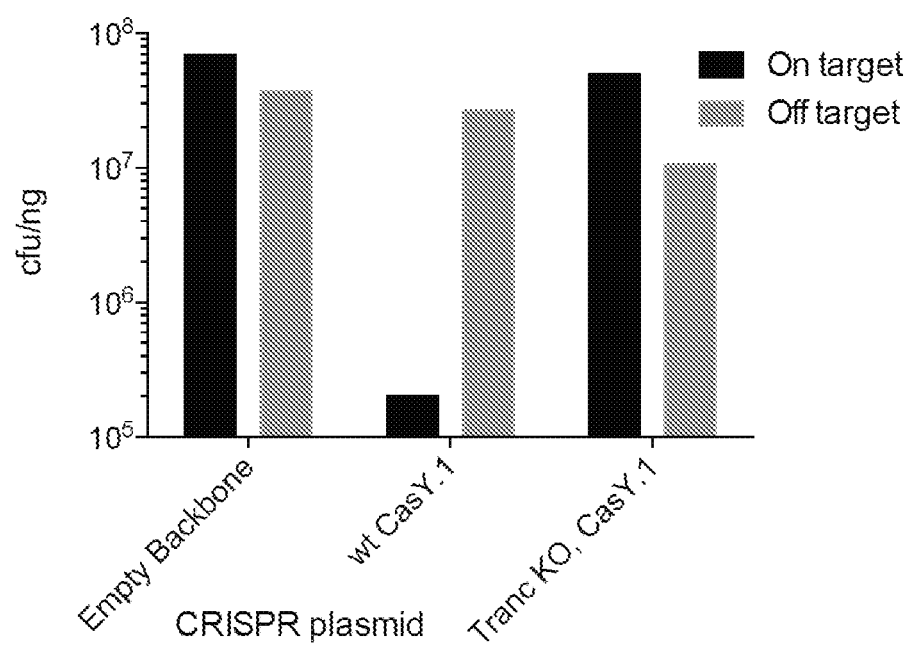
FIG. 10 presents data from CasY trancRNA deletion experiments.
Figure 11:
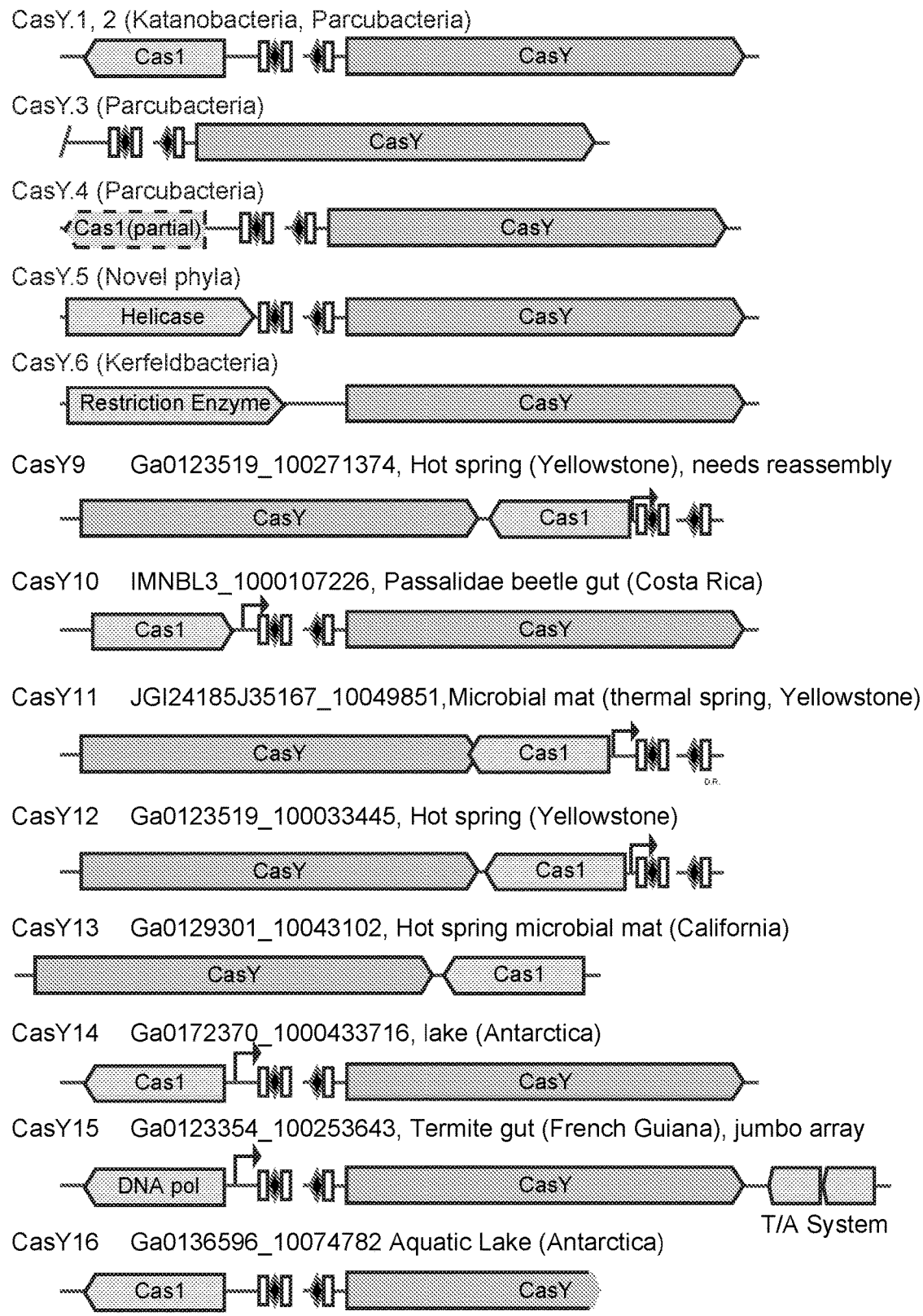
FIG. 11 depicts a schematic representation of natural CasY loci.

FIG. 10. Data from CasY trancRNA deletion experiments. A construct that includes the CasY1 locus was transferred into E. coli, and a target plasmid DNA was introduced. Transformants were quantified. The data show that in the presence of CasY trancRNA (CasY1 trancRNA in this particular example), the target DNA was cleaved efficiently (few transformants). In the absence of CasY trancRNA (CasY1 trancRNA in this particular example), the target DNA was not cleaved efficiently (many transformants).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising an engineered and/or non-naturally occurring complex comprising:
   (a) a CasY polypeptide, or a nucleic acid encoding said CasY polypeptide, wherein the CasY polypeptide comprises an amino acid sequence having 97% or more amino acid sequence identity to the amino acid sequence set forth in any one of SEQ ID NOs: 1-2, 4, and 57;
   (b) a CasY guide RNA, or a nucleic acid encoding said CasY guide RNA, wherein said CasY guide RNA comprises a guide sequence that is complementary to a target sequence of a target nucleic acid, and comprises a region that can bind to the CasY polypeptide; and
   (c) a CasY transactivating noncoding RNA (trancRNA), or a nucleic acid encoding said CasY trancRNA.

2. A kit comprising an engineered and/or non-naturally occurring complex comprising:

(a) a CasY polypeptide, or a nucleic acid encoding said CasY polypeptide, wherein the CasY polypeptide comprises an amino acid sequence having 97% or more amino acid sequence identity to the amino acid sequence set forth in any one of SEQ ID NOs: 1-2, 4, and 57;

(b) a CasY guide RNA, or a nucleic acid encoding said CasY guide RNA, wherein said CasY guide RNA comprises a guide sequence that is complementary to a target sequence of a target nucleic acid, and comprises a region that can bind to the CasY polypeptide; and (c) a CasY transactivating noncoding RNA (trancRNA), or a nucleic acid encoding said CasY trancRNA.

3. The composition of claim 1, characterized by at least one of:

(a) the nucleic acid encoding said CasY polypeptide comprises a nucleotide sequence that: (i) encodes the CasY polypeptide and, (ii) is operably linked to a heterologous promoter;

(b) the nucleic acid encoding said CasY guide RNA comprises a nucleotide sequence that: (i) encodes the CasY guide RNA and, (ii) is operably linked to a heterologous promoter; and (c) the nucleic acid encoding said CasY trancRNA comprises a nucleotide sequence that: (i) encodes the CasY trancRNA and, (ii) is operably linked to a heterologous promoter.

4. The composition of claim 1, wherein at least one of: the nucleic acid encoding said CasY polypeptide, the nucleic acid encoding said CasY guide RNA, and the nucleic acid encoding said CasY trancRNA, is a recombinant expression vector.

5. The composition of claim 1, wherein the CasY guide RNA and/or the CasY trancRNA comprises one or more of: a modified nucleobase, a modified backbone, a non-natural internucleoside linkage, a modified sugar moiety, a Locked Nucleic Acid, a Peptide Nucleic Acid, and a deoxyribonucleotide.

6. The composition of claim 1, wherein the CasY polypeptide is a variant CasY polypeptide with reduced nuclease activity compared to a corresponding wild type CasY protein.

7. The composition of claim 1, wherein at least one of: the CasY polypeptide, the nucleic acid encoding the CasY polypeptide, the CasY guide RNA, the nucleic acid encoding the CasY guide RNA, the CasY trancRNA, and the nucleic acid encoding the CasY trancRNA; is conjugated to a heterologous moiety.

8. The composition of claim 7, wherein the heterologous moiety is a heterologous polypeptide.

9. The composition of claim 1, wherein the CasY polypeptide has reduced nuclease activity compared to a corresponding wild type CasY protein, and is fused to a heterologous polypeptide.

10. The composition of claim 1, wherein the CasY polypeptide is fused to a heterologous polypeptide that: (i) has DNA modifying activity, (ii) exhibits the ability to increase or decrease transcription, and/or (iii) has enzymatic activity that modifies a polypeptide associated with DNA.

11. The composition of claim 1, wherein the CasY polypeptide comprises an amino acid sequence having 99% or more amino acid sequence identity to the amino acid sequence set forth in any one of SEQ ID NOs: 1-2, 4, and 57.

12. The composition of claim 1, wherein the CasY polypeptide comprises the amino acid sequence set forth in any one of SEQ ID NOs: 1-2, 4, and 57.

13. The composition of claim 1, wherein the trancRNA comprises a nucleotide sequence having 70% or more identity with:

(i)
(SEQ ID NO: 18)
CUCCGAAAGUAUCAAAAUAAAAAGGGUUUCCAGUUUUUAACUAAACUUUA

GCCUUCCACCCUUUCCUGAUUUUGUU;

(ii)
(SEQ ID NO: 18)
ACCUGCCAAAAUUUCGUUCAACGAAACUUAAGCAGGCAAGAAAAUUUAAA

AUUAAAUCCGCUGGUGGGCGGAUAAAGUC;
or (iii)
(SEQ ID NO: 19)
GGUAUUUCCGGACAGCGGCUUGACCGCAUCGUCCUCGCCUUUUCCUAAAA

U.

14. The composition of claim 1, wherein the CasY polypeptide is fused to a heterologous polypeptide that is a histone modifier.

15. The composition of claim 1, wherein the CasY polypeptide is fused to a heterologous polypeptide that is a transcriptional activator or a transcription repressor.

16. The composition of claim 1, wherein the trancRNA comprises a nucleotide sequence having 70% or more identity with SEQ ID NO: 151.

* * * * *